United States Patent
Wan et al.

(10) Patent No.: US 10,344,275 B2
(45) Date of Patent: *Jul. 9, 2019

(54) LINKAGE MODIFIED OLIGOMERIC COMPOUNDS

(71) Applicant: Ionis Pharmaceuticals, Inc., Carlsbad, CA (US)

(72) Inventors: W. Brad Wan, Fallbrook, CA (US); Michael T. Migawa, Carlsbad, CA (US); Michael Oestergaard, Carlsbad, CA (US); Eric E. Swayze, Encinitas, CA (US); Punit P. Seth, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,071

(22) Filed: Feb. 8, 2018

(65) Prior Publication Data

US 2018/0305687 A1    Oct. 25, 2018

Related U.S. Application Data

(63) Continuation of application No. 15/305,742, filed as application No. PCT/US2015/028076 on Apr. 28, 2015, now Pat. No. 9,926,556.

(60) Provisional application No. 62/114,153, filed on Feb. 10, 2015, provisional application No. 61/985,196, filed on Apr. 28, 2014.

(51) Int. Cl.
*C12N 15/11* (2006.01)
*C07H 19/067* (2006.01)
*C07H 19/167* (2006.01)
*C07H 21/02* (2006.01)
*C07H 19/06* (2006.01)
*C07H 19/16* (2006.01)
*C07H 21/00* (2006.01)
*C12N 15/113* (2010.01)

(52) U.S. Cl.
CPC .......... *C12N 15/111* (2013.01); *C07H 19/06* (2013.01); *C07H 19/067* (2013.01); *C07H 19/16* (2013.01); *C07H 19/167* (2013.01); *C07H 21/00* (2013.01); *C07H 21/02* (2013.01); *C12N 15/1135* (2013.01); *C12N 15/1136* (2013.01); *C12N 15/1137* (2013.01); *C12N 15/1138* (2013.01); *C12N 2310/11* (2013.01); *C12N 2310/315* (2013.01); *C12N 2310/321* (2013.01); *C12N 2310/3231* (2013.01); *C12N 2310/341* (2013.01); *C12N 2310/346* (2013.01); *C12N 2310/351* (2013.01)

(58) Field of Classification Search
None
See application file for complete search history.

*Primary Examiner* — Dana H Shin
(74) *Attorney, Agent, or Firm* — McNeill Baur PLLC

(57) ABSTRACT

The present invention provides oligomeric compounds comprising at least one neutral methoxypropyl phosphonate modified internucleoside linkage. Such oligomeric compounds have one or more improved properties such as selectivity, potency, improved toxicity profile and or improved proinflammatory profile. Such oligomeric compounds have enhanced stability to exposure to base during synthesis. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

21 Claims, 1 Drawing Sheet
Specification includes a Sequence Listing.

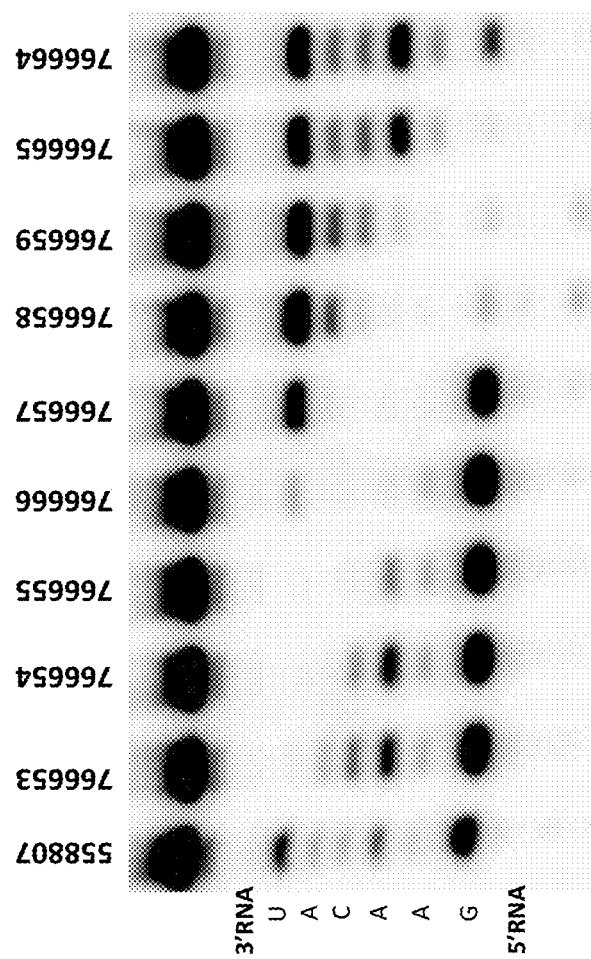

LINKAGE MODIFIED OLIGOMERIC COMPOUNDS

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CHEM0091USC1SEQ_ST25.txt, created Feb. 8, 2018, which is 284 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

The synthesis and biochemical properties of oligonucleotides containing phosphorus-modified phosphonoacetate and thio-phosphonoacetate deoxyribonucleotides have been described in scientific journals and patent literature (see Dellinger et al., *J. Am. Chem. Soc.* 2003, 125(4), 940-950; Sheehan et al., *Nucl. Acids Res.* 2003, 31(14), 4109-4118); also see published US patent applications (US 2004/0116687 and US 2002/0058802) and U.S. Pat. No. 6,693,187.

DNA or RNA containing oligonucleotides comprising alkylphosphonate internucleoside linkage backbone have been disclosed (see U.S. Pat. Nos. 5,264,423 and 5,286,717).

The synthesis of oligodeoxyribonucleotides containing a methyl phosphonate locked nucleic acid (LNA) thymine monomer has been described. The Tm values of the duplexes with their DNA or RNA complements have also been reported (see Lauritsen et al., *Bioorg. Med. Chem. Lett.* 2003, 13(2), 253-256).

Oligomeric compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134(28), 11618-11631).

Targeting disease-causing gene sequences was first suggested more than thirty years ago (Belikova et al., *Tet. Lett.* 1967, 8(37), 3557-3562), and antisense activity was demonstrated in cell culture more than a decade later (Zamecnik et al., *Proc. Natl. Acad. Sci. U.S.A.* 1978, 75(1), 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of 5'-substituted DNA and RNA derivatives and their incorporation into oligomeric compounds has been reported in the literature (Saha et al., *J. Org. Chem.* 1995, 60, 788-789; Wang et al., *Bioorg. Med. Chem. Lett.* 1999, 9(6), 885-890; and Mikhailov et al., *Nucleosides Nucleotides* 1991, 10(1-3), 339-343; Beigelman et al., *Nucleosides Nucleotides* 1995, 14(3-5), 901-905; and Eppacher et al., *Helv. Chim. Acta.* 2004, 87, 3004-3020). The 5'-substituted monomers have also been made as the monophosphate with modified bases (Wang et al., *Nucleosides Nucleotides Nucleic Acids* 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/US94/02993, Published on Oct. 13, 1994 as WO 94/22890).

The synthesis of 5'-$CH_2$—R substituted 2'-O-protected nucleosides and their incorporation into oligomers has been previously reported (see Wu et al., *Helv. Chim. Acta.* 2000, 83, 1127-1143 and Wu et al., *Bioconjug. Chem.* 1999, 10, 921-924).

Amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (De Mesmaeker et al., *Synlett* 1997, 11, 1287-1290).

A genus of 2'-substituted 5'-$CH_2$—R (or O) modified nucleosides and a discussion of incorporating them into oligonucleotides has been previously reported (see International Application Number: PCT/US92/01020, published on Feb. 7, 1992 as WO 92/13869).

The synthesis of modified 5'-methylene phosphonate monomers having 2'-substitution and their use to make modified antiviral dimers has been previously reported (see U.S. patent application Ser. No. 10/418,662, published on Apr. 6, 2006 as US 2006/0074035).

Various analogs of 5'-alkynylphosphonate ribonucleosides have been prepared and reported in the literature (see Meurillon et al., *Tetrahedron* 2009, 65, 6039-6046; Meurillon et al., *Nucleic Acids Symp. Ser.* 2008, 52(1), 565-566; Lera et al., *Org. Lett.* 2000, 2(24), 3873-3875).

The preparation of 5'-vinylphosphonate DNA and RNA monomers and their use to make dimeric compounds for oligonucleotide synthesis have been described. Their biochemical studies have also been discussed (see Whittaker et al., *Tet. Lett.* 2008, 49, 6984-6987; Abbas et al., *Org. Lett.* 2001, 3(21), 3365-3367; Bertram et al., *Biochemistry* 2002, 41, 7725-7731; Zhao et al., *Tet. Lett.* 1996, 37(35), 6239-6242 and Jung et al., *Bioorg. Med. Chem.* 2000, 8, 2501-2509).

Various BNA's have been prepared and reported in the patent literature as well as in scientific literature, see for example: Singh et al., *Chem. Commun.* 1998, 4, 455-456; Koshkin et al., *Tetrahedron* 1998, 54, 3607-3630; Wahlestedt et al., *Proc. Natl. Acad. Sci. U.S.A.* 2000, 97, 5633-5638; Kumar et al., *Bioorg. Med. Chem. Lett.* 1998, 8, 2219-2222; Wengel et al., PCT International Application WO 98-DK393 19980914; Singh et al., *J. Org. Chem.* 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 2004/0219565, 2004/0014959, 2003/0207841, 2004/0192918, 2003/0224377, 2004/0143114 and 2003/0082807; the text of each is incorporated by reference herein, in their entirety.

The synthesis of various cyclohexitol nucleoside analogs (tetrahydropyran nucleoside analogs) has been reported in the literature, see for example: Verheggen et al., *J. Med. Chem.* 1995, 38, 826-835; Altmann et al., *Chimia* 1996, 50, 168-176; Herdewijn et al., *Bioorg. Med. Chem. Lett.* 1996, 6(13), 1457-1460; Verheggen et al., *Nucleosides Nucleotides* 1996, 15(1-3), 325-335; Ostrowski et al., *J. Med. Chem.* 1998, 41, 4343-4353; Allart et al., *Tetrahedron.* 1999, 55, 6527-6546; Wouters et al., *Bioorg. Med. Chem. Lett.* 1999, 9, 1563-1566; Brown et al., *Drug Dev. Res.* 2000, 49, 253-259; published PCT application: WO 93/25565; WO 02/18406; and WO 05/049582; U.S. Pat. Nos. 5,314,893; 5,607,922; and 6,455,507. Various cyclohexitol nucleoside analogs (tetrahydropyran nucleoside analogs) have been described as monomers and have also been incorporated into oligomeric compounds (see for example: Published PCT application, WO 93/25565, published Dec. 23, 1993; Augustyns et al., *Nucleic Acids Res.* 1993, 21(20), 4670-4676; Verheggen et al., *J. Med. Chem.*, 1993, 36, 2033-2040; Van Aerschol et al., *Angew. Chem. Int. Ed. Engl.*, 1995, 34(12), 1338-1339; Anderson et al., *Tetrahedron Lett.* 1996, 37(45), 8147-8150; Herdewijn et al., *Liebigs Ann.* 1996, 1337-1348; De Bouvere et al., *Liebigs Ann./Recueil* 1997, 1453-1461; 1513-1520; Hendrix et al., *Chem. Eur. J.* 1997, 3(1), 110-120; Hendrix et al., *Chem. Eur. J.* 1997, 3(9), 1513-1520; Hossain et al, *J. Org. Chem.* 1998, 63, 1574-1582; Allart et al., *Chem. Eur. J.* 1999, 5(8), 2424-2431; Boudou et al., *Nucleic Acids Res.* 1999, 27(6), 1450-1456; Kozlov et al., *J. Am. Chem. Soc.* 1999, 121, 1108-1109; Kozlov et al., *J. Am. Chem. Soc.*, 1999, 121, 2653-2656; Kozlov et al., *J. Am. Chem. Soc.*, 1999, 121, 5856-5859; Pochet et al., *Nucleosides & Nucleotides*, 1999, 18 (4&5), 1015-1017; Vastmans et al., *Collection Symposium Series*, 1999, 2, 156-160; Froeyen et al., *Helv. Chim. Acta.* 2000, 83, 2153-2182; Kozlov et al., *Chem. Eur. J.*, 2000, 6(1), 151-155; Atkins et al., *Parmazie*, 2000, 55(8), 615-617; Lescrinier et al., *Chemistry & Biology*, 2000, 7, 719-731; Lescrinier et al., *Helv. Chim. Acta.* 2000, 83, 1291-1310; Wang et al., *J. Am. Chem.* 2000, 122, 8595-8602; US Patent Application US 2004/0033967; Published US Patent Application US 2008/0038745; Published and Issued U.S. Pat. No. 7,276,592). DNA analogs have also been reviewed in an article (see: Leumann, *Bioorg. Med. Chem.* 2002, 10, 841-854) which included a general discussion of cyclohexitol nucleoside analogs (under the name: hexitol nucleic acid family).

Oligomeric compounds having phosphodiester linked hexitol nucleic acids (HNA, or 1,5-anhydrohexitol nucleic acids, 3'-H tetrahydropyran nucleoside analogs) have also been prepared for evaluation in cell assays. The different motifs that have been evaluated are fully modified wherein each monomer is a phosphodiester linked hexitol nucleic acid analog and gapped wherein each monomer in the 3' and 5' external regions of the oligomeric compound are each phosphodiester linked hexitol nucleic acid analogs and each monomer in the internal region is a phosphorothioate linked deoxyribonucleoside (see: Kang et al., *Nucleic Acids Research*, 2004, 32(14), 4411-4419; Vandermeeren et al., 2000, 55, 655-663; Flores et al., *Parasitol Res.*, 1999, 85, 864-866; and Hendrix et al., *Chem. Eur. J,* 1997, 3(9), 1513-1520).

Oligomeric compounds having phosphodiester linked analogs having the 3'-OH group which are referred to in the art as ANA or D-altritol nucleic acids (3'-OH tetrahydropyran nucleoside analogs) have been prepared and evaluated both structurally and in vitro (Allart et al., *Chem. Eur.* 1999, 5(8), 2424-2431).

Chemically modified siRNA's having incorporated hexitol nucleotides (also referred to in the art as HNA, hexitol nucleic acids and tetrahydropyran nucleoside analogs) have been prepared and tested for silencing capacity (see: Published PCT application, WO 06/047842, published May 11, 2006.

Cyclohexenyl nucleic acids (ceNA) and analogs thereof have been reported in the scientific and patent literature as monomers as well as in oligomeric compounds, see for example: Robeyns et al., *J. Am. Chem. Soc.* 2008, 130(6), 1979-1984; Horváth et al., *Tetrahedron Lett.* 2007, 48, 3621-3623; Nauwelaerts et al., *J. Am. Chem. Soc.* 2007, 129(30), 9340-9348; Gu et al., *Nucleosides Nucleotides Nucleic Acids* 2005, 24(5-7), 993-998; Nauwelaerts et al., *Nucleic Acids Res.* 2005, 33(8), 2452-2463; Robeyns et al., *Acta Crystallogr. F Struct. Biol. Commun.* 2005, F61(6), 585-586; Gu et al., *Tetrahedron* 2004, 60(9), 2111-2123; Gu et al., *Oligonucleotides* 2003, 13(6), 479-489; Wang et al., *J. Org. Chem.* 2003, 68, 4499-4505; Verbeure et al., *Nucleic Acids Res.* 2001, 29(24), 4941-4947; Wang et al., *J. Org. Chem.* 2001, 66, 8478-82; Wang et al., *Nucleosides Nucleotides Nucleic Acids* 2001, 20(4-7), 785-788; Wang et al., *J. Am. Chem.* 2000, 122, 8595-8602; Published PCT application, WO 06/047842; and Published PCT Application WO 01/049687; the text of each is incorporated by reference herein, in their entirety.

The synthesis of 5'-phosphonate deoxyribonucleoside monomers and dimers having a 5'-phosphate group and their incorporation into oligomeric compounds have been described. Their physico-chemical properties including thermal stability as well as substrate activity toward certain nucleases have also been discussed (see Nawrot et al., *Oligonucleotides* 2006, 16(1), 68-82).

Nucleosides having a 6'-phosphonate group have been reported wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (see Fairhurst et al., *Synlett* 2001, 4, 467-472; Kappler et al., *J. Med. Chem.* 1986, 29, 1030-1038; Kappler et al., *J. Med. Chem.* 1982, 25, 1179-1184; Vrudhula et al., *J. Med. Chem.* 1987, 30, 888-894; Hampton et al., *J. Med. Chem.* 1976, 19, 1371-1377; Geze et al., *J. Am. Chem. Soc.* 1983, 105(26), 7638-7640 and Hampton et al., *J. Am. Chem. Soc.* 1973, 95(13), 4404-4414).

The synthesis and biochemical properties of oligonucleotides containing phosphorus-modified phosphonoacetate and thio-phosphonoacetate deoxyribonucleotides have been described in scientific journals and patent literature (see Dellinger et al., *J. Am. Chem. Soc.* 2003, 125, 940-950; Sheehan et al., *Nucleic Acids Res.* 2003, 31(14), 4109-4118); also see published US patent applications (US 2004/0116687 and US 2002/0058802) and U.S. Pat. No. 6,693,187.

DNA or RNA containing oligonucleotides comprising alkylphosphonate internucleoside linkage backbone have been disclosed (see U.S. Pat. Nos. 5,264,423 and 5,286,717).

The synthesis of oligodeoxyribonucleotides containing a methyl phosphonate locked nucleic acid (LNA) thymine monomer has been described. The Tm values of the duplexes with their DNA or RNA complements have also been reported (see Lauritsen et al., *Bioorg. Med. Chem. Lett.* 2003, 13(2), 253-256).

Oligomeric compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134(28), 11618-11631).

SUMMARY OF THE INVENTION

Provided herein are oligomeric compounds comprising at least one modified internucleoside linkage having Formula I.

In certain embodiments, the oligomeric compounds provided herein comprise gapped oligomeric compounds comprising at least one modified internucleoside linkage having Formula I. In certain embodiments, the oligomeric compounds provided herein hybridize to a portion of a target RNA resulting in loss of normal function of the target RNA. In certain embodiments, the oligomeric compounds disclosed herein provide improved selectivity for a target RNA. In certain embodiments, the oligomeric compounds disclosed herein provide improved selectivity for a target RNA relative to an off target RNA. In certain embodiments, the oligomeric compounds provide improved potency for a target RNA. In certain embodiments, the oligomeric compounds provided herein provide enhanced stability to base exposure. In certain embodiments, the oligomeric compounds provided herein provide enhanced stability to base exposure during synthesis of the oligomeric compound. In certain embodiments, the oligomeric compounds provided herein provide an enhanced off target profile.

The variables are defined individually in further detail herein. It is to be understood that the oligomeric compounds provided herein include all combinations of the embodiments disclosed and variables defined herein.

Provided herein are oligomeric compounds comprising a contiguous sequence of monomer subunits linked by internucleoside linking groups wherein at least one of the internucleoside linking groups has Formula I:

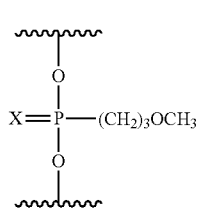

wherein each X is independently O or S;

and each ⁓⁓⁓ represents an attachment to a monomer subunit within said oligomeric compound.

In certain embodiments, each internucleoside linking group of Formula I forms a 3'-5' linkage between two monomer subunits comprising furanosyl sugar moieties within the oligomeric compound. In certain embodiments, one or more internucleoside linking groups of Formula I forms a 2'-3' and or a 2'-5' linkage between two monomer subunits comprising furanosyl sugar moieties within the oligomeric compound.

In certain embodiments, one or more internucleoside linking groups of Formula I forms a linkage between a 3' or a 5'-position on a monomer subunit comprising a furanosyl sugar moiety and a ring atom on a sugar surrogate group as disclosed herein. In certain embodiments, one or more internucleoside linking groups of Formula I form a linkage between two monomer subunits comprising sugar surrogate groups as disclosed herein.

In certain embodiments, oligomeric compounds are provided comprising a contiguous sequence of monomer subunits linked by internucleoside linking groups wherein at least one of the internucleoside linking groups has Formula I, wherein the oligomeric compound comprises a gapped oligomeric compound having a gap region of from 6 to 14 contiguous monomer subunits selected from β-D-2'-deoxyribonucleosides and modified nucleosides that are DNA-like that each adopt a 2'-endo conformational geometry located between a 5'-region and a 3'-region wherein the 5' and 3'-regions each, independently, have from 2 to 8 contiguous monomer subunits selected from RNA-like modified nucleosides that each adopt a 3'-endo conformational geometry.

In certain embodiments, oligomeric compounds are provided comprising from 12 to 24 monomer subunits. In certain embodiments, oligomeric compounds are provided comprising from 14 to 20 monomer subunits.

In certain embodiments, gapped oligomeric compounds are provided wherein the gap region has 10 contiguous monomer subunits and the 5' and 3'-regions each, independently, have 2, 3 or 5 contiguous monomer subunits. In certain embodiments, the gap region has 10 contiguous monomer subunits and the 5' and 3'-regions each have 5 contiguous monomer subunits. In certain embodiments, the gap region has 10 contiguous monomer subunits and the 5' and 3'-regions each have 3 contiguous monomer subunits. In certain embodiments, the gap region has 10 contiguous monomer subunits and the 5' and 3'-regions each have 2 contiguous monomer subunits. In certain embodiments, gapped oligomeric compounds are provided wherein the gap region has 8 contiguous monomer subunits and the 5' and 3'-regions each, independently, have 4 contiguous monomer subunits.

In certain embodiments, oligomeric compounds are provided comprising from 1 to 10 internucleoside linking groups of Formula I. In certain embodiments, oligomeric compounds are provided comprising from 1 to 5 internucleoside linking groups of Formula I. In certain embodiments, oligomeric compounds are provided comprising from 1 to 3 internucleoside linking groups of Formula I. In certain embodiments, oligomeric compounds are provided comprising 1 internucleoside linking group of Formula I. In certain embodiments, oligomeric compounds are provided comprising 4 internucleoside linking groups of Formula I. In certain embodiments, oligomeric compounds are provided comprising 3 internucleoside linking groups of Formula I. In certain embodiments, oligomeric compounds are provided comprising 2 internucleoside linking groups of Formula I.

In certain embodiments, oligomeric compounds are provided wherein internucleoside linking groups of Formula I are contiguous. Contiguous internucleoside linkages means that each successive linkage is an internucleoside linking groups of Formula I such as 2, 3, 4, 5 in a row or wherein each internucleoside linkage in an oligomeric compound is an internucleoside linking group of Formula I.

In certain embodiments, gapped oligomeric compounds are provided wherein each internucleoside linking group of Formula I is, independently, located in the gap region or between the gap region and the 5' or 3'-region. In certain embodiments, gapped oligomeric compounds are provided wherein each internucleoside linking group of Formula I is, independently, located in the gap region or between the gap region and the 5'-region or the 3'-region. In certain embodiments, gapped oligomeric compounds are provided wherein each internucleoside linking group of Formula I is, independently, located in the 5'-region, the 3'-region or between the gap region and the 5'-region or the 3'-region.

In certain embodiments, oligomeric compounds are provided wherein each internucleoside linking group of Formula I is, independently, located in the 5'-region. In certain embodiments, each internucleoside linking group of Formula I is, independently, located in the 3'-region. In certain embodiments, each internucleoside linking group of Formula I is, independently, located in the 5'-region or the gap region. In certain embodiments, each internucleoside linking group of Formula I is, independently, located in the 3'-region or the gap region. In certain embodiments, at least one internucleoside linking group of Formula I is located between the gap region and the 5'-region. In certain embodiments, at least one internucleoside linking group of Formula I is located in the gap region between monomer subunits 1 and 2 counting from the first monomer subunit at the 5' end of the gap region.

In certain embodiments, oligomeric compounds are provided having two internucleoside linking groups of Formula I wherein one internucleoside linking group of Formula I is located between the gap region and the 5'-region and the other internucleoside linking group of Formula I is located in the gap region between monomer subunits 1 and 2 counting from the first monomer subunit at the 5' end of the gap region.

In certain embodiments, oligomeric compounds are provided wherein at least one internucleoside linking group of Formula I is located in the gap region between monomer subunits 2 and 3 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 1 and 2 counting from the first monomer subunit at the 5' end of the gap region and the other internucleoside linking group of Formula I is located in the gap region between monomer subunits 2 and 3 counting from the first monomer subunit at the 5' end of the gap region.

In certain embodiments, oligomeric compounds are provided wherein at least one internucleoside linking group of Formula I is located in the gap region between monomer subunits 3 and 4 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 2 and 3 counting from the first monomer subunit at the 5' end of the gap region and the other internucleoside linking group of Formula I is located in the gap region between monomer subunits 3 and 4 counting from the first monomer subunit at the 5' end of the gap region.

In certain embodiments, oligomeric compounds are provided wherein at least one internucleoside linking group of Formula I is located in the gap region between monomer subunits 4 and 5 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 3 and 4 counting from the first monomer subunit at the 5' end of the gap region and the other internucleoside linking group of Formula I is located in the gap region between monomer subunits 4 and 5 counting from the first monomer subunit at the 5' end of the gap region.

In certain embodiments, oligomeric compounds are provided wherein at least one internucleoside linking group of Formula I is located between the gap region and the 3'-region. In certain embodiments, at least one internucleoside linking group of Formula I is located in the gap region between monomer subunits 1 and 2 counting from the first monomer subunit at the 3' end of the gap region. In certain embodiments, oligomeric compounds are provided having two internucleoside linking groups of Formula I wherein one internucleoside linking group of Formula I is located between the gap region and the 3'-region and the other internucleoside linking group of Formula I is located in the gap region between monomer subunits 1 and 2 counting from the first monomer subunit at the 3' end of the gap region.

In certain embodiments, oligomeric compounds are provided wherein at least one internucleoside linking group of Formula I is located in the gap region between monomer subunits 2 and 3 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 1 and 2 counting from the first monomer subunit at the 3' end of the gap region and the other internucleoside linking group of Formula I is located in the gap region between monomer subunits 2 and 3 counting from the first monomer subunit at the 3' end of the gap region.

In certain embodiments, oligomeric compounds are provided wherein at least one internucleoside linking group of Formula I is located in the gap region between monomer subunits 3 and 4 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 2 and 3 counting from the first monomer subunit at the 3' end of the gap region and the other internucleoside linking group of Formula I is located in the gap region between monomer subunits 3 and 4 counting from the first monomer subunit at the 3' end of the gap region.

In certain embodiments, oligomeric compounds are provided wherein at least one internucleoside linking group of Formula I is located in the gap region between monomer subunits 4 and 5 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 3 and 4 counting from the first monomer subunit at the 3' end of the gap region and the other internucleoside linking group of Formula I is located in the gap region between monomer subunits 4 and 5 counting from the first monomer subunit at the 3' end of the gap region.

In certain embodiments, oligomeric compounds are provided wherein each internucleoside linking group is, independently, a phosphodiester, a phosphorothioate or an internucleoside linking group of Formula I. In certain embodiments, oligomeric compounds are provided wherein each internucleoside linking group is, independently, a phosphorothioate or an internucleoside linking group of Formula I.

In certain embodiments, oligomeric compounds are provided wherein each monomer subunit comprises an optionally protected heterocyclic base moiety independently selected from thymine, cytosine, 5-methylcytosine, adenine and guanine.

In certain embodiments, oligomeric compounds are provided wherein each X is O. In certain embodiments, oligomeric compounds are provided wherein each X is S.

In certain embodiments, the chirality of each internucleoside linking group having Formula I is $R_P$. In certain embodiments, the chirality of each internucleoside linking group having Formula I is $S_P$.

In certain embodiments, gapped oligomeric compounds are provided wherein each modified nucleoside in the 5' and 3'-regions comprises a modified sugar moiety independently selected from a bicyclic nucleoside comprising a bicyclic furanosyl sugar moiety, a modified nucleoside comprising a furanosyl sugar moiety having at least one substituent group and a modified nucleoside comprising a sugar surrogate group. In certain embodiments, each modified nucleoside in the 5' and 3'-regions is, independently, selected from a bicyclic nucleoside comprising a bicyclic furanosyl sugar moiety having a bridging group between the 4' and 2' carbon atoms of the furanosyl ring independently selected from 4'-(CH$_2$)—O-2', 4'-(CH$_2$)$_2$—O-2', 4'-CH(CH$_3$)—O-2', 4'-CH$_2$—NCH$_3$—O-2', 4'-CH$_2$—C—(H)(CH$_3$)-2' and 4'-CH$_2$—C(=CH$_2$)-2' and a modified nucleoside comprising a ribofuranosyl sugar moiety having at least a 2'-substituent group independently selected from F, OCH$_3$, O(CH$_2$)$_2$—OCH$_3$ and OCH$_2$C(=O)—N(H)CH$_3$. In certain embodiments, each modified nucleoside in the 5' and 3'-regions is, independently, selected from a bicyclic nucleoside comprising a bicyclic furanosyl sugar moiety having a 4'-CH[(S)—(CH$_3$)]—O-2' bridging group and a modified nucleoside comprising a ribofuranosyl sugar moiety having a 2'-O(CH$_2$)$_2$—OCH$_3$ substituent group. In certain embodiments, each modified nucleoside in the 5' and 3'-regions is, independently, selected from a bicyclic nucleoside comprising a bicyclic furanosyl sugar moiety having a 4'-CH$_2$—O-2' or 4'-CH[(S)—(CH$_3$)]—O-2' bridging group and a modified nucleoside comprising a ribofuranosyl sugar moiety having a 2'-O(CH$_2$)$_2$—OCH$_3$ substituent group.

In certain embodiments, gapped oligomeric compounds are provided wherein the modified nucleosides in the 5' and 3'-regions comprise at least 2 different types of sugar moieties. In certain embodiments, one or more of the modified nucleosides in the 5' and 3'-regions comprises a sugar surrogate.

In certain embodiments, gapped oligomeric compounds are provided wherein essentially each monomer subunit in the gap region is a β-D-2'-deoxyribonucleoside. In certain embodiments, at least one monomer subunit in the gap region is a modified nucleoside.

In certain embodiments, gapped oligomeric compounds are provided comprising at least one 5' or 3'-terminal group. In certain embodiments, gapped oligomeric compounds are provided comprising one 5' or 3'-conjugate group. In certain embodiments, the conjugate group comprises a cell targeting moiety. In certain embodiments, the cell targeting moiety has the formula:

In certain embodiments, the cell targeting moiety has the formula:

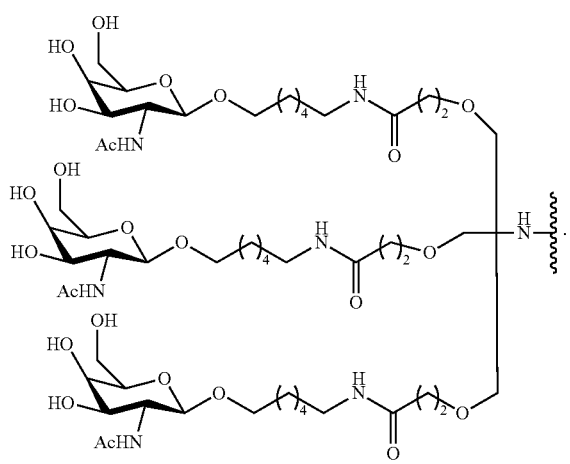

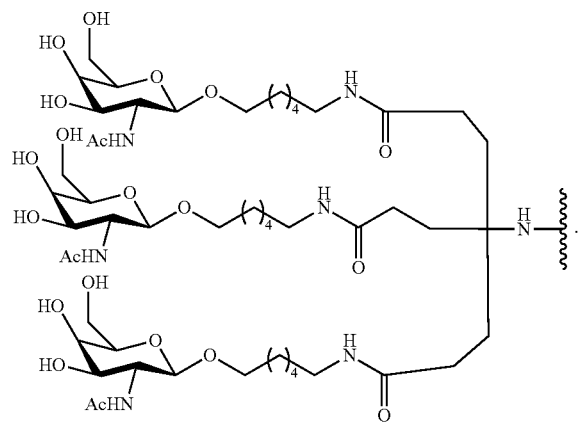

In certain embodiments, the attachment of the cell targeting moiety to the oligomeric compound includes a conjugate linker having the formula: —C(=O)—(CH$_2$)$_3$—C(=O)N(H)—(CH$_2$)$_6$—O—.

In certain embodiments, the attachment of the cell targeting moiety to the oligomeric compound includes a conjugate linker and a cleavable moiety. In certain embodiments, the cleavable moiety has the formula:

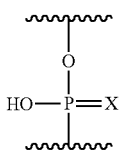

wherein X is O or S.

In certain embodiments, X is O. In certain embodiments, X is S.

In certain embodiments, attachment of the cell targeting moiety to the oligomeric compound includes a conjugate linker and a cleavable moiety.

In certain embodiments, the gap region has from 8 to 12 contiguous monomer subunits and the 5' and 3'-regions each, independently, have from 2 to 5 contiguous monomer sub-units. In certain embodiments, the gap region has from 9 to 10 contiguous monomer subunits. In certain embodiments, the gap region has 10 contiguous monomer subunits.

In certain embodiments, the 5' and 3'-regions each have 5 contiguous monomer subunits. In certain embodiments, the 5' and 3'-regions each have 2 to 3 contiguous monomer subunits. In certain embodiments, the 5' and 3'-regions each have 3 contiguous monomer subunits.

In certain embodiments, oligomeric compounds are provided comprising from 2 to 3 internucleoside linking groups of Formula I. In certain embodiments, the internucleoside linking groups having Formula I are contiguous.

In certain embodiments, each internucleoside linking group of Formula I is, independently, located in the gap region or between the gap region and the 5'-region or the 3'-region. In certain embodiments, each internucleoside linking group of Formula I is, independently, located in the 5'-region, the 3'-region or between the gap region and the 5'-region or the 3'-region.

In certain embodiments, oligomeric compounds are provided comprising only 1 internucleoside linking group of Formula I. In certain embodiments, oligomeric compounds are provided comprising a gapped oligomeric compound comprising only 1 internucleoside linking group of Formula I. In certain embodiments, the internucleoside linking group of Formula I is located in between two monomer subunits in the gap region.

In certain embodiments, oligomeric compounds are provided wherein each internucleoside linking group is, independently, a phosphodiester, a phosphorothioate or an internucleoside linking group of Formula I. In certain embodiments, each internucleoside linking group is a phosphorothioate or an internucleoside linking group of Formula I.

In certain embodiments, oligomeric compounds are provided wherein each monomer subunit comprises an optionally protected heterocyclic base moiety independently selected from a purine, substituted purine, pyrimidine or substituted pyrimidine. In certain embodiments, each heterocyclic base moiety is independently selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, oligomeric compounds are provided comprising a contiguous sequence of monomer subunits linked by internucleoside linking groups wherein at least one of the internucleoside linking groups has Formula I, wherein each X is O. In certain embodiments, each X is S.

In certain embodiments, the chirality of each internucleoside linking group having Formula I is R$_P$. In certain embodiments, the chirality of each internucleoside linking group having Formula I is S$_P$.

In certain embodiments, gapped oligomeric compounds are provided wherein each modified nucleoside in the 5'-region and the 3'-region provides enhanced hybridization affinity for an RNA target as compared to an unmodified nucleoside. In certain embodiments, each modified nucleoside in the 5' and 3'-regions comprises a modified sugar moiety. In certain embodiments, each modified nucleoside in the 5' and 3'-regions is, independently, a bicyclic nucleoside comprising a bicyclic furanosyl sugar moiety, a modified nucleoside comprising a furanosyl sugar moiety having at least one substituent group or a modified nucleoside comprising a sugar surrogate group. In certain embodiments, each modified nucleoside in the 5' and 3'-regions is, independently, a bicyclic nucleoside comprising a bicyclic furanosyl sugar moiety or a modified nucleoside comprising a ribofuranosyl sugar moiety having at least a 2'-substituent group.

In certain embodiments, one or more of the modified nucleosides in the 5' and 3'-regions comprises a modified sugar moiety having 2'-substituent group independently selected from halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—$CH=CH_2$, $O(CH_2)_2$—$OCH_3$, $O(CH_2)_2$—$SCH_3$, $O(CH_2)_2$—$OCF_3$, $O(CH_2)_3$—$N(R_3)(R_4)$, $O(CH_2)_2$—$ON(R_3)(R_4)$, $O(CH_2)_2$—$O(CH_2)_2$—$N(R_3)(R_4)$, $OCH_2C(=O)$—$N(R_4)(R_4)$, $OCH_2C(=O)$—$N(R_5)$—$(CH_2)_2$—$N(R_3)(R_4)$ and $O(CH_2)_2$—$N(R_5)$—$C(=NR_6)[N(R_3)(R_4)]$ wherein $R_3$, $R_4$, $R_5$ and $R_6$ are each, independently, H and $C_1$-$C_6$ alkyl. In certain embodiments, each 2'-substituent group is independently selected from F, $OCH_3$, $OCF_3$, $OCH_2CH_3$, $OCH_2CF_3$, $OCH_2$—$CH=CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ and $OCH_2$—$N(H)$—$C(=NH)NH_2$. In certain embodiments, each 2'-substituent group is independently selected from F, $OCH_3$, $O(CH_2)_2$—$OCH_3$ and $OCH_2C(=O)$—$N(H)CH_3$. In certain embodiments, each 2'-substituent group is $O(CH_2)_2$—$OCH_3$.

In certain embodiments, one or more of the modified nucleosides in the 5' and 3'-regions is a bicyclic nucleoside comprising a bicyclic furanosyl sugar moiety having a bridging group between the 4' and 2' carbon atoms of the furanosyl ring independently selected from 4'-($CH_2$)—O-2', 4'-($CH_2$)—S-2', 4'-($CH_2$)$_2$—O-2', 4'-$CH(CH_3)$—O-2', 4'-CH($CH_2OCH_3$)—O-2', 4'-C($CH_3$)$_2$—O-2', 4'-$CH_2$—N($OCH_3$)-2', 4'-$CH_2$—O—N($CH_3$)-2', 4'-$CH_2$—$NCH_3$—O-2', 4'-$CH_2$—C(H)($CH_3$)-2' and 4'-$CH_2$—C(=$CH_2$)-2'. In certain embodiments, each of the bridging groups is selected from 4'-($CH_2$)—O-2', 4'-($CH_2$)$_2$—O-2', 4'-$CH(CH_3)$—O-2', 4'-$CH_2$—$NCH_3$—O-2', 4'-$CH_2$—C(H)($CH_3$)-2' and 4'-$CH_2$—C(=$CH_2$)-2'. In certain embodiments, each bridging group is 4'-CH[(S)—($CH_3$)]—O-2'.

In certain embodiments, gapped oligomeric compounds are provided wherein each modified nucleoside in the 5' and 3'-regions have identical sugar moieties. In certain embodiments, the modified nucleosides in the 5' and 3'-regions have at least two different types of sugar moieties. In certain embodiments, the different types of sugar moieties are selected from bicyclic furanosyl sugar moieties and furanosyl sugar moieties having at least one substituent group. In certain embodiments, the different types of sugar moieties are selected from bicyclic ribofuranosyl sugar moieties having a 4'-CH[(S)—($CH_3$)]—O-2' bridging group and 2'-O($CH_2$)$_2$—$OCH_3$ substituted ribonucleosides.

In certain embodiments, gapped oligomeric compounds are provided wherein at least one modified nucleosides in the 5' and 3'-regions comprises a sugar surrogate.

In certain embodiments, gapped oligomeric compounds are provided wherein each monomer subunit in the gap region is a β-D-2'-deoxyribonucleoside. In certain embodiments, at least one monomer subunit in the gap region is a modified nucleoside.

In certain embodiments, oligomeric compounds are provided comprising at least one 5' or 3'-terminal group.

In certain embodiments, methods of inhibiting gene expression are provided comprising contacting one or more cells, a tissue or an animal with an oligomeric compound as provided herein wherein the oligomeric compound is complementary to a target RNA. In certain embodiments, the cells are in a human. In certain embodiments, the target RNA is human mRNA. In certain embodiments, the target RNA is cleaved thereby inhibiting its function.

In certain embodiments, methods of inhibiting gene expression are provided comprising contacting one or more cells or a tissue with an oligomeric compound as provided herein.

In certain embodiments, in vivo methods of inhibiting gene expression are provided comprising contacting one or more cells, a tissue or an animal with an oligomeric compound as provided herein.

In certain embodiments, oligomeric compound as provided herein are used in medical therapy.

BRIEF DESCRIPTION OF THE FIGURE

FIG. 1 is a picture of a polyacrylamide gel showing cleavage patterns resulting from RNaseH 1 treatment of RNA/ASO duplexes. The ASO strands are 3/10/3 cEt gapmers having 2 contiguous MOP linkages walked from the 5'-gap junction to the 3'-gap junction one nucleoside at a time (see Example 38).

DETAILED DESCRIPTION OF THE INVENTION

Provided herein are oligomeric compounds comprising at least one modified internucleoside linkage having Formula I. In certain embodiments, the oligomeric compounds provided herein comprise gapped oligomeric compounds comprising at least one modified internucleoside linkage having Formula I. In certain embodiments, the oligomeric compounds provided herein hybridize to a portion of a target RNA resulting in loss of normal function of the target RNA. In certain embodiments, the oligomeric compounds disclosed herein provide improved selectivity for a target RNA. In certain embodiments, the oligomeric compounds disclosed herein provide improved selectivity for a target RNA relative to an off target RNA. In certain embodiments, the oligomeric compounds provide improved potency for a target RNA. In certain embodiments, the oligomeric compounds provided herein provide enhanced stability to base exposure. In certain embodiments, the oligomeric compounds provided herein provide enhanced stability to base exposure during synthesis. In certain embodiments, the oligomeric compounds provided herein provide an enhanced off target profile.

The oligomeric compounds provided herein comprise a contiguous sequence of monomer subunits linked by internucleoside linking groups wherein at least one of the internucleoside linking groups has Formula I:

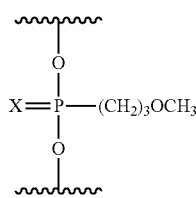

wherein each X is independently O or S.

In certain embodiments, the oligomeric compounds provided herein comprise gapped oligomeric compounds that each have a gap region of from 6 to 14 contiguous monomer subunits selected from β-D-2'-deoxyribonucleosides and modified nucleosides that are DNA-like that each adopt a 2'-endo conformational geometry located between a 5'-region and a 3'-region wherein the 5' and 3'-regions each, independently, have from 2 to 8 contiguous monomer subunits selected from RNA-like modified nucleosides that each adopt a 3'-endo conformational geometry.

The gapped oligomeric compounds provided herein have been shown to have improved properties. In certain embodiments, the activity of an otherwise unmodified gapped oligomeric compound against a target nucleic acid is enhanced by incorporation of one internucleoside linking group having Formula I in the gap region. In certain embodiments, at least one internucleoside linking group having Formula I is located in the gap but not at a gap junction. In certain embodiments, at least one internucleoside linking group having Formula I is located at the gap junction on the 5' side wherein the internucleoside linkage separates the gap region from the wing 5'-region. In certain embodiments, at least one internucleoside linking group having Formula I is located at the gap junction on the 3' side. In certain embodiments, at least one internucleoside linking group having Formula I is located in at least one of the 5' and 3'-regions. As indicated in the data provided in the example section herein, such properties include selectivity and potency.

In certain embodiments, a gapped oligomeric compound of interest is identified and then a series of identical oligomeric compounds are prepared with a single internucleoside linking group having Formula I walked across the gap region. If there are 8 monomer subunits in the gap then there will be 8 oligomeric compounds prepared having the internucleoside linking group having Formula I located at a different position in each of the oligomeric compounds which are subsequently assayed in one or more assays as illustrated herein to determine the lead from the series.

In certain embodiments, a gapped oligomeric compound of interest is identified and then a series of identical oligomeric compounds are prepared with two contiguous internucleoside linking group having Formula I walked across the gap region. If there are 10 monomer subunits in the gap then there will be 10 oligomeric compounds prepared having the internucleoside linking groups of Formula I located at a different positions in each of the oligomeric compounds which are subsequently assayed in one or more assays as illustrated herein to determine the lead from the series (such as a 3/10/3 gapmer, see for example, Example 38).

In certain embodiments, additional internucleoside linking groups having Formula I are incorporated into the gap region of the lead oligomeric compound and assayed in one or more assays as illustrated herein. In certain embodiments, the lead compound is further functionalized with one or more terminal groups such as for example a conjugate group. In certain embodiments, a gapped oligomeric compound of interest is identified and then a series of identical oligomeric compounds are prepared with blocks of at least two internucleoside linking group having Formula I walked across the gap region.

In certain embodiments, gapped oligomeric compounds having a single internucleoside linking group having Formula I are provided having enhanced or comparable ($IC_{50}$) and enhanced selectivity when compared to unmodified gapped oligomeric compounds and otherwise identical oligomeric compounds having a methyl phosphonate linkage. Oligomeric compounds comprising a single internucleoside linking group having Formula I have also been shown to have enhanced stability to aqueous ammonia during the deblocking and cleavage steps of oligomeric compound synthesis as compared to an otherwise identical oligomeric compounds having a methyl phosphonate linkage substituted for the internucleoside linking group having Formula I.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a 2'-deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl ring and that is capable of replacing the naturally occurring sugar moiety of a nucleoside, such that the resulting nucleoside sub-units or monomer subunits are capable of linking together and/or linking to other nucleosides or other monomer subunits to form an oligomeric compound which is capable of hybridizing to a complementary oligomeric compound such as a nucleic acid target. Such structures include rings comprising a different number of atoms than furanosyl (e.g., 4, 6, or 7-membered rings); replacement of the oxygen atom of a furanosyl with a non-oxygen atom (e.g., carbon, sulfur, or nitrogen, wherein replacement of the oxygen atom with sulfur in furanose is generally considered a modified nucleoside as opposed to a sugar surrogate but can be considered both); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols. The synthesis and incorporation of modified nucleosides that include a sugar surrogate is well known in the art (see for example: U.S. Pat. Nos. 8,530,640; 8,088,904; 8,604,192; and 8,536,320, each of which are commonly owned and is incorporated herein by reference in its entirety).

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose or modified furanose sugar group such as a 4'-S analog (4'-S-modified nucleoside and 4'-S-ribonucleoside refer to replacement of the furanose oxygen atom with S). Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-5-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH($CH_3$)—O-2' bridge. In certain embodiments, the cEt comprises a comprising a 4'-CH((S)—$CH_3$)—O-2' bridge. In certain embodiments, the cEt comprises a comprising a 4'-CH((R)—$CH_3$)—O-2' bridge.

As used herein, "locked nucleic acid nucleoside" or "LNA" means a nucleoside comprising a bicyclic sugar moiety comprising a 4'-$CH_2$—O-2'bridge.

As used herein, "2'-substituted nucleoside" means a ribofuranosyl nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H(H) furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside other than a β-D-ribose nucleoside that provides an A-form (northern) duplex when incorporated into an oligomeric compound and duplexed with a complementary RNA. RNA-like nucleosides are used as replacements for RNA nucleosides in oligomeric compounds to enhance one or more properties such as, for example, nuclease resistance and or hybridization affinity. RNA-like nucleosides include, but are not limited to modified furanosyl nucleosides that adopt a 3'-endo conformational geometry when put into an oligomeric compound. RNA-like nucleosides also include RNA surrogates such as F-HNA. RNA-like nucleosides include but are not limited to modified nucleosides comprising a 2'-substituent group selected from F, O($CH_2$)$_2$ $OCH_3$ (MOE) and $OCH_3$. RNA-like nucleosides also include but are not limited to modified nucleosides comprising bicyclic furanosyl sugar moiety comprising a 4'-$CH_2$—O-2', 4'-($CH_2$)$_2$—O-2', 4'-C(H)[(R)—$CH_3$]—O-2' or 4'-C(H)[(S)—$CH_3$]—O-2' bridging group.

As used herein, "DNA-like nucleoside" means a modified nucleoside other than a β-D-2'-doxyribose nucleoside that provides a B-form (southern) duplex when incorporated into an oligomeric compound and duplexed with a complementary DNA. DNA-like nucleosides provide an intermediate duplex when incorporated into an oligomeric compound and duplexed with a complementary RNA that is between A-form and B-form. DNA-like nucleosides are used as replacements for DNA nucleosides in oligomeric compounds to enhance one or more properties. DNA-like nucleosides include, but are not limited to modified nucleosides that adopt a 2'-endo conformational geometry when put into an oligomeric compound.

As used herein, the term "single-stranded" refers to an oligomeric compound that is not hybridized to its complement and that does not have sufficient self-complementarity to form a hair-pin structure under physiologically relevant conditions. A single-stranded compound may be capable of binding to its complement to become a double-stranded or partially double-stranded compound.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein the term "monomer subunit" is meant to include all manner of monomers that are amenable to oligomer synthesis. In general a monomer subunit includes at least a sugar moiety or modified sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—$CHR_a$-4' bridging group, wherein $R_a$ is H, alkyl or substituted alkyl), other modified nucleosides and nucleosides having sugar surrogates.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide or oligomeric compound wherein at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "RNAi compound" refers to an oligomeric compound that acts, at least in part, through an RNAi mechanism to modulate a target nucleic acid and/or protein encoded by a target nucleic acid. RNAi compounds include, but are not limited to double-stranded short interfering RNA (siRNA), single-stranded RNA (ssRNA), and microRNA, including microRNA mimics.

As used herein, "mRNA" means an RNA molecule that encodes a protein.

As used herein, "pre-mRNA" means an RNA transcript that has not been fully processed into mRNA. Pre-RNA includes one or more intron.

As used herein, "pdRNA" refers to a pre-selected RNA molecule that interacts with one or more promoter to modulate transcription.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.\

As used herein, "target microRNA" refers to a preselected non-coding RNA molecule about 18-30 nucleobases in length that modulates expression of one or more proteins or to a precursor of such a non-coding molecule.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is doublestranded.

As used herein, "seed region" refers to a region at or near the 5'end of an antisense compound having a nucleobase sequence that is import for target nucleic acid recognition by the antisense compound. In certain embodiments, a seed region comprises nucleobases 2-8 of an antisense compound. In certain embodiments, a seed region comprises nucleobases 2-7 of an antisense compound. In certain embodiments, a seed region comprises nucleobases 1-7 of an antisense compound. In certain embodiments, a seed region comprises nucleobases 1-6 of an antisense compound. In certain embodiments, a seed region comprises nucleobases 1-8 of an antisense compound.

As used herein, "microRNA seed region" refers to a seed region of a microRNA or microRNA mimic. In certain embodiments, a microRNA seed region comprises nucleobases 2-8 of a microRNA or microRNA mimic. In certain embodiments, a microRNA seed region comprises nucleobases 2-7 of a microRNA or microRNA mimic. In certain embodiments, a microRNA seed region comprises nucleobases 1-7 of a microRNA or microRNA mimic. In certain embodiments, a microRNA seed region comprises nucleobases 1-6 of a microRNA or microRNA mimic. In certain embodiments, a microRNA seed region comprises nucleobases 1-8 of a microRNA or microRNA mimic.

As used herein, "seed match segment" refers to a portion of a target nucleic acid having nucleobase complementarity to a seed region. In certain embodiments, a seed match segment has nucleobase complementarity to nucleobases 2-8 of an siRNA, ssRNA, natural microRNA or microRNA mimic. In certain embodiments, a seed match segment has nucleobase complementarity to nucleobases 2-7 of an siRNA, ssRNA, microRNA or microRNA mimic. In certain embodiments, a seed match segment has nucleobase complementarity to nucleobases 1-6 of an siRNA, ssRNA, microRNA or microRNA mimic. In certain embodiments, a seed match segment has nucleobase complementarity to nucleobases 1-7 of an siRNA, ssRNA, microRNA or microRNA mimic. In certain embodiments, a seed match segment has nucleobase complementarity to nucleobases 1-8 of an siRNA, ssRNA, microRNA or microRNA mimic.

As used herein, "seed match target nucleic acid" refers to a target nucleic acid comprising a seed match segment.

As used herein, "microRNA family" refers to a group of microRNAs that share a microRNA seed sequence. In certain embodiments, microRNA family members regulate a common set of target nucleic acids. In certain embodiments, the shared microRNA seed sequence is found at the same nucleobase positions in each member of a microRNA family. In certain embodiments, the shared microRNA seed sequence is not found at the same nucleobase positions in each member of a microRNA family. For example, a microRNA seed sequence found at nucleobases 1-7 of one member of a microRNA family may be found at nucleobases 2-8 of another member of a microRNA family.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein "positionally modified" means an oligomeric compound or portion thereof comprising any modification at any position. In certain embodiments, positionally modified is used to describe sugar or linkage modified nucleosides. In certain embodiments, the term positionally modified includes a sequence of β-D-ribonucleosides wherein the sequence is interrupted by two or more regions comprising from 1 to about 4 sugar modified nucleosides. The positionally modified motif includes internal regions of sugar modified nucleoside and can also include one or both termini. Each particular sugar modification within a region of sugar modified nucleosides is variable with uniform modification desired. The sugar modified regions can have the same sugar modification or can vary such that one region may have a different sugar modification than another region. Positionally modified oligomeric compounds are distinguished from gapped motifs, hemimer motifs, blockmer motifs and alternating motifs because the pattern of regional substitution defined by any positional motif is not defined by these other motifs.

As used herein, "uniform modified" or "uniformly modified" means an oligomeric compound or a portion thereof that comprise the same modifications. In certain embodiments, the nucleosides of the oligomeric compound or a region thereof will all have identical sugar moieties. In certain embodiments, the internucleoside linkages of the oligomeric compound or a region thereof will be identical. As such the term uniform modification applies to the sugar moieties and or the internucleoside linkages and is independent of the heterocyclic bases present in the oligomeric compound.

As used herein, "fully modified" or "fully modified motif" means an oligomeric compound or portion thereon wherein each nucleoside comprises a modified sugar moiety other than β-D-ribose or β-D-2'-deoxyribose. The modified sugar moieties of the nucleosides of a fully modified oligomeric compound may all be the same (uniformly modified) or one or more may be different from one another. As such the term fully modified applies to the sugar moieties and is independent of the heterocyclic bases present in the oligomeric compound.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N($R_{bb}$) ($R_{cc}$)), imino(=N$R_{bb}$), amido (—C(O)N($R_{bb}$)($R_{cc}$) or —N($R_{bb}$)C(O)$R_{aa}$), azido (—N$_3$), nitro (—NO$_2$), cyano (—CN), carbamido (—OC(O)N($R_{bb}$)($R_{cc}$) or —N($R_{bb}$)C (O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$) (=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S (O)$R_{bb}$), sulfonyl (—S(O)$_2R_{bb}$) and sulfonamidyl (—S(O)$_2$ N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. Alkyl groups as used herein may optionally include one or more further substituent groups.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

The term "phosphate moiety" means a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

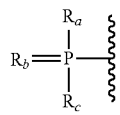

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ 1 S O or S.

Phosphorus moieties included herein can be attached to a monomer, which can be used in the preparation of oligomeric compounds, wherein the monomer may be attached using O, S, $NR_d$ or $CR_eR_f$ wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

B. Oligomeric Compounds

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups. In certain embodiments, oligomeric compounds comprise a contiguous sequence of monomer subunits wherein each monomer subunit comprises a heterocyclic base moiety and a sugar moiety. In certain embodiments, oligomeric compounds include one or more abasic sites. In certain embodiments, oligomeric compounds include one or more acyclic nucleosides.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

i. Certain Modified Nucleosides

Provided herein are oligomeric compounds comprising modified nucleosides. Such modified nucleosides comprise a modified sugar moeity, a modified nucleobase, or both a modified sugar moiety and a modified nucleobase.

a. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituents, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position are selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N (R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Zhou et al., J. Org. Chem. 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH (CH$_2$OMe)-O-2') BNA (also referred to as constrained MOE or cMOE) as depicted below.

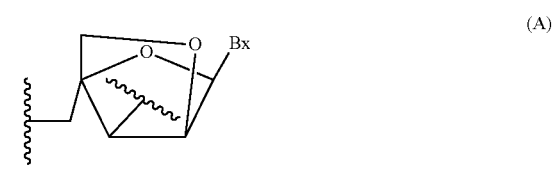

(A)

(B) 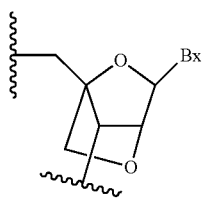

(C) 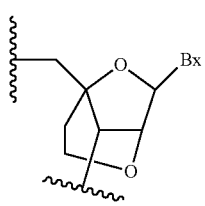

(D) 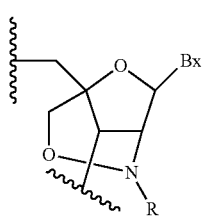

(E) 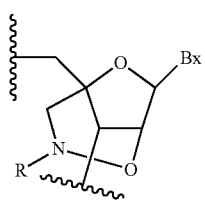

(F) 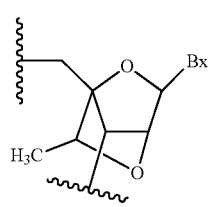

(G) 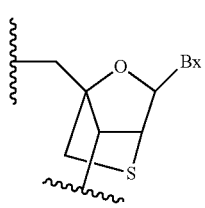

(H) 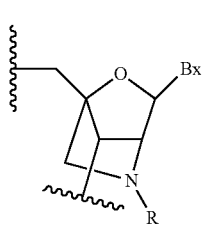

(I) 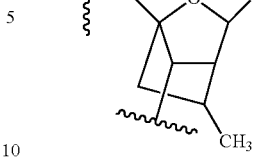

(J) 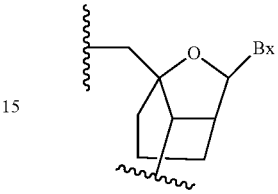

(K) 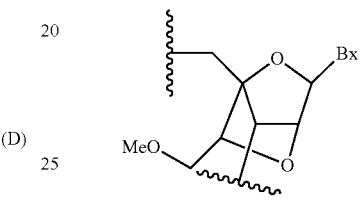

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.* 1998, 4, 455-456; Koshkin et al., *Tetrahedron,* 1998, 54, 3607-3630; Wahlestedt et al., *Proc. Natl. Acad. Sci. U.S.A.* 2000, 97, 5633-5638; Kumar et al., *Bioorg. Med. Chem. Lett.* 1998, 8, 2219-2222; Singh et al., *J. Org. Chem.* 1998, 63, 10035-10039; Srivastava et al. *J. Am. Chem. Soc.* 2007, 129(26) 8362-8379; Elayadi et al., *Curr. Opin. Investig. Drugs* 2001, 2, 558-561; Braasch et al., *Chem. Biol.* 2001, 8, 1-7; Orum et al., *Curr. Opin. Mol. Ther.* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Res.* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see, e.g., published U.S. Patent Application US 2005/0130923, published on Jun. 16, 2005) and/or the 5' position. By way of additional example, carbocyclic bicyclic nucleosides having a 4'-2' bridge have been described (see, e.g., Freier et al., *Nucleic Acids Res.* 1997, 25(22), 4429-4443 and Albaek et al., *J. Org. Chem.* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, *Bioorg. Med. Chem.* 2002, 10, 841-854), fluoro HNA (F-HNA, see e.g., U.S. Pat. Nos. 8,088,904; 8,440,803; and 8,796,437, F-HNA can also be referred to as a F-THP or 3'-fluoro tetrahydropyran), and including further compounds also having Formula VII:

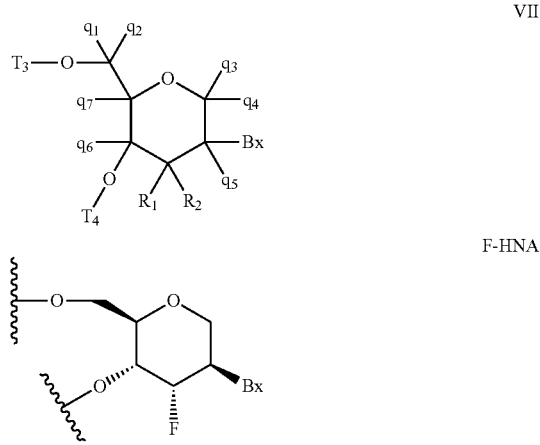

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H. In certain embodiments, the modified THP nucleoside is F-THP.

Many other bicyclo and tricyclo sugar surrogate ring systems are also known in the art that can be used to modify nucleosides for incorporation into antisense compounds (see, e.g., review article: Leumann, *Bioorg. Med. Chem.* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US 2005/0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleosides.

In certain embodiments, the oligomeric compounds provided herein include RNA-like nucleosides that have been modified to influence the sugar conformation to have predominantly 3'-endo conformational geometry. In certain embodiments, such modified nucleosides include synthetic modifications of the heterocyclic base moiety, the sugar moiety or both to induce a 3'-endo sugar conformation. In certain embodiments, RNA-like nucleosides are selected from RNA surrogates such as including, but not limited to, F-HNA or cyclohexenyl nucleic acid. RNA-like nucleosides are used to replace and mimic RNA nucleosides in an oligomeric compound so that particular properties of the oligomeric compound can be enhanced. Typically RNA-like nucleosides are used in the 5' and 3'-regions (wings) of gapped oligomeric compounds to improve stability in the presence of nucleases and also to increase the affinity for nucleic a nucleic acid target. Other properties that can also be enhanced by using RNA-like nucleosides include but aren't limited to modulation of pharmacokinetic properties through modification of protein binding, protein off-rate, absorption and clearance as well as chemical stability and specificity of the oligomeric compound (affinity and specificity for enzymes as well as for complementary sequences); and increasing efficacy of RNA cleavage.

In certain embodiments, RNA-like nucleosides include modified nucleosides comprising one or more 2', 3', 4' and 5' substituent groups, bicyclic nucleosides and RNA-surrogates. In certain embodiments, RNA-like nucleosides include, but are not limited to modified nucleosides comprising 2'-ribo-substituent groups selected from: F, $OCH_3$, O—$C_2$-$C_4$ alkyl, O—$CH_2CH$=$CH_2$, O—$(CH_2)_2$—O—$CH_3$ (MOE), O—$(CH_2)_3$—$NH_2$, O—$(CH_2)_2$—O—$N(R_1)_2$, O—$CH_2C(O)$—$N(R_1)_2$, O—$(CH_2)_2$—O—$(CH_2)_2$—$N(R_1)_2$, O—$(CH_2)_3$—$NHR_1$ and O—$CH_2$—$N(H)$—C(=$NR_1$)[$N(R_1)_2$] wherein each $R_1$ is, typically H, $C_1$-$C_{12}$ alkyl or a protecting group. RNA-like nucleosides also include but are not limited to modified nucleosides having a bicyclic furanosyl sugar moiety (bicyclic nucleosides) comprising a bridging group between the 4' and 2'-carbon atoms. Such bicyclic nucleosides include, but are not limited to bridging groups consisting of from 1 to 3 linked biradical groups selected from O, S, $NR_a$, $C(R_b)(R_c)$, C=O, $C(R_b)$=$C(R_c)$ and C[=$C(R_b)(R_c)$] wherein $C(R_b)$=$C(R_c)$ counts as 2 of said biradical groups wherein each $R_a$, $R_b$ and $R_c$ is, independently, H, $C_1$-$C_6$ alkyl, $C_1$-$C_6$ alkoxy, $C_2$-$C_6$ alkenyl or $C_2$-$C_6$ alkynyl. In certain embodiments, the bridging groups include, but are not limited to 4'-($CH_2$)—O-2', 4'-($CH_2$)—S-2', 4'-($CH_2$)$_2$—O-2', 4'-$CH(CH_3)$—O-2', 4'-CH($CH_2OCH_3$)—O-2', 4'-C($CH_3$)$_2$—O-2', 4'-$CH_2$—$N(OCH_3)$-2', 4'-$CH_2$—O—$N(CH_3)$-2', 4'-$CH_2$—$NCH_3$—O-2', 4'-$CH_2$—C(H)($CH_3$)-2' and 4'-$CH_2$—C(=$CH_2$)-2'. In certain embodiments, the bridging groups include, but are not limited to 4'-$CH_2$—O-2', 4'-($CH_2$)$_2$—O-2', 4'-C(H)[(R)—$CH_3$]—O-2' and 4'-C(H)[(S)—$CH_3$]—O-2'.

In certain embodiments, the oligomeric compounds provided herein include DNA-like nucleosides that have been modified to influence the sugar conformation to have predominantly 2'-endo conformational geometry. Such modified nucleosides can include synthetic modifications of the heterocyclic base moiety, the sugar moiety or both to induce the desired 2'-endo sugar conformation. These modified nucleosides are used to mimic RNA nucleosides so that particular properties of an oligomeric compound can be enhanced while maintaining the desirable 2'-endo conformational geometry.

In certain embodiments, DNA-like nucleosides include, but are not limited to 2'-substituted furanosyl nucleosides comprising: 2'=$CH_2$, 2'-ara-CN, 2'-ara-F, 2'-ara-Br or 2'-ara-Cl, 2'-ara-$N_3$, 2'-ara-OH, 2'-ara-O—$CH_3$ or 2'-dehydro-2'-ara-$CH_3$.

The C3'-endo and C2'-endo conformational geometries are shown below:

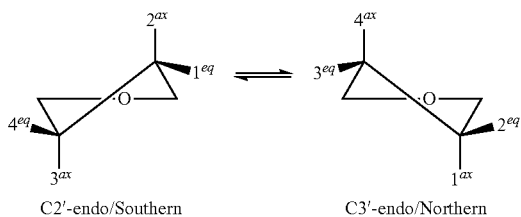

C2'-endo/Southern    C3'-endo/Northern ii. Certain Modified Nucleobases

In certain embodiments, nucleosides of the present invention comprise one or more unmodified nucleobases. In certain embodiments, nucleosides of the present invention comprise one or more modified nucleobases (heterocyclic base moieties).

In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methylcytosine, 6-N-benzoyladenine or 2-N-isobutyrylguanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302).

Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

ii. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

iii. Certain Motifs

In certain embodiments, oligomeric compounds comprise or consist of oligonucleotides. In certain embodiments, such oligonucleotides comprise one or more chemical modifications. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

a. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligomeric compounds provided herein comprise a gapmer sugar motif, which comprises two external regions or "wings" and a central or internal region or "gap" (also referred to as 5'-region and 3'-region). The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar moieties of the two wings are the same as one another (symmetric sugar gapmer). In certain embodiments, the sugar moieties of the 5'-wing differs from the sugar moieties of the 3'-wing (asymmetric sugar gapmer). In certain embodiments, the sugar moieties in the two wings are selected from at least two different types that are different from the sugar moieties in the gap and at least one of each are in each wing.

In certain embodiments, the term "gapped oligomeric compound" refers to an oligomeric compound having two external regions or wings and an internal region or gap (also referred to as 5'-region and 3'-region). The three regions form a contiguous sequence of monomer subunits with the sugar moieties of the external regions (wings) being different than the sugar moieties of the internal region (gap). In certain embodiments, the sugar moieties of each monomer subunit within a particular region is essentially the same. In certain embodiments, the sugar moieties of each monomer subunit within each wing region is selected independently from 2 different types of modified nucleosides. In certain embodiments, the sugar moieties of each monomer subunit within each wing region is selected independently from 3 different types of modified nucleosides. In certain embodiments, the sugar moieties of each monomer subunit within each wing region is selected independently from 4 different types of modified nucleosides. In certain embodiments, the sugar moiety of essentially each monomer subunit within the internal region is essentially the same. In certain embodiments, the sugar moiety of each monomer subunit within the internal region is a β-D-2'-deoxyribonucleoside, a nucleoside that is DNA-like and/or a nucleoside that supports RNaseH when in the gap region.

In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 2, 3, 4, 5 or about 6 monomer subunits) and the monomer subunits comprise non-naturally occurring sugar moieties with the internal region comprising β-D-2'-deoxyribonucleosides. In certain embodiments, the external regions each, independently, comprise from 2 to about 8 monomer subunits having non-naturally occurring sugar moieties and the internal region comprises from 6 to 14 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. A gapped oligomeric compound can further include one or more additional groups including but not limited to capping groups, conjugate groups and other 5' or 3'-terminal groups.

In certain embodiments, gapped oligomeric compounds comprise an internal region of β-D-2'-deoxyribonucleosides with a single internucleoside linkage having Formula I. In certain embodiments, gapped oligomeric compounds comprise an internal region of β-D-2'-deoxyribonucleosides having two internucleoside linkages having Formula I. In certain embodiments, gapped oligomeric compounds comprise an internal region of β-D-2'-deoxyribonucleosides having three internucleoside linkages having Formula I.

In certain embodiments, the 5' and 3'-wing regions of gapped oligomeric compounds comprise modified nucleosides wherein all the sugar moieties have the same type of modification such as cEt or MOE. In certain embodiments, the 5' and 3'-wing regions of gapped oligomeric compounds comprise two types of modified nucleosides having sugar moieties independently selected from 2'-substituted sugar moieties and furanosyl bicyclic sugar moieties. In certain embodiments, the 5' and 3'-wing regions of gapped oligomeric compounds comprise two types of modified nucleosides having sugar moieties independently selected from 2'-MOE substituted sugar moieties and furanosyl bicyclic sugar moieties each having a 4'-CH((S)—CH$_3$)—O-2' bridge.

In certain embodiments, gapped oligomeric compounds are provided that are from about 10 to about 30 monomer subunits in length. In certain embodiments, gapped oligomeric compounds are provided that are from about 12 to about 20 monomer subunits in length. In certain embodiments, gapped oligomeric compounds are provided that are from about 14 to about 20 monomer subunits in length. In certain embodiments, gapped oligomeric compounds are provided that are from about 14 to about 18 monomer subunits in length.

b. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

c. Certain Nucleoside Motifs

In certain embodiments, oligomeric compounds comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, oligomeric compounds are provided herein wherein most if not all of the nucleosides are selected from those having particular nucleobases. In certain embodiments, nucleosides are provided wherein each nucleobase is, independently, selected from adenine, guanine, thymine, cytosine, 5-methyl cytosine and uracil. In certain embodiments, nucleosides are provided wherein each nucleobase is, independently, selected from 6-N-benzoyladenine, 2-N-isobutyrylguanine, thymine, 4-N-benzoylcytosine, 5-methyl 4-N-benzoyl cytosine and uracil.

In certain embodiments, oligomeric compounds are provided herein wherein most if not all of the nucleosides are selected from those having particular sugar moieties. In certain embodiments, nucleosides are provided wherein each sugar moiety is, independently, selected from β-D-2'-deoxyribose, a ribofuranosyl sugar moiety having a 2' substituent group selected from F, OCH$_3$, MOE and NMA, a bicyclic sugar selected from LNA, cEt, R-cEt or S-cEt, and a sugar moiety comprising a F-substituted hexitol as in a F-HNA. In certain embodiments, nucleosides are provided wherein each sugar moiety is, independently, selected from β-D-2'-deoxyribose, a ribofuranosyl sugar moiety having a 2' substituent group selected from MOE and NMA, a bicyclic sugar selected from LNA or S-cEt, and a sugar moiety comprising a F-substituted hexitol as in a F-HNA. In certain embodiments, nucleosides are provided wherein each sugar moiety is, independently, selected from β-D-2'-deoxyribose, a 2'-MOE substituted ribofuranosyl sugar moiety, and a bicyclic sugar selected from S-cEt.

In certain embodiments, oligomeric compounds are provided herein wherein most if not all of the nucleosides are selected from those having particular sugar moieties. In certain embodiments, nucleosides are provided wherein each sugar moiety is, independently, selected from β-D-ribose, a ribofuranosyl sugar moiety having a 2' substituent group selected from F, OCH$_3$ and MOE, a 4'-thio ribofuranosyl sugar moiety and a 4'-thio-2'-modified nucleoside wherein the 2'-substituent is selected from F, OCH$_3$ and MOE. In certain embodiments, nucleosides are provided wherein each sugar moiety is, independently, selected from β-D-ribose and a ribofuranosyl sugar moiety having a 2' substituent group selected from F, OCH$_3$ and MOE.

In certain embodiments, oligomeric compounds provided herein include a 5'-stabilized nucleoside. In certain embodiments, the oligomeric compound is a single stranded RNAi compound. In certain embodiments, the 5'-stabilized nucleoside has the formula:

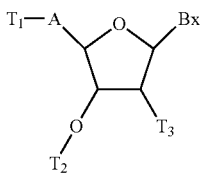

wherein:
$T_1$ is an optionally protected phosphorus moiety;
A has one of the formulas:

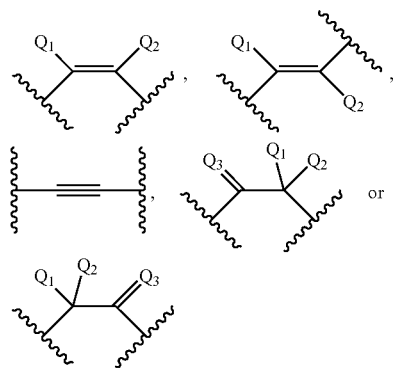

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
Bx is a heterocyclic base moiety;
$T_3$ is a 2'-substituent group; and
$T_2$ is an internucleoside linkage connecting the 5'-stabilized nucleoside to the remainder of an oligomeric compound.

In certain embodiments, the 5'-stabilized nucleoside has the configuration of the formula:

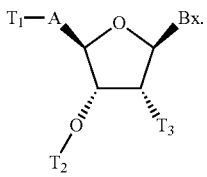

In certain embodiments, the 5'-stabilized nucleoside has the formula:

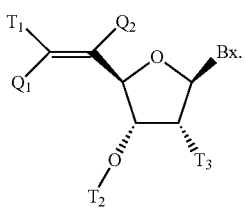

In certain embodiments, the 5'-stabilized nucleoside has the formula:

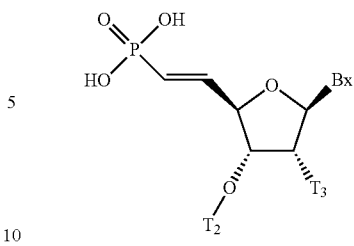

or a protected analog thereof.

In certain embodiments, the oligomeric compounds comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

d. Certain 5'-Wings

In certain embodiments, the 5'-wing of a gapmer consists of 2 to 8 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides. In certain embodiments, the 5'-wing of a gapmer consists of 7 linked nucleosides. In certain embodiments, the 5'-wing of a gapmer consists of 8 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside.

In certain embodiments, the 5'-wing of a gapmer has a nucleoside motif selected from among the following: ABBA; ABB; ABAA; AABAA; AAABAA; AAAABAA; AAAAABAA; AAABAA; AABAA; ABAB; AAABB; AAAAA; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type and each C is a modified nucleoside of a third type. In certain embodiments, such an oligomeric compound is a gapmer. In certain such embodiments, the 3'-wing of the gapmer may comprise any nucleoside motif.

1. Certain 3'-Wings

In certain embodiments, the 3'-wing of a gapmer consists of 2 to 8 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides. In certain embodiments, the 3'-wing of a gapmer consists of 7 linked nucleosides. In certain embodiments, the 3'-wing of a gapmer consists of 8 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside.

In certain embodiments, the 3'-wing of a gapmer has a nucleoside motif selected from among the following: ABB; ABAA; AAABAA, AAAAABAA; AABAA; AAAABAA; AAABAA; ABAB; AAAAA; AAABB; AAAAAAAA; AAAAAAA; AAAAAA; AAAAB; AAAA; AAA; AA; AB; ABBB; ABAB; AABBB; wherein each A is a modified nucleoside of a first type, each B is a modified nucleoside of a second type. In certain embodiments, an oligonucleotide comprises any 3'-wing motif provided herein. In certain such embodiments, the 5'-wing of the gapmer may comprise any nucleoside motif.

e. Certain Central Regions (Gap Regions)

In certain embodiments, the gap of a gapmer consists of 6 to 20 linked nucleosides. In certain embodiments, the gap of a gapmer consists of 6 to 14 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides. In certain embodiments, the gap of a gapmer consists of 13 linked nucleosides. In certain embodiments, the gap of a gapmer consists of 14 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like". In certain embodiments, "DNA-like" means that the nucleoside has similar characteristics to DNA, such that a duplex comprising the gapmer and an RNA molecule is capable of activating RNase H. In certain embodiments, modified nucleosides that are DNA-like are 2'-endo. For example, under certain conditions, 2'-(ara)-F have been shown to support RNase H activation, and thus is DNA-like and further has 2'-endo conformation geometry. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, the gap comprise a stretch of unmodified 2'-deoxynucleosides interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

f. Certain Gapmer Motifs

In certain embodiments, a gapmer comprises a 5'-wing, a gap comprising at least one internucleoside linkage of Formula I, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting table:

TABLE 1

Certain Gapmer Nucleoside Motifs

| 5'-wing region | Gap region | 3'-wing region |
|---|---|---|
| AAAAAAA | DDDDDDDDD | AAA |
| AAAAABB | DDDDDDDD | BBAAAAA |
| ABB | DDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABAB | DDDDDDDD | BBA |
| AA | DDDDDDDD | BBBBBBBB |
| ABB | DDDDDD | ABADB |
| AAAAB | DDDDDDD | BAAAA |
| ABBB | DDDDDDDD | AB |
| AB | DDDDDDDD | BBBA |
| ABBB | DDDDDDDD | BBBA |
| AB | DDDDDDDD | ABA | wherein each A is a modified nucleoside of a first type, each B is a modified nucleoside of a second type and each D is a β-D-2'-deoxyribonucleoside or a nucleoside that is DNA-like. Each gap region includes at least one internucleoside linkage of Formula I.

In certain embodiments, each A comprises a modified sugar moiety. In certain embodiments, each A comprises a 2'-substituted sugar moiety. In certain embodiments, each A comprises a 2'-substituted sugar moiety selected from among F, $OCH_3$, $OCH_2—C(=O)—N(H)(CH_3)$ and $O(CH_2)_2—OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A is a modified nucleoside comprising a sugar surrogate selected from morpholino, cyclohexenyl and cyclohexitol. In certain embodiments, each A is a modified nucleoside comprising a sugar surrogate selected from morpholino and F-tetrahydropyran (F-HNA). In certain embodiments, each A comprises a F-HNA surrogate modified nucleoside. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, OCH$_3$, OCH$_2$—C(=O)—N(H)(CH$_3$) and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B is a modified nucleoside comprising a sugar surrogate selected from morpholino, cyclohexenyl and cyclohexitol. In certain embodiments, each B is a modified nucleoside comprising a sugar surrogate selected from morpholino and F-tetrahydropyran (F-HNA). In certain embodiments, each B comprises a F-HNA surrogate modified nucleoside. In certain embodiments, each B comprises a modified nucleobase. In certain embodiments, each B comprises a modified nucleobase selected from among 2-thiothymidine nucleoside and 5-propyne uridine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B comprises a sugar surrogate selected from morpholino, cyclohexenyl and cyclohexitol and the other of A or B comprises a 2'-substituted sugar moiety. In certain embodiments, one of A or B comprises a sugar surrogate selected from morpholino, cyclohexenyl and cyclohexitol and the other of A or B comprises a 2'-MOE sugar moiety. In certain embodiments, one of A or B comprises a F-THP sugar surrogate and the other of A or B comprises a 2'-substituted sugar moiety. In certain embodiments, one of A or B comprises a F-THP sugar surrogate and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, each A and B is, independently, a modified nucleoside comprising a bicyclic sugar moiety comprising a 4'-CH(CH$_3$)—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(S)—(CH$_3$)]—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(R)—(CH$_3$)]—O-2' bridge or a modified nucleoside comprising a 2'-OCH$_2$CH$_2$OCH$_3$ (MOE) substituent group. In certain embodiments, at least one modified nucleoside comprising a 2'-OCH$_2$CH$_2$OCH$_3$ (MOE) substituent group and at least one modified nucleoside comprising a 4'-CH(CH$_3$)—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(S)—(CH$_3$)]—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(R)—(CH$_3$)]—O-2' bridge is located in each of the 3' and 5' wings.

g. Certain Internucleoside Linkage Motifs

In certain embodiments, oligomeric compounds comprise modified internucleoside linkages arranged along the oligomeric compound or region thereof in a defined pattern or modified internucleoside linkage motif provided that at least one internucleoside linkage has Formula I. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligomeric compounds having a gapped internucleoside linkage motif may or may not have a gapped nucleoside motif and if it does have a gapped nucleoside motif, the wing and gap lengths may or may not be the same.

In certain embodiments, oligomeric compounds comprise a region having an alternating internucleoside linkage motif. In certain embodiments, oligomeric compounds of the present invention comprise a region of uniformly modified internucleoside linkages. In certain such embodiments, the oligomeric compound comprises a region that is uniformly linked by phosphorothioate internucleoside linkages. In certain embodiments, the oligonucleotide is uniformly linked by phosphorothioate. In certain embodiments, each internucleoside linkage of the oligomeric compound is selected from phosphodiester and phosphorothioate. In certain embodiments, each internucleoside linkage of the oligomeric compound is selected from phosphodiester and phosphorothioate and at least one internucleoside linkage is phosphorothioate. In certain embodiments, at least one internucleoside linkage of the oligomeric compound is selected from other than phosphodiester and phosphorothioate.

In certain embodiments, oligomeric compounds comprise a positionally modified internucleoside linkage motif. In certain embodiments, oligomeric compounds as provided herein comprise a region of uniformly modified internucleoside linkages. In certain such embodiments, the oligomeric compound comprises one or more modified internucleoside linkages of one or more different types.

In certain embodiments, the oligomeric compound comprises at least 6 phosphorothioate internucleoside linkages. In certain embodiments, the oligomeric compound comprises at least 8 phosphorothioate internucleoside linkages. In certain embodiments, the oligomeric compound comprises at least 10 phosphorothioate internucleoside linkages. In certain embodiments, the oligomeric compound comprises at least one block of at least 6 consecutive phosphorothioate internucleoside linkages. In certain embodiments, the oligomeric compound comprises at least one block of at least 8 consecutive phosphorothioate internucleoside linkages. In certain embodiments, the oligomeric compound comprises at least one block of at least 10 consecutive phosphorothioate internucleoside linkages. In certain embodiments, the oligomeric compound comprises at least one block of at least one 12 consecutive phosphorothioate internucleoside linkages. In certain such embodiments, at least one such block is located at the 3' end of the oligomeric compound. In certain such embodiments, at least one such block is located within 3 nucleosides of the 3' end of the oligomeric compound. In certain embodiments, each internucleoside linkage a phosphorothioate internucleoside linkage.

h. Certain Modification Motifs

Modification motifs define oligonucleotides by nucleoside motif (sugar motif and nucleobase motif) and linkage motif. For example, certain oligonucleotides have the following modification motif:

AAADDDDDDDDBBB;

wherein each A is a modified nucleoside comprising a 2'-substituted sugar moiety; each D is a β-D-2'-deoxyribonucleoside or a modified nucleoside having B form conformation geometry and each B is a modified nucleoside comprising a bicyclic sugar moiety wherein at least one internucleoside linkage had Formula I. The following non-limiting Table further illustrates certain modification motifs:

TABLE 2

Certain Modification Motif

| 5'-wing region | Gap region | 3'-wing region |
|---|---|---|
| BB | DDDDDDDD | AAAAAAAA |
| ABB | DDDDDDDD | BBA |
| ABB | DDDDDDDD | BBA |

TABLE 2-continued

Certain Modification Motif

| 5'-wing region | Gap region | 3'-wing region |
|---|---|---|
| ABBB | DDDDDDDD | BBABB |
| ABB | DDDDDDDD | BBABB |
| BBABB | DDDDDDDD | BBA |
| ABB | DDDDDDDD | BBABBBB |
| AABAA | DDDDDDDD | BBA |
| AAABAA | DDDDDDDD | BBA |
| AABAA | DDDDDDDD | AABAA |
| AAABAA | DDDDDDDD | AABAAA |
| AAAABAA | DDDDDDDD | BBA |
| ABAB | DDDDDDDD | BABA |
| ABAB | DDDDDDDD | AABAA |
| ABB | DDDDDDDD | BABA |
| BBABBBB | DDDDDDDD | BABA |
| AAAAA | DDDDDDDD | AAAAA |
| AAAAA | DDDDDDD | AAAAA |
| AAAAA | DDDDDDDD | BBABBBB |
| AAABB | DDDDDDD | BBA |
| ABAB | DDDDDDD | BBA |
| ABAB | DDDDDDD | AAABB |
| AAAAB | DDDDDDD | BAAAA |
| BB | DDDDDDDD | AA |
| AA | DDDDDDD | AAAAAAAA |
| AAA | DDDDDDD | AAAAAAA |
| AAA | DDDDDDD | AAAAAA |
| AB | DDDDDDD | BBBA |
| ABBB | DDDDDDDD | BA |
| AB | DDDDDDDD | BBBA |
| AAABB | DDDDDDD | BBAAA |
| AAAAB | DDDDDDD | BAAAA |
| AABBB | DDDDDDD | BBBAA |
| AAAAB | DDDDDDD | AAAAA |
| AAABB | DDDDDDD | AAAAA |
| AABBB | DDDDDDD | AAAAA |
| AAAAA | DDDDDDD | BAAAA |
| AAAAA | DDDDDDD | BBAAA |
| AAAAA | DDDDDDD | BBBAA | wherein each A is a modified nucleoside of a first type, each B is a modified nucleoside of a second type and each D is a β-D-2'-deoxyribonucleoside or a nucleoside that is DNA-like. Each gap region includes at least one internucleoside linkage of Formula I.

In certain embodiments, each A comprises a modified sugar moiety. In certain embodiments, each A comprises a 2'-substituted sugar moiety. In certain embodiments, each A comprises a 2'-substituted sugar moiety selected from among F, OCH$_3$, OCH$_2$—C(=O)—N(H)(CH$_3$) and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A is a modified nucleoside comprising a sugar surrogate selected from morpholino, cyclohexenyl and cyclohexitol. In certain embodiments, each A is a modified nucleoside comprising a sugar surrogate selected from morpholino and F-tetrahydropyran (F-HNA). In certain embodiments, each A comprises a F-HNA sugar surrogate modified nucleoside. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, OCH$_3$, OCH$_2$—C(=O)—N(H)(CH$_3$) and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B is a modified nucleoside comprising a sugar surrogate selected from morpholino, cyclohexenyl and cyclohexitol. In certain embodiments, each B is a modified nucleoside comprising a sugar surrogate selected from morpholino and F-tetrahydropyran (F-HNA). In certain embodiments, each B comprises a F-HNA sugar surrogate modified nucleoside. In certain embodiments, each B comprises a modified nucleobase. In certain embodiments, each B comprises a modified nucleobase selected from among 2-thiothymidine nucleoside and 5-propyne uridine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B comprises a sugar surrogate selected from morpholino, cyclohexenyl and cyclohexitol and the other of A or B comprises a 2'-substituted sugar moiety. In certain embodiments, one of A or B comprises a sugar surrogate selected from morpholino, cyclohexenyl and cyclohexitol and the other of A or B comprises a 2'-MOE sugar moiety. In certain embodiments, one of A or B comprises a F-THP sugar surrogate and the other of A or B comprises a 2'-substituted sugar moiety. In certain embodiments, one of A or B comprises a F-THP sugar surrogate and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, each A and B is, independently, a modified nucleoside comprising a bicyclic sugar moiety comprising a 4'-CH(CH$_3$)—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(S)—(CH$_3$)]—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(R)—(CH$_3$)]—O-2' bridge or a modified nucleoside comprising a 2'-OCH$_2$CH$_2$OCH$_3$ (MOE) substituent group. In certain embodiments, at least one modified nucleoside comprising a 2'-OCH$_2$CH$_2$OCH$_3$ (MOE) substituent group and at least one modified nucleoside comprising a 4'-CH(CH$_3$)—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(S)—(CH$_3$)]—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(R)—(CH$_3$)]—O-2' bridge is located in each of the 3' and 5' wings.

b. Certain Antisense Activities and Mechanisms

Antisense mechanisms include any mechanism involving the hybridization of an oligomeric compound with a target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain antisense activities, hybridization of an antisense compound results in recruitment of a protein that cleaves a target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuranose sugar moieties in the nucleosides of the gap and modified sugar moieties in the nucleosides of the wings.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression. In certain embodiments, the invention provides antisense compounds that are sufficiently "DNA-like" to elicit RNase H activity. Such DNA-like antisense compounds include, but are not limited to gapmers. In certain embodiments, such gapmers comprise 2'-β-D-ribofuranose nucleosides in the gap and modified nucleosides comprising at least modified sugar moieties in the wings.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

iv. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 10, 11, 12, 13, 14, 15, 16, 17, 18, 19, 20, 21, 22, 23, 24, 25, 26, 27, 28, 29 and 30; provided that X≤Y. For example, in certain embodiments, the invention provides oligomeric compounds which comprise oligonucleotides consisting of 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

In certain embodiments, oligonucleotides of the present invention are characterized by their modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Provided herein are oligomeric compounds comprising modified nucleosides. Such modified nucleosides comprise a modified sugar moiety, a modified nucleobase, or both a modified sugar moiety and a modified nucleobase. In certain embodiments, oligomeric compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surogates may comprise one or more substitutions corresponding to those of substituted sugar moieties.

In certain embodiments, the present invention provides oligonucleotides comprising modified nucleosides. Modified nucleosides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleosides.

Oligomeric compounds are routinely prepared using solid support methods as a preferred method over solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods* 2001, 23, 206-217; *Oligonucleotides and Analogues, a Practical Approach*, F. Eckstein, Ed., Oxford University Press, New York, 1991; Gait et al., *Applications of Chemically synthesized RNA in RNA: Protein Interactions*, Smith, Ed., 1998, 1-36; Gallo et al., *Tetrahedron* 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "A$^{me}$CGAUCG," wherein $^{me}$C indicates a cytosine base comprising a methyl group at the 5-position.

v. Certain Oligonucleotides

In certain embodiments, oligonucleotides of the present invention are characterized by their modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

vi. Certain Terminal Groups/Conjugate Groups

In certain embodiments, the oligomeric compounds as provided herein are modified by covalent attachment of one or more terminal groups to the 5' and or 3'-end. Although terminal groups are generally attached at the terminal 3' or 5'-position, attachment at any available terminal or internal position is also possible. As used herein the terms "5'-terminal group", "3'-terminal group", "terminal group" and combinations thereof are meant to include useful groups known to the art skilled that can be placed on one or both of the terminal ends of an oligomeric compound or at another reactive position at a terminal end of an oligomeric compound. Such terminal groups are useful for various purposes such as enabling the tracking of an oligomeric compound (a fluorescent label or other reporter group), improving the pharmacokinetics or pharmacodynamics of an oligomeric compound (such as for example: uptake and/or delivery) or enhancing one or more other desirable properties of an oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

In certain embodiments, the oligomeric compounds as provided herein are modified by covalent attachment of one or more conjugate groups. As used herein, "conjugate group" means a radical group comprising a group of atoms that are attached to an oligomeric compound. In general, conjugate groups modify one or more properties of the compound to which they are attached, including, but not limited to pharmacodynamic, pharmacokinetic, stability, binding, absorption, cellular distribution, cellular uptake, charge and/or clearance properties. Conjugate groups are routinely used in the chemical arts and can include a conjugate linker that covalently links the conjugate group to an oligomeric compound.

In certain embodiments, conjugate groups include without limitation, intercalators, reporter molecules, polyamines, polyamides, polyethylene glycols, thioethers, peptides, carbohydrates, a vitamin moiety, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. U.S.A.* 1989, 86, 6553-6556); cholic acid (Manoharan et al., *Bioorg. Med. Chem. Let.* 1994, 4, 1053-1060); a thioether, e.g., hexyl-S-tritylthiol (Manoharan et al., *Ann. N.Y. Acad. Sci.* 1992, 660, 306-309; and Manoharan et al., *Bioorg. Med. Chem. Let.* 1993, 3, 2765-2770); a thiocholesterol (Oberhauser et al., *Nucleic Acids Res.* 1992, 20, 533-538); an aliphatic chain, e.g., do-decan-diol or undecyl residues (Saison-Behmoaras et al., *EMBOI* 1991, 10, 1111-1118; Kabanov et al., *FEBS Lett.* 1990, 259, 327-330; Svinarchuk et al., *Biochimie* 1993, 75, 49-54); a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.* 1995, 36, 3651-3654; Shea et al., *Nucl. Acids Res.* 1990, 18, 3777-3783); a polyamine or a polyethylene glycol chain (Manoharan et al., *Nucleosides Nucleotides,* 1995, 14, 969-973); an adamantane acetic acid (Manoharan et al., *Tetrahedron Lett.* 1995, 36, 3651-3654); a palmityl moiety (Mishra et al., *Biochim. Biophys. Acta* 1995, 1264, 229-237); an octadecylamine or hexylamino-carbonyl-oxycholesterol moiety (Crooke et al., *J. Pharmacol. Exp. Ther.* 1996, 277, 923-937); or a tocopherol group (Nishina et al., *Molecular Therapy Nucleic Acids,* 2015, 4, e220; doi:10.1038/mtna.2014.72, Published online 13 Jan. 2015; and Nishina et al., *Molecular Therapy,* 2008, 16(4), 734-740).

In certain embodiments, a conjugate group comprises an active drug substance including but not limited to aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

In certain embodiments, conjugate groups are directly attached to oligomeric compounds. In certain embodiments, conjugate groups are attached to oligomeric compounds by a conjugate linking group. In certain such embodiments, conjugate linking groups include bifunctional linking moieties which are known in the art and are useful for attaching conjugate groups to oligomeric compounds. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl group having at least two functional groups. One of the functional groups is selected to bind to a parent molecule or compound of interest and the other is selected to bind essentially any selected group such as chemical functional group or a conjugate group. In certain embodiments, the conjugate linking group comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In certain embodiments, bifunctional linking moieties include one or more groups selected from, but not limited to, alkyl, alkenyl, alkynyl, amino, amido, hydroxyl, thiol, acyl and carboxyl.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, one or more conjugate groups are attached to the 5'-end of an oligomeric compound. In certain embodiments, conjugate groups are near the 5'-end. In certain embodiments, conjugates are attached at the 5'end of an oligomeric compound, but before one or more terminal group nucleosides.

In certain embodiments, one or more conjugate groups are attached to the 3'-end of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, conjugate groups include a cleavable moiety that covalently links the conjugate group to an oligomeric compound. In certain embodiments, conjugate groups include a conjugate linker and a cleavable moiety to covalently link the conjugate group to an oligomeric compound. In certain embodiments, a conjugate group has the general formula:

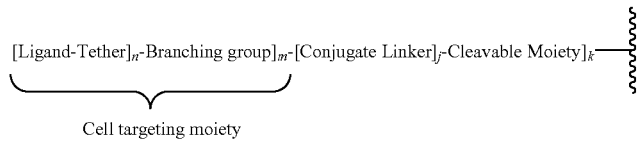

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an antisense oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyl adenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-acetylgalactosamine, 2-acetamido-2-deoxy-D-galactopyranose (GalNAc), 2-amino-3-O—[(R)-1-carboxyethyl]-2-deoxy-β-D-glucopyranose (β-muramic acid), 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from the group consisting of 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., *Bioconjug. Chem.* 2003, 14, 18-29, which is incorporated herein by reference in its entirety, or Rensen et al., *J. Med. Chem.* 2004, 47, 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

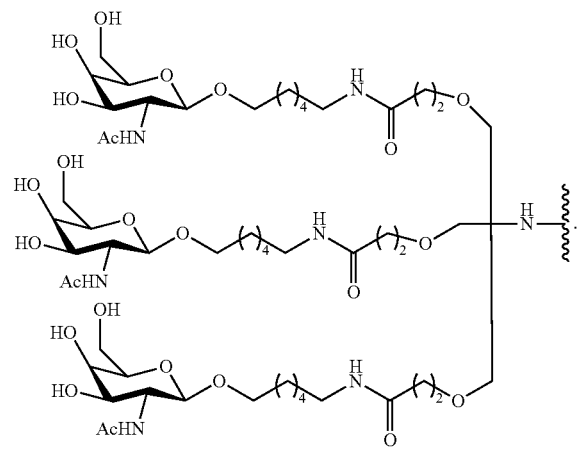

In certain embodiments, conjugate groups are provided wherein the cell-targeting moiety has the formula:

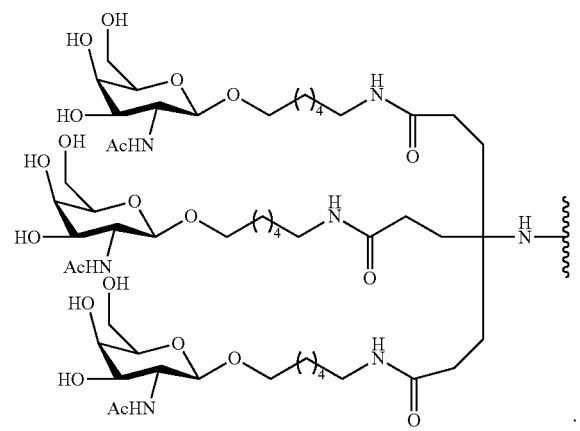

In certain embodiments, conjugate groups are provided wherein the cell-targeting moiety has the formula:

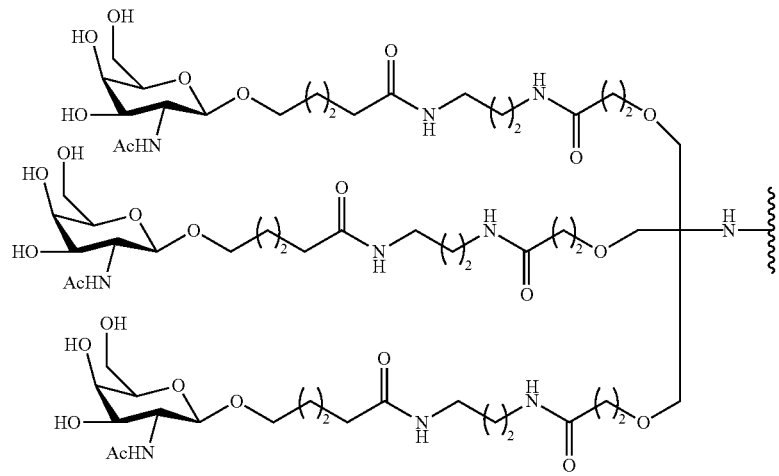

In certain embodiments, conjugate groups have the formula:

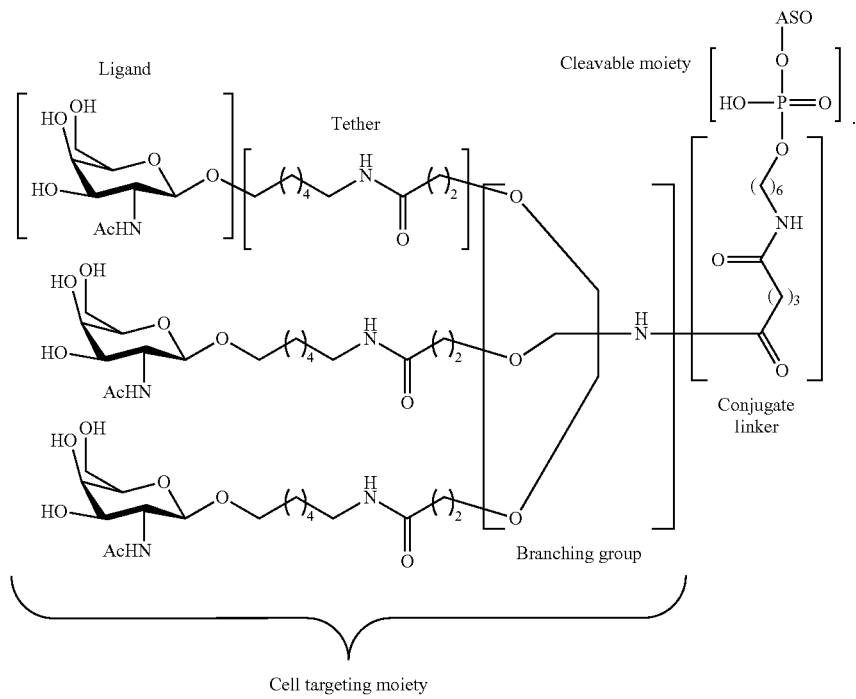

Representative United States patents, United States patent application publications, and international patent application publications that teach the preparation of certain of the above noted conjugates, conjugated oligomeric compounds such as antisense compounds, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated oligomeric compounds such as antisense compounds, tethers, conjugate linkers, branching groups, ligands, cleavable moieties as well as other modifications include without limitation, Biessen et al., *J. Med. Chem.* 1995, 38, 1846-1852; Biessen et al., *J. Med. Chem.*, 1995, 38, 1538-1546, Lee et al., *Bioorg. Med. Chem.* 2011, 19, 2494-2500; Rensen et al., *J. Biol. Chem.* 2001, 276(40), 37577-37584; Rensen et al., *J. Med. Chem.* 2004, 47, 5798-5808, Sliedregt et al., *J. Med. Chem.* 1999, 42, 609-618, and Valentijn et al., *Tetrahedron* 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, *Carbohydr Res.* 1978, 67, 509-514; Connolly et al., *J. Biol. Chem.* 1982, 257, 939-945; Pavia et al., *Int. J. Pep. Protein Res.* 1983, 22, 539-548; Lee et al., *Biochem* 1984, 23, 4255-4261; Lee et al., *Glycoconjugate J.* 1987, 4, 317-328; Toyokuni et al., *Tetrahedron Lett.* 1990, 31, 2673-2676; Biessen et al., *J. Med. Chem.* 1995, 38, 1538-1546; Valentijn et al, *Tetrahedron* 1997, 53, 759-770; Kim et al, *Tetrahedron Lett.* 1997, 38, 3487-3490; Lee et al., *Bioconjug. Chem.* 1997, 8, 762-765; Kato et al., *Glycobiol.* 2001, 11, 821-829; Rensen et al., *J. Biol. Chem.* 2001, 276, 37577-37584; Lee et al., *Methods Enzymol.* 2003, 362, 38-43; Westerlind et al., *Glycoconj. J.* 2004, 21, 227-241; Lee et al., *Bioorg. Med. Chem. Lett.* 2006, 16(19), 5132-5135; Maierhofer et al., *Bioorg. Med. Chem.* 2007, 15, 7661-7676; Khorev et al., *Bioorg. Med. Chem.* 2008, 16, 5216-5231; Lee et al., *Bioorg. Med. Chem.* 2011, 19, 2494-2500; Kornilova et al., *Analyt. Biochem.* 2012, 425, 43-46; Pujol et al., *Angew. Chemie. Int. Ed. Engl.* 2012, 51, 7445-7448; Biessen et al., *J. Med. Chem.* 1995, 38, 1846-1852; Sliedregt et al., *J. Med. Chem.* 1999, 42, 609-618; Rensen et al., *J. Med. Chem.* 2004, 47, 5798-5808; Rensen et al., *Arterioscler. Thromb. Vasc. Biol.* 2006, 26, 169-175; van Rossenberg et al., *Gene Ther.* 2004, 11, 457-464; Sato et al., *J Am. Chem. Soc.* 2004, 126, 14013-14022; Lee et al., *J Org. Chem.* 2012, 77, 7564-7571; Biessen et al., *FASEB J.* 2000, 14, 1784-1792; Rajur et al., *Bioconjug. Chem.* 1997, 8, 935-940; Duff et al., *Methods Enzymol.* 2000, 313, 297-321; Maier et al., *Bioconjug. Chem.* 2003, 14, 18-29; Jayaprakash et al., *Org. Lett.* 2010, 12, 5410-5413; Manoharan, Antisense *Nucleic Acid Drug. Dev.* 2002, 12, 103-128; Merwin et al., *Bioconjug. Chem.* 1994, 5, 612-620; Tomiya et al., *Bioorg. Med. Chem.* 2013, 21, 5275-5281; International applications WO 1998/013381; WO 2011/038356; WO 1997/046098; WO 2008/098788; WO 2004/101619; WO 2012/037254; WO 2011/120053; WO 2011/100131; WO 2011/163121; WO 2012/177947; WO 2013/033230; WO 2013/075035; WO 2012/083185; WO 2012/083046; WO 2009/082607; WO 2009/134487; WO 2010/144740; WO 2010/148013; WO 1997/020563; WO 2010/088537; WO 2002/043771; WO 2010/129709; WO 2012/

068187; WO 2009/126933; WO 2004/024757; WO 2010/054406; WO 2012/089352; WO 2012/089602; WO 2013/166121; WO 2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US 2011/0097264; US 2011/0097265; US 2013/0004427; US 2005/0164235; US 2006/0148740; US 2008/0281044; US 2010/0240730; US 2003/0119724; US 2006/0183886; US 2008/0206869; US 2011/0269814; US 2009/0286973; US 2011/0207799; US 2012/0136042; US 2012/0165393; US 2008/0281041; US 2009/0203135; US 2012/0035115; US 2012/0095075; US 2012/0101148; US 2012/0128760; US 2012/0157509; US 2012/0230938; US 2013/0109817; US 2013/0121954; US 2013/0178512; US 2013/0236968; US 2011/0123520; US 2003/0077829; US 2008/0108801; and US 2009/0203132; each of which is incorporated by reference in its entirety.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

B. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

i. Certain Antisense Activities and Mechanisms

Antisense mechanisms include any mechanism involving the hybridization of an oligomeric compound with a target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

One type of antisense mechanism involving degradation of target RNA is RNase H mediated antisense. RNase H is a cellular endonuclease which cleaves the RNA strand of an RNA:DNA duplex wherein the DNA strand may comprise modified nucleosides at one or more positions. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression. In certain embodiments, the invention provides antisense compounds that are sufficiently "DNA-like" to elicit RNase H activity. Such DNA-like antisense compounds include, but are not limited to gapmers. In certain embodiments, such gapmers comprise 2'-β-D-ribofuranose nucleosides in the gap and modified nucleosides comprising at least modified sugar moieties in the wings.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

ii. Selective Antisense Compounds

In certain embodiments, antisense compounds provided herein are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);
a modification motif comprising a long 3'-wing (longer than 5, 6, or 7 nucleosides);
a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

a. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

1. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

2. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleic acid is at positions 1, 2, 3, or 4 of the antisense compounds from the 5'-end of the wing region. In certain embodiments, a mismatch relative to the target nucleic acid is at positions 4, 3, 2, or 1 of the antisense compounds from the 3'-end of the wing region.

3. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXC'B'A';
ABCXXXXXXX(X/C')(X/B')(X/A');
(X/A)(X/B)(X/C)XXXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

4. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

C. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

i. Single-Nucleotide Polymorphism

Embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Feng et al., *Gene* 2006, 371(1), 68-74); the PrP gene encoding prion protein involved in Creutzfeldt-Jakob disease and in fatal familial insomnia (Chen et al., *Nat. Med.* 1997, 3, 1009-1015); GFAP gene encoding glial fibrillary acidic protein involved in Alexander disease (Hagemann et al., *J. Neurosci.* 2006, 26(43), 11162-11173); alpha-synuclein gene encoding alpha-synuclein protein involved in Parkinson's disease (Dawson et al., *J. Clin. Invest.* 2003, 111(2), 145-151); SOD-1 gene encoding the SOD-1 protein involved in amyotrophic lateral sclerosis (Bruijn et al., *Science* 1998, 281 (5384), 1851-1854); atrophin-1 gene encoding atrophin-1 protein involved in dentato-rubral and pallido-luysian atrophy (DRPA) (Margolis et al., *Trends Mol. Med.* 2001, 7, 479-482); SCA1 gene encoding ataxin-1 protein involved in spino-cerebellar ataxia-1 (SCA1) (Sen et al., *Protein Sci.* 2003, 12(5), 953-962); PLP gene encoding proteolipid protein involved in Pelizaeus-Merzbacher disease (Gow et al., *Neuromolecular Med.* 2003, 4, 73-94); DYT1 gene encoding torsinA protein involved in Torsion dystonia (Shashidharan et al., *Brain Res.* 2000, 877(2), 379-381); and alpha-B crystalline gene encoding alpha-B crystalline protein involved in protein aggregation diseases, including cardiomyopathy (Rajasekaran et al., *Cell* 2007, 130, 427-439); alpha1-antitrypsin gene encoding alpha1-antitrypsin protein involved in chronic obstructive pulmonary disease (COPD), liver disease and hepatocellular carcinoma (Carrell et al., *N. Engl. J. Med.* 2002, 346, 45-53); Ltk gene encoding leukocyte tyrosine kinase protein involved in systemic lupus erythematosus (Li et al., *Hum. Mol. Gen.* 2004, 13(2), 171-179); PCSK9 gene encoding PCSK9 protein involved in hypercholesterolemia (Abifadel et al., *Hum. Mutat.* 2009, 30(4), 520-529); prolactin receptor gene encoding prolactin receptor protein involved in breast tumors (Bogorad et al., *Proc. Natl. Acad. Sci. U.S.A.* 2008, 105(38), 14533-14538); CCL5 gene encoding the chemokine CCL5 involved in COPD and asthma (Hizawa et al., *Eur. Respir. J.* 2008, 32, 372-378); PTPN22 gene encoding PTPN22 protein involved in Type 1 diabetes, Rheumatoid arthritis, Graves disease, and SLE (Yu et al., *Proc. Natl. Acad. Sci. U.S.A.* 2007, 104, 19767-19772); androgen receptor gene encoding the androgen receptor protein involved in spinal and bulbar muscular atrophy or Kennedy's disease (Palazzolo et al., *J. Steroid Biochem. Mol. Biol.* 2008, 108(3-5), 245-253); CHMP4B gene encoding chromatin modifying protein-4B involved in progressive childhood posterior subcapsular cataracts (Shiels et al., *Am. J. Hum. Genet.* 2007, 81(3), 596-606); FXR/NR1H4 gene encoding Farnesoid X receptor protein involved in cholesterol gallstone disease, arthrosclerosis and diabetes (Marzolini et al., *Mol. Endocrinol.* 2007, 21(8), 1769-1780); ABCA1 gene encoding ABCA1 protein involved in cardiovascular disease (Mantaring et al., *Transl. Res.* 2007, 149(4), 205-210); CaSR gene encoding the calcium sensing receptor protein involved in primary hypercalciuria (Vezzoli et al., *Kidney Int.* 2007, 71, 1155-1162); alpha-globin gene encoding alpha-globin protein involved in alpha-thallasemia (De Gobbi et al., *Science* 2006, 312 (5777), 1215-1217); httlpr gene encoding HTTLPR protein involved in obsessive compulsive disorder (Xian-Zhang et al., *Am. J. Hum. Genet.* 2006, 78(5), 815-826); AVP gene encoding arginine vasopressin protein in stress-related disorders such as anxiety disorders and comorbid depression (Landgraf, *CNS Neurol. Disord. Drug Targets* 2006, 5(2), 167-179); GNAS gene encoding G proteins involved in congenital visual defects, hypertension, metabolic syndrome (Weinstein et al., *Trends Pharmacol. Sci.* 2006, 27(5), 260-266); APAF1 gene encoding APAF1 protein involved in a predisposition to major depression (Harlan et al., *Mol. Psychiatry* 2006, 11(1), 76-85); TGF-beta1 gene encoding TGF-beta1 protein involved in breast cancer and prostate cancer (Ewart-Toland et al., *Cancer Epidemiol. Biomarkers Prev.* 2004, 13(5), 759-764); AChR gene encoding acetylcholine receptor involved in congenital myasthenic syndrome (Webster et al., *Neurology* 2004, 62(7), 1090-1096); P2Y12 gene encoding adenosine diphosphate (ADP) receptor protein involved in risk of peripheral arterial disease (Fontana et al., *Circulation* 2003, 108, 2971-2973); LQT1 gene encoding LQT1 protein involved in atrial fibrillation (Lai et al., *Cardiology* 2003, 100, 109-113); RET protooncogene encoding RET protein involved in sporadic pheochromocytoma (McWhinney et al., *J. Clin. Endocrinol. Metab.* 2003, 88(10), 4911-4916); filamin A gene encoding filamin A protein involved in various congenital malformations (Robertson et al., *Nat. Genet.* 2003, 33(4), 487-491); TARDBP gene encoding TDP-43 protein involved in amyotrophic lateral sclerosis (Kabashi et al., *Hum. Mol. Genet.* 2010, 19(4), 671-683); SCA3 gene encoding ataxin-3 protein involved in Machado-Joseph disease (Alves et al., *PLoS One* 2008, 3(10), e3341); SCAT gene encoding ataxin-7 protein involved in spino-cerebellar ataxia-7 (Scholefield et al., *PLoS One* 2009, 4(9), e7232); and HTT gene encoding huntingtin protein involved in Huntington's disease (Persichetti et al., *Neurobiol. Dis.* 1996, 3(3), 183-190); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Daiger et al., *Adv. Exp. Med. Biol.* 2008, 613, 203-209)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

a. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

Table 3 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 3

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C | ii. Single-Stranded RNAi Compounds

In certain embodiments, oligomeric compounds as provided herein are particularly suited for use as single-stranded antisense compounds. In certain such embodiments, such oligomeric compounds are single-stranded RNAi (ssRNA) compounds. In certain embodiments, such oligomeric compounds are ssRNA compounds or microRNA mimics. In certain embodiments, ssRNA compounds comprise a 5'-stabilized nucleoside such as a 5'-terminal nucleosides described herein that provide enhanced nuclease resistance to such ssRNA compounds. Certain such 5'-terminal nucleosides are disclosed having a 5'-phosphate group wherein the 5'-nucleoside is modified to provide the enhanced stability. Certain such 5'-terminal nucleosides are disclosed wherein a 5'-phosphorus moiety provides the enhanced stability. Certain such 5'-terminal nucleosides are disclosed wherein a 5'-phosphorus moiety in combination with the modified 5'-nucleoside provides the enhanced stability. In certain embodiments, the 5'-terminal nucleoside provides enhanced RISC loading. In certain embodiments, the 3'-terminal nucleoside(s) is also selected to provide enhanced stability.

In certain instances, a single-stranded oligomeric compound comprising a 5'-phosphorous moiety is desired. For example, in certain embodiments, such 5'-phosphorous moiety is necessary or useful for RNAi compounds, particularly, ssRNA compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, modified nucleosides are disclosed that may be placed at the 5'-end of an oligomeric compound, resulting in stabilized phosphorous and or stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligomeric compound. Certain 5'-stabilized nucleosides comprising a 5'-phosphate, 5'-phosphorus moiety, modified 5'-nucleoside or combinations thereof have been previously disclosed (see US published applications US 2013/033961 and US 2013/0084576).

In certain embodiments, ssRNA oligomeric compounds comprise at least one modification at or between positions 6, 7 and 8 of the oligomeric compound (from the 5'-end) in addition to a 5'-terminal stabilizing nucleoside as described herein. Modification at or between positions 6, 7 and 8 is expected to alleviate distortion at position 6 which was observed from crystal structure data of an ssRNA Ago-2 complex. Chemical modifications in and or near this observed distortion is expected to improve one or more properties of the ssRNA oligomeric compound. Such properties, include, but are not limited to pharmakodynamic, pharmacokinetic, binding, absorption, cellular distribution, cellular uptake, charge and clearance. In certain embodiments, it is expected that chemical modification at or between positions 6, 7 and 8 will improve the loading of the ssRNA oligomeric compounds provided herein to Ago-2 protein and therefore improve slicer activity of the ssRNA oligomeric compound. Although certain oligomeric compounds as provided herein have particular use as single-stranded compounds, such compounds may also be paired with a second strand to create a double-stranded oligomeric compound.

In certain embodiments, oligomeric compounds as provided herein bind and/or activate one or more nucleases. In certain embodiments, such binding and/or activation ultimately results in antisense activity. In certain embodiments, an oligomeric compound of the invention interacts with a target nucleic acid and with a nuclease, resulting in activation of the nuclease and cleavage of the target nucleic acid. In certain embodiments, an oligomeric compound of the invention interacts with a target nucleic acid and with a nuclease, resulting in activation of the nuclease and inactivation of the target nucleic acid. In certain embodiments, an oligomeric compound of the invention forms a duplex with a target nucleic acid and that duplex activates a nuclease, resulting in cleavage and/or inactivation of one or both of the oligomeric compound and the target nucleic acid. In certain embodiments, an oligomeric compound of the invention binds and/or activates a nuclease and the bound and/or activated nuclease cleaves or inactivates a target nucleic acid. Nucleases include, but are not limited to, ribonucleases (nucleases that specifically cleave ribonucleotides), double-strand nucleases (nucleases that specifically cleave one or both strands of a double-stranded duplex), and double-strand ribonucleases. For example, nucleases include, but are not limited to RNase H, an argonaute protein (including, but not limited to Ago2), and dicer.

In certain embodiments, oligomeric compounds as provided herein interact with an argonaute protein (Ago). In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain embodiments, such oligomeric compounds comprise a modified 5'-phosphate group. In certain embodiments, the invention provides methods of modulating the expression or amount of a target nucleic acid in a cell comprising contacting the cell with an oligomeric compound capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, oligomeric compounds as provided herein interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one strand of a dicer duplex is an antisense oligomeric compound and the other strand is its sense complement.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3' overhangs of a dicer duplex comprise 1-4 nucleosides. In certain embodiments, such overhangs comprise two nucleosides. In certain embodiments, the nucleosides in the 3'-overhangs comprise purine nucleobases. In certain embodiments, the nucleosides in the 3' overhangs comprise adenine nucleobases. In certain embodiments, the nucleosides in the 3' overhangs comprise pyrimidines. In certain embodiments, dicer duplexes comprising 3'-purine overhangs are more active as antisense compounds than dicer duplexes comprising 3' pyrimidine overhangs. In certain embodiments, oligomeric compounds of a dicer duplex comprise one or more 3' deoxy nucleosides. In certain such embodiments, the 3' deoxy nucleosides are dT nucleosides.

In certain embodiments, the 5' end of each strand of a dicer duplex comprises a phosphorus moiety. In certain embodiments the antisense strand of a dicer duplex comprises a phosphorus moiety and the sense strand of the dicer duplex does not comprise a phosphorus moiety. In certain embodiments the sense strand of a dicer duplex comprises a phosphorus moiety and the antisense strand of the dicer duplex does not comprise a phosphorus moiety. In certain embodiments, a dicer duplex does not comprise a phosphorus moiety at the 3' end. In certain embodiments, a dicer duplex is cleaved by dicer. In such embodiments, dicer duplexes do not comprise 2'-OMe modifications on the nucleosides at the cleavage site. In certain embodiments, such cleavage site nucleosides are RNA.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

a. Dicer

In certain embodiments, oligomeric compounds as provided herein interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds. In certain embodiments, oligomeric compounds that interact with dicer are single-stranded RNAi compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one strand of a dicer duplex is an antisense oligomeric compound and the other strand is its sense complement.

In certain embodiments, the invention provides single-stranded oligomeric compounds that interact with dicer. In certain embodiments, such single-stranded dicer compounds comprise a 5'-stabilized nucleoside. In certain embodiments, single-stranded dicer compounds do not comprise a phosphorous moiety at the 3'-end. In certain embodiments, such single-stranded dicer compounds may comprise a 3'-overhangs. In certain embodiments, such 3'-overhangs are additional nucleosides. In certain embodiments, such 3'-overhangs comprise 1-4 additional nucleosides that are not complementary to a target nucleic acid and/or are differently modified from the adjacent 3' nucleoside of the oligomeric compound. In certain embodiments, a single-stranded oligomeric compound comprises an antisense oligonucleotide having two 3'-end overhang nucleosides wherein the overhang nucleosides are adenine or modified adenine nucleosides. In certain embodiments, single stranded oligomeric compounds that interact with dicer comprise a 5'-stabilized nucleoside.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

b. Ago

In certain embodiments, oligomeric compounds as provided herein interact with Ago. In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain such embodiments, the Ago is in a cell. In certain such embodiments, the cell is in an animal.

E. Certain Methods/Uses

In certain embodiments, the present invention provides compounds and methods for reducing the amount or activity of a target nucleic acid. In certain embodiments, the invention provides antisense compounds and methods. In certain embodiments, the invention provides antisense compounds and methods based on activation of RNase H. In certain embodiments, the invention provides RNAi compounds and methods.

In certain instances it is desirable to use an antisense compound that functions at least in part through RISC. In certain such instances unmodified RNA, whether single-stranded or double stranded is not suitable. Single-stranded RNA is relatively unstable and double-stranded RNA does not easily enter cells. The challenge has been to identify modifications and motifs that provide desirable properties, such as improved stability, without interfering with (and possibly even improving upon) the antisense activity of RNA through RNAi.

In certain embodiments, the present invention provides oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at to 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif of the present invention, may comprise another motif of modifications or may be unmodified.

It has been shown that in certain circumstances for single-stranded RNA comprising a 5'-phosphate group has RNAi activity if but has much less RNAi activity if it lacks such 5'-phosphate group. The present inventors have recognized that in certain circumstances unmodified 5'-phosphate groups may be unstable (either chemically or enzymatically). Accordingly, in certain circumstances, it is desirable to modify the oligonucleotide to stabilize the 5'-phosphate. In certain embodiments, this is achieved by modifying the phosphate group (phosphorus moiety). In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, oligonucleotides are provided comprising a phosphate-stabilizing modification and a motif described herein. In certain embodiments, such oligonucleotides are useful as single-stranded RNAi compounds (ss-RNA) having desirable properties. In certain embodiments, such oligonucleotides may be paired with a second strand to form a double-stranded RNAi compound. In such embodiments, the second strand may comprise a motif of the present invention, may comprise another motif of modifications or may be unmodified RNA.

The target for such antisense compounds comprising a motif and/or 5'-phosphate stabilizing modification of the present invention can be any naturally occurring nucleic acid. In certain embodiments, the target is selected from: pre-mRNA, mRNA, non-coding RNA, small non-coding RNA, pd-RNA, and microRNA. In embodiments, in which a target nucleic acid is a pre-RNA or a mRNA, the target may be the same as that of a naturally occurring micro-RNA (i.e., the oligonucleotide may be a microRNA mimic). In such embodiments, there may be more than one target mRNA.

In certain embodiments, the invention provides compounds and methods for antisense activity in a cell. In certain embodiments, the cell is in an animal. In certain embodiments, the animal is a human. In certain embodiments, the invention provides methods of administering a compound of the present invention to an animal to modulate the amount or activity or function of one or more target nucleic acid.

F. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

NONLIMITING DISCLOSURE AND
INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Synthesis of Nucleoside Phosphoramidites
The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds
The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. Nos. 5,256,775 or 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., *J. Biol. Chem.* 1991, 266(27), 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors
Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation
Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 3).

Forward primer:
                                                (SEQ ID NO: 4)
AATGGCTAAGTGAAGATGACAATCAT Reverse primer:
                                                (SEQ ID NO: 5)
TGCACATATCATTACACCAGTTCGT And the PCR probe:
FAM-TTGCAGCAATTCACTGTAAAGCTG-GAAAGG-TAMRA (SEQ ID NO: 6), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 2

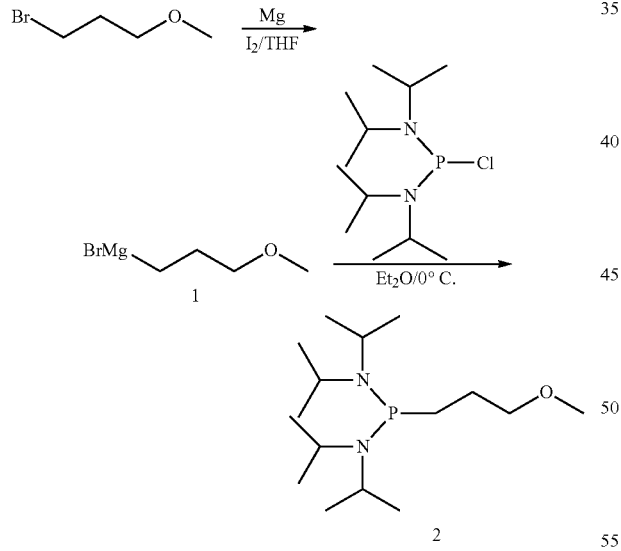

To a suspension of Mg/I$_2$ (297 mg, 8.25 mmol) in THF (16 mL) was added 1-bromo-3-methoxypropane (1.26 g, 8.25 mmol, commercially available) with stirring at room temperature for about 50 minutes to provide Compound 1. In a separate flask, bis(diisopropylaminochlorophos-phine (2.0 g, 7.50 mmol, commercially available) was dissolved in diethyl ether (125 mL) with cooling to 0° C. The solution of Compound 1 was cooled to about 0° C. and cannulated into the stirred solution of bis(diisopropylamino)chlorophos-phine with the temperature of the reaction mixture maintained at about 0° C. The reaction was monitored by $^{31}$P NMR. After about 1 hour the reaction mixture was allowed to warm to room temperature and filtered. The filtrate was concentrated under reduced pressure and the residue washed with hexane. The remaining residue was dissolved in acetonitrile and extracted with hexane. The hexane layers were combined, dried over Na$_2$SO$_4$, filtered and concentrated under reduced pressure to provide Compound 2 (1.7 g).

Reaction repeated starting with 22.0 g 1-bromo-3-methoxypropane to provide 22.5 g Compound 2 (76% yield). The structure of Compound 2 was confirmed by $^1$H NMR.

Example 14

Preparation of Methoxypropyl (MOP)-Diisopropylamino-phosphonamidite DMT-T, Compound 3

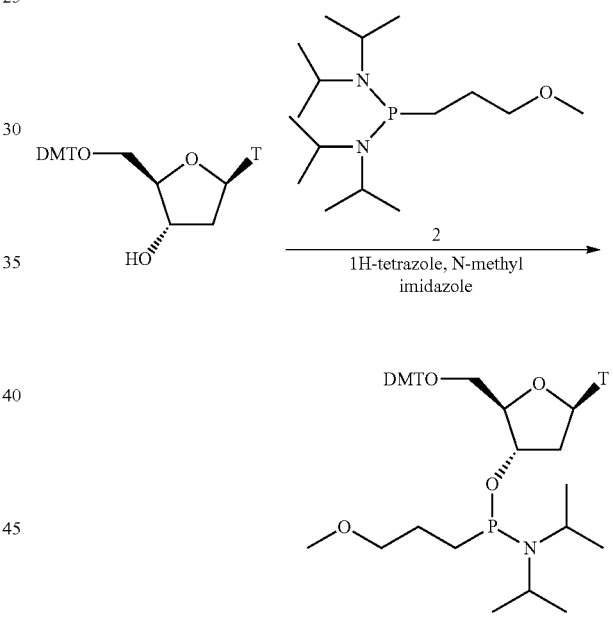

Dimethoxytrityl thymidine (3.0 g, 5.59 mmol, commercially available) and 1H-tetrazole (587 mg, 8.39 mmol) were dissolved in DMF (20 mL). N-methyl imidazole (116 mg, 1.40 mmol) and Compound 2 were added with stirring at room temperature for 1 hour at which time the reaction was complete by TLC. The reaction was diluted with ethyl acetate and quenched by addition of saturated NaHCO$_3$. The ethyl acetate layer was collected and dried over MgSO$_4$, filtered and concentrated under reduced pressure. The residue was purified by column chromatography (eluted with ethyl acetate/hexane 50/50 v/v) to provide Compound 3 (1.67 g, 78%). The structure of Compound 3 was confirmed by $^1$H NMR.

Example 15

Preparation of Protected MOP-Phosphonate Linked TT Dimer, Compound 4

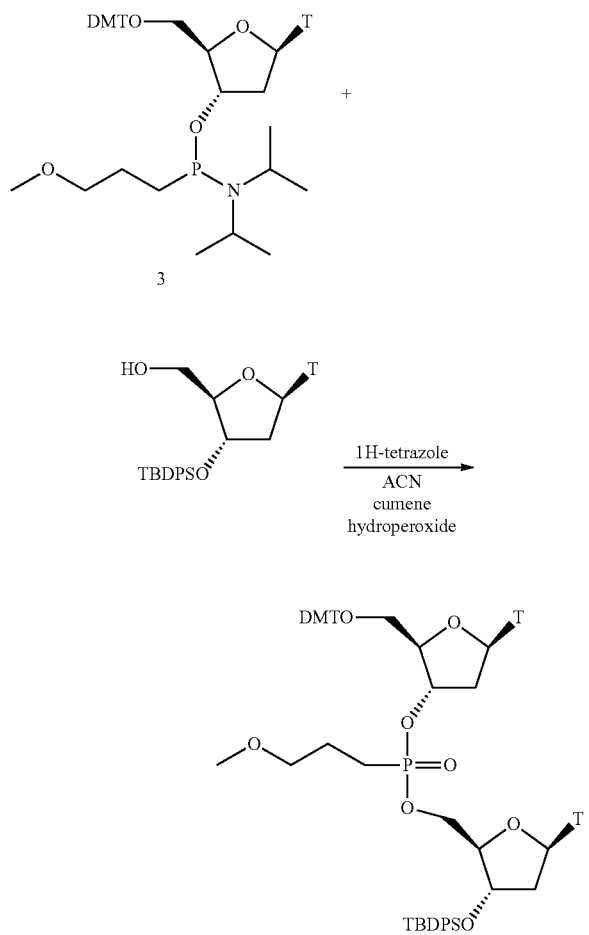

Dry 3'-O-t-butyldiphenylsilyl thymidine (400 mg, 0.832 mmol, commercially available) dissolved in ACN was cannulated into dry 1H-tetrazole (408 mg, 5.83 mmol) followed by Compound 3 (746 mg, 0.998 mmol) in ACN with stirring for 8 minutes. Cumene hydroperoxide (171 mg, 0.72 mL, 1.123 mmol) was added and the reaction was stirred for about 10 minutes. The reaction was quenched by addition of sodium bisulfite solution (1 g/mL) followed by extraction with ethyl acetate. Ethyl acetate layers were combined, dried over MgSO$_4$, filtered and concentrated under reduced pressure. The residue was purified by column chromatography to provide three fractions. The first fraction that eluted from the column (the fast fraction) was identified as the Rp isomer of Compound 4 (241 mg). The slower fractions were isolated and identified as the Sp isomer and the racemic mixture of Compound 4. The structure of Compound 4 was confirmed by $^1$H NMR.

Example 16

Preparation of 5'-ODMT MOP-Phosphonate Linked TT Dimer, Compound 5

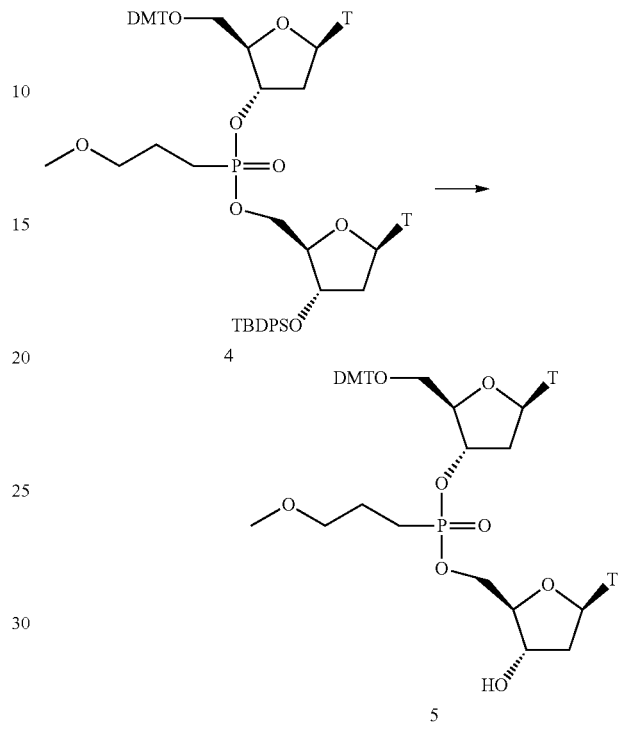

A solution of tetrabutylammonium fluoride (0.42 mL, 0.42 mmol, 1 N/THF) was added to a solution of Compound 4 (241 mg, 0.21 mmol) in THF (2 mL) with stirring for 2 hours. The reaction was diluted with water and extracted with ethyl acetate. The combined ethyl acetate layers were combined, dried over MgSO$_4$, filtered and concentrated under reduced pressure. The residue was purified by column chromatography (10% EtOH/ethyl acetate) to provide Compound 5 (146 mg, 76.8%).

Example 17

Preparation of 5'-ODMT-3'-Phosphoramidite MOP-Phosphonate Linked TT Dimer, Compound

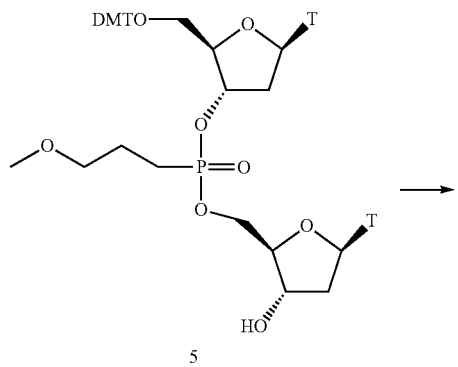

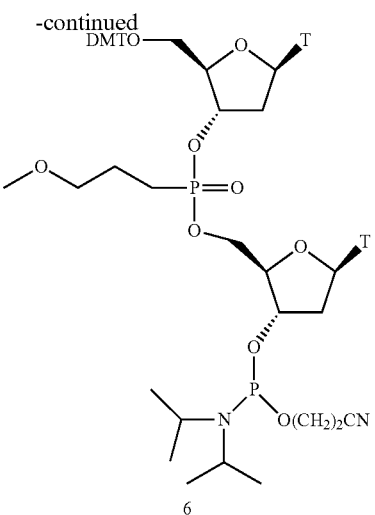

To a solution of Compound 5 in DMF (10 mL) was added 1H-tetrazole (127 mg, 1.82 mmol) followed by N-methyl imidazole (46 mg, 0.567 mmol) with stirring. 2-Cyanoethyl-N,N,N',N'-tetra-isopropylphosphorodiamidite (73 mg, 0.08 mL, 0.243 mmol) was added and the reaction mixture was stirred at room temperature for about 3 hours. The reaction was quenched by addition of saturated NaCl and extracted with ethyl acetate. The ethyl acetate layers were combined, dried over Na$_2$SO$_4$, filtered and concentrated under reduced pressure. The residue was purified by column chromatography (Biotage, 80% EtOAc/hexanes) to provide Compound 6 (90 mg).

Example 18

General Preparation of 5'-ODMT Methoxypropyl-Diisopropylaminophosphonamidite Nucleoside, Compound 8

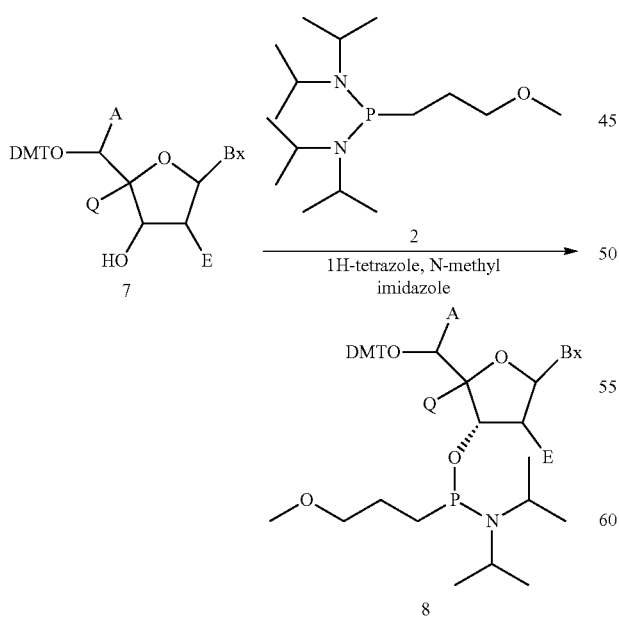

Following the procedures illustrated in Example 14 or optionally the procedures illustrated in Example 21, an optionally modified nucleoside having the formula of Compound 7 is converted to the methoxypropyl phosphonamidite having the formula of Compound 8. Many such optionally modified nucleosides represented by Compound 7 are disclosed herein and well known to the art skilled, many of which are commercially available. Included in Compound 7 are ribonucleosides and 2'-deoxyribonucleosides as well as optionally substituted analogs such as 2'-substituted nucleosides (A and Q are each H and E is a 2'-substituent group); 5'-substituted modified nucleosides (Q and E are H and A is a 5'-substituent group); 2',5'-substituted modified nucleosides (Q is H and E is a 2'-substituent group and A is a 5'-substituent group); and bicyclic nucleosides (A is H or an optional 5'-substituent group and Q and E together form a bridging group).

Modified nucleosides and or modified nucleosides that have been functionalized as methoxypropyl phosphonamidites can be incorporated into an oligomeric compound directly as the DMT phosphonamidite or as a DMT phosphonamidate dimer, prepared as per the procedures illustrated examples 15 to 17, following standard oligonucleotide synthesis protocols. Any nucleoside or modified nucleoside can be coupled to the DMT phosphonamidite to prepare the DMT phosphoramidite dimer such as the TT dimer illustrated in Example 17. The modified nucleoside can also have any heterocyclic base with uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine being preferred.

Example 19

General Preparation of Methoxypropyl Phosphonamidite Monomers Comprising a Sugar Surrogate Group, Preparation of F-HNA Methoxypropyl Phosphoramidite, Compound 10

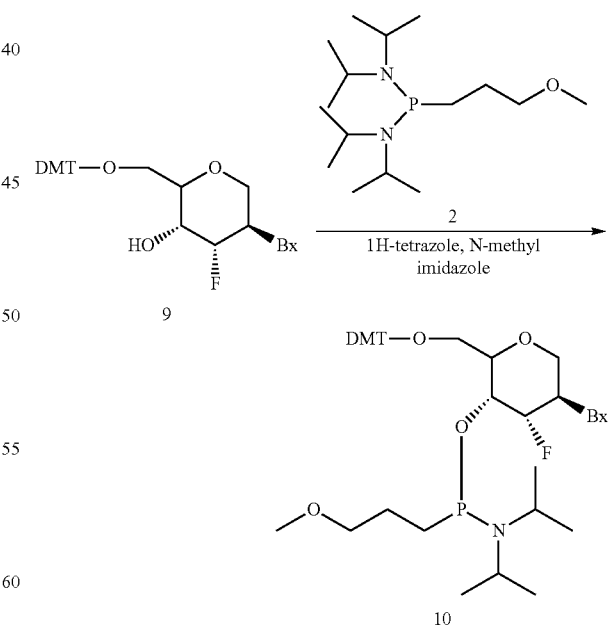

Following the procedures illustrated in Example 14 or optionally the procedures illustrated in Example 21, a DMT protected modified nucleoside comprising a sugar surrogate group having a free hydroxyl group (DMT-F-HNA, Formula 9 prepared as per U.S. Pat. No. 8,088,904) is converted to the methoxypropyl phosphoramidite of Formula 10. Such DMT protected modified nucleosides comprising a sugar surrogate group having a free hydroxyl group are disclosed herein and well known to the art skilled, many of which are commercially available.

Modified nucleosides comprising sugar surrogate groups that have been functionalized as methoxypropyl phosphoramidites can be incorporated into an oligomeric compound directly as the DMT phosphoramidite as per Formula 10 or as a DMT phosphoramidite dimer, prepared as per the procedures illustrated examples 15 to 17, following standard oligonucleotide synthesis protocols. Any nucleoside or modified nucleoside can be coupled to a DMT phosphoramidite comprising a sugar surrogate (such as Formula 10) to prepare a DMT phosphoramidite dimer such as illustrated in Example 17. The modified nucleoside can also have any heterocyclic base with uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine being preferred.

Example 20

Preparation of cEt Methoxypropyl Phosphonamidite, Compound 12

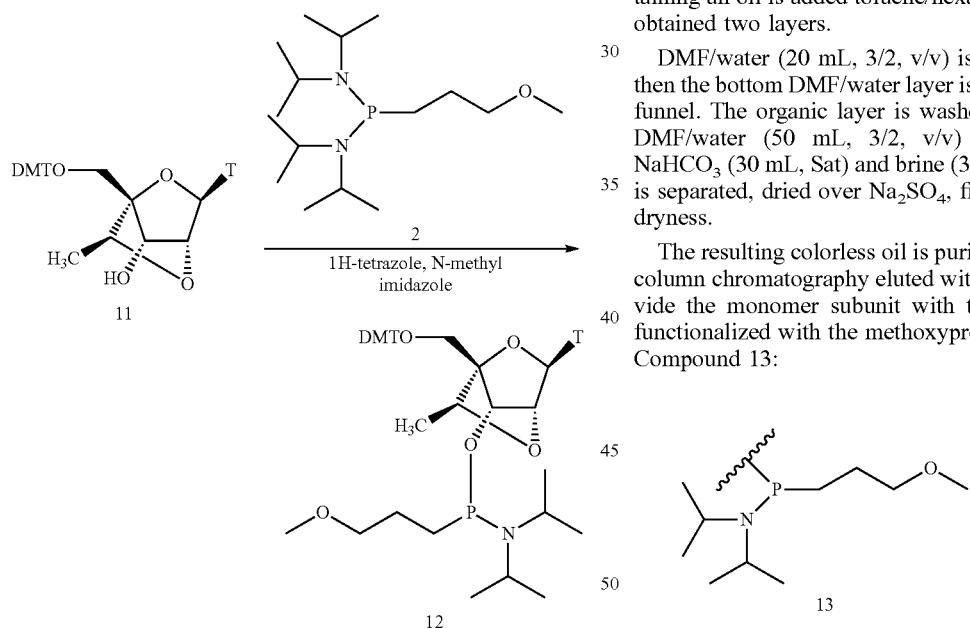

DMT cEt thymidine (Compound 11, prepared as per published literature procedures, 5.0 g, 8.43 mmol) and 1H-tetrazole (1.0 g, 14.3 mmol) were dried over phosphorus pentoxide for 4 hours and dissolved in DMF (20 mL) with stirring under nitrogen. N-methyl imidazole (350 mg, 4.26 mmol) and Compound 2 (7.0 g, 23.0 mmol) were added with stirring at room temperature for about 5 hours at which time the reaction was complete by TLC. The reaction was diluted with EtOAc (100 mL) and the organic layer was washed with half-saturated brine (200 mL), half saturated NaHCO₃ (2×200 mL), half saturated brine (1×200 mL), brine (1×100 mL), dried over MgSO4, filtered through a sintered glass funnel and concentrated under reduced pressure. Purify by biotage, 50 gram column pre-washed with 0.5% TEA in hexanes, then equilibrated in 2% EtOAc in hexanes. The crude material was loaded using ACN (~10 mL) and the column was washed with flash 3 CV of 2% EtOAc in hexanes followed by 20% EtOAc in hexanes over 5 CV and 80% EtOAc in hexanes. The fractions containing the desired compound were pooled and concentrated to give the final product was a white solid. The structure of Compound 12 was confirmed by $^1$H NMR.

Example 21

General Procedure for Preparation of Diisopropylamino-Methoxypropyl Phosphonate Monomer Subunits To a solution of 1H-tetrazole (1.5 eq), 1-methyl imidazole (0.4 eq) and a commercially available or synthesized monomer subunit such as a nucleoside, modified nucleoside or a nucleoside comprising a surrogate sugar group having a free hydroxyl group (5'-ODMT/or equivalent position, with optional base protection, 1.0 eq) dissolved in DMF (160 mL) is added dropwise a solution of Compound 2 (2.0 eq) dissolved in THF. The reaction is stirred at room temperature overnight and then the reaction was stopped by addition of Et₃N (0.5 mL) and then water (20 mL). The resulting milky solution is washed with hexane (3×100 mL) and the hexane layers were decanted. To the remaining aqueous layer containing an oil is added toluene/hexane (200 mL, 3/1, v/v) to obtained two layers.

DMF/water (20 mL, 3/2, v/v) is added with mixing and then the bottom DMF/water layer is removed in a separatory funnel. The organic layer is washed twice with additional DMF/water (50 mL, 3/2, v/v) followed by saturated NaHCO₃ (30 mL, Sat) and brine (30 mL). The organic layer is separated, dried over Na₂SO₄, filtered and evaporated to dryness.

The resulting colorless oil is purified using silica gel flash column chromatography eluted with ETOAc/hexane to provide the monomer subunit with the free hydroxyl group functionalized with the methoxypropyl phosphonate group, Compound 13:

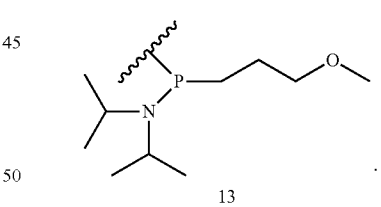

Example 22

Preparation of compound 15

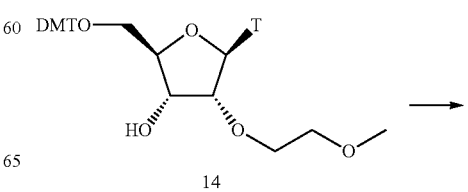

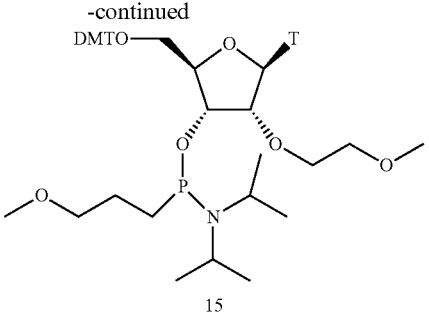

15

Compound 15 was prepared as per the procedure of Example 21 based on 1 eq., of Compound 14 (prepared as per published literature procedures, 10.0 g, 0.016 mol, 1.0 eq), Compound 2 (7.38 g, 0.024 mol, 2.0 eq), 1H-tetrazole (1.68 g, 0.024 mol, 1.5 eq), and 1-methyl imidazole (0.58 g, 0.007 mol, 0.4 eq). The resulting material was purified by passing through plug of silica gel eluted with ETOAc/Hexane (7/3, v/v) to afford 8.40 g of Compound 15 (63% yield). NMRs ($^1$H and $^{31}$P) were consistent Compound 15.

Example 23

Preparation of Compound 17

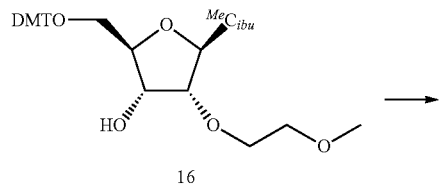

16

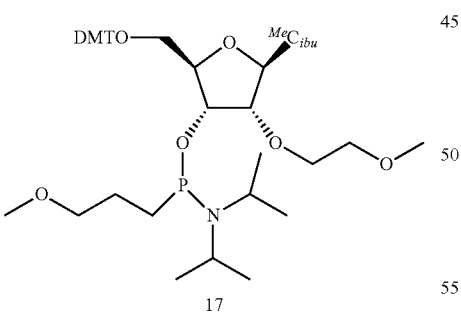

17

Compound 17 was prepared as per the procedure of Example 21 based on 1 eq., of Compound 16 (prepared as per published procedures, 10.0 g, 0.014 mol, 1.0 eq), Compound 2 (8.85 g, 0.029 mol, 2.0 eq), 1H-tetrazole (1.50 g, 0.021 mol, 1.5 eq), and 1-methyl imidazole (0.52 g, 0.006 mol, 0.4 eq). The resulting material was purified by passing through plug of silica gel eluted with ETOAc/hexane (7/3, v/v) to afford 7.70 g of Compound 17 (60% yield). NMRs ($^1$H and $^{31}$P) were consistent Compound 17.

Example 24

Preparation of Compound 19

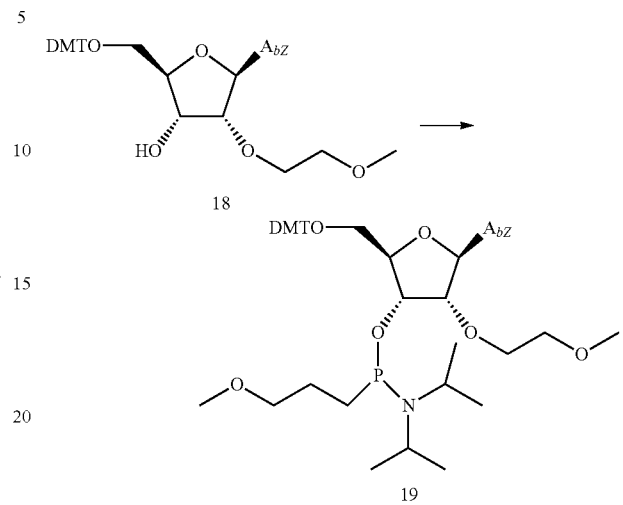

Compound 19 was prepared as per the procedure of Example 21 based on 1 eq., of Compound 18 (prepared as per published procedures, 10.0 g, 0.013 mol, 1.0 eq), Compound 2 (8.32 g, 0.027 mol, 2.0 eq), 1H-tetrazole (1.43 g, 0.020 mol, 1.5 eq), and 1-methyl imidazole (0.50 g, 0.006 mol, 0.4 eq). The resulting material was purified by passing through plug of silica gel eluted with ETOAc/hexane (7/3, v/v) to afford 3.51 g of Compound 19 (27% yield). NMRs ($^1$H and $^{31}$P) were consistent Compound 19.

Example 25

Preparation of Compound 21

Compound 21 was prepared as per the procedure of Example 21 based on 1 eq., of Compound 20 (prepared as per published procedures, 10.0 g, 0.014 mol, 1.0 eq), Compound 2 (8.53 g, 0.028 mol, 2.0 eq), 1H-tetrazole (1.47 g, 0.021 mol, 1.5 eq), and 1-methyl imidazole (0.50 g, 0.006 mol, 0.4 eq). The resulting material was purified by passing through plug of silica gel eluted with ETOAc/hexane (7/3, v/v) to afford 9.65 g of Compound 21 (75% yield). NMRs ($^1$H and $^{31}$P) were consistent Compound 21.

Example 26

Preparation of Compound 23

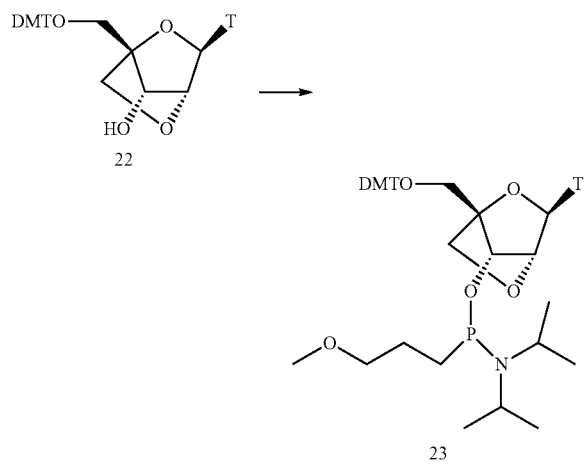

Compound 23 was prepared as per the procedure of Example 21 based on 1 eq., of Compound 22 (prepared as per published procedures, 3 g, 0.005 mol, 1.0 eq), Compound 2 (4.78 g, 0.015 mol, 3.0 eq), 1H-tetrazole (0.55 g, 0.007 mol, 1.5 eq), and 1-methyl imidazole (0.190 g, 0.002 mol, 0.4 eq). The resulting material was purified by passing through plug of silica gel eluted with ETOAc/hexane (7/3, v/v) to afford 2.7 g of Compound 23 (67% yield). NMRs ($^1$H and $^{31}$P) were consistent Compound 23.

Example 27

Preparation of Compound 25

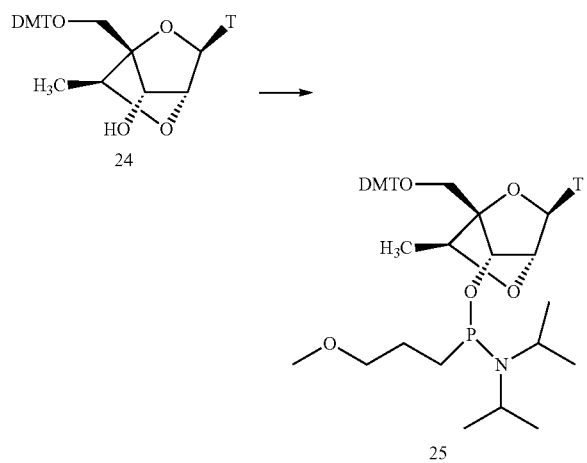

Compound 25 was prepared as per the procedure of Example 21 based on 1 eq., of Compound 24 (prepared as per published procedures, 10.0 g, 0.014 mol, 1.0 eq), Compound 2 (8.70 g, 0.029 mol, 2.0 eq), 1H-tetrazole (1.50 g, 0.021 mol, 1.5 eq), and 1-methyl imidazole (0.46 g, 0.006 mol, 0.4 eq). The resulting material was purified by passing through plug of silica gel eluted with ETOAc/hexane (7/3, v/v) to afford 11.13 g of Compound 25 (88% yield). NMRs ($^1$H and $^{31}$P) were consistent Compound 25.

Example 28

General Procedure for Synthesis of Oligomeric Compounds Comprising at Least One Methoxypropyl Phosphonate Internucleoside Linkage, Synthesis of Oligomeric Compounds ISIS-619442 to ISIS-619444

Oligomeric compounds were synthesized on a 2 µmol scale on an ABI 394 DNA/RNA synthesizer using MOE $^mC^{Bz}$ loaded primer support (loading: 215 µmol/g). Oligomeric compounds ISIS-619441 and ISIS-619442 were prepared using the thymidine methoxypropyl phosphoramidite monomer prepared as per the procedures illustrated in Example 14 and oligomeric compounds ISIS-619443 and ISIS-619444 were prepared using the thymidine methoxypropyl phosphoramidite dimer prepared as per the procedures illustrated in example 15 to 17. The other phosphoramidites (optionally protected: dA$^{bz}$, dG$^{DMF}$, d$^m$C$^{Bz}$, cEt A$^{Bz}$ and cEt $^m$C$^{Bz}$) were incorporated using standard solid-phase synthesis, i.e. 3% dichloroacetic acid in DCM for deblocking, 1 M 4,5-dicyanoimidazole 0.1 M N-methylimidazole in acetonitrile as activator, acetic acid in THF and 10% 1-methylimidazole in THF/pyridine for capping, 0.2 M phenylacetyl disulfide in pyridine:acetonitrile 1:1 (v:v) for thiolation and 10% tert-butyl hydroperoxide in acetonitrile for MOP oxidation. DNA and MOE amidites were dissolved to 0.1 M in acetonitrile while S-cEt amidites were dissolved to 0.2 M in acetonitrile:toluene 1:1 (v:v). DNA amidites were coupled for 2 times 4 min. while DNA MOP, MOE and S-cEt amidites were coupled for 2 times 6 min.

After synthesis was complete cyanoethyl groups were removed by treatment with trietylamine:acetonitrile 1:1 (v:v) for 25 min. The remaining protecting groups were cleaved in aq. conc. ammonia at room temperature for 6 h. The resulting oligomeric compounds were purified by strong anionic ion-exchange high performance liquid chromatography using a linear gradient of buffer A to B. Buffer A: 50 mM NaHCO$_3$; Buffer B: 50 mM NaHCO$_3$ 1.5 M NaBr, both buffers in acetonitrile:water 3:7 (v:v). Purified oligomeric compounds were desalted using a C18 reverse-phase cartridge. The identity of the oligomeric compounds was determined by electrospray ionization mass spectrometry.

| SEQ ID NO./ ISIS NO. | Composition (5' to 3') | Linkage/ isomer |
|---|---|---|
| 09/619441 | T$_e$A$_k$A$_k$ATT$_q$GT$^m$CAT$^m$CA$_k$$^m$C$_k$$^m$C$_e$ | MOP |
| 09/619442 | T$_e$A$_k$A$_k$AT$_q$TGT$^m$CAT$^m$CA$_k$$^m$C$_k$$^m$C$_e$ | MOP |
| 09/619443 | T$_e$A$_k$A$_k$AT$_{q\,(S)}$TGT$^m$CAT$^m$CA$_k$$^m$C$_k$$^m$C$_e$ | MOP/Sp |
| 09/619444 | T$_e$A$_k$A$_k$AT$_{q\,(R)}$TGT$^m$CAT$^m$CA$_k$$^m$C$_k$$^m$C$_e$ | MOP/Rp |

Between adjacent nucleosides subscript "q" indicates a methoxypropyl phosphonate modified internucleoside linkage (—P(CH$_3$O—(CH$_2$)$_3$—)(=O)—, MOP) between adjacent nucleosides and all other internucleoside linkages are phosphorothioate internucleoside linkages. Subscript "(R)" or "(S)" indicates the isomer of the internucleoside linkage as Rp or Sp respectively. Each nucleoside followed by a subscript "e" indicates a 2'-O-methoxyethyl (MOE) modified nucleoside and each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^mC$" is a 5-methyl cytosine modified nucleoside. Nucleosides followed by subscripts "e" or "k" are further illustrated below.

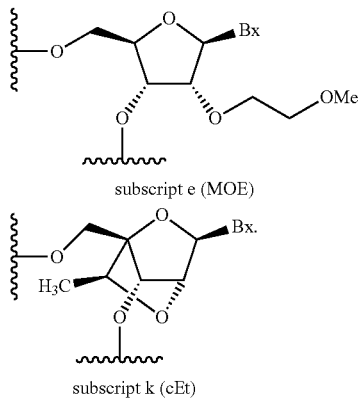

subscript e (MOE)

subscript k (cEt)

Example 29

Modified Methods for Deprotection and Cleavage of Oligonucleotides with Modified Internucleoside Linkages (Synthesis of ISIS 736646)

The SRB-1 targeted oligonucleotide ISIS 736646 (see examples 34 and 35) was synthesized using standard methods on a 40 μM scale. The first base ($^mC_k$, 3'-end) was pre-loaded on VIMAD solid support via succinate at 326 μmol/gram. For the modified methods non-standard protecting groups were used for particular amidites. The exocyclic amino groups of 2'-deoxy $^mC$ and $^mC_k$ were protected with isobutyryl groups and the exocyclic amino group of 2'-deoxy G was protected with DMF.

| SEQ ID NO./ ISIS NO. | Composition (5' to 3') | Linkage |
|---|---|---|
| 12/736646 | $T_kT_k{}^mC_kAGT^mCATGA^mCTT_{kx}{}^mC_{kx}{}^mC_k$ | MP |

MW 5638.325 (DMT on), MW 5335.325 (DMT off)

Between adjacent nucleosides subscript "x" indicates a methyl phosphonate modified internucleoside linkage (—P(CH₃)(=O)—, MP) and all other internucleoside linkages are phosphorothioate internucleoside linkages. Each nucleoside followed by a subscript "k" is a bicyclic nucleoside having a 4'-CH((S)—CH₃))—O-2' bridging group (cEt) and all other nucleosides are 2'-deoxyribonucleosides. Each "$^mC$" is a 5-methyl cytosine nucleoside.

400 mg fully protected oligo on VIMAD resin was placed in a glass pressure vial with a magnetic stir bar. Dry THF (5 mL) was added, and the mixture was allowed to stir and swell for 15 minutes. Ethylenediamine (EDA, 5 mL) was added via syringe with stirring at room temperature. The reaction was heated 55° C. with stirring in an oil bath for 15 minutes. The reaction was cooled in an ice bath and diluted with THF (5 mL). The reaction was centrifuged (3000 rpm, 5 minutes), and the solvent was removed via pipette. The residue was re-suspended in dry THF (7 mL) and was stirred vigorously for 5 minutes, followed by centrifugation and removal of solvent. The THF rinse process was repeated a third time. The pellet was suspended in 50% EtOH in H₂O (7 mL) with vigorous stirring (5 minutes). The spent resin was removed by filtration, and was rinsed with 50% EtOH (15 mL). The crude cleavage solution was diluted to a final volume of 25 mL. Quantification of the crude cleavage solution (UV, 260 nm) indicated 19.54 μmol recovery (crude, 50%).

The modified cleavage and deprotection methods are amenable to any of the modified internucleoside linkages, including those disclosed herein such as the methoxypropyl phosphonate modified internucleoside linkages (—P(CH₃O—(CH₂)₃—)(=O,S)—, MOP) and are merely exemplified for ISIS 736646.

Example 30

Thermal Stability Assay

A series of modified oligomeric compounds were evaluated in a thermal stability ($T_m$) assay. A Cary 100 Bio spectrophotometer with the Cary Win UV Thermal program was used to measure absorbance vs. temperature. For the $T_m$ experiments, oligomeric compounds were prepared at a concentration of 8 μM in a buffer of 100 mM Na+, 10 mM phosphate and 0.1 mM EDTA (pH 7). The concentration of the oligonucleotides was determined at 85° C. The concentration of each oligomeric compound was 4 μM after mixing of equal volumes of test oligomeric compound and complimentary RNA strand. Oligomeric compounds were hybridized with the complimentary RNA strand by heating the duplex to 90° C. for 5 minutes followed by cooling to room temperature. Using the spectrophotometer, $T_m$ measurements were taken by heating the duplex solution at a rate of 0.5° C./min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The oligomeric compounds were hybridized to complementary RNA (ISIS 606581). The results are presented below.

| SEQ ID NO./ ISIS NO. | Composition (5' to 3') | Tm | ΔTm | Linkage/chemistry |
|---|---|---|---|---|
| 07/606581 | UCGAGAACAUCC | n/a | | PO/RNA complement |
| 08/606339 | GGATGTTCTCGA | 49.4 | std. | PO/DNA unmodified |
| 08/614338 | GGATGT$_x$TCTCGA | 47.5 | -1.9 | MP |
| 08/614362 | GGATGT$_{x(S)}$TCTCGA | 45.2 | -4.2 | MP(Sp) |
| 08/614361 | GGATGT$_{x(R)}$TCTCGA | 48.9 | -0.9 | MP(Rp) |

-continued

| SEQ ID NO./ISIS NO. | Composition (5' to 3') | Tm | ΔTm | Linkage/chemistry |
|---|---|---|---|---|
| 08/618681 | GGATGT$_q$TCTCGA | 48.7 | -0.7 | MOP |
| 08/619024 | GGATGT$_{q(S)}$TCTCGA | 44.8 | -4.6 | MOP(Sp) |
| 08/619025 | GGATGT$_{q(R)}$TCTCGA | 48.9 | -0.9 | MOP(Rp) |
| 08/606346 | GGATGT$_k$TCTCGA | 54.7 | 5.3 | PO/cEt |
| 08/614341 | GGATGT$_{kx}$TCTCGA | 53.5 | 4.1 | MP/cEt |
| 08/614365 | GGATGT$_{kx(S)}$TCTCGA | 50.2 | 0.8 | MP(Sp)/cEt |
| 08/614366 | GGATGT$_{kx(R)}$TCTCGA | 54.2 | 4.8 | MP(Rp)/cEt |
| 08/618684 | GGATGT$_{kq}$TCTCGA | 53.9 | 4.5 | MOP/cEt |
| 08/606349 | GGATGT$_k$T$_k$CTCGA | 62.3 | 6.5 | cEt (x2) |
| 08/614342 | GGATGT$_{kx}$T$_k$CTCGA | 59.6 | 5.1 | MP/cEt (x2) |
| 08/618685 | GGATGT$_{kq}$T$_k$CTCGA | 59.4 | 5.0 | MOP/cEt (x2) |

Between adjacent nucleosides subscript "x" indicates a methyl phosphonate modified internucleoside linkage (—P(CH$_3$)(=O)—, MP), subscript "q" indicates a methoxypropyl phosphonate modified internucleoside linkage (—P(CH$_3$O—(CH$_2$)$_3$—)(=O)—, MOP) and all other internucleoside linkages are phosphodiester (PO) internucleoside linkages. Subscript "(R)" or "(S)" indicates the isomer of the internucleoside linkage as Rp or Sp respectively. ΔTm's are calculated relative to 606339. Each nucleoside followed by a subscript "k" is a bicyclic ribofuranosyl nucleoside having a 4'-CH((S)—CH$_3$))—O-2' bridging group.

Example 31

Thermal Stability Assay

A series of modified oligomeric compounds were evaluated in a thermal stability (T$_m$) assay following the procedures illustrated in Example 30. The results are presented below.

| SEQ ID NO./ISIS NO. | Composition (5' to 3') | Tm | ΔTm | Linkage |
|---|---|---|---|---|
| 07/606581 | UCGAGAACAUCC | n/a | | PO (RNA) |
| 08/606339 | GGATGTTCTCGA | 49.4 | std. | PO (DNA) |
| 08/748260 | GGAT$_q$GTTCTCGA | 54.2 | 4.8 | MOP |
| 08/748261 | GGATGT$_q$TCTCGA | 52.9 | 3.5 | MOP |
| 08/748262 | GGATGTT$_q$CTCGA | 54.9 | 5.5 | MOP |
| 08/748263 | GGATGTTCT$_q$CGA | 52.5 | 3.1 | MOP |
| 08/748256 | GGAT$_x$GTTCTCGA | 55.0 | 5.6 | MP |
| 08/748257 | GGATGT$_x$TCTCGA | 52.3 | 2.9 | MP |
| 08/748258 | GGATGTT$_x$CTCGA | 55.0 | 5.6 | MP |
| 08/748259 | GGATGTTCT$_x$CGA | 52.6 | 3.2 | MP. | between adjacent nucleosides subscript "x" indicates a methyl phosphonate modified internucleoside linkage (—P(CH$_3$)(=O)—, MP), subscript "q" indicates a methoxypropyl modified internucleoside linkage (—P(CH$_3$O—(CH$_2$)$_3$—)(=O)—, MOP) and all other internucleoside linkages are phosphodiester internucleoside linkages. Each nucleoside followed by a subscript "l" is a bicyclic ribofuranosyl nucleoside having a 4'-CH$_2$—O-2' bridging group (LNA). ΔTm's are calculated relative to 606339.

Example 32

Stability of Modified Linkages to Aqueous Ammonia

To evaluate internucleoside linkage stability under conditions similar to those encountered during deblocking and cleavage steps of oligomeric compound synthesis a comparative assay was performed with 2 sets of 2 identical oligomeric compounds wherein the only difference in each set is that one of the oligomeric compounds had a single methoxypropyl phosphonate modified internucleoside linkage (—P(CH$_3$O—(CH$_2$)$_3$—)(=O)— MP) and the other oligomeric compound had a single methylene phosphonate modified internucleoside linkage (—P(CH$_3$)(=O)—, MP). The stability was measured up to 16 days.

Each oligonucleotide was subjected to standard deprotection conditions used for automated oligonucleotide synthesis (ammonium hydroxide aqueous). Each oligonucleotide listed (10 nmol) is dissolved in concentrated aqueous ammonia (0.5 mL) and mixed at room temperature. Aliquots are taken out at the time points indicated and analyzed using LCMS.

| SEQ ID NO./ISIS NO. | Composition (5' to 3') | Linkage/isomer |
|---|---|---|
| 09/619442 | T$_e$A$_k$A$_k$AT$_q$TGT$^m$CAT$^m$CA$_k$$^m$C$_k$$^m$C$_e$ | MOP full PS |
| 09/558256 | T$_e$A$_k$A$_k$AT$_x$TGT$^m$CAT$^m$CA$_k$$^m$C$_k$$^m$C$_e$ | MP full PS |
| 08/748262 | G$_o$G$_o$A$_o$T$_o$G$_o$T$_o$T$_{lq}$C$_o$T$_o$C$_o$G$_o$A | MOP full PO |
| 08/748258 | G$_o$G$_o$A$_o$T$_o$G$_o$T$_o$T$_{lx}$C$_o$T$_o$C$_o$G$_o$A | MP full PO |

Between adjacent nucleosides subscript "x" indicates a methyl phosphonate modified internucleoside linkage (—P(CH$_3$)(=O)—, MP), subscript "q" indicates a methoxypropyl phosphonate modified internucleoside linkage (—P(CH$_3$O—(CH$_2$)$_3$—)(=O)—, MOP), subscript "o" indicates a phosphodiester (PO) internucleoside linkage and all other internucleoside linkages are phosphorothioate (PS) internucleoside linkages. Each nucleoside followed by a subscript "k" is a bicyclic nucleoside having a 4'-CH((S)—CH$_3$))—O-2' bridging group, each nucleoside followed by a subscript "1" is a bicyclic nucleoside having a 4'-CH$_2$—O-2' bridging group and all other nucleosides are 2'-deoxyribonucleosides. Each "$^m$C" is a 5-methyl cytosine nucleoside.

contains 3 modified nucleosides. For each of the modified oligonucleotides a modified internucleoside linkage was placed between nucleosides 5 and 6, from the 5'-end. The modified oligonucleotides were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to the control ISIS 460209 which was identical to the other oligonucleotides but did not include a modified linkage. The

| SEQ ID NO./ | % Cleavage | | | | | | |
|---|---|---|---|---|---|---|---|
| ISIS NO. | Day-1 | Day-2 | Day-3 | Day-4 | Day-8 | Day-16 | Linkages |
| 09/619442 | <1 | | | 2 | 7 | 12 | MOP (PS) |
| 09/558256 | <1 | | | 4 | 35 | 43 | MP (PS) |
| 08/748262 | 40 | 57 | 75 | | | | MOP (PO) |
| 08/748258 | 86 | 95 | 100 | | | | MP (PO). |

To determine the effect of ammonium hydroxide treatment on the overall yield of various oligomeric compounds, a series of oligomeric compounds were prepared for comparison. The oligomeric compounds were prepared in pairs that differ only in having either MOP or MP internucleoside linkages at the same locations. The demonstrated degradation caused by treatment with ammonium hydroxide also results in a reduction in yield during the standard deblocking and cleavage steps. The lability of each oligomeric compound will depend on the chemistry and position of each modified internucleoside linkage. The oligomeric compounds listed below were prepared having either MOP or MP internucleoside linkages located at selected positions. The syntheses were performed on 40 μmol scale. It is shown that overall the MOP internucleoside linkage leads to a higher yield.

position on the oligonucleotides opposite to the SNP position, as counted from the 5'-terminus is position 8.

The modified oligonucleotides were tested in vitro using heterozygous fibroblast GM04022 cell line was used (from Coriell Institute). Cultured GM04022 cells at a density of 25,000 cells per well were transfected using electroporation with 0.1, 0.4, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 μM from ABI), 1000 uL water and 40.4 uL RT MIX. To each well was added 15 uL of this mixture and 5 uL of purified RNA. The

| SEQ ID NO./ ISIS NO. | Composition (5' to 3') | Linkage | |
|---|---|---|---|
| 12/736674 | T$_k$T$_{kq}$$^m$C$_{kq}$AGT$^m$CATGA$^m$CTT$_k$$^m$C$_k$$^m$C$_k$ | MOP | 24% |
| 12/736645 | T$_k$T$_{kx}$$^m$C$_{kx}$AGT$^m$CATGA$^m$CTT$_k$$^m$C$_k$$^m$C$_k$ | MP | 10% |
| 12/736648 | T$_k$T$_k$$^m$C$_k$A$_x$G$_q$T$^m$CATGA$^m$CTT$_k$$^m$C$_k$$^m$C$_k$ | MOP | 21% |
| 12/582074 | T$_k$T$_k$$^m$C$_k$A$_x$G$_x$T$^m$CATGA$^m$CTT$_k$$^m$C$_x$$^m$C$_k$ | MP | 11% |
| 12/736649 | T$_k$T$_k$$^m$C$_k$AGT$^m$CATGA$^m$C$_q$T$_q$T$_k$$^m$C$_k$$^m$C$_k$ | MOP | 21% |
| 12/736673 | T$_k$T$_k$$^m$C$_k$AGT$^m$CATGA$^m$C$_x$T$_x$T$_k$$^m$C$_k$$^m$C$_k$ | MP | 5% |
| 12/736675 | T$_k$T$_k$$^m$C$_k$AGT$^m$CATGA$^m$CTT$_{kq}$$^m$C$_{kq}$$^m$C$_k$ | MOP | 16% |
| 12/736646 | T$_k$T$_k$$^m$C$_k$AGT$^m$CATGA$^m$CTT$_{kx}$$^m$C$_{kx}$$^m$C$_k$ | MP | 31% |
| 12/736676 | T$_k$T$_{kq}$$^m$C$_{kq}$AGT$^m$CATGA$^m$CTT$_{kq}$$^m$C$_{kq}$$^m$C$_k$ | MOP | 19% |
| 12/736647 | T$_k$T$_{kx}$$^m$C$_{kx}$AGT$^m$CATGA$^m$CTT$_{kx}$$^m$C$_{kx}$$^m$C$_k$ | MP | 11%. |

Example 33

Modified Oligonucleotides Comprising a Methoxypropyl Phosphonate Internucleoside Linkage Targeting HTT SNP In Vitro Study Modified oligonucleotides were designed based on ISIS 460209, having a 3/9/3 gapmer motif wherein each internucleoside linkage is a phosphorothioate, the gap region contains nine β-D-2'-deoxyribonucleosides and each wing mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The half maximal inhibitory concentration (IC$_{50}$) of each oligonucleotide is presented below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity as expressed in "fold" was calculated by dividing the IC$_{50}$ for inhibition of the wild-type HTT versus the IC$_{50}$ for inhibiting expression of the mutant HTT mRNA and the results are presented below.

The modified oligomeric compounds were also evaluated in a thermal stability (T$_m$) assay using the procedure illustrated in Example 30. The oligomeric compounds were hybridized to a complementary region of an RNA 30mer (ISIS 539568). The results are presented below.

| SEQ ID NO./ ISIS NO. | Composition (5' to 3') | Tm/ΔTm | Linkage (isomer) |
|---|---|---|---|
| 09/460209 | T$_e$A$_k$A$_k$ATTGT$^m$CAT$^m$CA$_k^m$C$_k^m$C$_e$ | 54.7/— | unmodified (full PS) |
| 09/558256 | T$_e$A$_k$A$_k$AT$_x$TGT$^m$CAT$^m$CA$_k^m$C$_k^m$C$_e$ | 53.8/−0.9 | MP |
| 09/622261 | T$_e$A$_k$A$_k$AT$_{x(S)}$TGT$^m$CAT$^m$CA$_k^m$C$_k^m$C$_e$ | 51.3/−3.4 | MP(Sp) |
| 09/622262 | T$_e$A$_k$A$_k$AT$_{x(R)}$TGT$^m$CAT$^m$CA$_k^m$C$_k^m$C$_e$ | 53.1/−1.6 | MP(Rp) |
| 09/619442 | T$_e$A$_k$A$_k$AT$_q$TGT$^m$CAT$^m$CA$_k^m$C$_k^m$C$_e$ | 53.6/−1.1 | MOP |
| 09/619443 | T$_e$A$_k$A$_k$AT$_{q(S)}$TGT$^m$CAT$^m$CA$_k^m$C$_k^m$C$_e$ | 51.7/−3.0 | MOP(Sp) |
| 09/619444 | T$_e$A$_k$A$_k$AT$_{q(R)}$TGT$^m$CAT$^m$CA$_k^m$C$_k^m$C$_e$ | 53.8/−0.9 | MOP(Rp) |

| SEQ ID NO. | Sequence (5' to 3', RNA complement) | | |
|---|---|---|---|
| 10/539568 | AGACUUUUCUGGUGAUGACAAUUUAUUAA | RNA (full PO) | |

Between adjacent nucleosides subscript "x" indicates a methyl phosphonate modified internucleoside linkage (—P(CH$_3$)(=O)—, MP), subscript "q" indicates a methoxypropyl phosphonate modified internucleoside linkage (—P(CH$_3$O—(CH$_2$)$_3$—)(=O)— MOP) and all other internucleoside linkages are phosphorothioate internucleoside linkages except that each internucleoside linkage for the RNA complement (539568) is a phosphodiester internucleoside linkage. Subscript "(R)" or "(S)" indicates the isomer of the internucleoside linkage as Rp or Sp respectively. Each nucleoside followed by a subscript "e" indicates a 2'-O-methoxyethyl (MOE) modified nucleoside and each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" is a 5-methyl cytosine modified nucleoside. ΔTm's are calculated relative to 460209.

| SEQ ID NO./ ISIS NO. | Mut IC$_{50}$ (µM) | Wt IC$_{50}$ (µM) | Fold Selectivity (mut vs. wt) | Modified linkage |
|---|---|---|---|---|
| 09/460209 | 0.50 | 2.5 | 5.0 | Positive control (3/9/3) |
| 09/558256 | 0.34 | 4.76 | 14 | MP |
| 09/622261 | 0.62 | 8.86 | 14 | MP(Sp) |
| 09/622262 | 0.45 | >10 | >22 | MP(Rp) |
| 09/619442 | 0.44 | >10 | >34 | MOP |
| 09/619443 | 1.14 | 9.46 | 8.3 | MOP(Sp) |
| 09/619444 | 0.33 | 8.25 | 25 | MOP(Rp). |

Example 34

Modified oligonucleotides targeting SRB-1 in vitro study

Modified oligonucleotides were designed based on the control oligonucleotide ISIS 449093, having a 3/10/3 gapmer motif wherein each internucleoside linkage is a phosphorothioate, the gap region contains ten β-D-2'-deoxyribonucleosides and each wing contains 3 cEt bicyclic nucleosides. Either 2 or 4 methoxypropyl modified internucleoside linkages were positioned in each of the modified oligonucleotides which were tested for their ability to inhibit SRB-1 mRNA expression levels. The potency of the modified oligonucleotides was evaluated and compared to the control oligonucleotide.

The modified oligonucleotides were tested in vitro in primary mouse hepatocyte cells. Cells at a density of 35,000 cells per well were transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR wherein the SRB-1 mRNA levels are adjusted according to total RNA content, as measured by RIBOGREEN®.

| SEQ ID NO./ ISIS NO. | Composition (5' to 3') | Linkage |
|---|---|---|
| 17/463290 | AA<u>GGAAGUCAUGACUGAAGC</u> | RNA (full PO) |
| 12/449093 | $T_kT_k{}^mC_k$AGT${}^m$CATGA${}^m$CTT$_k{}^mC_k{}^mC_k$ | unmodified (full PS) |
| 12/736674 | $T_kT_{kq}{}^mC_{kq}$AGT${}^m$CATGA${}^m$CTT$_k{}^mC_k{}^mC_k$ | MOP |
| 12/736648 | $T_kT_k{}^mC_kA_qG_qT{}^m$CATGA${}^m$CTT$_k{}^mC_k{}^mC_k$ | MOP |
| 12/736649 | $T_kT_k{}^mC_k$AGT${}^m$CATGA${}^mC_qT_qT_k{}^mC_k{}^mC_k$ | MOP |
| 12/736675 | $T_kT_k{}^mC_k$AGT${}^m$CATGA${}^m$CTT$_{kq}{}^mC_{kq}{}^mC_k$ | MOP |
| 12/736676 | $T_kT_{kq}{}^mC_{kq}$AGT${}^m$CATGA${}^m$CTT$_{kq}{}^mC_{kq}{}^mC_k$ | MOP |

Between adjacent nucleosides subscript "q" indicates a methoxypropyl phosphonate (MOP) modified internucleoside linkage (—P($CH_3O$—($CH_2$)$_3$—)(=O)—) and all other internucleoside linkages are phosphorothioate internucleoside linkages. Each nucleoside followed by a subscript "k" is a bicyclic nucleoside having a 4'-CH((S)—$CH_3$)—O-2' bridging group (cEt) and all other nucleosides are 2'-deoxyribonucleosides. Each "${}^m$C" indicates that this nucleoside comprises a 5-methyl cytosine heterocyclic base. The hybridizing region of the RNA complementary strand is underlined.

| SEQ ID NO./ ISIS NO. | Tm, °C | ΔTm, °C | $IC_{50}$ free uptake | $IC_{50}$ electroporation |
|---|---|---|---|---|
| 12/449093 | 70.4 | n/a | 1.0 | 9.9 |
| 12/736674 | 64.9 | −2.8 | 12.1 | 22.9 |
| 12/736648 | 68.1 | −1.2 | 2.0 | 14.2 |
| 12/736649 | 68.8 | −0.8 | 2.9 | 13.7 |
| 12/736675 | 68.4 | −1.0 | 2.9 | 10 |
| 12/736676 | 66.0 | −1.1 | 12.5 | 23.3 |

The half maximal inhibitory concentration ($IC_{50}$) of each oligonucleotide listed above is calculated by plotting the concentrations of oligonucleotides used versus the percent inhibition of SRB-1 mRNA expression achieved at each concentration, and noting the concentration of oligonucleotide at which 50% inhibition of SRB-1 mRNA expression is achieved compared to the control. ΔTm's are calculated relative to 449093.

Example 35

Modified Oligonucleotides Targeting SRB-1 In Vivo Study

Modified oligonucleotides were designed based on the control oligonucleotide ISIS 449093, having a 3/10/3 gapmer motif wherein each internucleoside linkage is a phosphorothioate, the gap region contains ten β-D-2'-deoxyribonucleosides and each wing contains 3 cEt bicyclic nucleosides. Either 2 or 4 methoxypropyl (MOP) modified internucleoside linkages were positioned in each of the modified oligonucleotides which were tested for their ability to inhibit SRB-1 mRNA expression levels. The study included unmodified oligonucleotide 449093 for comparison. The potency of the modified oligonucleotides was evaluated and compared to the control oligonucleotide.

Six week old BALB/C mice (Jackson Laboratory, Bar Harbor, Me.) were injected subcutaneously once at dosage of 3, 10, 30 or 100 mg/kg with the modified oligonucleotides targeted to SRB-1 mRNA. The mice were sacrificed 72 hrs following administration. Liver tissues were homogenized and mRNA levels were quantitated using real-time PCR as described herein for comparison to untreated control levels (% UTC). Organs (liver, kidney and spleen) were collected for PK.

| SEQ ID NO./ ISIS NO. | Composition (5' to 3') | Linkage |
|---|---|---|
| 12/449093 | $T_kT_k{}^mC_k$AGT${}^m$CATGA${}^m$CTT$_k{}^mC_k{}^mC_k$ | full PS |
| 12/736674 | $T_kT_{kq}{}^mC_{kq}$AGT${}^m$CATGA${}^m$CTT$_k{}^mC_k{}^mC_k$ | MOP |
| 12/736648 | $T_kT_k{}^mC_kA_qG_qT{}^m$CATGA${}^m$CTT$_k{}^mC_k{}^mC_k$ | MOP |
| 12/736649 | $T_kT_k{}^mC_k$AGT${}^m$CATGA${}^mC_qT_qT_k{}^mC_k{}^mC_k$ | MOP |
| 12/736675 | $T_kT_k{}^mC_k$AGT${}^m$CATGA${}^m$CTT$_{kq}{}^mC_{kq}{}^mC_k$ | MOP |
| 12/736676 | $T_kT_{kq}{}^mC_{kq}$AGT${}^m$CATGA${}^m$CTT$_{kq}{}^mC_{kq}{}^mC_k$ | MOP |

Between adjacent nucleosides subscript "q" indicates a methoxypropyl phosphonate (MOP) modified internucleoside linkage (—P($CH_3O$—($CH_2$)$_3$—)(=O)—) and all other internucleoside linkages are phosphorothioate internucleoside linkages. Each nucleoside followed by a subscript "k" is a bicyclic nucleoside having a 4'-CH((S)—$CH_3$)—O-2' bridging group (cEt) and all other nucleosides are 2'-deoxyribonucleosides. Each "${}^m$C" indicates that this nucleoside comprises a 5-methyl cytosine heterocyclic base.

| SEQ ID NO./ ISIS NO. | $ED_{50}$ | MTD | TI | Linkage |
|---|---|---|---|---|
| 12/449093 | 3.2 | 10 | 3.1 | full PS |
| 12/736674 | 13 | >100 | >7.7 | MOP |
| 12/736648 | 7.6 | >100 | >13 | MOP |
| 12/736649 | 11.3 | >100 | >8.8 | MOP |
| 12/736675 | 5.7 | 30 | 5.3 | MOP |
| 12/736676 | 28 | >100 | >3.6 | MOP |

The $ED_{50}$, is the effective dose, for 50% of the animals receiving the drug. The $ED_{50}$ is commonly used as a measure of the reasonable expectancy of a drug effect. The $ED_{50}$s listed in the table below were calculated by plotting the concentrations of oligonucleotides used versus the percent inhibition of SRB-1 mRNA expression achieved at each concentration, and noting the concentration of oligonucleotide at which 50% inhibition of SRB-1 mRNA expression was achieved compared to the control.

The mean tolerable dose (MTD) is the lowest dose wherein the ALT is normal (generally less than 3 times the value of the saline treated animal).

The therapeutic index (TI) is calculated as the MTD divided by the $ED_{50}$.

| SEQ ID NO./ ISIS NO. | ALT 3 mg/kg | ALT 10 mg/kg | ALT 30 mg/kg | ALT 100 mg/kg |
|---|---|---|---|---|
| saline | 38 | | | |
| 12/449093 | 92 | 47 | 473 | 2246 |
| 12/736674 | 53 | 66 | 51 | 41 |
| 12/736648 | 68 | 35 | 35 | 74 |
| 12/736649 | 55 | 73 | 63 | 55 |
| 12/736675 | 43 | 42 | 55 | 297 |
| 12/736676 | 108 | 58 | 56 | 35. |

Example 36

Modified Oligonucleotides Targeting FXI In Vitro Study

Modified oligonucleotides were designed based on the control oligonucleotide ISIS 464917, having a 3/10/3 gapmer motif wherein each internucleoside linkage is a phosphorothioate, the gap region contains ten β-D-2'-deoxyribonucleosides and each wing contains 3 cEt bicyclic nucleosides. Two methoxypropyl phosphonate modified internucleoside linkages were positioned in each of the modified oligonucleotides which are tested for their ability to inhibit FXI mRNA expression levels. The potency of the modified oligonucleotides are evaluated and compared to the control oligonucleotide.

The modified oligonucleotides are tested in vitro in primary mouse hepatocyte cells. Cells at a density of 35,000 cells per well are transfected using electroporation with 0.015, 0.056, 0.234, 0.937, 3.750 and 15.000 μM concentrations of each of the oligonucleotides listed below. After a treatment period of approximately 24 hours, RNA is isolated from the cells and mRNA levels are measured by quantitative real-time PCR and the SRB-1 mRNA levels are adjusted according to total RNA content, as measured by RIBOGREEN®.

| SEQ ID NO./ ISIS NO. | Composition (5' to 3') | Linkage |
|---|---|---|
| 11/464917 | $G_kT_k{}^mC_k$TGTG${}^m$CAT${}^m$CT${}^m$CT$_k{}^mC_k{}^mC_k$ | full PS |
| 11/718411 | $G_kT_{kq}{}^mC_{kq}$TGTG${}^m$CAT${}^m$CT${}^m$CT$_k{}^mC_k{}^mC_k$ | MOP |
| 11/718413 | $G_kT_k{}^mC_kT_qG_q$TG${}^m$CAT${}^m$CT${}^m$CT$_k{}^mC_k{}^mC_k$ | MOP |
| 11/718416 | $G_kT_k{}^mC_k$TGTG${}^m$CAT${}^m$CT$_q{}^mC_qT_k{}^mC_k{}^mC_k$ | MOP |
| 11/718417 | $G_kT_k{}^mC_k$TGTG${}^m$CAT${}^m$CT${}^m$CT$_{kq}{}^mC_{kq}{}^mC_k$ | MOP |
| 11/718418 | $G_kT_{kq}{}^mC_kT_q$GTG${}^m$CAT${}^m$CT${}^m$CT$_k{}^mC_k{}^mC_k$ | MOP |

Between adjacent nucleosides subscript "q" indicates a methoxypropyl phosphonate (MOP) modified internucleoside linkage (—P(CH$_3$O—(CH$_2$)$_3$—)(=O)—) and all other internucleoside linkages are phosphorothioate internucleoside linkages. Each nucleoside followed by a subscript "k" is a bicyclic nucleoside having a 4'-CH((S)—CH$_3$)—O-2' bridging group (cEt) and all other nucleosides are 2'-deoxyribonucleosides. Each ""C" indicates that this nucleoside comprises a 5-methyl cytosine heterocyclic base.

The half maximal inhibitory concentration ($IC_{50}$) of each oligonucleotide listed above is calculated by plotting the concentrations of oligonucleotides used versus the percent inhibition of FXI mRNA expression achieved at each concentration, and noting the concentration of oligonucleotide at which 50% inhibition of FXI mRNA expression is achieved compared to the control.

Example 37

Modified Oligonucleotides Targeting CXCL12 In Vitro Study

Modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides. Methoxypropyl phosphonate internucleoside linkages were positioned at various positions within gap of the oligonucleotides as illustrated below. The resulting modified oligonucleotides were tested for their ability to inhibit CXCL12 (Chemokine ligand 12) and Raptor mRNA expression levels. The potency of the modified oligonucleotides was evaluated and compared to the control oligonucleotide. The table is divided into 6 sections to reflect that 6 separate assays were performed (3 assays targeting CXCL12 and 3 assays targeting Raptor).

The modified oligonucleotides were tested in vitro in mouse b.END cells by electroporation. Cells at a density of 20,000 cells per well are transfected using electroporation with 0.027, 0.082, 0.25, 0.74, 2.22, 6.67 and 20 uM concentrations of each of the oligonucleotides listed below. After a treatment period of approximately 24 hours, RNA is isolated from the cells and mRNA levels are measured by quantitative real-time PCR and the CXCL12 mRNA and Raptor mRNA levels are adjusted according to total RNA content, as measured by RIBOGREEN®.

| SEQ ID NO./ ISIS NO. | Composition (5' to 3') | Tm/ΔTm ° C. | Linkage |
|---|---|---|---|
| 15/558807 | $G_k{}^mC_kA_k$TGTT${}^m$CT${}^m$CA${}^m$CAT$_kT_kA_k$ | 63.7/std | full PS |
| 15/766653 | $G_k{}^mC_kA_kT_qG_q$TT${}^m$CT${}^m$CA${}^m$CAT$_kT_kA_k$ | 60.3/-1.7 | MOP/PS |
| 15/766654 | $G_k{}^mC_kA_kTG_qT_qT{}^m$CT${}^m$CA${}^m$CAT$_kT_kA_k$ | 60.0/-1.9 | MOP/PS |
| 15/766655 | $G_k{}^mC_kA_k$TGT$_qT_q{}^m$CT${}^m$CA${}^m$CAT$_kT_kA_k$ | 61.9/-0.9 | MOP/PS |
| 15/766666 | $G_k{}^mC_kA_k$TGTT$_q{}^mC_q{}^m$CA${}^m$CAT$_kT_kA_k$ | 61.2/-1.3 | MOP/PS |

| SEQ ID NO./ ISIS NO. | Composition (5' to 3') | Tm/ΔTm °C. | Linkage |
|---|---|---|---|
| 15/766657 | $G_k{}^mC_kA_k$TGTT${}^mC_qT_q{}^mCA{}^mCAT_kT_kA_k$ | 60.1/-1.8 | MOP/PS |
| 15/766658 | $G_k{}^mC_kA_k$TGTT${}^mCT_q{}^mC_qA{}^mCAT_kT_kA_k$ | 54.5/-4.6 | MOP/PS |
| 15/766659 | $G_k{}^mC_kA_k$TGTT${}^mCT{}^mC_qA_q{}^mCAT_kT_kA_k$ | 61.0/-1.4 | MOP/PS |
| 15/766665 | $G_k{}^mC_kA_k$TGTT${}^mCT{}^mCA_q{}^mC_qAT_kT_kA_k$ | 61.6/-1.1 | MOP/PS |
| 15/766664 | $G_k{}^mC_kA_k$TGTT${}^mCT{}^mCA{}^mC_qA_qT_kT_kA_k$ | 61.3/-1.2 | MOP/PS |

Between adjacent nucleosides subscript "q" indicates a methoxypropyl phosphonate modified internucleoside linkage ($-P(CH_3O-(CH_2)_3-)(=O)-$, MOP) and all other internucleoside linkages are phosphorothioate internucleoside linkages. Each nucleoside followed by a subscript "k" is a bicyclic nucleoside having a 4'-$CH((S)-CH_3))-O-2'$ bridging group (cEt) and all other nucleosides are 2'-deoxyribonucleosides. Each "${}^mC$" indicates that this nucleoside comprises a 5-methyl cytosine heterocyclic base. Tm's were performed following essentially the procedures illustrated in Example 30.

The half maximal inhibitory concentration ($IC_{50}$) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control.

| SEQ ID NO./ ISIS NO. | $IC_{50}$/CXCL12 | Linkage |
|---|---|---|
| 15/558507 | 150 | full PS |
| 15/766653 | 200 | MOP/PS |
| 15/766654 | 250 | MOP/PS |
| 15/766655 | 250 | MOP/PS |
| 15/558807 | 200 | full PS |
| 15/766666 | 200 | MOP/PS |
| 15/766657 | 200 | MOP/PS |
| 15/766658 | 350 | MOP/PS |
| 15/558807 | 100 | full PS |
| 15/766659 | 100 | MOP/PS |
| 15/766665 | 100 | MOP/PS |
| 15/766664 | 100 | MOP/PS |

| SEQ ID NO./ ISIS NO. | $IC_{50}$/Raptor | Linkage |
|---|---|---|
| 15/558807 | 3000 | full PS |
| 15/766653 | >20000 | MOP/PS |
| 15/766654 | >20000 | MOP/PS |
| 15/766655 | >20000 | MOP/PS |
| 15/558807 | 4000 | full PS |
| 15/766666 | >20000 | MOP/PS |
| 15/766657 | 6000 | MOP/PS |
| 15/766658 | 6000 | MOP/PS |
| 15/558807 | 2500 | full PS |
| 15/766659 | 2000 | MOP/PS |
| 15/766665 | 1500 | MOP/PS |
| 15/766664 | 2000 | MOP/PS |

Addition modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides for evaluation in the above illustrated assays.

| SEQ ID NO./ ISIS NO. | Composition (5' to 3') | Linkage |
|---|---|---|
| 15/558807 | $G_k{}^mC_kA_k$TGTT${}^mCT{}^mCA{}^mCAT_kT_kA_k$ | full PS |
| 15/766676 | $G_k{}^mC_kA_kT_g$GTT${}^mCT{}^mCA{}^mCAT_kT_kA_k$ | MOP/PS |
| 15/766677 | $G_k{}^mC_kA_k$TG$_q$TT${}^mCT{}^mCA{}^mCAT_kT_kA_k$ | MOP/PS |
| 15/766678 | $G_k{}^mC_kA_k$TGT$_q$T${}^mCT{}^mCA{}^mCAT_kT_kA_k$ | MOP/PS |
| 15/766679 | $G_k{}^mC_kA_k$TGTT$_q{}^mCT{}^mCA{}^mCAT_kT_kA_k$ | MOP/PS |
| 15/766680 | $G_k{}^mC_kA_k$TGTT${}^mC_qT{}^mCA{}^mCAT_kT_kA_k$ | MOP/PS |
| 15/766681 | $G_k{}^mC_kA_k$TGTT${}^mCT_q{}^mCA{}^mCAT_kT_kA_k$ | MOP/PS |
| 15/766682 | $G_k{}^mC_kA_k$TGTT${}^mCT{}^mC_qA{}^mCAT_kT_kA_k$ | MOP/PS |
| 15/766683 | $G_k{}^mC_kA_k$TGTT${}^mCT{}^mCA_q{}^mCAT_kT_kA_k$ | MOP/PS |
| 15/766684 | $G_k{}^mC_kA_k$TGTT${}^mCT{}^mCA{}^mC_qAT_kT_kA_k$ | MOP/PS |
| 15/766685 | $G_k{}^mC_kA_k$TGTT${}^mCT{}^mCA{}^mCA_qT_kT_kA_k$ | MOP/PS |
| 16/558765 | $A_k{}^mC_kA_kT{}^mCTT{}^mCAGAT{}^mCA_kT_kT_k$ | full PS |
| 16/766686 | $A_k{}^mC_kA_kT_q{}^mC_qTT{}^mCAGAT{}^mCA_kT_kT_k$ | MOP/PS |
| 16/766687 | $A_k{}^mC_kA_kT{}^mC_qT_qT{}^mCAGAT{}^mCA_kT_kT_k$ | MOP/PS |
| 16/766688 | $A_k{}^mC_kA_kT{}^mCT_qT_q{}^mCAGAT{}^mCA_kT_kT_k$ | MOP/PS |
| 16/766689 | $A_k{}^mC_kA_kT{}^mCTT_q{}^mC_qAGAT{}^mCA_kT_kT_k$ | MOP/PS |
| 16/766690 | $A_k{}^mC_kA_kT{}^mCTT{}^mC_qA_qGAT{}^mCA_kT_kT_k$ | MOP/PS |
| 16/766691 | $A_k{}^mC_kA_kT{}^mCTT{}^mCA_qG_qAT{}^mCA_kT_kT_k$ | MOP/PS |
| 16/766692 | $A_k{}^mC_kA_kT{}^mCTT{}^mCAG_qA_qT{}^mCA_kT_kT_k$ | MOP/PS |
| 16/766693 | $A_k{}^mC_kA_kT{}^mCTT{}^mCAGA_qT_q{}^mCA_kT_kT_k$ | MOP/PS |
| 16/766694 | $A_k{}^mC_kA_kT{}^mCTT{}^mCAGAT_q{}^mC_qA_kT_kT_k$ | MOP/PS |
| 16/766695 | $A_k{}^mC_kA_kT_q{}^mCTT{}^mCAGAT{}^mCA_kT_kT_k$ | MOP/PS |
| 16/766696 | $A_k{}^mC_kA_kT{}^mC_qTT{}^mCAGAT{}^mCA_kT_kT_k$ | MOP/PS |
| 16/766697 | $A_k{}^mC_kA_kT{}^mCT_qT{}^mCAGAT{}^mCA_kT_kT_k$ | MOP/PS |
| 16/766698 | $A_k{}^mC_kA_kT{}^mCTT_q{}^mCAGAT{}^mCA_kT_kT_k$ | MOP/PS |
| 16/766699 | $A_k{}^mC_kA_kT{}^mCTT{}^mC_qAGAT{}^mCA_kT_kT_k$ | MOP/PS |
| 16/766700 | $A_k{}^mC_kA_kT{}^mCTT{}^mCA_qGAT{}^mCA_kT_kT_k$ | MOP/PS |
| 16/766701 | $A_k{}^mC_kA_kT{}^mCTT{}^mCAG_qAT{}^mCA_kT_kT_k$ | MOP/PS |

-continued

| SEQ ID NO./ ISIS NO. | Composition (5' to 3') | Linkage |
|---|---|---|
| 16/766702 | $A_k{}^mC_kA_kT{}^mCTT{}^mCAGA_qT{}^mCA_kT_kT_k$ | MOP/PS |
| 16/766703 | $A_k{}^mC_kA_kT{}^mCTT{}^mCAGAT_q{}^mCA_kT_kT_k$ | MOP/PS |
| 16/766704 | $A_k{}^mC_kA_kT{}^mCTT{}^mCAGAT{}^mC_qA_kT_kT_k$ | MOP/PS. |

Example 38

Stability and Cleavage Patterns of Modified Oligonucleotides (RNA/ASO Duplexes) Subjected to RNaseH 1 Treatment Modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides. Methoxypropyl phosphonate internucleoside linkages were positioned at various positions within gap of the oligonucleotides as illustrated below. The resulting modified oligonucleotides (ASOs) were hybridized to complementary RNA strands to provide RNA/ASO duplexes that were then treated with Human RNase H1.

Human RNase H1 (1:100 dilution) was prepared by adding Human RNase H1 (1.0 µL) to RNase H1 dilution buffer (72 µL) (RNase H1 dilution buffer: glycerol 30%; 20 mM Tris pH7.5; 50 mM NaCl) and RNAseOUT (8 The dilution was allowed to incubate for 1 hour prior to use.

RNA/ASO duplexes were prepared by heating a buffered solution of each of the modified oligonucleotides (400 nM) listed in the table below with the complementary RNA (IDT, 200 nm unlabeled and 1 nm 5'-$^{32}$P labeled) to 90° C. for 2 minutes. The buffered solution is prepared having 20 mM Tris pH 7.5; 50 mM NaCl; 2 mM MgCl; 0.2 mM TCEP; and 2 µL RNAseOUT.

To each of the RNA/ASO duplexes (20 µL) is added the Human RNase H1 solution (1 µL) in a heat block at 37° C. for 30 minutes. The samples are then quenched with urea (20 µL, 8M) and heated to 90° C. for 2 minutes.

The percent cleavage at the 30 minute is shown below.

Between adjacent nucleosides subscript "q" indicates a methoxypropyl phosphonate modified internucleoside linkage (—P(CH$_3$O—(CH$_2$)$_3$—)(=O)—, MOP) and all other internucleoside linkages are phosphorothioate internucleoside linkages. Each nucleoside followed by a subscript "k" is a bicyclic nucleoside having a 4'-CH((S)—CH$_3$))—O-2' bridging group (cEt) and all other nucleosides are 2'-deoxyribonucleosides except for the complementary RNA sequence Seq Id No.: 17. Each "$^m$C" indicates that this nucleoside comprises a 5-methyl cytosine heterocyclic base. The complementary RNA was purchased from IDT.

The cleavage products were resolved on polyacrylamide gel and quantitated further quantitated using GE Image quant software. The polyacrylamide gel is shown in FIG. 1.

Example 39

Modified Oligonucleotides Targeting Malat1 In Vitro Study

Modified oligonucleotides were designed based on the control oligonucleotide ISIS 602056, having a 5/10/5 gapmer motif wherein each internucleoside linkage is a phosphorothioate except that 3 of the oligonucleotides have some of the phosphorothioate internucleoside linkages replaced with phosphodiester internucleoside linkages (mixed backbone), the gap region contains ten β-D-2'-deoxyribonucleosides and each wing contains 5 2'-MOE modified nucleosides. Methoxypropyl phosphonate internucleoside linkages are positioned at various positions within the oligonucleotides as illustrated below. The resulting modified oligonucleotides are tested for their ability to inhibit Malat1 mRNA expression levels. The potency of the modified oligonucleotides is evaluated and compared to the control oligonucleotide.

The modified oligonucleotides are tested in vitro in primary mouse hepatocyte cells. Cells at a density of 35,000 cells per well are transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR wherein the Malat1 mRNA levels are adjusted according to total RNA content, as measured by RIBOGREEN®.

| SEQ ID NO./ ISIS NO. | Composition (5' to 3') | Cleavage % | Linkage |
|---|---|---|---|
| 17/IDT | UAAUGUGAGAACAUGC | n/a | RNA |
| 15/558807 | $G_k{}^mC_kA_kTGTT{}^mCT{}^mCA{}^mCAT_kT_kA_k$ | 36.80 | full PS |
| 15/766653 | $G_k{}^mC_kA_kT_qG_qTT{}^mCT{}^mCA{}^mCAT_kT_kA_k$ | 50.10 | MOP/PS |
| 15/766654 | $G_k{}^mC_kA_kTG_qT_qT{}^mCT{}^mCA{}^mCAT_kT_kA_k$ | 48.60 | MOP/PS |
| 15/766655 | $G_k{}^mC_kA_kTGT_qT_q{}^mCT{}^mCA{}^mCAT_kT_kA_k$ | 44.30 | MOP/PS |
| 15/766666 | $G_k{}^mC_kA_kTGTT_q{}^mC_qT{}^mCA{}^mCAT_kT_kA_k$ | 45.00 | MOP/PS |
| 15/766657 | $G_k{}^mC_kA_kTGTT{}^mC_qT_q{}^mCA{}^mCAT_kT_kA_k$ | 48.70 | MOP/PS |
| 15/766658 | $G_k{}^mC_kA_kTGTT{}^mCT_q{}^mC_qA{}^mCAT_kT_kA_k$ | 44.40 | MOP/PS |
| 15/766659 | $G_k{}^mC_kA_kTGTT{}^mCT{}^mC_qA_q{}^mCAT_kT_kA_k$ | 40.30 | MOP/PS |
| 15/766665 | $G_k{}^mC_kA_kTGTT{}^mCT{}^mCA_q{}^mC_qAT_kT_kA_k$ | 44.40 | MOP/PS |
| 15/766664 | $G_k{}^mC_kA_kTGTT{}^mCT{}^mCA{}^mC_qA_qT_kT_kA_k$ | 50.30 | MOP/PS |

| SEQ ID NO./ ISIS NO. | Composition (5' to 3') | Linkage |
|---|---|---|
| 13/602056 | $G_e{}^mC_eC_eA_eG_eG^m$CTGGTTATGA$_e{}^mC_eT_e{}^mC_eA_e$ | full PS |
| 13/766753 | $G_{eq}{}^mC_e{}^mC_{eq}A_eG_{eq}G^m$CTGGTTATGA$_e{}^mC_eT_e{}^mC_eA_e$ | MOP/PS |
| 13/766754 | $G_{eq}{}^mC_{eq}{}^mC_{eq}A_eG_eG^m$CTGGTTATGA$_e{}^mC_eT_e{}^mC_eA_e$ | MOP/PS |
| 13/766755 | $G_e{}^mC_e{}^mC_{eq}A_{eq}G_{eq}G^m$CTGGTTATGA$_e{}^mC_eT_e{}^mC_eA_e$ | MOP/PS |
| 13/766756 | $G_e{}^mC_e{}^mC_{eq}A_eG_{eq}G^m$CTGGTTATGA$_e{}^mC_eT_e{}^mC_eA_e$ | MOP/PS |
| 13/761957 | $G_e{}^mC_e{}^mC_eA_eG_eG^m$CTGGTTATGA$_{eq}{}^mC_eT_{eq}{}^mC_eA_e$ | MOP/PS |
| 13/766757 | $G_e{}^mC_e{}^mC_eA_eG_eG^m$CTGGTTATGA$_e{}^mC_{eq}T_{eq}{}^mC_{eq}A_e$ | MOP/PS |
| 13/766758 | $G_e{}^mC_e{}^mC_eA_eG_eG^m$CTGGTTATGA$_{eq}{}^mC_{eq}T_{eq}{}^mC_eA_e$ | MOP/PS |
| 13/766759 | $G_e{}^mC_{eq}{}^mC_{eq}A_{eq}G_{eq}G^m$CTGGTTATGA$_{eq}{}^mC_{eq}T_e{}^mC_eA_e$ | MOP/PS |
| 13/766766 | $G_{eq}{}^mC_{eo}{}^mC_{eo}A_{eo}G_{eo}G^m$CTGGTTATGA$_{eo}C_{eo}T_{eq}{}^mC_{eq}A_e$ | MOP/PO/PS |
| 13/766761 | $G_{eq}{}^mC_{eq}{}^mC_{eo}A_{eo}G_eG^m$CTGGTTATGA$_{eo}{}^mC_{eo}T_{eq}{}^mC_{eq}A_e$ | MOP/PO/PS |
| 13/766762 | $G_{eq}{}^mC_{eo}{}^mC_{eq}A_eG_eG^m$CTGGTTATGA$_e{}^mC_{eq}T_{eo}{}^mC_{eq}A_e$ | MOP/PO/PS |
| 13/766763 | $G_{eq}{}^mC_{eq}{}^mC_{eq}A_{eq}G_{eq}G^m$CTGGTTATGA$_e{}^mC_eT_e{}^mC_eA_e$ | MOP/PS |
| 13/766764 | $G_e{}^mC_e{}^mC_eA_eG_eG^m$CTGGTTATGA$_{eq}{}^mC_{eq}T_{eq}{}^mC_{eq}A_e$ | MOP/PS |
| 13/766765 | $G_{eq}{}^mC_{eq}{}^mC_{eq}A_{eq}G_{eq}G^m$CTGGTTATGA$_{eq}{}^mC_{eq}T_{eq}{}^mC_{eq}A_e$ | MOP/PS |
| 13/766767 | $G_e{}^mC_e{}^mC_eA_eG_eG_q{}^mC_q$TGGTTATGA$_e{}^mC_eT_e{}^mC_eA_e$ | MOP/PS |
| 13/766768 | $G_e{}^mC_e{}^mC_eA_eG_eG^mC_qT_q$GGTTATGA$_e{}^mC_eT_e{}^mC_eA_e$ | MOP/PS |
| 13/766769 | $G_e{}^mC_e{}^mC_eA_eG_eG^m$CT$_qG_q$GTTATGA$_e{}^mC_eT_e{}^mC_eA_e$ | MOP/PS |
| 13/766770 | $G_e{}^mC_e{}^mC_eA_eG_eG^m$CTG$_qG_q$TTATGA$_e{}^mC_eT_e{}^mC_eA_e$ | MOP/PS |
| 13/766771 | $G_e{}^mC_e{}^mC_eA_eG_eG^m$CTGG$_qT_q$TATGA$_e{}^mC_eT_e{}^mC_eA_e$ | MOP/PS |
| 13/766772 | $G_e{}^mC_e{}^mC_eA_eG_eG^m$CTGGT$_qT_q$ATGA$_e{}^mC_eT_e{}^mC_eA_e$ | MOP/PS |
| 13/766773 | $G_e{}^mC_e{}^mC_eA_eG_eG^m$CTGGTT$_qA_q$TGA$_e{}^mC_eT_e{}^mC_eA_e$ | MOP/PS |
| 13/766774 | $G_e{}^mC_e{}^mC_eA_eG_eG^m$CTGGTTA$_qT_q$GA$_e{}^mC_eT_e{}^mC_eA_e$ | MOP/PS |
| 13/766775 | $G_e{}^mC_e{}^mC_eA_eG_eG^m$CTGGTTAT$_qG_qA_e{}^mC_eT_e{}^mC_eA_e$ | MOP/PS |
| 13/766784 | $G_e{}^mC_e{}^mC_eA_eG_eG_q{}^m$CTGGTTATG$_qA_e{}^mC_eT_e{}^mC_eA_e$ | MOP/PS |
| 13/766785 | $G_e{}^mC_e{}^mC_eA_eG_eG_q{}^mC_q$TGGTTAT$_qG_qA_e{}^mC_eT_e{}^mC_eA_e$ | MOP/PS |
| 13/766787 | $G_e{}^mC_e{}^mC_eA_eG_eG_q{}^mC_qT_qG_q$GTT$_qA_qT_qG_{Ae}{}^mC_eT_e{}^mC_eA_e$ | MOP/PS |
| 13/766776 | $G_e{}^mC_e{}^mC_eA_eG_eG_q{}^mC_qT_q$GGTTATGA$_e{}^mC_eT_e{}^mC_eA_e$ | MOP/PS |
| 13/766777 | $G_e{}^mC_e{}^mC_eA_eG_eG^mC_qT_qG_q$GTTATGA$_e{}^mC_eT_e{}^mC_eA_e$ | MOP/PS |
| 13/766778 | $G_e{}^mC_e{}^mC_eA_eG_eG^m$CT$_qG_qG_q$TTATGA$_e{}^mC_eT_e{}^mC_eA_e$ | MOP/PS |
| 13/766779 | $G_e{}^mC_e{}^mC_eA_eG_eG^m$CTG$_qG_qT_q$TATGA$_e{}^mC_eT_e{}^mC_eA_e$ | MOP/PS |
| 13/766780 | $G_e{}^mC_e{}^mC_eA_eG_eG^m$CTGG$_qT_qT_q$ATGA$_e{}^mC_eT_e{}^mC_eA_e$ | MOP/PS |
| 13/766781 | $G_e{}^mC_e{}^mC_eA_eG_eG^m$CTGGT$_qT_qA_q$TGA$_e{}^mC_eT_e{}^mC_eA_e$ | MOP/PS |
| 13/766782 | $G_e{}^mC_e{}^mC_eA_eG_eG^m$CTGGTT$_qA_qT_q$GA$_e{}^mC_eT_e{}^mC_eA_e$ | MOP/PS |
| 13/766783 | $G_e{}^mC_e{}^mC_eA_eG_eG^m$CTGGTTA$_qT_qG_qA_e{}^mC_eT_e{}^mC_eA_e$ | MOP/PS |

Between adjacent nucleosides subscript "q" indicates a methoxypropyl phosphonate (MOP) modified internucleoside linkage ($-P(CH_3O-(CH_2)_3-)(=O)-$) and all other internucleoside linkages are phosphorothioate internucleoside linkages. Each nucleoside followed by a subscript "e" is a 2'-O-methoxyethyl (MOE) modified nucleoside and all other nucleosides are 2'-deoxyribonucleosides. Each "$^mC$" indicates that this nucleoside comprises a 5-methyl cytosine heterocyclic base.

The half maximal inhibitory concentration ($IC_{50}$) of each oligonucleotide listed above is calculated by plotting the concentrations of oligonucleotides used versus the percent inhibition of Malat1 mRNA expression achieved at each concentration, and noting the concentration of oligonucleotide at which 50% inhibition of Malat1 mRNA expression is achieved compared to the control.

Example 40

Modified Oligonucleotides Targeting Androgen Receptor In Vitro Study

Modified oligonucleotides were designed based on the control oligonucleotide ISIS 585268, having a 4/8/4 gapmer motif wherein each internucleoside linkage is a phosphorothioate, the gap region contains 8 β-D-2'-deoxyribonucleosides and each wing contains 4 modified nucleosides independently selected from 2'-MOE modified nucleosides and bicyclic nucleosides having a 4'-CH((S)—CH$_3$))—O-2' bridging group. Additional similar motifs are also provided. Methoxypropyl phosphonate internucleoside linkages are positioned at various positions within the oligonucleotides as illustrated below. The resulting modified oligonucleotides are tested for their ability to inhibit Androgen receptor mRNA expression levels. The potency of the modified oligonucleotides is evaluated and compared to the control oligonucleotide.

The modified oligonucleotides are tested in vitro in primary mouse hepatocyte cells. Cells at a density of 35,000 cells per well are transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR and the Androgen receptor mRNA levels are adjusted according to total RNA content, as measured by RIBOGREEN®.

| SEQ ID NO./ISIS NO. | Composition (5' to 3') | Linkage |
|---|---|---|
| 14/585268 | A$_k$A$_e$G$_k$T$_e$TGTAGTAGT$_e$$^m$C$_k$G$_e$$^m$C$_k$ | full PS |
| 14/766788 | A$_k$A$_{eq}$G$_{kq}$T$_e$TGTAGTAGT$_{eq}$$^m$C$_k$G$_e$$^m$C$_k$ | MOP/PS |
| 14/766789 | A$_k$A$_{eq}$G$_{kq}$T$_e$TGTAGTAGT$_{eq}$$^m$C$_{kq}$G$_e$$^m$C$_k$ | MOP/PS |
| 14/766790 | A$_k$A$_{eq}$G$_{kq}$T$_{eq}$TGTAGTAGT$_{eq}$$^m$C$_k$G$_e$$^m$C$_k$ | MOP/PS |
| 14/766791 | A$_k$A$_{eq}$G$_{kq}$T$_e$TGTAGTAGT$_{eq}$$^m$C$_{kq}$G$_e$$^m$C$_k$ | MOP/PS |
| 14/766793 | A$_{kq}$A$_{eq}$G$_{kq}$T$_{eq}$TGTAGTAGT$_e$$^m$C$_k$G$_e$$^m$C$_k$ | MOP/PS |
| 14/766794 | A$_k$A$_e$G$_k$T$_e$TGTAGTAGT$_{eq}$$^m$C$_{kq}$G$_{eq}$$^m$C$_k$ | MOP/PS |
| 14/766795 | A$_{kq}$A$_{eq}$G$_{kq}$T$_{eq}$TGTAGTAGT$_{eq}$$^m$C$_{kq}$G$_{eq}$$^m$C$_k$ | MOP/PS |
| 14/766796 | A$_{kq}$A$_{eq}$G$_{kq}$T$_e$TGTAGTAGT$_e$$^m$C$_{kq}$G$_e$$^m$C$_k$ | MOP/PS |
| 14/766797 | A$_k$A$_{eq}$G$_k$T$_{eq}$TGTAGTAGT$_{eq}$$^m$C$_k$G$_{eq}$$^m$C$_k$ | MOP/PS |
| 14/549372 | A$_k$A$_k$G$_k$TTGTAGTAGT$^m$C$_k$G$_k$$^m$C$_k$ | MOP/PS |
| 14/766798 | A$_{kq}$A$_{kq}$G$_{kq}$TTGTAGTAGT$^m$C$_k$G$_k$$^m$C$_k$ | MOP/PS |
| 14/766799 | A$_k$A$_k$G$_k$TTGTAGTAGT$^m$C$_{kq}$G$_{kq}$$^m$C$_k$ | MOP/PS |
| 14/766800 | A$_{kq}$A$_{kq}$G$_{kq}$TTGTAGTAGT$^m$C$_{kq}$G$_{kq}$$^m$C$_k$ | MOP/PS |
| 14/766801 | A$_k$A$_k$G$_k$T$_q$T$_q$GTAGTAGT$^m$C$_k$G$_k$$^m$C$_k$ | MOP/PS |
| 14/766802 | A$_k$A$_k$G$_k$TT$_q$G$_q$TAGTAGT$^m$C$_k$G$_k$$^m$C$_k$ | MOP/PS |
| 14/766803 | A$_k$A$_k$G$_k$TTG$_q$T$_q$AGTAGT$^m$C$_k$G$_k$$^m$C$_k$ | MOP/PS |
| 14/766804 | A$_k$A$_k$G$_k$TTGT$_q$A$_q$GTAGT$^m$C$_k$G$_k$$^m$C$_k$ | MOP/PS |
| 14/766805 | A$_k$A$_k$G$_k$TTGTA$_q$G$_q$TAGT$^m$C$_k$G$_k$$^m$C$_k$ | MOP/PS |
| 14/766806 | A$_k$A$_k$G$_k$TTGTAG$_q$T$_q$AGT$^m$C$_k$G$_k$$^m$C$_k$ | MOP/PS |
| 14/766807 | A$_k$A$_k$G$_k$TTGTAGT$_q$A$_q$GT$^m$C$_k$G$_k$$^m$C$_k$ | MOP/PS |
| 14/766808 | A$_k$A$_k$G$_k$TTGTAGTA$_q$G$_q$T$^m$C$_k$G$_k$$^m$C$_k$ | MOP/PS |
| 14/766809 | A$_k$A$_k$G$_k$TTGTAGTAG$_q$T$_q$$^m$C$_k$G$_k$$^m$C$_k$ | MOP/PS |
| 14/766800 | A$_{kq}$A$_{kq}$G$_{kq}$TTGTAGTAGT$^m$C$_{kq}$G$_{kq}$$^m$C$_k$ | MOP/PS |
| 14/766810 | A$_{kq}$A$_{kq}$G$_{kq}$TTGTAGTA$_q$G$_q$T$_q$$^m$C$_e$G$_e$$^m$C$_e$ | MOP/PS |
| 14/766811 | A$_{kq}$A$_{kq}$G$_{kq}$TTGTAGTAG$_q$T$_q$$^m$C$_{kq}$G$_e$$^m$C$_e$ | MOP/PS |
| 14/766812 | A$_e$A$_{kq}$G$_e$T$_q$TGTAGTAGT$_e$$^m$C$_{kq}$G$_e$$^m$C$_k$ | MOP/PS |
| 14/642460 | A$_q$A$_q$G$_q$TTGTAGTAGT$^m$C$_q$G$_q$$^m$C$_q$ | MOP/PS |
| 14/642461 | A$_{kq}$A$_{kq}$G$_{kq}$TTGTAGTA$_q$G$_q$T$_q$$^m$C$_e$G$_e$$^m$C$_e$ | MOP/PS |
| 14/642462 | A$_{kq}$A$_{kq}$G$_{kq}$TTGTAGTAG$_q$T$_q$$^m$C$_{kq}$G$_e$$^m$C$_e$ | MOP/PS |
| 14/642463 | A$_e$A$_q$G$_e$T$_q$TGTAGTAGT$_e$$^m$C$_q$G$_e$$^m$C$_q$ | MOP/PS |
| 14/642464 | A$_q$A$_e$G$_q$T$_e$TGTAGTAGT$_e$$^m$C$_q$G$_e$$^m$C$_k$ | MOP/PS. |

Between adjacent nucleosides subscript "q" indicates a methoxypropyl phosphonate modified internucleoside linkage (—P(CH$_3$O—(CH$_2$)$_3$—)(=O)—, MOP), subscript "o" indicates a phosphodiester internucleoside linkage (PO) and all other internucleoside linkages are phosphorothioate internucleoside linkages (PS). Each nucleoside followed by a subscript "e" is a 2'-O-methoxyethyl (MOE) modified nucleoside, each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" indicates that this nucleoside comprises a 5-methyl cytosine heterocyclic base.

The half maximal inhibitory concentration (IC$_{50}$) of each oligonucleotide listed above is calculated by plotting the concentrations of oligonucleotides used versus the percent inhibition of Androgen receptor mRNA expression achieved at each concentration, and noting the concentration of oligonucleotide at which 50% inhibition of Androgen receptor mRNA expression is achieved compared to the control.

The invention claimed is:

1. An oligomeric compound comprising a contiguous sequence of monomer subunits linked by internucleoside linking groups wherein at least one of the internucleoside linking groups has Formula I:

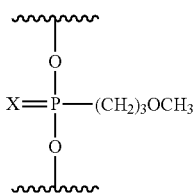

wherein each X is independently O or S.

2. The oligomeric compound of claim 1 comprising from 12 to 24 monomer subunits.

3. The oligomeric compound of claim 1 comprising from 14 to 20 monomer subunits.

4. The oligomeric compound of claim 1 comprising from 1 to 10 internucleoside linking groups of Formula I.

5. The oligomeric compound of claim 1 comprising from 1 to 5 internucleoside linking groups of Formula I.

6. The oligomeric compound of claim 1 comprising from 1 to 3 internucleoside linking groups of Formula I.

7. The oligomeric compound of claim 1 comprising 4 internucleoside linking groups of Formula I.

8. The oligomeric compound of claim 1 comprising 3 internucleoside linking groups of Formula I.

9. The oligomeric compound of claim 1 comprising 2 internucleoside linking groups of Formula I.

10. The oligomeric compound of claim 1 wherein each X is O.

11. The oligomeric compound of claim 1 wherein each X is S.

12. The oligomeric compound of claim 11 wherein the chirality of each internucleoside linking group having Formula I is $R_P$.

13. The oligomeric compound of claim 11 wherein the chirality of each internucleoside linking group having Formula I is $S_P$.

14. The oligomeric compound of claim 1 further comprising one 5' or 3'-conjugate group.

15. The oligomeric compound of claim 14 wherein the conjugate group comprises a cell targeting moiety.

16. The oligomeric compound of claim 15 wherein the cell targeting moiety has the formula:

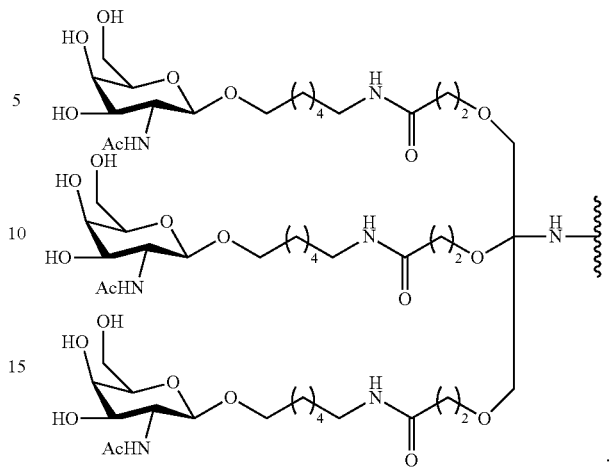

17. The oligomeric compound of claim 15 wherein the attachment of the cell targeting moiety to the oligomeric compound includes a conjugate linker having the formula:

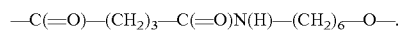

18. The oligomeric compound of claim 15 wherein the attachment of the cell targeting moiety to the oligomeric compound includes a conjugate linker and a cleavable moiety.

19. The oligomeric compound of claim 18 wherein the cleavable moiety has the formula:

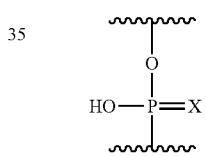

wherein X is O or S.

20. The oligomeric compound of claim 19, wherein X is O.

21. A method of inhibiting gene expression comprising contacting one or more cells, a tissue or an animal with the oligomeric compound of claim 1, wherein said oligomeric compound is complementary to a target RNA.

* * * * *

SEQUENCE LISTING

<160> NUMBER OF SEQ ID NOS: 18

<210> SEQ ID NO 1

<211> LENGTH: 202001
<212> TYPE: DNA
<213> ORGANISM: Homo sapiens

<400> SEQUENCE: 1

```
gcccagcagg tgtcagcctc attttacccc gcccctattc aagatgaagt tgttctggtt      60
ccaacgcctc tgacatatta gctgcatcat tttacatttc tttttttttt ttccttttaa     120
atggggtctt gctctgtcac ccaggctgga gtgctgtggt atgatctcgg ctcactgcaa     180
tctccacctc cgaggttcca gcgattctct tgcctcagcc tcccgagtag ctgggactac     240
aggcacccac catcatactg gctaatttt tgtgttttta gtagagatgg gtttccccca     300
tgttgcccag gctgatctca aactcctggg cttaagcaat acagccgcgt tggcctccca     360
aagtgttggg attacaagca tgagctaccc cacccagctc attttacatt tccacttgtt     420
aaactgaaaa ctggcccgag aaagcttctg tactgccatc cttgcgtcct tgcagatgaa     480
tcgtaaccta gcatagtagg taggcagact gaaaacctaa cttagcagta ggcttctgta     540
acaacagctg tgtctcagcc agttcctgca gccagacttc aaccactcac aggccgcaaa     600
ctgttcaaac tgtgttcgga aaggcgaat tcatctggct gttaacgtgc ctcacttctg     660
cttctgtgg ccactttccc ttttctgtcc ataaatttgc tttgaccaca cagcatccct     720
agagtctccc tgaatctgct gtgattctgg gacctgcacc attgtgaat tgtttttttt     780
ttccttgatc agctaaactc tgttcaattc aatttgttgg aagttttaa cataccaatg     840
gtgcaccaag gttccaattt ctccacttcc tcataaataa gtcattttaa atggcttttc     900
agtattccaa tatttggaag tattaatgtt ctaccaatt ttctattttt ggacattgag     960
gttgtttcat tttttttttc tttttttgag acagagtctc gctccgtcac ccaggctgga    1020
gtgcagtggc ctgatcccgg cccactgcaa cctccacctc cctcctcagc ctcctgagta    1080
gctgggatta caggtgcatg caccaccaca cccagctaat ttttgtattt ttagtagaga    1140
tggggtttca ccatgttggt caggctggtc tcaaactcct gacctcaggt ggtccacctg    1200
ccttggcctc ccaaaatgct gggattacag gcctgagcca ctgcgcctgg cctcatcttc    1260
ttgatattaa tgttgcttta acatctttgt ccctgtgttt tttgtttttt ttttgagac    1320
ggagtctcat tcattctgtc acccaggctg gagttcagtg gcgtgatctc agctcactgc    1380
aacctctgtc tcctgggttc cagtgattct cctgcgtcgg tctcctgagt agctgtgttc    1440
ctgggtcttt cgatggttat ttaatacttc cctacagtaa tgccctgtgc gtacatgcta    1500
agtgtgatga atggttggc acagttaaat cttttgaaag acattgccaa gtcactcttc    1560
agaaaagtga taggaggtca tagcaatttt aagaagtcct catttctaca tttccttact    1620
aatctcggtt ggtgtctctt caatctttcc tcacactttt cttgggtttt tcctgaatca    1680
tgagtctact acatttacac attttaaagc atctttagaa acaggatctc attttgttgc    1740
ccaggctaga gttggtggc atgattatag ctcctcatac tcctgggctc aagtgatcct    1800
tccacctctg aaaccccaaa atttgagaaa ggtctcattt aatttagaaa gtttattttg    1860
ccaaggttga gggtgcacac ctgtgatgat atacgagtta aaagaaatt atttaggcag    1920
atactgaggg taagaaagtc ctcggtaagg ttttcttttc aatgaaaagc agcccccaag    1980
cattttcttt tctaacaaag agcagcctgt aaaatcgagc tgcagacata cacaagcaag    2040
ctggaagctt gcacaggtga atgctggcag ctgtgccaat aagaaaaggc tacctggggc    2100
caggcagatc caacatggcg gctccatctt cccttccttt gtcaaccatg tgcacagtaa    2160
ggagcaggca acatagtgtc ccccgagtag agaccaattt gcataataaa aggtgagggt    2220
```

```
agggtgggca gcttctttgc atgctatgta aacattatgc ctggtccaac caatctttgg    2280
gccctgtgta aattagacac cacctcctca agcctgtcta taaaaccctg tccattctgc    2340
cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc aggagagag cttctaggtc     2700 acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180 gaaacccat ctctactaaa aaatacaaaa aactagctgg gtgtggtggc gagcacctgt     3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaaa aagagagag agaatatgca tctatctcag     3420
tgagcagaag gatgactttg aatggaatgg gagcagttcc tagcttgaac ttccccttta    3480
gcttcagtga tttgggggct caaggtatgt tcctttcaca tacctcagcc tcccaagtag    3540
ctgggaccac aagtgcatgc caccacacgt ggctaatgtt ttatttttt tgtaggaata    3600 gggtctcact atgtgtccag gctggtctaa aaccccctgag ctcaaatggt cctcccgcct   3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc    4020 ccctttctct tctgcttggc gtgttgttca tcaccactgt gcactgctga gggtaagtgc    4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac ctttttactaa agagatcttc ctgatcctcc    4380
tccccaggcc aggggagggg tcctccctgg ggttggagcc tttagtaggg ggtcggagac    4440
acgacgtagc cttcatgaca ttcatagtct agttacacga tccctgtaag ggtcagttga    4500
agtaagtgct acaaaggaag ggaggtgctc agtggagagg gctctctttt atgtattata    4560
```

```
tttctttcat ggggagggat atggatcagg gatcagcaga ggtgtttcag tcccgaggga    4620
aagaaagtca gcgtggcttg ggagttggga gcagcaagac agtggctcaa gatatcttaa    4680
gactagtgga gtacaccttg catgttaaaa gccttgctca gggctgcctg gttcttgtag    4740
gacgacagag atggcctagc tctgcatact gcaccccccag gggctcagaa cagtgcaaat   4800
gtcagtctat ctgtcagtgg cagagccagc cttggagcag gggtgcaagg aggtctctgc    4860
actggccagg catgcagaac attctgttca gtagcactgg acagaaggcc ccatctagat    4920
gagacagagc tggtggggca ggacaaagac tcctggcagc tcaaacggcc tggcagatgc    4980
ttggagagag ggggcttctt gagacagcac catttctggg aagagagtca cctgggaggg    5040
atgaggccac gctccggctt ggaggtgaag agaggggctg ctgcaagaaa gaattagaga    5100
catgccagcc tttgctgtgt tgcccaggct ggtcatgaac tcttggcctc aagcaatctt    5160
cccacctcag cctccccaag cgctgggatt atagacatga gcccccatgc tggccaataa    5220
aagatgattt tatggagggg atggtggtga aggttgtggg tggtatgaaa tagtaagaaa    5280
tatatattgg tctgcaccca gttcctgcca cagagctcct aaaatcctga gaacttcctg    5340
ggtgagcatc ttttgttcta atgaggtgac tcttggtggc tcctggatag gagtgaatca    5400
ccagaaagat caagccagag ttagaagcag aaagtgctgg ctataacaca ggaaagctgt    5460
aacacaaata ataaagtttt tttttttttt tttgagatgg agcctcactc tgttgcccag    5520
gctggagtgc aatggtgcaa tctcagctca ctacaagctc tgcctccag gttcaagtga     5580 ttctcctgcc tcagcctcct gagcagttgg gactacaggt gtgtgccacc acatctggct    5640
aatttttgta ttttttagcag agacggggtt tcaccatatt aaccaggctg gcctcaaact    5700
ccttaccttg tgatccgcct gcctcagcct cccaaagtgc tgggattaca ggcatgagcc    5760
accgtgcctg gccaaaagac attgttctta aagaatcaa ctaactaacc aaataaataa     5820
aaatctaacc taattaagaa actaaaaata cacaaaaatt aatttcaagg ggagaaaaat    5880
catgtaaaga gagaaagata atgaatactt tgcagaaatt tatgaacata acataaaaac    5940
ttggatgaaa tgcatttcta ggaaaacata atttatcaaa actaaccaca agtaaaatag    6000
aagcctaaat aggatatttt caagagaaga agtaaagttg tcaaagtgct acccttcaaa    6060
aaaacaccag gctcaaacaa tctgacatgg gaatgttagc acaccttaga gagcaaataa    6120
aactttgaat gggcttgaaa tattccagac tctagaaaaa caaaacttcc caattctttt    6180
tataaagcaa gtataaattg ataccaaaat cttataaaga cctatacaa aacttcatac     6240 caatctcttt tatgaataca aaaccccttaa taaagtatta ccagacagaa cccaacaata    6300
cataaaaatg tcacatcata acatagtggg gtttatttca ataatgcatg gatggttcaa    6360
tacaaggaaa ttcagtaaca caatataata gatcatgtga atatacccaa agaaaaaata    6420
gattattttc atagatgctg taaaggcatt tgaccaaatt caacacctac ttttttaggtg   6480 gtcaataaaa taaattagtt actccttctt tagcatgata aaatatattt atcagcccag    6540
aaggcatcat tttacccgat aagggcacac gctggaggga ataatgttaa aattaggaat    6600
aagaggatag ctagtttctt tcttcttttt tttttttgag acggagtctt gctctgttgc    6660
caggctggag tgcagtggtg caatgttggc tcactgcacg ccccccgcct cccaggttca    6720
agcgattctc ctgcctcagc ctcccgagta gctgggacta caggcgcgca ccaccatgcc    6780
cggctaattt ttttttgtat tttagtagag atggggtttc accatgttgg tcaggctggt    6840
cttgaactcc caacctcacg tactgggatt accggtgtga gccaccacgc cagcccaact    6900
actttcaaca ttatccttaa tactgatgct tattgactta ctatggggtt acctctagat    6960
```

| | |
|---|---|
| aaatccataa taagttgaaa atataagtaa aaaatgccct taatacacct aacctaccaa | 7020 |
| acatcatagc tgagcccagc ctgccttagc tatgctcaga cactgacgtc agcctacaat | 7080 |
| tggcaaaatc acacagcagc acagtctact gcagagcatc tgctgtttgc ccttgtgact | 7140 |
| gcgtggctgc ctgggagctt cccagcttca caagacagta ttacgtagca catcactagc | 7200 |
| ctggggaaag atcaaagttg aaaatttgaa gtgtggtttc cattgaatgt gtactgcttt | 7260 |
| tgcaccatca tcaagtcaaa aaattttagt tgaaccagcc taagtttggg accatcttta | 7320 |
| ttttcaggag gaacttccat gtacattgat gacggacgat agaatccgtt tctatcatcc | 7380 |
| taatgaacat aatgaataaa tccagacaaa cataaacatt aacagagtaa gcagctttcg | 7440 |
| gggctggaag ccagaagagg gtgggagcgc agagagagag gccaaacacc agggctgctt | 7500 |
| ctgctttgcg ggtatttgct gatctggaca aggtatctgg aaggctgagc taagcctcct | 7560 |
| ttttttttga ggtggcgtct cactctgttg ccaggctgga gtgcaatggt gcgatctcag | 7620 |
| ctcactgcaa cctccacctc cctggttcaa gcgattctcc tgcctcagcc tcccgagtag | 7680 |
| ctgggattac aggctcccgc cactacaccc agctgatttt tgtaatttta gtagagacgg | 7740 |
| ggtttcacca tgttggccag gatggtctcg atctcttgac gtcatgatct gtccacctcg | 7800 |
| gcctcccaaa gtgctgggat tataggcgtg acccaccgtg ccccgtctga gctaagcctc | 7860 |
| ttgagcatag gggactaaaa atgaaatcta gcgcatgcca agtttagggt cccaggcaat | 7920 |
| tccttttccac tttggggtcc actttggggt ccaccccacc caagaagaag gatgacttgg | 7980 |
| aagtaaacca gctctgaaat atggatggtc tctgggacc ataccaatcc cttcatatca | 8040 |
| accacatcca gttcctcaaa actggaactt ggattaagat ggcctaggac ttctagtgtc | 8100 |
| ccaggagcct ggcattgcaa acaaaaatcc tctccggaag aagataatac cttaagcttc | 8160 |
| aaatgactct ctaataaatt tcaaatacaa tgtccagcac acaaacacaa attaccagga | 8220 |
| acgtgatatg aggcctgatg gatgggaatt agcagaaact tcaggcatga gaaacatacc | 8280 |
| ctcagaggcc tagaatctat ctagtgtcta gataatggag atatgaaata cagacactta | 8340 |
| aacaactatg tttcccatgt tcaaagagga aatttgcaaa acttgaaagt gttggcagga | 8400 |
| aatcagaaac tataaaatgt gacaacagca tactttagag tcagtataaa ttacggtccc | 8460 |
| gaaaactgca gaattccaga acttaatggt aaagcaaggg tttaacagca gaatagaaat | 8520 |
| agccagagag aactaggaag taagtcagat gacactaccc agaataaggc actgagaggc | 8580 |
| caaggaatgg aaaatgcaga agaaaggata tggtgagagg atctaatata catttatttg | 8640 |
| gagtaccagg gagagagaga aggagaagaa cagaagccgt gtttcaagga cggtgactga | 8700 |
| gaggcttcga aactgatgaa agccatcagt tcacaaattc aaagcccagt gaattccaag | 8760 |
| gagaaaaaaa gaaatcccata ctgtgaaagc aagtccagac aatgacaaac accatcaaca | 8820 |
| atacacagga caggcataag atgcatttaa tggggacact cagaggcaga gggttatcag | 8880 |
| aaggaggcac ttctctccca gttctcatc atcccaggc cagggacagc tggtcacacc | 8940 |
| ttagggagtt cactaggaga gggatctggc ttcttgtcat tctgggtatt tgtagggaaa | 9000 |
| ttggaaggga accagagca cctagccaat cgcatagcaa tgggagattt caggctgtgg | 9060 |
| ggaatgtctt tgctggtgaa aagaacatcc tgaccttaga aatctttcac cgaggggat | 9120 |
| ctgcgttcca gaacttctgg agctggtata ggtaaggctt tgagctttcc tactgagcca | 9180 |
| gcctgttgct aggttaccaa aggggacctc gagggccatc tggccaacaa gcagacttgt | 9240 |
| ctctccttac accccagac gtatcactgc aaaactacag aaaaccaaag acagagaaaa | 9300 |

```
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaattag    9540
tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaa aaaaaaaaa aaagggtgac     9720
gaagcttcaa tctcctgaaa ggaagcaact gccgcctttg attcgatacc caccaaaatc   9780
cgtgaagaag gaaggcaaaa taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatggaa aattcggggg   9960
ccaatttaaa caaagctgac tgctctacta actgttgtgt ctctatcttt tgtaacatat  10020
atgtgtgtgt agcttttttt tttttttttg tcaagatgga ttctcactct gtcgcccagg  10080
ctacagtgaa atggcacggt ctcggctcac tgcaacctct gccccttggg ctcaaatgat  10140
tctcttgcct cagcctcctg agtagctgag attacaggtg cctggcacaa tgcctggcta  10200
attttttgtat ttttactaga gatgggattt ctccatgttg gccaggctgg tcttgaacac  10260
ctgacctcag gtgatccacc tgcctgggcc tcccaaagtg ctaggattac aggcgcgagc  10320
cactgcatct ggcctatgtg tgtgtttata tggaattaaa acacatggca ataatacccct 10380
ccaaattggg agaaaccaaa aatagcattt aaatgttgta agctccctgc ataatcaaga  10440
agagaataga tttacgttag attttgatac ctggaggatg aatgttgtaa tttctagggt  10500
gaccatgaaa agaggagaca acggtgtatg tttttttttt tttgagatgg agtctcacctt 10560
tgtcacccag gctggagtgt tgtggtgtga tcttggctca ctgcaacctc ctcctcttgg  10620
gttcaggcca tcctcccacc taggcctcca gagtaggtgg gatcacaggc acctgccacc  10680
acacctggct aattttttttt tttttttaaa tatttagtag agatggggtt tcaccatgtt  10740
ggccaggctg tcttgaact cctgacctca ggcgatctgc ctacctctgc ctctcaaagt    10800
gctgggatta caggtgtgag ccatcgcgcc cggccaacag tgatcacttt caaactaaca  10860
gaggttcaaa aataaaatca gacttaacca aaaaccaggt aacagagctg gtaggatata  10920
cagaaagact gacctcacgt atatcaacga ttacagttaa tattaatgaa ggaaatgctc  10980
tagtttaaaa acgaggggttg tcaaagaccc cacataagaa gctccttacc agcggtgcac  11040
ctagaaccta aggaaacagg acagatgaag gaggacgcgc cccgccgct gtcctgcgcc    11100
tcagccatcc tatgagacgg gaaaggtttc tgtctgcagc tgggcccgtg ctctttacca  11160
gctcctggct ttcttctctg gaaggttcct gcctgttttg ccctcacacc tgctcctctc  11220
tcagccctct caggggtggg gctggaggcc accaaagagc ctcctctgct ctccagttgc  11280
tcgactgctc ctcatttccc cctggggtct gcgtcagggt ttccttcttt tccagcccca  11340
ccccgcgtgc atcccacctg gtctcgggtc ggggctgctc ccgcttactg cccccctgccc 11400
aggctggtgt gcacccccctc tggctgcttt caaggcctct tctctcttct cggcaggaca  11460
ggcacaggca ggtggccagg tgtcatgctt agctccccgc ccagtgagat tctttcattt  11520
aacaatcttc ccctgaatag ttcatgttca ttgctgaaaa tttgaaaaat atggaaaagc  11580
acaaagatta agatataaac cgccctcaat tcccctgccc agagagagtc actgctatga  11640
cttggtgact aggaacctta tttctctctc gctcttttt tttttttga gacagagtct    11700
```

```
tgctctgtca cccaggctgg agtgcagtgg ctcgatctca gctcactgca acctccgcct   11760
cctgggttca agcgattctc ctgcctcagc ctcttgagta gctgggatta caggcacctg   11820
ccaccatgcc cggctaattt ttgtattttt agttgagaga gggtttcatc ttgttggtca   11880
ggcggacttg aactcctgac ctcaggtgat cagcccacct cggcctccca aagtgctggg   11940
attacaggtg tgagccactg cgccttcatc tctcttctgt gtatgtgtac gctgtttttt   12000
ctttagaatg ggggacgtta tcaggctcta catggtgtgt agtcggctag catgttgtaa   12060
gcctttccct gtgtcacaag tgctcatctg gaacaggatt ctaatgactg cctgtggcta   12120
tgttgggatt cctttaactc agctccttct gcccagcatc tatcttttt ccatctttg    12180 tcctaagtgt tgctataata aatcattgat cacacatgcc tgactgtttg cataggataa   12240
attacgggaa atgttttgc tgttcaggga ctgtgcccat ttttaggcct cagagacacc    12300
atgccagact gcccagtatt gatctttact ctttttagat gatgccaaac ttttctgtga   12360
actttaaaaa cctgtgtctt gacagtccat ttctgtaagt ctttcacatt agatttcctg   12420
tcaggatgat agtcaattct aggcagatga tgttttctca gccatggctg aagcagttgt   12480
gatttgttgt ggccatgtaa agtcccgatg atccattgcc tccctggatg ggttggaata   12540
atttggtttg ggagcatata acagaatgac ctggagtcac agcagctcag acggaagtgt   12600
atttctccct tacagatgaa agaattccag gccaggctgg aatgacaact gcacacagtc   12660
atctgggccc cctccttcca gctcccatca ccccaggatg tggcttttat gcagatgatc   12720
caaaatggct gctcaagtcc cagccaacac atcccattcc agggagcagg aaaaaggtgt   12780
gtctttccct tcattttatg tgattccttt ctagaagtac tactcattac ttctgcttgc   12840
atctccctgg ctagcactta cttagttata tggccatagc tagctgaagg aaggacaggg   12900
actgtcatac actagctaag aggcaaactg cttagataaa aaggtctcta aagaaggtca   12960
gagcggctgc tagggtgcaa ctctattact tattgttatg ggacgaactg tgtccctcat   13020
tcaggttgat gtcctaagcc ccagaacctc agaatgggat tgtatttgga gacaggttct   13080
ttaaggaggt aaggaggcta aaatgagatc attagggtgg gccataatcc gactgatgtc   13140
ttacaagaag agattaggac acggacatgc tcagagggac ggccacgtga ggacaccaag   13200
aaaggcagct gtctgcaagt caaggacagg gctcagggga aaccaacctt gccaacacct   13260
tcatctcgga cttctagcct ctaggaccat gagaagatac atttctgttg tttaagctgc   13320
ccggtctgtg gtactttgtt atggcagccc aagtaaacaa atacagtcat ctgctgctgg   13380
aacaaatcac cccagcactg tggcttggca gcacacatgt ctagtcatag agttatatgt   13440
agttacgtgt agagccatat gtatcgtcac acgttctgtg ggtcaggaat ttggacccag   13500
cttaaccagc tccacttctc gccagggttc agtcaaatac cagctgcctc ccacctgaga   13560
gctcagccgg ggaagggtcc ctttccaatc tcacgtggtg ttggcaggat ccagttcctc   13620
atggcctgct ggactgagaa cctcagttct cactgcctgt tggccagagg ccgcctttat   13680
gtcctcgcca tgtgggcctc tccaacatgg cagctgactt catcagagca tccatgccaa   13740
gaaggcaaca gagagggcca gggagactga agtcataccc ttttgcgacc tagtcatggg   13800
gtgacattcc atcacctttg cccattggtt agaagcaggc caccaggtac agcccaagct   13860
cacggggagg ggtcatacaa gggtgtcaat accaggaggt gaggggtgct ggggccatct   13920
tatgagtctg cccactgagg taactaacaa ccttgaggcc tgacacagtg gacaaaggcc   13980
cttattaaca gcagagaact gggaacttta tttatttatt tattttgag acagagtctc   14040
```

```
actcttgtca cccaggctgg agtgcaatgg catgatcttg gctcactgca acctccacct   14100
cccaggttca agcaattctg cctcagcctc cggaatagct gggactacag gcatgcacca   14160
ctacacccgg ctaattttttg tatttttagt agagacaggg tttcgccatg ttggccaggc  14220
tggtctcgaa ctcctgacct ctggtgatct gcctgccttg gcctcccaaa gtgctgggat   14280
tacaggcgtg agccaccgca cctcgctgga acttaatttt tttagagaca gtgtcgctct   14340
atcacccaag ctggagtgca gtggtgcaat cctagctcac ttgcagcctc aaattcctgg   14400
gttcaggtga tcctcccaca tcagcctccc aagaactggg aactaacagc tgtttctctg   14460
ctgtccttct caagaaaagg gaggctactg ctaccccact ggggacaatg ctgggtttcc   14520
ctttaggaca ggctctgaga caaggcggag gtgctgtttg tggccacaga gcaggggact   14580
ctgggttgca ggtgtggcct ggctaaagta ggctttactg ggctcctctc tgcctgcatc   14640 acccccccggc tgggcggttg tctctgaggc caaccttact ccctgctggg caggctggac  14700
agctgccctc tccgtttgcc cctctaccac ccaaaaggca ggaggctctg gagaccagga   14760
ccctgcccgc cacggcctgt gtcccaggcg tgagggggtg ccccacagac ctctgctgag   14820
ctgctgctga atgacgcccc ttggggggtcc tgccggaagg tcagagcagg ggtgcactcc  14880
cataaagaaa cgcccccagg tcgggactca ttcctgtggg cggcatcttg tggccatagc   14940
tgcttctcgc tgcactaatc acagtgcctc tgtgggcagc aggcgctgac cacccaggcc   15000
tgccccagac cctctcctcc cttccggggc gctgcgctgg gaccgatggg gggcgccagg   15060
cctgtggaca ccgccctgca ggggcctctc cagctcactg ggggtggggt gggggtcaca   15120
cttggggtcc tcaggtcgtg ccgaccacgc gcattctctg cgctctgcgc aggagctcgc   15180
ccaccctctc cccgtgcaga gagccccgca gctggctccc cgcagggctg tccgggtgag   15240
tatggctctg gccacgggcc agtgtggcgg gagggcaaac cccaaggcca cctcggctca   15300
gagtccacgg ccggctgtcg ccccgctcca ggcgtcggcg ggggatcctt tccgcatggg   15360
cctgcgcccg cgctcggcgc cccctccacg gccccgcccc gtccatggcc ccgtccttca   15420
tgggcgagcc cctccatggc cctgcccctc gcgcccccac cctcccctcg ccccacctct   15480
caccttcctg ccccgccccc agcctcccca ccctcaccg gccagtcccc tcccctatcc    15540
cgctccgccc ctcagccgcc ccgcccctca gccggcctgc ctaatgtccc cgtccccagc   15600
atcgccccgc cccgccccg tctcgccccg ccctcaggc ggcctccctg ctgtgccccg     15660
ccccggcctc gccacgcccc tacctcacca cgcccccgc atcgcacgc cccccgcatc     15720 gccacgcctc ccttaccatg cagtcccgcc ccgtcccttc ctcgtcccgc ctcgccgcga   15780
cacttcacac acagcttcgc ctcaccccat tacagtctca ccacgccccg tcccctctcc   15840
gttgagcccc gcgccttcgc ccgggtgggg cgctgcgctg tcagcggcct tgctgtgtga   15900
ggcagaacct gcgggggcag gggcgggctg gttccctggc cagccattgg cagagtccgc   15960
aggctagggc tgtcaatcat gctggccggc gtggccccgc ctccgccggc gcggccccgc   16020
ctccgccggc gcagcgtctg ggacgcaagg cgccgtgggg gctgccggga cgggtccaag   16080
atggacggcc gctcaggttc tgcttttacc tgcgcccag agcccccatt cattgccccgg   16140 tgctgagcgg cgccgcgagt cggcccgagg cctccgggga ctgccgtgcc gggcgggaga   16200
ccgccatggc gaccctggaa aagctgatga aggccttcga gtccctcaag tccttccagc   16260
agcagcagca gcagcagcag agcagcagca gcagcagcag cagcaacagc                16320
cgccaccgcc gccgccgccg ccgccgcctc ctcagcttcc tcagccgccg ccgcaggcac   16380
agccgctgct gcctcagccg cagccgcccc cgccgccgcc cccgccgcca cccggcccgg   16440
```

```
ctgtggctga ggagccgctg caccgaccgt gagtttgggc ccgctgcagc tccctgtccc   16500
ggcgggtccc aggctacggc ggggatggcg gtaaccctgc agcctgcggg ccggcgacac   16560 gaaccccgg ccccgcagag acagagtgac ccagcaaccc agagcccatg agggacaccc    16620 gcccctcct ggggcgaggc cttccccac ttcagcccg ctccctcact tgggtcttcc      16680
cttgtcctct cgcgagggga ggcagagcct tgttggggcc tgtcctgaat tcaccgaggg   16740
gagtcacggc ctcagccctc tcgcccttcg caggatgcga agagttgggg cgagaacttg   16800
tttcttttta tttgcgagaa accagggcgg gggttctttt aactgcgttg tgaagagaac   16860
ttggaggagc cgagatttgc tcagtgccac ttccctcttc tagtctgaga gggaagaggg   16920
ctgggggcgc gggacacttc gagaggaggc gggggtttgga gctggagaga tgtgggggca  16980
gtggatgaca taatgctttt aggacgcctc ggcgggagtg gcgggcagg ggggggcgg     17040 ggagtgaggg cgcgtccaat gggagatttc ttttcctagt ggcacttaaa acagcctgag   17100
atttgaggct cttcctacat tgtcaggaca tttcatttag ttcatgatca cggtggtagt   17160
aacacgattt taagcaccac ctaagagatc tgctcatcta agcctaagtt ggtctgcagg   17220
cgtttgaatg agttgtggtt gccaagtaaa gtggtgaact tacgtggtga ttaatgaaat   17280
tatcttaaat attaggaaga gttgattgaa gttttttgcc tatgtgtgtt gggaataaaa   17340
ccaacacgtt gctgatgggg aggttaattg ccgagggatg aatgaggtgt acattttacc   17400
agtattccag tcaggcttgc cagaatacgg ggggtccgca gactccgtgg gcatctcaga   17460
tgtgccagtg aaagggtttc tgtttgcttc attgctgaca gcttgttact ttttggaagc   17520 tagggggtttc tgttgcttgt tcttggggag aattttttgaa acaggaaaag agagaccatt  17580
aaaacatcta gcggaacccc aggactttcc ctggaagtct gtgtgtcgag tgtacagtag   17640
gagttaggaa gtactctggt gcagttcagg cctttctctt acctctcagt attctatttc   17700
cgatctggat gtgtcccaga tggcatttgg taagaatatc tctgttaaga ctgattaatt   17760
tttagtaata tttcttgttc tttgtttctg ttatgatcct tgtctcgtct tcaaagttta   17820
attagaaaat gattcggaga gcagtgttag cttatttgtt ggaataaaat ttaggaataa   17880
attattctaa aggatggaaa aacttttttgg atatttggag aaattttaaa acaatttggc   17940
ttatctcttc agtaagtaat ttctcatcca gaaatttact gtagtgcttt tctaggaggt   18000
aggtgtcata aaagttcaca cattgcatgt atcttgtgta aacactaaac agggctcctg   18060 atggaagga agacctttct gctgggctgc ttcagacact tgatcattct aaaaatatgc    18120
cttctctttc ttatgctgat ttgacagaac ctgcatttgc ttatcttcaa aatatggta    18180 tcaagaaatt cctttgctg ccttgacaaa ggagatagat tttgtttcat tactttaagg    18240
taatatatga ttaccttatt taaaaaattt aatcaggact ggcaaggtgg cttacacctt   18300
taatccgagc actttgggag gcctaggtgg acgaatcacc tgaggtcagg agtttgagac   18360
cagcctggct aacatggtga aaccctgtct ctactaaaaa tacaaaaatt agctggtcat   18420
ggtggcacgt gcctgtaatc caagctacct gggaggctga ggcaggaaaa tcgcttgaac   18480 ccggaggca gagtctgcag tgagttgaga tcacgccact gcactccagc ctgggtgaca   18540
gagcgagact ctatctcaaa aaaatttttt ttaatgtat tatttttgca taagtaatac    18600
attgacatga tacaaattct gtaattacaa aagggcaata attaaaatat cttccttcca   18660
cccctttcct ctgagtacct aactttgtcc ccaagaacaa gcactatttc agttcctcat   18720
gtatcctgcc agatataacc tgttcatatt gtaagataga tttaaaatgc tctaaaaaca   18780
```

```
aaagtagttt agaataatat atatctatat attttttgag atgtagtctc acattgtcac   18840
ccaggctgga gtgcagtgat acaatctcgg ctcactgcag tctctgcctc ccaggttcaa   18900
atgcttctcc tgcctcagcc ttctgagtag ctgggattac aggcgcccac caccatgtcc   18960
agctaatttt tgtatttttta gtagagatgg ggtttcacca tgttggccag gctggtcttg   19020
aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg tttatttata gttttatagt tattttaaat aaaatgcata tttgtcatat   19200
ttctctgtat tttgctgttg agaaaggagg tattcactaa ttttgagtaa caaacactgc   19260
tcacaaagtt tggatttgg cagttctgtt cacgtgcttc agccaaaaaa tcctcttctc    19320
aaagtaagat tgatgaaagc aatttagaaa gtatctgttc tgtttttatg gctcttgctc   19380
tttggtgtgg aactgtggtg tcacgccatg catgggcctc agtttatgag tgtttgtgct   19440
ctgctcagca tacaggatgc aggagttcct tatgggctg gctgcaggct cagcaaatct     19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcagggc tcagcagtga   19680
gcagacaaag ctctgccctc gtgaagcttt cattctaatg aaggacatag acagtaagca   19740
agatagataa gtaaaatata cagtacgtta atacgtggag gaacttcaaa gcagggaagg   19800
ggatagggaa atgtcagggt taatcgagtg ttaacttatt tttattttta aaaaaattgt   19860
taagggcttt ccagcaaaac ccagaaagcc tgctagacaa attccaaaag agctgtagca   19920
ctaagtgttg acatttttat tttattttgt tttgttttgt tttttttgag acagttcttg   19980
ctctatcagc caggctggag tgcactagtg tgatcttggc tcactgcaac ctctgcctct   20040
tgggttcaag tgattctcat gcctcagcct cctgtttagc tgggattata gacatgcact   20100
gccatgcctg ggtaattttt tttttttccc ccgagacgga gtcttgctct gtcgcccagg   20160
ctggagtgca gtggcgcgat ctcagctcac tgcaagctcc gcttcccgag ttcacgccat   20220
tctcctgcct cagtctccca gtagctggg actacaggcg cctgccacca cgtccagcta    20280
atttttttgt attttaata gagacggggt ttcaccgtgt tagccaggat gatcttgatc    20340
tcctgacctc gtcatccgcc gaccttgtga tccgcccacc tcggcctccc aaagtgctgg   20400
gattacaggc atgagccact gtgcccggcc acgcctgggt aattttttgta ttttagtag   20460 agatggggtt ttgccatgat gagcaggctg gtctcgaact cccggcctca tgtgatctgc   20520
ctgccttggc ctcccaaagt gctaggatta caggcatgag ccaccatacc tggccagtgt   20580
tgatatttta aatacggtgt tcagggaagg tccactgaga agacagcttt ttttttttt    20640 tttttggggg ttgggggca aggtcttgct ctttaaccca ggctggaatg cagtatcact    20700
atcgtagctc acttcagcct tgaactcctg ggctcaagtg atcctcccac ctcaacctca   20760
caatgtgttg ggactatagg tgtgagccat cacacctggc cagatgatgg cttttgagta   20820
aagacctcaa gcgagttaag agtctagtgt aagggtgtat gaagtagtgg tattccagat   20880 gggggaaca ggtccaaaat cttcctgttt caggaatagc aaggatgtca ttttagttgg    20940
gtgaattgag tgagggggac atttgtagta agaagtaagg tccaagaggt caagggagtg   21000
ccatatcaga ccaatactac ttgccttgta gatggaataa agatattggc atttatgtga   21060
gtgagatggg atgtcactgg aggattagag cagaggagta gcatgatctg aatttcaatc   21120
ttaagtgaac tctggctgac aacagagtga aggggaacac cggcaaaagc agaaaccagt   21180
```

```
taggaagcca ctgcagtgct cagataagca tggtgggttc tgtcagggta ccggctgtcg   21240
gctgtgggca gtgtgaggaa tgactgactg gattttgaat gcggaaccaa ctgcacttgt   21300
tgaactctgc taagtataac aatttagcag tagcttgcgt tatcaggttt gtattcagct   21360
gcaagtaaca gaaaatcctg ctgcaatagc ttaaactggt aacaagcaag agcttatcag   21420
aagacaaaaa taagtctggg gaaattcaac aataagttaa ggaacccagg ctctttcttt   21480
tttttttttt tgaaacggag tttcgctctt gtcacccggg ctggagtgca atgatgtgat   21540
ctcagctcac taaaacctct acctcctggg ttcaagtgat tcttctgcct cagcctccca   21600
agtaactggg attacaggcg tataccacca tgcccagcta atttttgtgt ttttagtaga   21660
gatggggttt caccatgttg gccaggctgg tctcgaactt ctgacctcag gtgatccact   21720
cgcctcagcc tgccaaagtg ctgggattac aggtttgggc cactgcaccc ggtcagaacc   21780
caggctcttt cttatactta ccttgcaaac ccttgttctc attttttccc tttgtatttt   21840
tattgttgaa ttgtaatagt tctttatata ttctggatac tggattctta tcagatagat   21900
gatttgtaaa aactctccct tcctttggat tgtctttta cttctttgat agtgtctttt   21960
gaagtgtaaa agtttttaat tttgatgaag tcgagtttat ctattttgtc tttggttgct   22020
gtgcttcaag tgtcatatct aagaaatcat tgtctaatcc aaagtcaaaa aggtttactc   22080
ctatgttttc ttctaagaat tttagagttt tacatttaag tctgatccat tttgagttaa   22140
tttttatata tggttcaggt agaagtccaa ctttattctt ttccatgtgg ttattcagtt   22200
gtcccagcac tgtttgttga agagactatt cttttcccat ggaattatct tagtacccctt  22260 gttgaaaatt aatcgtcctt aattgtataa atttatttct agactgtcag ttctacctgt   22320
tggtctttat gtcgatcctg tgccagtacc atacagtctt gattactgaa gtttgtgtca   22380
cagtttaaat tcatgaaatg tgagttctcc aactttgttc cttttcaaga ttgatttggc   22440
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc tttttttttt ttttttttt ttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt attttagta gagacggggt ttctccatgt tggtcaggct ggtcttgaac   23160
tcctgacctc aggtgatcca cccgcctcag cctcccaaag tgctgggatt acagggtgtg   23220
agccaccaca ccctgctgga aagcattct ttttggctg ttttgtttt ttttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
agtgtttctt gtgtcttctt cccagatttt aatatgcata tacaagcatt taaatgtgtc   23460
attttttgtt tgcttgactg agatcacatt acatatgtat tttttactt aacaatgtgt   23520
```

| | |
|---|---|
| catagatatt gttccatagc agtacctgta attcttatta attgctatgt aatatttag | 23580 |
| aatttctttt taaaagagga cttttggaga tgtaaaggca aaggtctcac attttgtgg | 23640 |
| ctgtagaatg tgctggtgac atattctctc taccttgaga agtccccatc ccatcacct | 23700 |
| ccatttcctg taaataagtc aaccacttga taaactacct ttgaatggat ccacactcaa | 23760 |
| aacatttagt cttattcaga caacaaggag gaaaaataaa ataccttata aagcactgtt | 23820 |
| taatattgta ttaaattgga tcaatttggg ggctagaatg tatgttagag acatgatatg | 23880 |
| tccataggtc cttgctatca cagtgaggtc tcagggacag tcgtttggta tcatttggga | 23940 |
| tctcataagc agactctctc tgcttgacct gacaaatcag agtctgtgtt ttaacaggtt | 24000 |
| cagtgagtga cttacatgca cattggagtt tgggaagctc cactgtaggt gcttagacct | 24060 |
| tacctttgtt gttgctaata acaatgcaag catttgggag gaagacctgt gttgctcata | 24120 |
| tgtgtccagg tgtagctgag gtggccttgc ttatctgctg tagggccgtt gagcatttct | 24180 |
| gtagctgtga tgagtgagct gaggtgagcc tgcggagagc tcccagccat tggtagtggg | 24240 |
| actcgcttag atgaactgga aggacccttt catctgagca gccactatgg agaaaaacaa | 24300 |
| ccgaatgagg ggagagacaa tgtgcaattt tatttagggc acaaaggaga gctgtggtta | 24360 |
| gaaggtgaca tttgagtgga aagggggcaa gccatgtgta tagcgggaga agagaggtcc | 24420 |
| aggcagagtt aacagaaggc agaaatgctt tccatgtttg agaaccagta aggaggccag | 24480 |
| tggctgaagt aaggtgaagg gcagaaataa ggatgaggct gcgagagatg agaggttaga | 24540 |
| gacgagcgtc ttgtgcacca agataagctt gtgtggtcaa aacaagtagt ttaatttatg | 24600 |
| ttttttaaaag atcattttgg ctgggcacaa tggttcatgc ctgtaatacc agtagtttga | 24660 |
| gacggtgtgg tgggaggatt gcctgaggcc agacgaccag catagccaac atagcagcac | 24720 |
| ctataaggtc tctacaaaaa actttaaaaa attagctggg catagtggtg tgtgcctgta | 24780 |
| gtcccagcta ctcaggaggc tgaggaggct ggaggattgc ttgagtccag gagtttgagg | 24840 |
| ctgcagtgag ctatgattat gccactacac tacaacctgg gcaagagagt gagaccctgt | 24900 |
| ctctaaatat acacacacac acacacacac acacacacac acacacacac acacacacac | 24960 |
| acacacatat atatgtatat atatgcattt agatgaaaag atcactttga caataccaca | 25020 |
| tgctggtgag gatttagaaa aactaggtca cttattgctg gtgggaatat aatatagtac | 25080 |
| ggccactctg gaaaacagtt tggcagtttg tcataaaact gaacataccg ttagtataca | 25140 |
| gcccagcagc aactacaatc ctgggcatta atcctagaga aatgaaacct taatgttcac | 25200 |
| ataaaaacct atactcaagt atgcatagca gctttacccca taatatctaa gaactggaat | 25260 |
| cagctcagat gtccttcaac aggtgaatgg ttaaactact cagtaataaa aaggaatgag | 25320 |
| ctactgatag catgcaacag tttaggtgaa gttatgctaa tgaaaaaagc caatcccaaa | 25380 |
| aggttataca tactgtatga ttctatgttt ttttgcaatg gcacagtttt agggatggag | 25440 |
| aatagattag tggttgcctg gggttagaga tggggtagta gagtaggtta gtggtggcag | 25500 |
| aggagagaaa agagagggag gtgaatgtgg ttataaaagg acaacacagg ggaatacttg | 25560 |
| taatggaaat gctttgtctt ttttttttt tttttttttt tggcgacaga gtcttgctct | 25620 |
| gttgcccagg ctggagtgca gtggcatgat cttttctcac tgcaacctct gcctcctggg | 25680 |
| ttcaagtgat acttgtgtct cagtctccca tgttcagagt gaaacaaacc agaggtaatg | 25740 |
| ttcatccaaa taatccaaca cacatgacat taaaacatca agatcaggtc ggacgtggtg | 25800 |
| gctcatgcct gtaatcccag cacttttggg aggccaaggt gggcagatca cttgaggtca | 25860 |
| ggagttcgag accagccggg ccaacatgat gaaacccccat cttgactaaa aatacaaaaa | 25920 |

```
ttagccgggc atggtggtgt gcacctgtag tcccagctac ttgggaggct gaggcaagag   25980
aactgcttga acccgagggg cagaggttgc agtgagctga gagtgcgcca ttgcacttca   26040
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaa aaaattagcc gggtatagtg gtgggtgcct gtagtcccag   26280
ctacttggga ggctgaagca ggagaatggt gtgaacccgg gaggcagagc tggcagtgag   26340
ctgagatcgc gccactgcac tccagcctgg gcgacagagc aagactccgt ctcgggggaa   26400
aaaaaaaaat aaataaatag aatgctgtag tgtccttgag tttacatgcc cctccttacg   26460
cttgtgtgcc cgtgcagatt gcttgattac acaattagag gaggctggcg gaggattgtt   26520 ttaattttt tttttttgag acagtctggc tctgttcccc aggctagagt gcaatggcgc   26580
aatcttggtg cactgcaacc tctgcctcct gggttcaagc agttcttctg ccgcagcctc   26640
ccgagtagct gggattatag gcgcccgcca ccacgcccaa ctattttttg tattttagt   26700 agagcagcgt ttcaccatgc tggccaggct ggtctcgaac tcctgacctc agatgatctg   26760
ctgccccagc ctcccaaagt gctgggatta caggcgtgag ccacacctgg ccgtttgttt   26820
taattttgaa ggtgaagtga aagtgactac atttaccaaa agtgattgaa aagccaggac   26880
tgttcttacc ctgttttttcc agttcttgct cagagcaagg tggtttctt ttcacttaat   26940 caccatactt acttttcatg tagaacaagt cagtttgagt tatcagttca tcatcttaac   27000
taaattccat gggggaagga attagttta gtttcttaaa cttccaggtt tgcttattgg   27060
acaaaatgag atagcaaggc agtgttttta agttagattt tttatttctt tggtaataca   27120
attttctcag aaacttagta gtcttttagt ttagttgttt ttagttggtc ctatgttttg   27180
gatcacccct ctctacttta ttttgatagt gccaactgtg aagacatctg aagccatagg   27240
tttggatggg aaggaggcat ctttagcctg atcatcttcg ccaggctgtt tatctccttt   27300
tgcttggctg agaagtctta ataggaggct tattcccagc tatttgggga catgaaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata tttgaaaaa   27900 attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaataaag taaatgggg   28080 gaaatgaact gctttagtaa catcatctgt tttttctgtg agcagcgtag cttgacagcc   28140
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
```

```
aactaagtgg agtgggtaat tcaacacata ttaatttcct tcttttttttt attttagaa      28320
agaaagaact ttcagctacc aagaaagacc gtgtgaatca ttgtctgaca atatgtgaaa      28380
acatagtggc acagtctgtc aggtaattgc actttgaact gtctagagaa aataagaact      28440
ttgtatattt tcagtcttaa tgggctagaa tattctttgt gtcccagcta ttttaaatgg      28500
attcagaaat ccatttaaga tgaagaagga ccctttttccc atatttctgg ctatatacaa     28560
ggatatccag acactgaaat gaataatgtt ccctttttgt aatcttttat gcaaaaatta     28620
aaaccattat ggtaattgaa caacatgttt atgtttagtt aacacccttta gcaactatag     28680
ttattttaaa accatctatg gtttgatatt tttgcatttg ttgcaatagt aggaacagca     28740
caagacagtt cagtttgtct ctcttatttg ctttttcttg gcagtttgct gtcctattgt     28800
acctctgctc ctagcagtgg ctggagccca ctcctctgtg cttcgggatt agtggggatc     28860
gtggggcatt gactgtaggt cagcttttcct tgcttgatct ttctcactgg gatgaactag    28920
cagcaccttc ttttgtagct gctttgcttt tgactatctt tctgaccgtt gttcctagta     28980
gctgtagatg gtaaatatat ttaggcctgt ttccaatggc tcagtaggag acatattcac     29040
ctatgatatc tgaattctgt tacccacatg ggcatgcgtg aaatagttgc cttgccttac     29100
tttcccttgg aataaataat tcatgttatt ctcctggtag aagctagaaa aagcctttat     29160
agtcagtcag aaaaaaattt ttagacaaat aatcttgatt ttagtactga caaaacgtg     29220
tggtgattct tttttttaatt tttttttgag acggagtttc actcttgttg cccaggctgg    29280
agtgcaatgg cgtgatctcg gctcactgca acctctgcct cctgggttca agtgattctc     29340
ctgcctcagc ctcccaagta gctggagtta caggcatgtg ctactgtgcc cagctaattt     29400
tgtattttta gtagagatgt tggtcaggct gatctcgaac tcccaaccttt aggtgatctg     29460
cccgcctcag cctcccaaag tgctgggatt acaggcgtga gccagggcgc ccggtgattc     29520
atttgttttt tcaaaaaatt tcctcttggc cattgctttt cactttttgtt ttttttttt    29580
ttttgagacg gagtcacgat ctgtcaccca ggctggagtg cagtggcatg atcttggctt     29640
actgcaagct ctgcctccca ggttcacgcc attctcctgc ttcagcctgg cgagtagctg     29700
ggactacagg tgctcgccac cacacccggc tatttttttg tatttttagt agagatgggg    29760
tttcaccgtg gtcttgatct cctgacctca tgacccgctc aactcagcct cccaaagtgc     29820
tgggattaca ggcgtgagcc accgcgcccg gccctctctt gtcttttttat tgtggtaaaa    29880
tgcacataaa attgactgtc ttaaccatttt ttaggggtac agttcagtat atatattcgt     29940
aatgttgtac agccatcact gccatctact tcataagttt ttcttctgtc aaaactgaac     30000
atctgtcttc attaaactcc ctatcatcca ttctttcctg tagtcccttt ctactttctg     30060
tctgtatgag tgtaactgct ctggagacct catgtaagtg gattcctaca ggatttgtgt     30120
ttttttttttg gtgatctgct tatttttaat gcctctgtgc atttgtatta tatactttca    30180
aagtgatttc acaaaaccgt ttcattttag gttaactcat ttctgttgtt tgtgaaatac     30240
tgtgtatgat tctgttctgt ttctgtctaa ttttgtgaaa tgttgtggga agaaaatgaa     30300
ataacaaatg agcatatgtc ctgaaaataa aaatataaaa attctaagtt agcatgctat     30360
tgtagaatac aacgctatga taaaagtagg aaaaaaaaag gtttgaattc tatctctgct     30420
acctgtgtaa gctgggtgac tttagataag ctgtaacgtg tttgagcctt actggctcat     30480
ttttgaaatg taatccctag ttacacagtt cttgtgggat cagatggtac atgtgaaaca     30540
ctgtgaaaaa gcaactgcat agatatgttc attagccacc tgagcgggaa gcgtatccca     30600
ttgcgatgcc catcatccaa agctatatgt tatctttact tttttttttt tgagacagag     30660
```

```
tcttgctctg ttgcccaggc tagagtgcag tggtgcaatc tcagctcact gcaagctcca   30720
cctcccgggt tcacgctatt ctcctgcccc agcctcccaa gtagctggga ctacaggcac   30780
ccgccaccat gcctggctaa attttttgtat ttttagtaga gatggggttt caccgtgtta   30840
gccaggatgg tcttgatctc ctgacctcgt gatccgccg cctcggcctc ccaaagtgct   30900
gggattacag gcgtgagcca ctgcccctgg ccatctttac ttttttttgtg aaatgacttt   30960 aaatacttgg caaacatttg gtcattgttc atctgatctc caccatccag gtctcagaga   31020
acataatttc tctctgaaag cttattgacc caggaaataa gatctctttc aatctgagtg   31080
cgtcaggctt tattcttgtc attttgtctt ttgataattt tcaaatggaa ttcatggaat   31140
gttggcttat attcatatat tagtaaagta tgttgagaca tcttaagatt gatttgtggt   31200
tctatatgcc atattaaatc aaaataatag ctgttaatgg ttttcacatt agtcgtgtctc   31260 ttgtttttat ggagtaatgc tgagagttca ttatgcttgt tctacagaag agcatgttaa   31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttggaactt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc ctttttccca   31740
aacatacttc tgcattctgt ttgagtaggt agggactaca catttttcac aagtatcctc   31800
ttgggaatac ccaggaatgc ttacttgagc aacctcttac taatatgtac cttgataagg   31860
tggctaggta aacataaata tacaaaaatc catagatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgtttct gaaagatata   32040
ggtgaccact ttctagatag gaagatttta tattactaag ttgaatttc tctaaattaa   32100 cacagaaatt taaaataatc ttgatcaaaa ttctagtaga ggtattttg aacttgttca   32160 ctgcaagaat aaatacataa ttgcaaagaa tatctcaaaa tcatcaccag gcctggtgtg   32220
gtggcccatg cctgtaatcc cagcactttg ggaggctgag gcaggcagat cacctgaggt   32280
caagagtttg agaccagctg gaccagtgcg gtgaaacact gcctctacta aaaatacaaa   32340
aattagctgg gtgtggtggt gcatgcctgt agtcccagct acttgggagg ctgaggcagg   32400
agaattgctt gaacccagga ggtacaggtt gcggtgagcc tagatcgcac cactgcattc   32460
cagcctgggc gacaagagca aaattctgtc tcaagaaaaa agagaaaaaa gaaaagaaa   32520 tcaacactaa tatggtgaga cttaatgtat gtgacattaa aatagtgatt ggatgttaaa   32580
acaggtatag aacagaaaga agagtgtatg tgtgtatctg tatgaattta tgatgggtgt   32640
aacatatatg tattagggaa atgagggaaa tgatacattt ctctgacttt gggagaacat   32700
tatatctcta cctcatattg caaacaaaca taaagttcag attaattacc taaatgtgaa   32760
aaaatgaaat aatttctta aaaaatgtaa tcttagtttg aggaaggtta acattataaa   32820
ggaaaaaact gttttgagtg aatatagtt caatatgtca aaatccacct tcaacaaaat   32880
tgaaagtaaa ttgaacttgg ggaaagtatt gacagcatat agatcaaagg ttactagcct   32940
gtgtaaagag cagttataaa tatcgttaag aaaaacactg tcgacctgtc ggcaccttgt   33000
```

```
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga acaaaaata agaacctttt ttacctgtca aattggcaaa cattaagaat     33180
attcagattt tgtcagagg tgatacaacc ttctaagaag gcaatttggg aaaatataaa     33240
gctttagatt attatatgtc tgacctagca gttttaccte tagggtgctt acccctagga    33300
aagtgtgtaa tgatattggt gcagtgccct tcatcccatt agaaaattaa aaataacctt   33360
aatggcctac cactaaaagg ggattgaaaa tttaagatat atttatttat gtgtttattg    33420
agatggagtc ttgcactgtc cgcctgggcc agagtgcaat ggtgcgatct cggctcactg    33480
caacctctgc ttcccgggtt catgtgattc tcctgcctca gcctcctgag tagctgggat    33540
tacaggctca caccaccgca cccggctaat ttttgtatt tttagtagag atggggtttc     33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aatttttttt    33780
tagagacagg atcttactct gtcacccagg caggatgcag ttgcacaatc atagcccact   33840
gcagcctgaa ctcctgggct taagtgatcc ttctgcctca gccttttgag tacctggggg    33900
actttaggca gtgctactat acctggctaa tttttaaatg ttttatagat gagatcttgc    33960
tgtattgccc aggctggtct agaattcctg ggcccaagtg atcctccac cttggcctcc     34020 caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacggaag aaatatatgt aacagtggtt ttcaagttat tgggcatcag gcaaagaaga   34260
atagttatcc caggaaaatg aatgtggaga gccctacaat ttccttacat tactgcctgg    34320
tcatggcaag aggaaaaact gagagggagac tgaggctgag ccagtggttt gctgggttga   34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
atgtgtgtag ctgagtactg acgagcactt gcttgtgcgg aaatgaccca gggctggagg    34560
tagagccacc tgaaaggatt agaaggaaca gttgctgaaa gtcacacagg gccaggaaga    34620
atttctaatc acaccagttg gagtggaaaa cctcagctct catagagcag gtagggtact    34680
cagaagggtt tgcccaccta gccccagact aagtttcgtt actctgaccc tacctaatat    34740
taaaaagaga ttaattaaat tgttcgcaac aaaaataata tatttcagtg tttgtaacac    34800
gtagaagtga attgtatgac aatagcataa aggctggaag agcagaaatt gacatgtatt    34860
tgcgctgggc agaataatgc tcccctcttt ccccaaaaga tatcaagtcc taatccctgg    34920
agcctgtaaa tattacttta tatggaaaat tgttttatga tgtgattaaa ttcaggatct    34980
tgagatgagg gggctatctt ggatgatctg ggtaggcact aaatgcaatc acatatatat    35040
aaaaaggagg cagagggaga ttttacacac agagagaagg ccctgtgaag atggaacaga    35100
aagatttgaa ggtgctggcc ttgaaaattg gagtgatgaa gctataagcc aaggaatgca    35160
gcagccacca aagctggaag aggcacggag cagttctcat ttagagccta ctccagaggg    35220
aatgtggtgc tgccaattcc ttttttttt ttttttttaa gatatcattt accccttaa      35280 gttggttttt ttttttttt tttttttta gtatttattg atcattcctg ggtgtttctt      35340
ggagaggggg atttggcagg gtcataggac aatagtggag ggaaggtcag cagataaaca    35400
```

-continued

```
tgtaaacaaa ggtctctggt tttcctaggc agagggccct gccacgttct gcagtgtttg   35460
tgtccctggg tacttgagat tagggagtgg tgatgactct taacgagtat gctgccttca   35520
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga attttctta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt acacctccca   35820
gatggggtgg cggccgggca gagggctcc tcacttccca gatggggcgg ccgggcagag    35880
gcgcccccca acctcccaga cggggcggcg gctgggcggg ggctgccccc cacctcccgg   35940
acggggcggg tggccgggcg ggggctgccc accacctccc ggacggggcg gctggccggg   36000
cgggggctgc cccccaccctc ccggacgggg cgggtggccg ggcggggggct gcccccacc   36060
tcccggacgg ggcggctggc cgggcggggg ctgccccca cctcccggac ggagcggctg     36120
ccgggcggag gggctcctca cttcccggac ggggcggctg ctgggcggag gggctcctca   36180
cttctcagac ggggcggctg gtcagagacg ctcctcacct cccagacggg gtggcagtgg   36240
ggcagagaca ttcttaagtt cccagacgga gtcacggccg gcagaggtg ctctttcacat   36300
ctcagacggg gcgcggggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg gcaacactg agcactgagt gagcgagact ccgtctgcaa tcccggcacc   36660
tcgggaggcc gaggctggca gatcacttgc agtcaggagc tggagaccag cccggccaac   36720
acggcgaaac cccgtctcca ccaaaaaaca cgaaaaccag tcagacatgg cggtgcgtgc   36780
ctgcaatccc aggcacttgg caggctgagg caggagaatc aggtagggag gttgcagtga   36840
gtagagatgg tggcagtaca gtccagcctt ggctcggcat cagagggaga ctgtgcgagg   36900
gcgagggcga gggcgaggga attccttaat ttcagtttag tgatactaat tttggactct   36960
ggcctctaaa actgtgaaag aaaaaatttt ttgtttgttt gtttctttta agccacatag   37020
tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga aagaaagagc ttgatggtag   37260
atttcaacct aactatgtca aaaaggacat tacatgtaaa aggcagcgat ttttcagatt   37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaaggctct   37500
tgcccaggat gagatggtca tttcataatg atgaagggga ttcgttcatc agcctggcat   37560
agcaagctga aatgtttatg caccggacta cagagctaaa atacatgaag caaagcctga   37620
cagaactaca agtagaaaca gacaaatcca cagtgataga gatttcagta gccgctctca   37680
atgatttgta gaacacgtag ccataatatc tggatctaga acacttgacc aacactgtcc   37740
```

```
cctgtgcaac ctcattggca tttacaggac actccaccca gcaccagcag aagagacact   37800
ctctcaagtg ctcacagaat gtttgccaag atagagcaga tgctgggcca taaaacaagt   37860
ctctaaatta aaagcattca aattattcag agtatgtttt ctgacctcag tatcattaag   37920
ttggaatata ttataggaag ataacctgga aaagcctcag atatgtggaa aaacccatt t  37980
ccacatggcc catgggtcag aagtgaagtc aaaagggaaa tttgaaagtc ttttggattg   38040
actgatataa aaacaataga tttctaaact tgtggggtgc tgttacagca tagtaaatgg   38100
aaatttctag cattaaatgc ctgttttagg aaagaaagat ttcaaatcaa tgacctcagc   38160
ttctaccttt ggaaacttga aaatgacaag caaatggaat ccagagttac cagaagggcc   38220
aggtacggtg gcttatgcct gcagttctgc cactttggga ggccgaggca ggtggattgt   38280
ttgagactgg cagttgaaga ccagcctggg cagcctaggg agaccccata tctacaaaaa   38340
acaaaaaaat tagccaggtg tggtggcatg tgcctgtagt cccagctaac caggagtcta   38400
aggtgggagg attgcttgag tctgggaggt tgaggctgca gtgaactgtg attgtgccac   38460
tgtgttccat cctgggcaac agaatgagac cctgtctcaa aaacaaaaac agttactaga   38520
agaatggaca tcataaagat aggagcagaa gtcagtaaaa tagaaaacaa aaatacatag   38580
gaaatcaata aaaccaaaag ctggttcatc aagaacatca ataaattggt aaagctgata   38640
ggaaaaacag tgaagtcaca aattagcaat atcaggaatg agggagatga cagtagtata   38700
gattatatag atattaaaag gactgtatga ggcaggtgtg gtggttcacg cctgtaatcc   38760
cagcaccttg ggaggccgag gtggacagat cacctgaggt caggagtttg ggaccagcct   38820
ggccaacatg gtgaaactct gtctctacta aaaatacaaa aattagttgg tcgtggtgct   38880
gtgtgcctgt aatcccagct acttgggagg ctgaggcagg agaattgctt gaacctggga   38940
ggcggaggtt gcagtgagct gagattgtgc cgttgcactc cagcctgggt gacagagcaa   39000
gactccatct caaaacaaat aaataaataa aaaggactat atggtaatat tatgaacaac   39060
tttatgccaa taaatttgac aacttataga tgaaatggat gagttccttg aaagacacag   39120
aaactattaa agctctctca agaagatata gataagctga ttagccctat atctatttta   39180
ttgaatttaa atgtaaaaat caatatttag ttactggaaa acttttaagt gtggttggaa   39240
atggtatacg aacttttttca actgaatttt atgaagtcta atcacaggta aaggttttct   39300
gatgaaaatt tagtgtctga attgagatat actgtaaaaa atgttatata tcttaattat   39360
ttcttcacat taattacatg ttgaaataat actttgggtg tattgggtta aattaaatat   39420
tatgaaaatc ttgcctgttt tctttttact tttgatgcgt cagctaggaa atataaaagt   39480
gtagctcaca ttctgtttct gttgacagta ctgctttgga gcacagtgtt tgaatgatct   39540
atcatttcaa agacctttcc tcagttcgtt attcatggct gtctgtattc cacatagata   39600
aggtctgaaa tactgctaag tggcatgttt tgttttatgc ttttataagt ttgttgatca   39660
ttactgatgt ggacttttgg tgcctcttag gctcattgct atcttccaac cattgtttgc   39720
aattttttacc tagagataaa gagaaagaga catttggttt cagagtagtt agattgggat   39780
catgaaagag caacctcatt ttgatgcttc aaaaatagca catccccgt attactggga   39840
tttgctattc ttgggattac ttcaagaaca tccttgtgtt actggtttgg atgcttctga   39900
atgctgtgaa gtcagtttca tgtacatggc tcatcagttt agctctctct tggctttgtt   39960
tagacagttg gagcatgatg gcctaaacag cttcttccaa ttaaacatttt taaaatagtt   40020
tacaaatagt aaacaaactc cagttttttgt gactctttgt ctcgcacaac aaaaacacaa   40080
tctgaccatg atcatctggc atcttagggt gaaatatggt tatactttgg cccataccga   40140
```

```
aagcaagatt aaaaaggggc aggagagata gactgctgaa ctgattttca aggttccaag   40200
aatattgtag gttaagagta aaagtaaact tttggtagaa agcagtgggt tgtctaggat   40260
tgaagtatct gaagttttta aacgaaaatt taaaaagaaa aatgagaatt gccttacaag   40320
tacaatctct tctttttttaa aaataaact ttattttgaa atagttttag atttatagaa   40380
aaaaattaga tagggtagga agttttcata taccctacat ccagttaccc cagttattat   40440
catcctaatt tagtgtgaga cattttcatg tttaatgaat caatattgat atgctattaa   40500
cttaagtcca gactttattc agattttctt aatttctatg taatgtcctt tttctgttcc   40560
agaattccat gcaggacacc ggatacctca ttacatttca ttgtcatgtc accttaggct   40620
cctcttgaca gtttctcttc ttttttttgct tagaaattct ccagaatttc agaaacttct   40680
gggcatcgct atggaacttt ttctgctgtg cagtgatgac gcagagtcag atgtcaggat   40740
ggtggctgac gaatgcctca acaaagttat caaagtaaga accgtgtgga tgatgttctc   40800
ctcagagcta tcattgttgt aggctgagag aagaagcgat cattgagtgt tcttctgttt   40860
tgagtccctg aggatgtctg cacttttttc ctttctgatg tatggtttgg aggtgctctg   40920
ttgtatggtt tggaggtgct ctgttgtatg gtttggaggt gctctattgt atggtttgga   40980
ggtgctctgt tgtatggttt ggaggtgctc ttgtatggtt tggaggtgct cttgtatggt   41040
ttggaggtgc tctgttgtat ggtttggagg tggtcttgta tggtttgcag gtgctctatt   41100
gcatggtttg caggtgctct attgtatggt ttggaagtgc tcttgtatgg tttggaggtg   41160
ctcttgtatg gtttggagat gctctattgt atggtttgca ggtgctctat tgtatggttt   41220
ggaagtgctc ttgtatggtt tggaggtgct cttgtatggt tggaggtgc tctgttgtat   41280 ggtttggagg tgctctgttg tatgttttgg aggtgctctt gtatggtttg gaggtgctct   41340
attgtatggt ttggagatgc tctggtatct gcctgcattg cttccacac ctgcccggtc   41400 agaaggcgct atgttgacaa ttgtgcctgc acgtgccta ggtcaatgaa gggaaccgat   41460
ggtagccact ggatgctcct gggaaaatgt cactacaggc accagagaag ccagagctat   41520
gcccaaattt ctatgagtct cagttttctt aaccataaaa tgggatcaat gttttttgtgg   41580 catgtgtatg agtgtgtgtc tgtgtatgtg tgaggattaa attgtgtatg tgtgaggact   41640
aattgccact actggatcct caaagtggta agaagtgttc ttattaataa tgacatcctt   41700
acactcttac ccagcaagat tgatgggtgt ggcactgctt ctcttttcc atcacatggt   41760 ttccatggta tccttttgcc cagggaatct ttgctttgtg gctagcactt tgttgtttgg   41820
ctaatcacgc tttctgtggt caggacgctg gcttctctgg agccatggga ttctagctcc   41880
ctgtcttgtc cctagagtgg tcactgtctt ctctctccgc ttgcaattcc tgctttgctc   41940
gcatctcact tatgcagtga cgtatatcag tttcaccttg ttctccgtgc ctgctgatca   42000
ttggcaccac ttgcatggtg ccatttaggg cctgcttcca gttaagcttg cttctccaca   42060
ggcctaaata tccttgcttg ctttctttat tctcactggc aggaccaggg cggtctgtct   42120
ttgcatgaga cagggtctcg ctcagtcacc caggctggag tgcagtggct gatcacggct   42180
cattgcagcc ttgagctacc gggctcaagc tatcctcctg gcttggcccc ttgagtagct   42240
gggactacag gcgtgcacca ccatgcccag ctaattttta aaattatttg tagagatggg   42300
atctcgccag gttgcccagg ctggtcttga acgcctgggc tcaagtgatc ctccctcctt   42360
ggtttcccaa agtgctggga tcacaggtgt gagccactgt gcctggccct tgatgtttca   42420
gttcttgata tttgatcctc agagtcagaa aatctaaaaa gagggctatc ccaggttgcc   42480
```

| | |
|---|---|
| ttggttcatg gcaaatggga cgttaagagg gcagagagaa tatgaacaga aactgttcta | 42540 |
| atattggtca tttaatgtgt aagtattgtt cttttttaaa cctccttcat ttttttttcca | 42600 |
| ggaattgctg gacacagtgg cttggtgtgt gtctgaggac tgtaggccat ggccctaggt | 42660 |
| tgtggtttta ggtctcaggt gctcttcctg gctgtctcct tgcttctttc ccatgtcctc | 42720 |
| ttctttgttt ccagccattt ctcccttatg cttaagtttg gtgcagcagg gtttggctgc | 42780 |
| tctcagattc ctgcttcctc agatgctgta gttgtcaggc ccagcgggct ggcagcggga | 42840 |
| tcaggatctg gctaggtttg ctctcactgt ggcagagtag ggggaggcgt gggagagcac | 42900 |
| gtgtgacccc aggccagctg tagggagcat aggcatggtc acgtagcctt caggtcctag | 42960 |
| actttgtctt ctcatgagta tggctgtgtg tgtatggtga aaactaggtt ctacttagcc | 43020 |
| caagaaaatg ggcacatttt gcatgtggtt tctgtagaga aatgcactgg gtatctgaca | 43080 |
| tagcctggca gcatgcctcc ctcaggtagg ttagtctcag gcggtgaagc acgtgtgtcc | 43140 |
| agcaagaact tcatatgtgg cataaagtct ccgttctgtg aggtgctggc aaatcaccac | 43200 |
| caccgtcaag aggctgaagt gattttttgtc tagggaggca ggaaaggctt cctgagtca | 43260 |
| gcagccagta ggtgaaagag tagattggag accttcttaa tcatcaccgc ctcttgtctc | 43320 |
| aaggggtgcc aggaagctgt ggaggctgaa cccatcttat gctgccagag agtgggacac | 43380 |
| catgagggtc aggtcaaggg gttgtacctt gtttggtaga gaattagggg ctcttgaaga | 43440 |
| ctttggatgt ggtcagggga gtgtatcatt taggaagagt gacccggtga ggacgtgggg | 43500 |
| tagaggagga caggtgggag ggagtccagg tgggagtgag tagacccagc aggagtgcag | 43560 |
| ggcctcgagc caggatggtg gcagggctgt gaggagaggc agccacctgt gtgtctgcgg | 43620 |
| aagcaggggc aagagggaag aggccagcag cgtgctgcca tcacccagcg actggcgtag | 43680 |
| attgtgagag accattccct gctcttagga ggggctgagt tttagttttc tcttgttata | 43740 |
| caataagctt ggtatttgtt tacaaaacat ttgtaaagct aaatcaaggt ttgataaggc | 43800 |
| ttctagtttt atttaagaag taatgttgaa ataaatgttt gtccaattcg ctttgctcat | 43860 |
| ttaaggactt tcagtacaaa ctgcaacaac aggattagga tttaaacgtt tctgagatgt | 43920 |
| ttttactcct cagaatttcc cagaatgtga tctggttttg attttcaagc ttgctgaccc | 43980 |
| aataggttaa cccacaagtt ttacgaagac catctcagtc cacttacatc aactgcccat | 44040 |
| gccacggtta aagagatcat cgactgatgt ttggcacagc ttcctccctc ttgggtgggc | 44100 |
| aagcatttgg aagagaaggc tcctatgggt gagagtgggg caccaaagtc ttccctgtcc | 44160 |
| catcccctag cttgagaagc ccttctctaa tgtggacttt gtgccgttag catcgttact | 44220 |
| agcttgaagt tgaccatctg gacgtacttt ctggtttagc ctcacaagtg agcaaggagg | 44280 |
| gttgagagat gtgctgtgag gaatgtgggg ccccagctgg cagcaggctc tgggtcaggg | 44340 |
| gggcagggac cacgggcata cctgacagtg aggaggggcc acacctgcag aaaaggatgc | 44400 |
| aggactccgc cttgggaagt gttctaggcc agagcgaggg tctgtggttt ataagtacac | 44460 |
| ccacagtgct cgggaccctg cagatgtcca gggtgccgtc tgagcccgta tcatccaaca | 44520 |
| gaatgttctg ctagtgaaga ttaaagattt actccagggg ctttaggatt tattatatat | 44580 |
| atataaatcc tatatatata attttttttt tttttttttt tgagatggag tttcgctctt | 44640 |
| gttgcccagg ctggagtgca atggcgtgat cttggctcac tgcaacctcc gcctcccggg | 44700 |
| ttcaaactat tctcctgcct cagcctctcg agtagctggg attacaggcg cccaccacca | 44760 |
| cacccggcta atttttgtat ttttttagtag agacggagtt tctccatgtt ggtcaggctg | 44820 |
| gtcttgaact cctgacctca ggtgatctgc ccgccttggc ctcccaaagt gctgggatta | 44880 |

```
caggcatgag ccaccccacc tggccaggat ttattgtatt tgaaccatct accattttaa    44940
ttttgatgtt atgtagtatt tgatgataat gaaagttaaa ttgttttttct ttccattttt    45000 ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagtttcctt ttagctcgtt ttagaactag tgatgggatg tgtcttccat    45180
aaatctcttg tgatttgttg taggcttttga tggattctaa tcttccaagg ttacagctcg    45240
agctctataa ggaaattaaa aaggtgggcc ttgcttttct tttttaaaaa tgttttaaat    45300
tttaaatttt tataggtaca cgtattttgt aggtacatgt aaatgtatat atttatgggg    45360
tacatgagat attttgatac aggtatacaa tacataataa tcacaccatg gaaagttgga    45420
tatccatgcc ctcaagcatt tatcctttgt gttacaaaca atccagttac atgctttact    45480
tattttattt tattttttgag acagagtctt gctttcaccc atgctagagt acagtggcat    45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcatttgggg aggctgaggc aggtgatcac ctgagatcag    45780
gagttcgaga ccagcctggc caacatggag aaaccctgtc tctactaaaa atacaaaaat    45840
tagccaagtg tggtggcggg cgcctgtaat cctggctact cgggaggctg aggtaggga    45900 atcgcttgaa cctgggggtg gaggttcag tgagccgaga tcacgccact gcattccagc    45960
ctgagcgaca gagtgagact ttgtctcaaa aaataaaaat gaaataaaat tgggccgggt    46020
gtggtggctc acaccttagt cccagcactt tgggaacctg aggcaggtgg atgcttgaga    46080
ccaggagttt gagaccagca tggcaacat ggcaaaacgc tgtctgtaca gaaattagct    46140
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aacaaaaaa acaaaaaaca aaccactatt    46320
atcgactata tattattgtc tatgatccct ctgctgtgct gtcgaatacc aggtcttggg    46380
cccttatttc catcactgag caaacttcac tctgttaagc agcaggtgtg ggatttcatc    46440
gttattcagt aattcacaat gttagaagga atgctgtttt ggtagacgat tgctttactt    46500
ttcttcaaaa ggttactctt tattagatga gatgagaatt aaaaatggta acttacttta    46560
tatctttata attgaagccc actagacctt aaagtagtta ccagatgttt tatgcattta    46620
aatggccttt tctctaaaat tagaaagtaa caaggaaaga aaatgcttcg tttctatgca    46680
accctcttgg tgactagtat gtgactctta atgcaaccct cattgcaccc cctcagaatg    46740
gtgcccctcg gagtttgcgt gctgccctgt ggaggtttgc tgagctggct cacctggttc    46800
ggcctcagaa atgcaggtaa gttgtacact ctggatgttg gttttgtcg ggggccagct    46860 gctactgatc ctttatgtct cagctcagat gtcatttcaa aagtctgctc tgccctctcc    46920
aaattgcagt cgaccttgcc ctgtttatgt ttccctcata gcactaatcc atgtcagaaa    46980
ttgtcacgta cagtctatct gtgtgcttgt ttattttcta tcccacccctt ccgcaagaga    47040 cttatgggat gtgtgcccca ggacagcagg ggtcttactg tcttatgctc tgttgcagcc    47100
cagcagcgat aacagtgtct gcacatagta cttgcttaaa agatacttgc caaattgttg    47160
aaggttgagg taccaattc attattgctg actataggag ttatagcaaa atatccattt    47220
```

```
gtctgttaca tgagttaaaa atatggttgt tgcactgtga atagtttggt ttagtcaaaa    47280
cagttgtatc ttaacggatt gagaaacaaa agcaggacca cttttcatca gctccctcct    47340
tctccttaac cagcaataca tgctgatgct gatatcccat agaccctcag ctccatcctg    47400
agtcactggg aatgtggtct aaaccctcac tattaatatg aactgagttt caataagaat    47460
cttatatggg tcgggcatag tggctcatac ctttgatccc agcacttcag gaggccaagg    47520
caggtggatt gcttgaccca gactaggcaa catggtgaaa cgccgcctct acaaaaaata    47580
caaaacttag ccaggcatgg tggtgcgtgc ctgtggtcac agccactcga gaggctgagg    47640
tgggaggatc acttgagcct gggaggtgga ggtcgtgttg agccaagatc gcaccactgc    47700
actccagcct gggcaacaga gtgagacctg tctcaaaaaa accaaaatcc agaaaagaac    47760
ttatatggct gcagaggtat aatcactaag gaaatttcct tttgtataat ctttttttctt    47820 ttactatcat ttaaaaaaat gtgttatatt tctgaagcaa cacatccagg ttctgcacat    47880
agcagccaaa gtgaccttaa agaatataac tgggtcttgt cattcccttta tttaaactct    47940 tgtacccatt tcccagtgcc gtttagatag agattccaga ctcgtcaatg gctctgtcac    48000
ctcagacacc ctgcattgac tcattagtct gattagagtc aggttttttct tcctcctgat    48060 ggttttttttt tcccccttag ttctcagcgg aacagtcact tccttaggga ggtttcccca    48120
gccaccctct gaggccgtgc ttgttgccag actctgccac tagagggcag ggctgcacca    48180
ctcctggcac ctcgcacccg gcctgccctg tcactctgtg tgttgggtga attcctgtga    48240
tctgtgactc actgctctgt gtcctacaca ttcggctttt cttctctccc cacaacccca    48300
ttttataatt ctccttttttc aggaaagctt tattcccatt taaaaatttt tgttttttaaa    48360 atggtatttt cttacactta ttttctaatt aaaaatgagt gttttaagaa gtattatgat    48420
ttactgcaaa taatttttaa acccagcctt ttagatcctc tgtgatcata agagaaatga    48480
aggatgtctc ccaacacttg agcttcatcc acatttcatc ctcctgttct ttcagctgag    48540 tttttcccccat cccattaggg actgttggaa tataaaactg gcttttcccct aacagggaat    48600 gaattgcttc tgtttctcct gaaggagagc tggaagaatg acttgcgttc ttttgcatac    48660
acaggcctta cctggtgaac cttctgccgt gcctgactcg aacaagcaag agacccgaag    48720
aatcagtcca ggagaccttg gctgcagctg ttcccaaaat tatggcttct tttggcaatt    48780
ttgcaaatga caatgaaatt aaggtatgat tgttgcctca ggtcacaaac atgcgagtga    48840
tgctgtgagt gagtctgtgg agggtgaggg cttctgaaca gggagtcctg tgggagtgct    48900 tcttgggggta tgttgtatgt cgtaatttag actaccatca tttgtgttat ttttgaggca    48960
cctaaggact tcttttccact tctcattct tactgtgggg tgaagagttg aattgggaga    49020
tggtttctag atgcaaattg aaaaggcatt tttccagagc agatttgttt tcggcgtact    49080
agagtgactc tttaacctag ctgcgggaag atgactgtgc caagactgca ggtaggagaa    49140
agctcactga cgaggccttg tgggtctgaa cgtcctgcag ctatcagagc ctgttggctt    49200
cctgttgtgc attccaacaa atcatcttca aacccacttt agtgttttgt ttataatgtc    49260
cagaaatagt gaccctgtca catgctctac agattacagg attcttagcc tcttcctttt    49320
tggtaggtca gtcctgggtt tgagcccaag tgaccctcct gggaggtgat gatacacact    49380
gggtagagtg gaatcagatg gacttggatt agaattctgt cctctttact agttattttc    49440
ctctaggcaa actgcccaac agctctaagc tatttccttc gtattctgaa aaataagcct    49500
taatgggacc catatagggc aactctgaga gtaaaataaa ggaatatgtg ttagagtgta    49560
gcatagtcac ccacgggaag ggcttagatg ttagctgcta ctgctcttat tagctgaatg    49620
```

```
atttggaata aactgttagc ctctctcatg ttttttctct tgagcttcga agttttcttg   49680
ttaatactaa ggagatattc aaactagtca tggggttttg gaatgacgaa gggagatgat   49740
gaatctaaag aatttagtgt aatatttctt catgctcagt aaatggtagt ttctgctgct   49800 gttatttta ttaccatctc tttggaatgg gagtaggtgc tcctttgtgg tcagaggctg    49860
tgagagctcc acagcgccag tttgcccatc tgtacactgg ggtctgttga aggcagtccc   49920
ctctgtgata tctctggctg tcagagctca gatgatagat ggtatttttg tactcttagt   49980
tctcatcatt ttcatgattt cgatcaccat ttgagtatga tgatgctaac actttgttga   50040
acgtagaatc cgttaattac ttccttcctg aacctttggc attaaaaaaa atctattctg   50100
ctacctctct gctcatttat ggttattcaa atttattatc aagagcctgg tacagtggct   50160
tgtgcctata attgtagcta cttgggaggc tgaggtagga ggattgcttg aggcaggag    50220 tttgagacca gcctgggcaa gatagtgaga ccctatctct aaaaaaactg aaaaaaaatt   50280
agctggacat gatggcatgt gcctgtggtc ctagctactc aggaggctga gacaggaggc   50340
tcggttgagc ccaggagttg gagttcgagg ctacactgag ctgtgattgt gccaccacac   50400
tccagcatgg gtggtaaaac aagatgccat ttcttaaaaa aaaaaaatat atatatatat   50460
attatcaatg aaattcagta gtaccaacag gattataaac aaagatagta gttcccttcc   50520
tactttttct cttaatcctt gtgtctcaca ggcaaacata actcttagta tttcttccaa   50580
tatttacttt catgtttctt tctttctttc ttttttttc tttgagatgg agttttgctc    50640
ttgttgccaa ggctggagtg caatgacgca atcttggctc accacaacct ctgtctcccg   50700
ggttcaagcg attctcctgc ctcagcctcc tagtagctgg gattacaggc atgcatcacc   50760
acgctcggct aattttgtac ttttagtaga gatggggttt ctccggggttg gtcaggctgg   50820 tctcgaactc ctgacctcag gtgatcctcc cacctcagcc tcccaaagtg ctgggattac   50880
aggcgtgagc cactgcgccc agcaacttcc acatttctaa ataacatgct tctactgcta   50940
tttttttttt caattttaga cattttttta ctttcactat agttctatca gaattcagtg   51000
tgtacgttat tatgcctaag taaatagtca tggttgctta cgtattatat ttctttgatt   51060
gtgtttctta tttgatgaga aagctgtgtt ttttgctctg ggttgaaact ggagagagga   51120
cctggggagg aggaggagga cagatgaagt tggtgactgt accttcatgg ccatagctgg   51180
gttctcagca cccggggatc tgctgatcac ctactcatag gccaggcccc tatcgaagtt   51240
ctaggtgacc cagtgctggg gacggggggg ccacctgcaa ggtctaatca tggaggtggg   51300
ggctacagtg ttggcttgtg ctggggccag catccttagg aaggcatctt ggaggtggag   51360
gagacagccg cccacttctt gattggggcc ttcagcagca ccagcttctt gggcaggctg   51420
gtgctggctt tcatcaccat gtcgtgttca atcttcttcc agatcctgac ttctaggttc   51480
agctttcctc agaccctggt tcctttcaga ggccattgct gctgccttgc tctttgctgg   51540
cttgtgcctt gattatatgt ctttgtacaa ctttttgttt tcctggagtt aatcttcaca   51600
tctgttttct tggagttaat cgttacctct atatcgcttg cttattattc tttggccttt   51660
ttgtcttctc acaccttcca acttctttgt aatatgtgtt tagtacaatt tttcatgaca   51720
ggtagtttac tgaatcagtt tttccccagt gtggtcatcc aacttgagtt atccagctct   51780
ctgccccagt ctgggcaggt tgatcttcag gtctgtagta cacttgtatc ctaggacttc   51840
tctttgccat tagcctggaa tttccttttgc agttctcccg ttggatgccc agttcctaga   51900
tgccatatgt ttttctatcg tctagtagct tcctgagaga agatgaatgg gagggaaatt   51960
```

```
gtatgaggtt ttgcattcat aaaaatgcca ttttttttcc tgtacacttg gctgggtatg    52020
gtgttctggg gtagaaatca ttttccctca gaaatgcaaa gtctttgccc tgttgtctta    52080
aaatctccaa cgtgacccga ttccttaacc tatgaatgta cttttctttg gaagctttcc    52140 attttttgggg aggtgaagtg ctaggtactt agtaggcctt ttaatttgga aacttacatc    52200
ccttcagttc tgggaaaatt ttcttaacat ttctctgaga agttcttgcc ttttattttc    52260
tgtgttctct cctgaaattg gttagttgga tgttggtcct cctagattga ctcacatctt    52320
acctttttct tttcttttc tggtacttt tagatatcca tctcaaactc ttctattcat    52380
tgttatgttt ttaacttctt tcttttcttt gtctcttgat ggggtcttgc cctgttgccc    52440
aggttgtggt gcagtggtgc gatcatagct cactgcagcc tcaaattcct gggctcaagc    52500
agctgttctg cctcaccctc ccaagtagtt gggactacag gtatgcacca ccacgtccag    52560 ctatttctt tactttttt ttttttttt tgagatggag tcctactctg tcgcccaggc    52620
tagagtgcgg tggtgggatt ttggctcact taagcctctg cctcccaggt tcaagcagtt    52680
ctcctgcctc agcctctcaa gtagctggga ttacaggtgt gcaccaccat gcccggctaa    52740 ttttttgtatt tttagtagag ccagagtttc accatgttgg ccaggctggt ctcgaacgcc    52800
tgacctcagg tgatccgcct gccttggcct ccgaaagtgc cgggattaca ggcgtgagcc    52860
catcattaga tctttaaata ccagtatcta taagtctttt cctcttgagt cagctagtat    52920
ccctggaagg aaaattactca ttttcctgct tggaggctat aagcttggct atgtttatcc    52980
tgcaaccggg gactggaagg gaggggactg acagtgttgc tggtcagggt gccctcttac    53040 ttttttgtttt ctgtgtgcat ctcacgtctg tcctcagcct atgtaaacac ctcttgagat    53100
tatccctctc aatctttgcc ggaggtgggg gaggggctgc ttcctgggct gccttggatt    53160
ggagggaaga cctcaggtga gtgggtggga atttgcccaa ggagccatga gaccagccac    53220
tatttcaccc tctccatccc tccactttca gatgtatgtg gcgcctccaa agcccgagct    53280
cttcttggcg tctgtggctt caataagctt gcttttgct ggtatccctc ctaccctccc    53340
ctgtccccag caaagcttgc atttgaactt cttcctacgg gctaacaaat cagtcagtta    53400
tgtagctctt gttactttt agcttccgaa gttttgttga cacccgtagt ctgctaatgt    53460
ccctgttctg ttctttctgt tcgtgtaaat atatgcttta tacaacttct ttacatgatt    53520
tttgtggggt ttctgggtag cagagcttca caagttcaat ccagcgtgtt ggattagaaa    53580
tctcccaccc tctggtttat tcttattctc aaaattacct gccaaacact gatactccct    53640 tgttttcct tttcctgaca ggaaatgtac ataccataca ggacagaaat cattagtgta    53700
tcccttggtg aataaccaca aagtgaactt aaccttgta accgccaccc aggtcaagac    53760
agaatattac caagcactca gaagcctctc ccctattccc ccgtcactgc tcctgccttc    53820
ctccccaagg tcatgactgc tggcttctaa ttccagagtc tgttttaaa ttctgtgtac    53880 atagaccatg gattaagtgt tcttttgtc tggtttattt tggtcgacat taagttcatg    53940
agagtcttct atattatcgt gtgtattagt attcctgtag ttttaggagc ttcatagcat    54000
tccattgtag ggatatacca cagtttattc attgtattat cactgggttg tttctagttc    54060
ttggctattg cgagcagtgc tactgtgacc actcttaggt gtgtcttttg gagtacatgt    54120
gcaggtttcc atcttgcaca gctagaggtg gagttgttgg gtgatagggt gtgtgcatct    54180
cagctgcagt agaaactgcc aaatagcttt ccttgagtgc ttgtaccagc tcacccttt    54240 gccactgtgt atgggattc caggagctct ggtcctcgct agcacttgga attgctgatg    54300
cttttactct tagccttcct gatgggtgtt ttctggaatc acattatgat tttaatttcc    54360
```

```
attccttaaa gtacccttgg ctctgaagtt taatgattca tgcatctctt ccctttttgaa   54420 gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattcttggg attgtagaga ttagacctga ggaggcccct tggagctctc   54600
tgactaaatt ttattcttta ttattccaaa ctatttaagc tcaccgtgtg ctgactcatc   54660
ataataatga gtagctctca ttgtgcttgt ctatttggac tcatacaatg atttttttttt   54720 tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtattttta gtagagacgg   54900
ggtttcacca tgttggccag gttggtctca aactcctgac ctcaagtgat ctgccttctt   54960
cagcctccca aagtgctggg attacaggtg tgagccactg agcttggcca aagtagtttt   55020
ttaagatgtt agtatctttt cttgcagcta aaaaagtttg tcagagatga ttctactttg   55080
ttctccaggt gttttctcag ggagaaattg gaggcagtaa gccactgggg gagtcctgtg   55140 gctgggggg ggggtagtcc tgtggctcct tgtcagggag tcctgtggct ggcaaggaga   55200
gaagtcctgt ggctgggttg ggagggagtc ctgtggctgg ggtctcatcc tgtgcctaac   55260
agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
gcctttagag ctgagagccc tgaacagaga tttacсccaca tatttattaa tagcaaacca   55440
gtcattagca ttgtttctat agatgttaaa ttaactaaaa gtatcсccttа tgggaaacga   55500 ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
accctgggtg ggccaggtgt tccttgccct cattcctgtc aacccacaac cttccagtgt   55680
gggcattagg gccattatga acatgttaca gtgcttcaga gatttttgttt atggccagtt   55740 ttggggccag tttatggcca gattttgggg ggcctgctcc caatacagag gtctcgtgta   55800
aattccctgg gaggcgataa gcctctgaga aacagactat gctaaccacg ccatgaaaga   55860
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agttttgaat aatgggaaat ggatgttctt aagtaacata   56040
gtcaccaaga taatgcgact agctgggtca ccccttttca attttaggat attttttatca   56100 agatttaaat ggccatcatt agagttatag cactttctcc tttggattgt cctagaggcc   56160
catgagaaag tattccctaa tttcttagga gaacagtttg tgggtagtat gcggtcatgt   56220
ccagttaaat tgcagatatt tccgatcgaa gatgttccag tcctgagaac ttcgtgacat   56280
tagcaggact tctacaagcc atctcttagg gtggggcatt tactgcagtt ggctagtact   56340
cttttctcct taactttgtc atttgttgat ttttttttaa ctgtccccaa atactgtggg   56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
ttgcaagaat tggaaacttc taattcacgt taagttttat gtaatacatg ataagcttca   56640
taggagcttc atcttttatc tacttggact tttgcttccg taggttttgt taaaggcctt   56700
```

```
catagcgaac ctgaagtcaa gctcccccac cattcggcgg acagcggctg gatcagcagt    56760
gagcatctgc cagcactcaa gaaggacaca atatttctat agttggctac taaatgtgct    56820
cttaggtaag gtggaggcat atgagtggaa gagtctccag catgtactca agatagacct    56880
ttgaaataaa taaaaccaga tgatccctca gcttctagac caggctattt ggcactggtt    56940
gattgaatgt gaactgcact ggggctgctg tgagcccgca tgggtctctg tgaccctgca    57000
gatgcagccg tgcccaggga ctgggcagtg ggtgtgggct ggtgtgagcc ctgtctgcca    57060
cccagggcct ggccctctgt ctgtgtcggc catgactatg gtgagtcttg taggcttgag    57120
actgtgcctc gggttcctgc gggttctctg taggtcagtt gacagtttct cctgttgttt    57180
gggtaactgt ggaaacgaac actggcaagt gctgaagcga gcatgtggac gtgcgatatg    57240
aaataacgac ctggctttca aaggcagtga ggctctctgg aaaggacctt gctgagctag    57300
ggatgtgggt gtgtagccat tcccagtggg cctcatggcg tactcgttca tgatcatgtt    57360
tgtgccatct tgatctctca ggatctcttc ttttttaaca gattaagccg ggaatctcca    57420
aacagtgagt cagatgttaa gatgtcttgc ttccacccccc acaggcttac tcgttcctgt    57480
cgaggatgaa cactccactc tgctgattct tggcgtgctg ctcaccctga ggtatttggt    57540
gcccttgctg cagcagcagg tcaaggacac aagcctgaaa ggcagcttcg gagtgacaag    57600
gaaagaaatg gaagtctctc cttctgcaga gcagcttgtc caggtaggag cacagggttt    57660
actctaggcc ctgcatgtga atgactgaca ttcaaagaac cgattaattt ggaagagaag    57720
cggcagaacc gagagttaga ggtgtggact ctggagctgc gctgctcgtt tccaacccta    57780
ggtgctgacc tctagctgtc ttccctctgt atgtccctgt caccgtgagt caaatgcggg    57840
tgatgcctcc tcaggtgccg tgttacctaa gcctctcaga gaccactgct accctgtttc    57900
taaaaccaga ggtcacgata tgtgttcatc cacccagtaa atactgattg agcacccact    57960
gtgtgctagg ctctgggata ggggctgggt atacaatggt gagtatttca gctgcagctt    58020
ctgcccgtg gaggctgtgg cctagcacac tggtctaggc acggtggtat atgctcactc    58080
aaggagatag ggacgtggtc gtttgggtg tcggaacaaa atgtcggaac ttctcttccc    58140
aatgcagaga aaccttgcag taattctaat gtactgtgat tggcagttga cttcagttct    58200
ttgtagcacg cttactcagg ttatttcact aactatgtaa ccatgcagcc tcatttaag    58260
caattggatt ttttgaactt tacttaaaat gttatgtcag gttttttatt gtgcttaatg    58320
tgtgccattt agctaagttt tgtaggatac gaaattgtaa gtggcttaaa atgattctta    58380
atagaatcat gaattgaaga taatgctaat aatttaagca ctgagttagg tagtgtttgt    58440
aaaatgctta gaatgcttcc tggcacatgt taaggccatg taagtgctgc gtgttgataa    58500
acagctgagc aaaagtggac tcttaagaaa gtattgggc tgagagttct gttccaacca    58560
gctgcccttt ggttattttt cagaataaaa gcagagtctc atgggatatg acatttatat    58620
ttccttcaca aaaacactg ctgagtgttt tgttgagtaa aaagggtgta gccatggtaa    58680
taatacattt aaaatatagt ttatttcatc tttaccttgc cttgtttttt ttttaagcta    58740
gcttttatt gagaattcca cacatacaaa agtatcaact catgaccagt tatatttcat    58800
ttataatcct acttctcct tttttatta tttgaaagca aacccaatt atcctcttat    58860
ttcatctata agtatttcag tatctctata gatgaggact cttctttatt tttaaaactt    58920
tatttttaaa atgatggtca gatgcagtgt tcatgcctgt aatcccagaa ctttgggagg    58980
ccaagctggg cggatcactt gaacctggga gtttgagacc agcccgggaa acatggcgaa    59040
accccatgtc ttaaagaaaa aaatcagcca agtgtggtga tgcatgcctg tagtcccagc    59100
```

```
tacttgggag gctgagatgg gagggtcaca tgagcctgga agatcaaggc tgcagtgatc   59160
catgattgta ccactgcact ccatcctggg tgatggagca agattctgtc tcaaaaaaac   59220
aaaactgcaa aacaacgtca caaaacagtg ccattgttag acctgaaaat attaaacatt   59280
tcctacatca aatacccacc aactcattat caattttttct ctctactctt ttggaatcag   59340
catctaaata aaattggtcg ataaggattg taaatctctt tgatgaactg gttcccctcc   59400
atcccagttt ttttccctta gagttcattt attgagaaac cagattgttt gtcttctaag   59460
ttttcctgtg gtctgatata ctgcttccat ctccactgtg taaattaaca cctttttctc   59520
ttctctgtat ttcctgtaaa tcaataattg gaggaaaagc cttgtcagat ttagtgtata   59580
ttttatatct gagtccagta tttcttatat aatattttaa gataagtgta ctcttttaaa   59640
aagtattgaa actatatgct caatttttt taactgatgc ttttaagaag gctgcttgat   59700
cataaaagtt tagagatcat tggtctgatg ggaaaagcaa ataattacta aaccgtttag   59760
caaggttgag gtgcacatgg tggggcctgg agaagttcag tcatgagccg tcacttatgg   59820
gcacgtggaa tctgacccgg cacagagttg ggagaagaca ggagctttat agacagaaaa   59880
tgtggtcttt gctaagtccc aggagtgaaa gggtgagaca gtgctcacag cacacgagtg   59940
tgggtgcgta gacagagcaa gggtgggtcc tgaaaaggcc tgcaggcttt ctcatagatt   60000
agcaagagtg ctggttacgg aggtttctaa catttgtgaa cagatcgaaa ctgtgttaaa   60060
ttgggattgc agtaatcctg gaaggacagg gatagagggt gaagggggaaa aagggtatg   60120
gatgtgagac ttaattgctg attttcttaa gaccttttctc caaagtaaat aaatgatgtg   60180
gcacattttt gaactggcaa attctaaact ctagatatga ttatctctat aacatatctt   60240
actccatctt cttttgacta aaaactgttc ttaattaaat taccatgaga cgttcaattc   60300
agcaaatgta gtttggctaa ccatatttaa ttagaattta atataatcct aggcctggcc   60360
aaactattaa gcaagtgtgg gcaaaatatt gataattta gatatgcagg aacttagttt   60420
gctttccatg tgtgcttttc gaaaaggaa taaattgaaa aatagaggaa gccctgaaat   60480
ccaagaagca aactctctca cctaggcatg cagtaaaagc aattctagga tgattgctgt   60540
ttggcgcgta gttcgtatta gaaaccattc ttccttgaata aatagtatgt ttaagaagct   60600
gggcagaggg aaggcatatg catatattat caacaaggag ggagaaaaag gcaattagta   60660
accatccata ggagggtcag caagatttat aaaggaaatt tgtgatccaa gtatgaagca   60720
aaataaggtg cagaataaat tttaagcaag taatagatta gagtaagaga acccatttga   60780
ccattaacct tgggacattc tctttcaaat gacatggagt agtactgaaa tctttctttc   60840
tttctgagtc taggttattg tgactggact cagaaagaaa tatttcatta ttgcagtgaa   60900
taacatttgt gaacattatt gttcataaat tatgcagtga ataacattta tgaacacgtg   60960
atgtgtaaga tacatactgt ttatttttag ttaagttttt tggctcaact tctaggcaga   61020
gaacattaaa tgtaaatagt gttacctagg agcatgtaaa tggaaatctc catagtatga   61080
aagcagtgct gttgctaaca gaatttagga gggggcagat gaggtgaagg aaatgtgggt   61140
gctgatttcc ttattacatt gagaggagcc aggagattct tgttcaaaa tggatggctt   61200
aagaagtcaa agtataagct gattacgtag agcaggtacc caaaaatgtt ttgtgtaagg   61260
ggccagatag taaatatttt cagtcttgca ggccatccca agtctgtggc agctactcaa   61320
cactaccttt gtagcatgaa agcagccaca ggcagcccat aaatgtggct ctgttccggt   61380
gaaactttag gtacaaaagc aggtgcaggc cagacctgac ctgtgcactg tggtttgctg   61440
```

```
acctgggatt cagggtata aagttacca tcagaagagc taaaagtgag acttttact    61500
ttatactctt ctacactgtc tgattttgaa aaaagaaac atgtattta taatattaaa   61560
gatagggttg gcaaatagca aataaaaata cagaatacca gtgaaatttg aacttcagat  61620
acattatgag taatttatg gtgtaagtat attccaaatc atgtgggaca tacttacact   61680
acaaaattat ttgttgtttg tttacagttt aaatttgagt gccttgtatt ttatctggca  61740
actgtaatta aagggaaaaa gaataaaattc attatgttca tataatgtga tatagcaggg  61800
gtccccaacc cccaggctgc agagtggtac tggtccatgg gtccccaacc cccaggctgc  61860
agagcggtat tggtccatgg cctgttagga accaggctgc ccagcaggaa gtgagcagca  61920
ggtgagctgg cattcccacc tgagcaccgc ctcctgtcag atcagtggca gcattagatt  61980
cccataggag tgcaaaccct attgtgaact gcacatgtga ggggtctagg ttgtgcgctc  62040
cttatgagaa tctaatgcct gatgatctga ggtggaacag tctcgtcttg aaaccatccc  62100
ctggccctgt ggaaaaattg tctcccatga accagtctc tggtgccaga aaggttgggt    62160
agcactgtga tatagtatta aaagtgctaa taaatatggc atactgcctt taaaatgtct  62220
ggtagctctt tctcagtggc actcataata gtgttttttg attttaaat gtgtgtcaag   62280
ctgactctcc cctccgtgta tgctgggctt tatttccct ttcctagtca ccagttttgg    62340
gaaatagaga tcttcattct catgctgctc ctctagtgca agtgctccat ttatttaa    62400
ggaattaata taacaaaaa tcatgggaat ttagaaaaca acatgaaagc taatgatcac   62460
attggtggaa gtgatagga aatatttagg gggagaagtt aaggtataaa ctttgtcaat   62520
gaagtcctat taaaacaac aaaaagtga agcttaggat gcattttata aactctgacc    62580
agaacacctg tgtttctctg tttctaggtt tatgaactga cgttacatca tacacagcac  62640
caagaccaca atgttgtgac cggagccctg gagctgttgc agcagctctt cagaacgcct  62700
ccacccgagc ttctgcaaac cctgaccgca gtcggggca ttgggcagct caccgctgct    62760
aaggaggagt ctggtggccg aagccgtagt gggagtattg tggaacttat aggcaagtta  62820
ttagcaaggt ctactcttac aattaacttt gcagtaatac tagttacact ctattgatta  62880
tgggcctgcc ctgtgctaag cagtctgcat tccatcttcc ttgccaaaac ttataataca  62940
aatttcatct ttatttata aataggggag ttgggctggg tgtggtggct cacgcctgta   63000
atttcagcac tttggaagga tcgcttcagc ccaggagttt gagacaacct ggccaagtga   63060
gaccctgtct ctacaaaaaa aaaaaaaaa aaaaaattag ctgggcatgg tggcacatgc   63120
ctgtagtccc agctgctttg gaggctgagg tggtaggatt gcttaagccc aagaggttga   63180
ggctgcagtg aatcttgatg gcagctgcac tgagcctggt gacagagcaa gatgctgtct   63240
caaaataaat ttaaaaataa aataagagaa ttaaagttta gcaggttggg tggcaaaatg   63300
aggccacaca tttaaagccc ctcctcctga ttcttttctc tgccttggct gcctcctgtg   63360
gcattttagg tgctgagaaa tgaaaacagt agggaaaata gttccaggat cctcatgtta  63420
atttgccaga aatggcatct tcaagtcgtc agagggatct gagagttcct tcctggcctg  63480
acttgagaaa atccgtctgt ccccagctct gcgtctgcct ccactgccca gtcacctcct   63540
ctccatgctc ttggggctgg gccctacccc accatgcagt gctgccctgg agcagtgagc  63600
ttggtgggtc ctgtctggca tgagagctgc ctttgggagc tggatcccag cctctaccac   63660
tgggtctggt gcctagcagg ctatggataa acttctgctg actccggcct ctcctaagcc  63720
actgcaacgt ggtcggtgta gtgcacagtg tgtgtgcagc gtggccttac tcacagcctc   63780
cacattagag agaatctgac tgaagtctta ctgctgcctc gtgtgaacat aaatgttgc   63840
```

```
cagaaccatg agcaggaaat gttaatctgc cttgtttcct gtcctttaca cggaagaatt   63900 ttttctgta tggaatgcgt gccttacaaa taatgagtgg aaatacccat cgctaatgaa   63960
aagttatact tgactgttag tcagctaaat aatctgagat ttctaatact tttaatttgg   64020
cttttacaat gcaatttatc ttagcttttt tgatttctta ggtcatatct ttagaactat   64080
atatttgaat gttaatgtaa ttttcatatt gaaattaaaa tgttgaactg cgatgttaag   64140
tgtttcctgt ggaaaaacgt tcacattttc tctagtttta aagttgaatc aagctgtttg   64200
aagattttca catttcttct agattttatc agcttgttac tttatctgtc actttctgtg   64260
atttgcagct ggagggggtt cctcatgcag ccctgtcctt tcaagaaaac aaaaaggtga   64320
ttatttcaga aatcagagtc ttgtgttgaa tcttactgat tttcttgtat ttctgtaatg   64380
taatgtatct tgtatttctt gtaatactgt attggactct gtgtatatct cttctcagat   64440
gagtgattat atgtgtgaat gttgctggaa tctgataacc aggcctgaat agttttgtag   64500
ggtggctttt aaaaattact ttcatatcag aattgctttg tcataaattt tgaacgcatc   64560
ataaatttct aatgttcggg gtcagcagac tttttttgta aagggacaga gtgtaaacat   64620
cttagcttta tgggccatat ggtctctttt gcaacattca gctctgccct gtgacaggaa   64680
tgcagttgta aagacatgag ctactggcca gctatgttcc agtagaactt tacttacaga   64740
aacagacagg ctgtagtttg ccaatacctg ccttagggaa tgtgttgtta tattttgtga   64800
gttaccttct cagtaaattt tatttagtat tagtcaggaa tattattaag tagcttcttt   64860
tccagcctgg tcaacatagt gagacccggt ctctaccaaa acaaaacaaa acaaaaaaac   64920
agccacgcat gtggcatgtg cctgtagcct cagctgctgc tcaggggct gaggcaagag   64980 gattgtttga gcccaggagt ttgaggtcac agtgagctgt agtcatgcca ctgcactcca   65040
gcctaggcaa cagaatgaga ccttgtgtct taaaaaaaaa aagtttcctt tgttgggtta   65100
ttttaatttg gacctggtta tcattttca gccatattta actttgtaca tatcagaatg   65160
ttctgataaa acttaacttt tattaaagtg tttgtgatat aatctgctag ttttggtaca   65220
cattatcttt tgcaatgcca gttattttct tttccagtgt gggttgcat aggaaaagaa   65280 ttgctgtcac tttctatttt gaaatcttaa aagactgatc cttttttgtg tcatgatttg   65340
agtatttaat tgagagccta atgcctaata ttatttgcag tattaaatgg gatcttaaca   65400
ggaatagcat tctagccttc attgaattaa gtaaacattt cttaagagaa cttggaatct   65460 ataaatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttcc   65640 agtggcggta agaacgaaga tgactgattc acattgctca gatgagttta tcctcttctg   65700
gctgggacat gggatatatc ctgtctcttt taagccttt tggtattttt cccccattga   65760
gagctgtgtc ttcaaactct tctgttatag ctggaaaatc cttttaagt gaatctgcc   65820 caaattataa gacagatgaa ggtagagttg tgttggatat aggattaggg tgaaagtagt   65880
gggggtgtcc tggagcctct cttcggtgg cagcctagct cttgtgcctt tgaggaaatt   65940
accctgggga cggctctgtg gaacatattt gcaaaccact gatttggaag atagagatgg   66000
cttttgttaa gatctgaatt cacctttttg gcatttatt tgatttctca aggtaaagaa   66060
cttattttgt aataaagttt cctattattt agtagatagg ccaagttgct gtgttaattc   66120
catgtagatt ttgggttttcc tttgctcatt ttttcactct taatctcaca tcattgtaag   66180
```

```
tttatggaag ttatcatact tctgactttt tctttgaaga gcagaaatta gaaattccca    66240
ataattattt tgatagtgtc atttaatgac actcacatgt gatgtagcca caaagattta    66300
atgagttcag ttttaaatca tattaagact gttggtttca tttgttctca ttaatgtaat    66360
tctgaagatg aacaataaaa tgtattttta gaactttcaa atgaaatatt atttcatcct    66420
tccagatcat ataatgctta agttctgatt gttaatcata aagtctagaa aattaaaaga    66480
taataaaatg aaagtgactt ttaggtatta gagttttatt ataaattctg gtgtgtcatt    66540
ggagctatga catgaatatt tcaaaggcca atagcattgg atctttacag ttataactta    66600
ccatttttaa gtttaagtag taatatagat tatttaataa tcaaaatcaa taaatattaa    66660
ttattaaaat gttttgtggt atagtttgag aatcattgct tttaactttt tccatatagg    66720
tttattgact ttaatagcat tctaaacata acatctctac attctttgtg tttaatactg    66780
tggaggtata aaaatactta tatatgatga taaactatat tagagtaaat taaatattct    66840
tatgagtttc attttagagt gcatttactt aattttgaag tccttatttt tagcaaacta    66900
aaaggaatgt tggtacatta tttactaggc aaagtgctct taggagaaga agaagccttg    66960
gaggatgact ctgaatcgag atcggatgtc agcagctctg ccttaacagg tagttctcac    67020
tagttagccg ctggtgtgga ccttcactgt ctgccttcca cccccttgccc ttcctgctcg    67080 tcccctgca cctggtggac agcacgactg ggggcagcag tggagccagg ttgcttaaat    67140
ggggcatatt cgggcttctt ttataatact tactctgaag cttgtgtgtc tgtggtgttt    67200
gcatcatata tttgttgttt tccatggttt aggctgtttt aaaattaggt ttatggcttg    67260
agcatagggc tttgtgagta ggggatggca ggtcgaaaca tctcatgagt tggatggggtt    67320 atgctggggg ttgggaaatg ggatgaaaaa ttatgggatg aaaaattgcc tatggatagt    67380
ttaacttgaa agaatctgcc tttgtttaca gatagttatc ttttttcttt tttgagatag    67440
agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acgggttttt gccatgttgg tcaggctggt cttgaactcc tgacctcaag tgatctgcct    67680
gcctcagcct cccacagtgc cgggattaca ggagtgagcc actgtgcccg gccagttaca    67740
gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga ttttttttttg attacacaaa ttaaacaaca    67980 ataaacatc acagcaatcc ggatactata aagctcacat gcttaccgac ccaactgccc    68040
caggagtgac cactgccaac agcttcatgt cgaccttttt gccataattt ttatatagcc    68100
ttttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gcccctgact aggctgcccc ttaattacaa atgtctttat    68340
atattgctcc agctaaggct tggagtagtc ggttaagaac ttgaacttcg gttttgcag    68400 tgaaacagca tttgagaata tcaccttctg ataagcctta ttttataagg tgggtactgt    68460
agtgggaggc agtgtgagag atgcttgaag gatgcactgc tgtcctgcat ttcagcatct    68520
tcaggatgct gtgcagctga aacatttgat aacggtggaa ctgttcgtta ttttgcaagc    68580
```

```
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt accccttcag acagttctga aattgtaagt gggcagaggg    69000
gcctgacatc tttttttttta ttttttattt gagacagagt ctcactccat agtgcagtgg    69060
aggccgggca caggggctca tgcctgtaat cccagcactt gggagactg aggcaggcgg     69120 atcacttgag gtcaggagtt cgagaccagc ctggccaaca tggtgaaacc ctgtctctac    69180
taaaaataca aaaattagtt gggcgtggtg gcacatgtct gtagtcccag ctgttaggga    69240
ggctgaggca ggagaattgc ttgagcctgg gaggcagagg ttgcaatgag ccagatcgt     69300 gacactgcac tccagcccgg gcaacagagc aagactccat ttcaaaaaaa ataaaaaaat    69360
aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggtttca ccatgttggc caggctggtc tcaaactcct    69540
gaccttagat gatccaccca ccttggcctc ctaaagtatt gggattatag ttgtgagcca    69600
ccatgcccgg ccctgccacc tgccatcttt tgagttcttc cctggagacc tagacctgaa    69660
ccctcctgct tgttctcttg ttatctaata cccctattga cagcgcagct tagatcatta    69720
atggagagct tgacctcatc tgataccttc actgaaggaa acaacttagt gtcttttgtg    69780
ttgaacactg aggtaaaaaa ttggaatagt tgattatatg aactctgcta aaattgagtg    69840
cattttacat ttttttaaggc cttgttgggc cctggttaaa taattatttt taaaaatcct    69900
taaggagcct attataaaca gatctgtggt cttaatgaaa tgtgattaat actgtgcatt    69960
attttaagaa cttttgactt ttcaaaaaac ttttacaaca tttcccattt gatagcggca    70020
taggtttaag cacttctcat ctctaagtta gtggacaaaa aaccctcatg gatagtctaa    70080
taatgtttgc tacaagtcca tgttgagttt tatactccat tttattttca gttttaaaaa    70140
ctgtggttaa atatgtgtaa cataaaattt atgttcttaa ccatttttg cgtatacagt     70200 tcgctggtat taaatacatt taaataatgt catggaatca ttgctaccac ccatctctgt    70260
aaccttttga tcatgtaaca ctgaagctct gttcccattg aactctattc ctcctttccc    70320
gccaagtccc tggcaaccac gattcttctt tctgtcttct gaatttgact actttgggtt    70380
ctcatatact ttaggagtca cacagtattt gttttactta gcataatgtc cccaaagctc    70440
atgcatgttg tagcctatgt tagaacttcc taatgtttca ggccaaatac tattccattg    70500
tatggatagg ccacatttg ctttttccatt cctctgtcca tggacacttg tattgcttca     70560
tgttttagcc attgtgaatc atgctgttat gaacgtgggt gtacagatag ctcctggaga    70620
ctctgctttc cattttttttg gctaaatacc cagaaatgga gttgcttta cattccaatt     70680 ttaatttaaa acattcatat cattgagtgt tttacttaat agtatagtag ttaacaaact    70740
taataaaata gtattttggt aataatttgc tggtagtcca ttgttcagtt tttttaggta    70800
aattacacag gacatttcaa gtggacatga aacatcttgt gatgtggaat catgccccaa    70860
gctgatggct aaacatatga aataccatac cctaaattta gtagatttag tctttgcaat    70920
```

```
ttaggagata acctgttata ttgttaggtt tttgtcgaaa agctttgtcc tcatatttcc    70980
aacttgctgt aaaatttgtt tgtgaagaca aatattttg tatgggtttt ttcttttca     71040 tattaaaaag aaatgtccac attggaattt ttttggagtt tttagagcta atagagcttt   71100
tcataatgta gtgggaatga gtgatcagta agctcttagc agtttccatg cgtgcatttc   71160
tgtgccttga aataaatgac agatgagtac atttgtgttc tgtgtgtaaa atgtgctctt   71220
tcctcattgc acttccatgt tggagggctt gtctcttggt gatcacactt caaaattctc   71280
acagcccccc ttgaaccgtt taggtgttag acggtaccga caaccagtat ttgggcctgc   71340
agattggaca gccccaggat gaagatgagg aagccacagg tattcttcct gatgaagcct   71400
cggaggcctt caggaactct tccatgggta tgtggactac aggtgatgcg ctacaaagtg   71460
gtttgtattc agacctggac atcttaatta tatctttgct tccaagaaga agtcctttga   71520
tactgttttc tgagttctga atagctgatg aaaatgacca attgaggaat aatcatactt   71580
tttcttgatc taaatcttat acttttgagt tatcttagca taaatgtata attgtatttt   71640
aagtggaaat ttgtcactta atcttgattt ctctgttttt aaagcccttc aacaggcaca   71700
tttattgaaa aacatgagtc actgcaggca gccttctgac agcagtgttg ataaatttgt   71760
gttgagagat gaagctactg aaccgggtga tcaagaaaac aaggtgaggg acataggctt   71820
gagacgactt ggtgtttctg agcttgtgtg aggatttaaa atcgccctgg ctactgtcta   71880
ctttattgct ttcccatccc tgggccttta aatttcccct ttaaatacca gctcttccca   71940
ggcctgttgt tttctgcctt tccaggtact acccacagcc ttgagaattg cctgagttct   72000
gcctcctttg agagtgtgcc ccagacaaat ctattctgta ctgaatgttt ccttgtctga   72060
tttcttggat cattcatttg atggttgcgt atggcctgca acgtttcttg ttttggttct   72120
actgaactgt tctaaaagtc tctcttcata ttatcttttt acatgtaaat gtaactgtct   72180
tcacttttaa ttcctcaagg acaaggaata gcgtttcaca gttcgtccca tcaatcagaa   72240
ttatagcctt tggcatctcc ctatctacca ggcccacttc ctcttagatt tgggcttccc   72300
caggctgttg cctttcccca gtagcttct gcttgtcctg tagaagacct ttcatgcttt    72360
gcttctgcag cagccgttcc tgaatgccta gtgtcaactg ccttcttacc acgcccaccc   72420
tccctgcatg ctgcatttat cccctgccac agccctgtga ccctgtgtcc tgctgcctct   72480
gacttgtctg tttctgcttg gccatggtct ctgtgaggtc aggtgtgcat atgggcacaa   72540
accagggcat ctctttatcc ccagcacctg gcttaagtgc tgctctggaa ctatctgttg   72600
aatgaactaa tgcatgaatg tattgttgag tatgagacaa acaagtgtca ttgtctcctt   72660
tctagccttg ccgcatcaaa ggtgacattg gacagtccac tgatgatgac tctgcacctc   72720
ttgtccattg tgtccgcctt ttatctgctt cgttttgct aacaggggga aaaatggtg     72780 agtacaaaag gggatgtgca cagttgaagg aaataactag gtttcagagg tcagcttggt   72840
ggcctgtttt tgccttgcgt gcagcagagg aagtagaatc tgaggatgag tttggttttc   72900
actagccgag gggagggagg aaatgatggg agcaggtagg ttattgggtc tggttttgtt   72960
catttgaaaa caatctgttg tttgaggctg aaggtggctt gggtgatttc ttggcagtgc   73020
tggttccgga cagggatgtg agggtcagcg tgaaggccct ggccctcagc tgtgtgggag   73080
cagctgtggc cctccacccg gaatctttct tcagcaaact ctataaagtt cctcttgaca   73140
ccacggaata ccctggtatg ttaaaagttc acatcttatt ttctcagatt taatcattat   73200
tgtaaaaact atttcagtat tgactatttt agttttagag cagtaagtgt tttgagttca   73260
tttgggatat ttgacctgcg ttgtagctct tcagaaaaca catgaatagt gaagttcttt   73320
```

```
gtttcatggg ttcccttag atgaaaccca tagaggagaa aagtagaaac ctcagcacgt   73380
aagagccaac atatatacac atcggattta aacctaaagc acaaattgtg cctggtcgca   73440
gtggcgctga gtcgcactca gccaggccag gcattcacac tcagggtgag tgggaaccag   73500
gactggctga ggcagcagtg gacccaagtc tccatcgcgc ccatgcttac tatggagcct   73560
tctcgttctc tcttttttct tgggtgagag ggtacacttg tgttttgaa tttatatgag    73620 gtaagtgtgt aatagggttt tttctaatct tttttaagtg gaatctggaa ttttaatcag   73680
atttattatc tgacaaccta gaattataat ccagaaagtc tgtggtattg aggacatatt   73740
ggcaatatga tgaatctcta attcttaaat cctgaaactt ttttttttt aatcacttag    73800 ggttattata gtgaagtcat ttctgaattt ggatcttctc ttcacacctc ttttctctt    73860 tcctgagaat taagctttg tttcgagtta gaaagttgat agtagggaat tgttccatgg    73920
ctgagcaatt tatctccaca gaggaacagt atgtctcaga catcttgaac tacatcgatc   73980
atggagaccc acaggttcga ggagccactg ccattctctg tgggaccctc atctgctcca   74040
tcctcagcag gtcccgcttc cacgtgggag attggatggg caccattaga accctcacag   74100
gtaacggcca gttttcagc tgtgtttttt ctagttatgc ttactaaggt ttaagtttag    74160
atgatgatgt ttgttgcttg ttcttctggt taggaaatac attttctttg gcggattgca   74220
ttcctttgct gcggaaaaca ctgaaggatg agtcttctgt tacttgcaag ttagcttgta   74280
cagctgtgag ggtgagcata atcttctgtg aaccatttc ttcacttagt ggacattta     74340 tcattgctac aattaaaatt ggagcttaat aggaaatatt tccatgcact ctaaagctgt   74400
aaccagtaat acccaccatg tatccatctc tcagctttag aaagaaaacg ttgccagtaa   74460
agttaatgct tcataaactt cagtttaagt tctaattctc agaatatttg tttgaaatag   74520
acctcttcct aaaggatata tttagaaata acctatcatt aagtgtaaag tctgttgaat   74580
atgctgggca cggtgactca cacctgtaat ctgaccactt tgggaggcca aggtggaagg   74640
attgcttgag cccaggagtt caagactatg ggcaacatag ttgaccctgt ccctacagaa   74700
aattaaaaaa aaaaaaaaaa aaagtagctg gtatggtgg tgcatacctg tagtctcagc    74760
tactcgggaa gctgaggtgg agggggatt gcttgagccc cagagatcaa ggctgcagta    74820
aggcgtggtt acaccactgc cctctagcct gggcaacaga gtgagactgt ctcaaaaata   74880
atagtaataa taatcagttg aattaaaaaa aaaaaaaaa aaaccactgt gctaggccca    74940
tagtatggta agagttaaag tgagccttag ggattatta ctcaacctct gtttctgtat    75000
aaagtggaat aggctcaatt ctttaagtga tagcatgttg aacctttcca taccaactgg   75060
ctcataagtc acaactggcc agtcaacaag agtaaaaatt aactggtaaa aatcaaagca   75120
aaaaacctac aattgtcaaa tttgtgggat aactccccct tttaaaatgt catgcctgac   75180
agtaatttct ctctagtttc caggttttca gtcagttgtg tctttttga gcagaaggaa    75240 gcatgctaag agctcaatct tgtggctagc tggggtctt tgtgtcagcc atgcatgtga    75300
tggtgcccct gggtgcttgg ggctgcaggg gagggtaca gcagtagggg cctgttctgt    75360
tctctcgtgc tgtggagtac atagtgacat agtggggtgg tccttggtgt aggtcccttg   75420
ttcctacccc tgggtctgag atttatttag aagtggtgtt ggggctgtgc ggcaggcccc   75480
tctgtaactg atcaatgttt gtgaagttgc tgtttgagag ttgaaccat gacataagca    75540 gaaatggaag gaagaaagaa ccagttatgt gaaagggaca catttacttt taagcttgta   75600
tttactgaga taaagtattc ttaatcaatg ttcttgagag gtgtgggaaa aatgcaacat   75660
```

```
cctggttgca gttaaaccca gaacattgtg tgttgaagag tgacggttct caaaccgtca    75720
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctggaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttgctg     76080 aactttgccc tatgcttgga attttatttt attttattat ttatttagag acaagatctt    76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta gatttttttt    76440
tttggtagtc ctcgtcattt aagtattctg gatagtggga ataaaagagc ttagaatttt    76500
tcatctttgt cttaaacttt taaaaaaatg tagcttatat taattctgct tgttaaaaa     76560 gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaataaca tgagctgtgt tggcactttc     76740
attttctaag agtagttttg gctggagaag ttttctttca gtactttctt ttagaaggga    76800 aatttttcctt tataatttag ggtttgtttt ttttttttcc aagccacctt ttatagagcc   76860
cttgtgggtt atttcattta atccttagaa tgtttataaa tctgggcttg ttctcggctc    76920
cacccacaga tagggacgct gagcgtgcat gagtgggcag caagatagca ggttatggag    76980
ggcccagctc acccccttctg tggcttgagc caatttata gggcacttac agagtctttt    77040
gaaatagtat ttattttgaa gaaaagaaa aacagtttac tgagtactgt cttattgagt     77100
ctggaattgt gagaggaatg ccacctctat ttatttaaag ccattggcct tttttgttgt    77160
tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttggg aggcaaaagc agaaaactta cacagagggg ctcatcatta    77340 tacagggta agcggtttat ttttgtgaga tgctgtttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttcctttttt ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
gtaaaaattt tggactatag agaatagtac taagaagaaa aaaaaaatca ccttcaattc    78000
tgctgccacc tggaggtaat cactgttaat attttgctat atactctatg agtttcttgt    78060
```

```
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
gttgggataa aattttatat actttttttg gcaattactt attatacata aatgtttgtg    78240 tatagtttc tttttctgag aattcctgga agttgagtta ccaggcccgg ctttgaattt     78300 tttttttat tttttttttg agacagagtc ctgctctatt gtccaggtgc tatctcggct     78360
cactgcaacc tctgtctccc tggttcaagc gattctcctg cctcagcctc ccgagtagct    78420
gggattacag gggcacacca ccacgcccaa ttaattttg tattttagt agagacaggg      78480 tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aattttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140
ttttgcattt ggcttctttt acttaattgt gagattggtt cttgttgtag catgtatcag    79200
tagtttgttc atttttattg gcgaaagtat tctattatat gaataatacc atatttatc    79260 tatccatcag atggatatta tagagttcat gttttggcta atttatgaat tatggtactg    79320
tgaacatttg cctgcaagat tttgtgtaga catgtcttca tttctcttga gtagatcacc    79380
tagaagtgga ttttaaata attttggtac ttactgtgaa actgctcttc aaaaacatac     79440
cattgttcct tccttccttc cttccttcct tccttccttc tttccttcct ccctttcctcc   79500 ctcccttccc tacttccctc tccctttccc tttcccttcc ccttttccct tccccttccc    79560
gcctgcctgc ctgcctgcct tccttccttc cttccttcgt ttctttctac atatacacat    79620 tttttaaat ttcaatggtt tttggggtac aagtggtttt tggttacatg gctgaatttt     79680
ggttacatgg tgaagtctga gattttagta cacctgtcac ccgagtagtg taccttgtac    79740
ccaatatgta gttttttgtc cctccacctt cagccttccg ccttgtgagt ctccaatgtc    79800
cattatacca cactgtatgc ccttgcgtac ccacagctca gctcccactt ctgagaacat    79860
atagcagaaa catgccaaag tatactccca ctaccagaat gtgattgtgc ctgattcttc    79920
tcaccagtac aaatatttca aaaaagtta aatatgtatc agttttttgg gcagaagttg     79980
atacttctct ttatttattt atttttttg agatagggtc tcattctatg atgcccagcc     80040
tggagtgtgg tggtgcgatc tcggctcact gcagtctctg cctcccaggt tcaagtgatt    80100
cccacgtcag cctcccagga agctggaatt acaggcgagg ccaccactg ccagctaatt     80160 tttgtatttt ttggtagaga tggggtttca ccatgttggc cagactggtc tcaagctcct    80220
gacctcaagt gatccacctg ccttggcctt ccaaagtgct gggattacag gcgtgagcta    80280
ccacacccgg ctgatatttc tttttaaaat aacttacctt cttttgaaag taatacatgt    80340
ttaatgaaca gaatttaagg aaaatataaa aaaacgaaat aatctttgta atcaaactac    80400
```

```
tgaaaagaaa accaaagtta cattttggtg catattcttt tcattttca tcattgtaat    80460 ttgcatttct ttgattactt gtgagacact cctttcattt acttaatagg tttatatgac    80520
ttgcctattc agagattttg cagctttacc attttctgca aatgatagca acttcttttt    80580
gtttgtttgt ttgtggagac agagtctcgc tctgtcactc aggcaggaat gcagtggtgg    80640
aatcttggct cattgcaact attgcctcct gggttcaagc gattttcctg cctcagcctc    80700
ccaagtagct gggattacag gagtgtgcca ccatgcccgg ctaattttg tatctttagt    80760 agagatgggg ttttgccatg ttggccgggc tgatcttgaa ctcctggcct caagcggtcc    80820
ccctgtctcg gcctcccaaa gtgctgggat tacaggcgtg agccaccgta cccagccagt    80880
agttacttct tatattctag aaaaaattct actcatgatc aagtctccat gaggaaagag    80940
actttaattg aagatcatgg ggcttgcaga ccaatatgat aaaatagttc attgtttcta    81000
aaagtattac tgagtgttga tggcagatat gaacccttt gttttgtag aaaatgtta     81060 cccgtattct ccatttgaat tcagtttaga tttgttagga atcgcagctt aagctttgcc    81120
atctgggagt gtttgggaca gttttgcaga caaaattgca aaagtgccta aggaatgcag    81180
ctggcattca gacctgctct gtgctcagta ctctgtggac agacactgtt cagcacttgt    81240
tgatcagaag gtttagaaag agaactttca aagttggttt ttaattaaag catttaatag    81300
tgtaaataga aagggattaa attttatgac agacaaaaga aagtacagca cccagctggg    81360
cgtgggggct cacgcctgta atccagcact atggggggct gaggtgggtg gatcacgagg    81420
tcaggagttc aagagttcaa gaacagcctg gccaaggtga tgaaaccctg tctctactaa    81480
aactacaaaa attagccggg cgcggtggca ggcgcctgta atcccagcta ctcaggaggc    81540
tgaggcagga gaatcacttg aacctggacg gcagaggttg cagtgagcca agattgcacc    81600
attgtactcc ggcctgggcc acagagtgac attctgtctc aaaaaaaaaa aaaaaagaaa    81660 aaagaaagt acagcaccca gttatgtccg agtgggtgca tgagagtgac cctgagattg    81720
gagacaacgc tgtcacgtgc ttgaagaacg ccacctgaga aaggggcga gaagtggtgt    81780 ccgctggtaa ccagaggtgt tggcttagcc atctgcaggg aggagggtgg tctatcacag    81840
gtgagtttca tctactttct taagcaaatt aaccttactt ttgtgttagg cttgtcccaa    81900
agctgtttta taaatgtgac caaggacaag ctgatccagt agtggccgtg gcaagagatc    81960
aaagcagtgt ttacctgaaa cttctcatgc atgagacgca gcctccatct catttctccg    82020
tcagcacaat aaccaggtat gctgacccag tggcatcttc acattgtcgg gaaaatgccc    82080
tttcctgatg cctttcttta ggctttaatt gaaaacattt tattttctag aaaaaagctt    82140
cagctcagga tgtttgagtg taggtcagtc ctttgatagg atattatcat tttgaggatt    82200
gaccacacca cctctgtatt taagctctgc cacaatcact cagctgtgac actgtaaatc    82260
tcttaatagt ttattacatt ccatgtgctg acagttgtat ttttgtttgt gacacttacg    82320
tattatctgt taaacatttt tcactttagt tgtgttacct ttaaagagga ttgtattcta    82380
tcatgcctgt tgatttttttg gtgagcgggc tattaaagtc agtgttattt agggttatcc    82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620
cttgtgcttt ttaattttgt cttttaaatg ttatttaaa aattggcttt atatgatact    82680 cttttttct gctgagtaac agtgttttac aaaacttgga ctaaatgact tctaagctta    82740
aatgatcact tgatgctttt tttctgaatt aggaactcag cttatcaaat atcaaagtca    82800
```

```
taattcctga ataaataacg tcttttttca tgtaaagact gctttaaaaa acacatggaa  82860
ggctgggtgc ggtggctcac gcctgtaatc ctaacacttt gggaggccca ggtgggcagg  82920
tcgcttgagc tcaggggttc aagaccaccc agggcaacat ggcaaaaccc acctctactc  82980
aaatacaaaa aattagccag gcgtggtggc gggcccctgt aatcccagct actcgggagg  83040
ctgagggatg agaatcactt gagccccgga ggcagaggtt gcagtgagcc aagattgtgc  83100
cattgcactc ccagcttggg ctacagagtg agactctgtc tcaaaaaaag acacacacac  83160
aaacaaaaaa aacatggaga catttttttg gccaccttaa tatttcccct cagataattt  83220
cctttgttta aactcagaac tggcattttc tctcttggag aagattcagg acaaatactc  83280
ctttaagata agtagaagca gtgaaagagg atttgattat caggaatttg ataagcttag  83340
aataaattgt tgcttcttaa tgtcatttca gaagatgaat atttattaat agatgccaac  83400
tgagatatca ttaaaattga ttactaacta ctacttggaa aagtctccca gttccaaact  83460
tcagcaggcc tcttgacaat tcagctgtgg tcaattgggt cttgcgtgat agatacaatg  83520
accaattgtg cagcagagtg tgctgcttag ctgcctattc tgttagcatt catgtgttaa  83580
cttaaaatca taatctcctt agttttgttg agtgtctccg tggacaagac actgtgaggg  83640
atacaaaatc agattggctt tattcaaacc actggggtat tataattcat ttataattta  83700
ttttattttt tgccttttt ccatgtgttc taaaggaatt agagtttgta tataactata   83760
atgggggata gaaattgaca tgtgccatga agggaatgca aaaagtgcc gtgggagatg   83820 agaagtggag aaaggaattt cttttttctt ggaagcagga ataacttcat gaagcatgta  83880
tttcaactta aacagatagt aggcaacgct gtaagggag tatggctgca gcaaaagtgt   83940
tcggggcaga ctgggaggaa gggagggaat aaattcagcc attgttatgg aataatgatc  84000
aaaatttatt ttcagcccgt ttcacttaaa agttgagact gcttaacttt ttttaatctt  84060
taatcttaaa cttttaaatg ccatttgatc tttaaaaata tatgttttaa tagtgtattt  84120
taagtctcta tattttttgtt attagaatat atagaggcta taacctacta ccaagcataa  84180
cagacgtcac tatggaaaat aacctttcaa gagttattgc agcagtttct catgaactaa  84240
tcacatcaac caccagagca ctcacagtaa gtctctttct tgatcggtct tactgacatt  84300
gtaatagttt ttggtagctt gtatggccag ttagttgtat ggtcatctta cggtgaggtg  84360
cttgtcttac agctcttact tatccatgag gcttgctaag aaattgtgct tctgtgaaaa  84420
gaatctcagc ttactccagg aatgtaaatg actatgtttt ttctgattat taaagtaata  84480
cacgcccaaa ataaaaaaat tcagccaatt taggaagaca caacaattaa aataagccag  84540
gcatggtggc tcatgcctgt aatcccagca ctttgggagg ccaaggttgg gggctcactt  84600
gaggtcagga gtcggatacc agcctggcca acgtggtgaa accccatctc tactaaaaat  84660
acaaaaatta gctgggcgtg gtggcgggcg cctgtaatcc cagctactca ggaggctgag  84720
gcaggagaat cgcttgaacc tgggaggtag aggttgcagt gagctgaggt caagccactg  84780
cactccagcc tgtgcaatag agcgagactc tgtctcaaaa aaaaaaaaa aaaagaaaa    84840 gaaaaagta aactactgtc acctgcattg gtaatgtatc agaagtttaa aatgtctaga   84900
ttataattaa ctcagtgacc tggtaatata tactaaggga aaaatattta aatttacat   84960 ttttacattt ttattttttt aatttttatta tttttttttt gagacagagt tttgctcttg  85020
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
```

```
gcccggctaa ttttgtattt ttagtagaga cagggtttct ccatgttggt caggctggtc    85200
tcaaactccc aacctcaggt gatccgccct cctcgacccc ccaaagtgct gggattacag    85260
gtgtgagcca ccatgcctgg ccttacattt ttataataag aatttatgtt gctgacatta    85320
gaaaagaacc ataatatcca agaatccaag aataattaaa ttatgtacat atgctagtat    85380
atagtgtgat gctttggaga attttttaaca atatggagat gtataatctg gattgtaata    85440
ttgagtgaaa aaaggcagaa tacaaacctg gtggggtat agtcggattt cagttaagaa    85500
aaataatatt tacatatata catttctcac actggcagat aatcaccaag ataaattttg    85560
ggattgtgga tgatttttttt cttcttata tttttcagat attctcaaat tttctaaaat    85620
gagcaagtat aacttttgtt atcagaaaaa aataatatac aaaagtaatg ttaatttgct    85680
ggtgaccagg ttaaaccttt ttattttttat tttttgagat ggaatctcac tctgttgccc    85740
aggctagagc acagtggcat gatcttggct cactgcagcc tccgcttcct gggttcaaat    85800
gattctctgg ccccagcctc ctgagtggct ggaattacag gcgtgtggca ccacacctgg    85860 ctaattttttg tatttttagt agaggtaggg tttcaccagg ttggtcaggc tggtctcgaa    85920
ctcctgacct cgtgatccac ccacctcggc ctcccaaagt gctgggatta caggcgtgag    85980
ctactgcgcc cagccagacc ttttttatttt attttgacaaa agaaatactt ccatgttata    86040
gaagactaaa tattgtttgg gctgtctgca gtatggtctt cccttgattt gttcaaaata    86100
tcgtaaactt tgcttattta tttttattgt ggccgactgt gtcgggcact gttgtaggct    86160
tgggatggaa aaacaggatt cctgccctta gggtttctgc aggctggtca gggagacgat    86220
gtggtaagct ggagctcagc tcctaaggat gtgcaggggc agttgagagg cggaagggtg    86280
ggagatcatt ccagggtgtg ggcagcacag gaacctctct tcattgggat ataattgcca    86340
ttctgataac acgtgtttga ggtgtctaaa gtaggaagtt gtaccatggt gggacagata    86400
tcctgtggtt atcatacaca gatctcagtt ttcttctcat tgtttgtact ttttataaag    86460
ggtaacagga gatataattc aataaaacctt tgtggtgttt gggtgtgatt ttattgtttc    86520
tttcttctca gtttggatgc tgtgaagctt tgtgtcttct ttccactgcc ttcccagttt    86580
gcatttggag tttaggttgg cactgtgggt atgtattttc ctcagtatat attaatagtt    86640
gtctacaaca gtatgacata aacatagtta ttaggatgcc cttttctttt cttttttaagt    86700 cttttatcaa tttggcttttt tggaaaaata tctgatggaa tacttgtttc tgctatatta    86760
gctgtgtgag actagtgaca ggagctgtgg gaaatgaatg ccaaatgttc ttaggcattg    86820
atgggaattt cagggtgtgg tcttcaagtt catttaaggg aattttcata tgctggcaaa    86880
aggcttttct cattagcttg actctttcca aaattatttg ctgtgaatta aagtttagg    86940 aaccttttttt cacttaattg tgacctagca tacgaaatgg tgatgattta ggaactactg    87000
ttcttgtatt aacagctttt atttaaaaat gattttcctc cagtagatgg ccctactagc    87060
atctgggaaa taatttcaag tcttctccag cattcaggaa taggctttca ttttgtgtat    87120
caattactga gaatgatttt ggtgactcac atcacatttg agaagtaaac ctgcagattt    87180
cttgtgtgtg tcagcaaatg accaactgat atttgcttga agtggattac attatctgct    87240
ctagaatgat tgctttccca ccttcctcac atacagactg agcagctacg gtttctaatc    87300
ataggtctgg cactagactt cacttctggg caactttggc attggagtaa aatgtattaa    87360
tttaaagaaa gttaaaaatc cgttcaagta aacatacagt tctaatactt tttacaatttt    87420 aaaatataga tttaaatgat aaaataaaaa agaaaatatg ggtagacacc ataatcctcg    87480
tttctgcatc tgttcacaag gggttgatat ttatgagttc tattctccat atccattcta    87540
```

```
tgttctctta atgctcagtc agcacctcag gtggttggag ttcaatgctt ggtagtttga   87600
cttacactgt ctttctagg ggattgagcc ctgggtagtc ctgcttattt gaggttgcaa   87660 tttgtcttc aataactttt actacaagat atggcgtgtt aaaggatacc attggggaac    87720
caacataata atatcaggaa aactaaccac gtcagacctg ccccattgtg tatcaagtac   87780 actattttc catagtaata aagagttcac cccagccaat tctctttat tttgtgcctg     87840 tttactcaat ggcattaaca tgcccaaatg tctgggtagc tgtctcatct ccagttcagc   87900
agaaccattg tcatatgccc tagtaaaagc attccttcat tggacactta ggccccaata   87960 cttcattca gatctactac ctgatttcat ttctcaaatg attttatgg agctctgatt     88020 tataggaaag atgttagttg attaaaaata aaacaatttc tgagctggta taaaatgtat   88080
tgtgacatgc cttcctcttg gaattgcaag agaaaggaag actgttgttt gcttaaaaat   88140
tgtctataat ttgactttgc aaatgtctgc ttccagagtg cctccactga gtgcctcaga   88200
tgagtctagg aagagctgta ccgttgggat ggccacaatg attctgaccc tgctctcgtc   88260
agcttggttc ccattggatc tctcagccca tcaagatgct ttgattttgg ccggaaactt   88320
gcttgcaggt actggtactg agttgaaaca gggactccag gacttggatt ttgatttcct   88380 taggggaat ggggtggtg agcatatgag gggaaaatac tataaggtca ttgccagtga     88440
tggcttgtcc ctttagtcaa atttcagatg ttacctatat gcataaacac atgcagttgg   88500
cagctgttct gtgctgagta ttttaaagta gcctcttccc aatatagccc ctcagttaac   88560
tacaagtaaa ctcattttga atttcatttt aatgggcacc atatgccagt actccctcgg   88620
gcactgggat gttaagaaag tataatgtat ggacttcatt ctcaagttag ttttagatta   88680 gaggggata cacgtaaaca aaagtgcagt ggtcacacag agtggcccta atcactctcc    88740
ttgggcagat ttatgggctg gtaggaaaga gcacaacacg gagagggtgt agcaccttgg   88800
cgatgataat ggaggatgtg gccagcaagg aagacggagt ccattgaaat tgattttggg   88860
agaagttgcc aatctccatg aaagaattgg ggcctgtgct atttgcttca gggggctata   88920
ggagagtttc gtgaaaggga ctaaaagatg agtattttaa taagatcatt catccaactt   88980
gaacatgggc tggaggagaa ggtagggaga ctcaggagat taatgttgat gctaaggcaa   89040
gataatggct ttgggactgt agggaagaca ctgattgtaa gagaatgaag gaggcagaat   89100
tgccaggcct ggttcaccaa ctgaacttcg gttgtgaaga caaagaaacc tgggatgact   89160
tcacatcctg gcaggtgtg tggtggtgac agtcatggaa attgggaaca cagatttgtg    89220
cgggaaacat cagtttcagt ttgagttgg cttatcagtt gaatatcagg cacagatgtc    89280
tggccaactc tcaacatagg gtcttaaatg acttcagttc cccaagcaat ttgtccttcc   89340
catgctattg gggtggagag gtaatgtctg tgcccatatc acagccagtg ctcccaaatc   89400
tctgagaagt tcatgggcct ctgaagaaga agccaaccca gcagccacca agcaagagga   89460
ggtctggcca gccctggggg accgggccct ggtgccatg tgtggagcagc tcttctctca    89520 cctgctgaag gtgattaaca tttgtgccca cgtcctggat gacgtggctc ctggacccgc   89580
aataaaggta atgtcccact tgggtgctgg attcatacag ccttaatgac tatgggtttc   89640
cagactacct ttgtttagta atctgtccct tctttattct cttttgctt taaatgaaca    89700 aaattgctca gattgtgaca ctaaatttaa catcaaaatg tgaccatgtg gatgggtgca   89760
gtggctcgtg cctgttattc cagcactttg ggagactgag gcaagtggat cacttggagc   89820
caagagttcg agaccagcct gggcaacatc acgaaacccc ctctctacta aaaatacaaa   89880
```

```
aaattagatg ggttgggccg ggcgtggtgg ctcaagcctg taatcccagc actttgggag    89940
gccgaggtgg gcggatcacg aggtcaagag atcaagacca tcctggctaa cacagtgaaa    90000
ccccgtctct actaaaaata caaaaaatt atctgagcat ggtggcgggc gcctgtagtc     90060
ccagctgctc gggaggctga ggcaggagaa tggcgtgaat ccgggaggcg gagcttgcag    90120
tgagccgaga tcgtgccact gcactccagc ctgggtgaca gagcgagact ccgtctcaaa    90180
aaaaaaatta gatgggcatg gtggtgcgtg cctgtaatcc cagctacttg ggaggctgag    90240
gcaagagagt tgcttgaacc tgggaggcgg agtttgcagt aagccttgat tgtgccgctg    90300
cactccagcc tgggtgacag agtcagactc tttccaaaag aagaaaaaaa tgtgaccatg    90360
tgttttatag ctcttttagt atcatcagtc actgttatcc ctaagaggga aatacctagc    90420
tttagtttta ggtttccagc attagccaag aaagctcaga attgatgttc ctggccaagt    90480
acctcattgc tgtctcctta aatcttggtt aatggctact gtcctggcta gcatagttat    90540
ggagcatttc catggttgta gaatgttctg ccaatctcag ggacagtttt gctttctgt     90600 gaagcaataa aatcaacttc aaaacaaatg ttaactattt gtacaatgga tttaagatag    90660
accagttcac atacttttt tttttttttt ttttgagatg gagtttcatt cttgttgcct     90720
gggctggagt gcaatggtgt gatctcagct cactgcaact tctgcctcct gggttcaaac    90780
gattcttctg cctcagcctc tcgaggcaga ttacagctgg gattacaggc atgcaccacc    90840
acacccagct aatttttttg tagttttagt agagacgggg tttcaccatg ttggtcaggt    90900
tggtctcaaa ctcctgacct gaagtgatct atccgcttcg gcctcccaaa gtgttgggat    90960
tacgggcatg agccaccacg cccagcctaa gatagaccag ttcacttact gtttatatct    91020
gattactctc tctttgcctt gtcttctacc tttaaaaatc tccctactaa cttcccattc    91080
tcctttagct gccatcagtc ttctcccttc tctgcaaaca tctctggaga gtcccagcct    91140
cagcccacag agcttcccac tgctctgagg tggaccttgt ttgcaaggct tctttggctc    91200
tcttggcctg gaccctgtct actacttcag ccatccttcc ttaaccctg ctggtggttt     91260 ctgttgccac actccatagc agcgtttccc gcccagatca tgtctttaca tctctgggca    91320
ctgctctggt cctgcctgcc tttccctctt tgtatcctgc aggctgctac ccccatcttg    91380
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaattta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagcttcctg tcctcctccc    91920
cacatctgcc cctgccccat ttaccccact ttgtgtctta tcaagctaga aacaggtcac    91980
cacaagtctt catttccact caccaagtct tttgtttccc ctactaaata ttttgcgaga    92040
agaaagtgtg tacctttgta ttcacataca tgtacatgca catatacatg cacatatgca    92100
ggggtcccca acctctgtta aaaccggac tgcaggccgt gcgtggtggc tcacgcctgt     92160
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
```

| | | | | | |
|---|---|---|---|---|---|
| tggtggcggg | cgcccatagt | cccagctacc | tgggaggctg | atgcaggaga | acggcgtgaa | 92340 |
| cctgggaggc | ggagcttgca | gtgagccgag | attgtgccat | tgcactccag | cctgggcgac | 92400 |
| agagcgagac | tctgtctcaa | aaacaaaaca | aacaaaaaa | aaaaaaaacc | aggctgcaca | 92460 |
| ggaagaagtg | agcaagcatt | accatctgag | ctctatctcc | tctcaggcca | gtggtggcat | 92520 |
| tagattctca | taggagcgtg | tatgagttcg | ttctcacact | tctgtaaaga | catacctgag | 92580 |
| acatataaag | aaaagaggtt | taattggctc | acagttctgc | aggctgtaca | ggcttctgtt | 92640 |
| tctgggaagg | cctcaggaaa | cttgcagtca | tggcagaagg | tgaaggggaa | gtaggcacat | 92700 |
| cttcacatgg | cccacaggaa | aaagagagaa | ggagagagag | agagagacag | agagagagag | 92760 |
| agaaaaagaa | agattgagag | ggagagagga | gggagaaagg | agagtgcctg | taggggagt | 92820 |
| tgctacacaa | aggagcacca | gggggatggt | gctcaaccat | tagaaactac | ccccatgatc | 92880 |
| caatcacctc | ccaccaggcc | ccacctccga | cactggagat | tacaattcag | catgagattt | 92940 |
| gggtggggac | acagagccaa | accatatcag | agcatgaacc | ctattgtgaa | ctgcacattt | 93000 |
| gagggatcta | ggttgcatgc | tccttatgag | aatctaatgc | ctgatgatga | tttgaggtgg | 93060 |
| aacagtttca | tcccgaaacc | atcccccgcc | aaccctggtt | tgtggaaaaa | ttgtcttcca | 93120 |
| cagaaccggt | ccctggtgcc | aaaaagtttg | gggacctctg | cacatatgca | tgcacctgta | 93180 |
| catggacaca | taatacatgt | acatatgcat | actttatatt | ctctgccact | tctggtccag | 93240 |
| actgatatac | tatctcattt | ggattactgc | actagccttt | tgttttggaa | acagcatttt | 93300 |
| ttaaaaaatt | taatttaatt | tttttgagat | agggtgtcat | tctgttgccc | agcttggagt | 93360 |
| gcagtgtcat | gatcatagct | cactgcggcc | tcgatctccc | aggctcaagt | gatccttctg | 93420 |
| cctcagcctt | ctcagtagtt | gggactacag | gcatacccac | catgcccagc | taatttttg | 93480 |
| attttttttt | tttttgaga | cagagtctca | gcctgtcgcc | caggctggag | tgggttggcg | 93540 |
| cgatctcagc | tcactgcaac | ttctgcctcc | caggttcaag | tgattctcct | gcctcagcct | 93600 |
| cccgagtagt | tgggattaca | ggcgcctgcc | accacaccca | gctaactttt | tgtattttta | 93660 |
| gtagagacgg | ggtttcacca | tgttggccag | gctggtctcg | aacttgtgac | ctcgtgatta | 93720 |
| gcccgcctcg | gcctcccaaa | gtgctgggat | tacaggcgtg | agctaccgct | cccagccagg | 93780 |
| aaacagcatt | cttgagataa | ttcatataat | tcacccattt | aaagtatata | attcattctc | 93840 |
| tttagtatgc | ccacagagtt | gtacagccat | caccagaatc | agttttagaa | cccataaagg | 93900 |
| aactctgtac | tctttaccca | aaacctccat | gcctccagct | gcaggcagcc | actaacctgc | 93960 |
| cttctgtctc | tgtgactcta | cgtcttctgg | acattactgt | ggatgggctc | atacagtcag | 94020 |
| tgagcttgtg | actggtgcct | tctaccaagc | agggttttca | gtgtagcagc | ctctctgttt | 94080 |
| ttctttttt | tttaaattgt | gacggaactt | ctgcctccg | ggttcaagcg | attctcctgc | 94140 |
| ctcagcctcc | cgagtggctg | ggactacagg | cccatgtcac | catgcctggc | taattttttt | 94200 |
| tttttttttt | tttagtagag | atgggttttca | acatgttagc | cagggtggtc | tcgatctcct | 94260 |
| gacttcatga | tccgcctgcc | tcggcctccc | aaagtgctgg | gattacaggc | gtgagccacc | 94320 |
| atgcccggct | aacctttcat | ttactgtctg | catttcttcc | ctgatgcctt | ccagtccatg | 94380 |
| cacccgattg | tagccattca | tcctattatg | gtttaaggtg | actgtcttag | tcagcatggg | 94440 |
| ttgccataac | aaaataccat | agcctgggtg | gcttcaacaa | cagaatttac | ttctcacact | 94500 |
| tctggaggtt | gggaagtcca | agatccagga | ctttcgcctt | gccctcatgt | ggtgaggggg | 94560 |
| tgaggaagct | ctgtggggcc | tcttatatat | ggatgctaat | ctcattcatg | agggtctgc | 94620 |

```
cctcatgacc cagtcacctc ccaaaggccc cacctcctaa taccatcacc ctggtaatta   94680
agtttcagtg tataaatttg ggggactata gacattgaaa ccataacaag cacttttcta   94740
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg gcgtgtgcct gtggtcccat ctactctgga ggctgaggtg gaggattgc   95220 ttgagcccag gaggttgagg ctacaatgaa atatgattgc accccatcct gggtgacgag   95280
tgagaccctg tctcaaaaaa gaaaaaaaaa atgctgcttt gtaccccttt catgtcatgg   95340
cgtcatggcc aacatagaat gccctggttg tttgctgttg gagggcatgg gcctgggggc   95400
tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaaat gagtgacatg ggttagctct ttttaataaa   95580
tggtaaaacc aaatattcta attttcagtt ttgttatact tccatcacat gttttgtttt   95640
ttttgttttt tgttttttgtt tttctatttt aggcagcctt gccttctcta acaaaccccc   95700
cttctctaag tccatccga cgaaggggga aggagaaaga accaggagaa caagcatctg   95760
taccgttgag tcccaagaaa ggcagtgagg ccagtgcagg taggaaacag cgtggggaag   95820
ggagggacat gagtgcagca tctgtcatgt agaaacatag gatttaagta acttggtgtt   95880
ttagagaaat aaatataata cacatcagta aagtgagaga aagtttctcc aggtgcggtt   95940
caagatatta gaaactaatg actgatgtac acagaccacc ttttggtctg aagcattct   96000 aagtgccact ggctgacatg cagcccctac agcctccagg cttccagccc tagcatggag   96060
catcactctc ctatgcttcc ctggttgcag gtgatggctg gagaggcctc ctgattttca   96120
gtaagggaag tggtgtagat gcttaggaat agatgtagtg agtgaaaaaa ctgattctga   96180
tatgtcaaaa attctgattg gaaatggaat atttacattt ggaagagcta aaggcgagag   96240
aaagtgggga taaagtcatc tgagttggag gagcttaaac cattcacaag tttggaggac   96300
ctttttttac ccatgaaaag gtcagaacag aaggggctag gatttaggtg tgactgcagt   96360
ttattgaatt cccatccata ctgctctcgg tgggcagtgg caggggcagg agaggagcct   96420
ggcaaagcat gaagtgactg ctgctgcctc tgctatctgg gacgcctggc cacctgtctg   96480
tacagtctcc ctccagaccc attctcacgc tgtctcttgg cacccagggg ccagtgatgg   96540
ttctcccatt tgttttgtgt atatagcatt tatatcaagg ctatttattt atttatttat   96600
tttatttatt tatttttttg agacagagtc tcactctgtc acccaggctg gagtgcagtg   96660
gtgcaatctc ggctcagtgc aagctctgcc tcctgggttc aagcaattct cctgcctcag   96720
cctcctgagt agctgggact acaggtgtgc accaccacac ctggctaatt ttttgtattt   96780
tttattagtg gagacggggt ttcaccttgt tggccaggat ggtcttgatc tcctgacctc   96840
gtgatccgtc cacctcagcc tctcaaagtg ctgggattac aggcatgagt cactgtaccc   96900
ggcctattta tttattttta attgacaaaa ttgtatatat ctgtaatata caacatgatg   96960
tttgaaatat gtgtacattg gccaggcgtg gtggctcaca cctgtaatcc cagcactttg   97020
```

```
ggaggctgag gtgggcggat cacgaggtcg ggagttcaag accaaactgg ccagcatggt    97080
gaaatcctgt ctctactaaa aataccacaa aaaaaaaaaa aaaaaaaaaa agccgggcat    97140
ggtggctcgc gccagtcgtc ccagctactt gggaggctga ggcaggagaa ttgcttgaat    97200
ctggcaggtg gaggttgcag tgagctgagt tcatgccact gcactctagc ctgggcgata    97260
gagcgagact ccgtctcaaa aaaaaaaaaa aagaagaaaa tacatatgca ttgtggaatg    97320
gctaattaac ctgtgcatca cctcacgtat cattgttttg tggtgagaac acttaaaatc    97380
tactctttca gtgatttttct tgcatatggt acattgctat taactgcagt caccatgcta    97440
tacagtagat ctcttgaact cattcctcct gtctataaat gaaattttgt atccttgacc    97500
aacacattca aggttttttt tgagatggag tcttcttcac ccaggctgga gtaccatggc    97560
acgatctcat ctcactgcaa cctccgcctc ccaggttcaa gcaattctcc tgcctcagcc    97620
tcctgagtag ctgggattac aggcacatgc tactgcacct ggctaatttt tgtattttta    97680
gtagaagtgg agtttcacca tgttggccag gctggtctcg aactcctgac ctcaagtgat    97740
ccgcctgcct tggcctgcca aagtgctggg attacaggtg tgagccactg cacccggcct    97800
caagcgtttt aaaagatgct cttttctaag gattgactgt agtacaggag gaagattgac    97860
ctgttgaaaa gcctcagcct ttacaagtgt aaaattatca gtatattact atcatctttc    97920
tgatgaatta aataaactaa ggactccaag tcaaaagtct tcaaactgaa gtagaatagt    97980
tgtatatagt gcttggcact ttaatattta gtatcggttt aatgataatg tttgtgcctt    98040
tgccgtcttt aaaacatttt tacatcatcc ctgtttgatt acttggtgtg ctcatgaagt    98100
tgttggccac taaggaatct taggctcaga gaggttctgg aattggccag tggtccttga    98160
atcagctgct cctatgattc tctaactgat ttctcacaaa gcaaacaagc aatcataaca    98220
aaacaactgt gcacactgct cttcttattt tgttatttaa aaagtactta ggctctactt    98280
atgtttgtta gtcaatttct cattacttct agttaatcaa aaggtcagag gaaatacttg    98340
aatattttca tactagaata cttttaaaaaa tcatgatttc cagtaatctc tttaaaactt    98400
ggcaagttat tttgatctaa aagtttatct tttgtgtgca tattttttaaa gcttctagac    98460 aatctgatac ctcaggtcct gttacaacaa gtaaatcctc atcactgggg agtttctatc    98520
atcttccttc atacctcaaa ctgcatgatg tcctgaaagc tacacacgct aactacaagg    98580
tatgggcctc tgcatctttt aaaaatatat atgcacacat acttacgtct aatggatagt    98640
tgatgttttt cttatgattt gtaggatgta taagcccttt gagatatgag ttacatttag    98700 tttttttcaag tttgtttgtc tttcagcttt gtttatgata gcttctatca tacaggtgtt    98760 ttggatttc atattgtttg tactcacagc taagattgat tacagtgaca gagctaggat    98820
gtgcagccag gttataggg gaagtggccc tggtggagtc tggagggatc cgtgtacagg    98880
cttccttccc tcccgtgagg ctcacacaaa aatacagcaa catgctggtc ctgcaggtac    98940
cctctgccta acatgagcca caattccaga ctcacagaag aaaagcaggt gttcggcata    99000
aaccatgtgt ttcaaatagt ctgggcatgg tgagccactt gttatcagct agggaaagtt    99060
tatgtcagcg taagaaactg ttcaccagat accccaaga gccagccttt ctgtctaggg    99120 atgtttttagt tttttagttc attttttttt ttaactttaa aattttctgt tcatctgcaa    99180
tttgttagat atgaagtatg tgtctaattt aattttttgtt tttggttgtc cccaataatg    99240
tttacagaag aattttttctg cactaattgg cttgagttac ttacattctc atagttctct    99300
agtttcagta gtttcattta ttattttgtt atatcaatct atctgtctgc tcatctatta    99360
```

```
gaagcatcct tgttttttt tttcttttt tagacagagt cttgctctgt ccccaggttg    99420
gagtgcagtg gtgcaaccat gcctccctgc agtctcaggg ctcaagtgat cctcccacct    99480
cagctcctga gtacctggga ctaccggcat gtgccaccac acccagctaa ttttttacatt    99540 ttttgtagag acagggtctc cctaagttgc ctgggctggt ctcaagctcc tggcttaagt    99600
aatcctccct ccttggcctc ccaaagtgct gggattacag gtgtgagcaa ctgcacccgg    99660
ctacaagtat acttcttaat tattgtagct taatggtatt tatgagggga tcagttcccc    99720
tgttgttctt tagaattttc tggatattct tctttattga ttttgggatg tgaacaatag    99780
aatcaacttc tacttgtaga ttgatttagg gagaacttat acctcagatg ttaagtcacc    99840
ctgtccagaa tgtgggatgc tttcctattt gttcagaact ttttaaatta cctcagaagc    99900
acatgaaatt taaaggattt taaaaaaaac ttaaagatta tttcacatag ctcttgcaca    99960
tttcttgata aatgaatcct caggtattcc tctgtttttg ttactaatag ttacttctta   100020
tgggtttttt ttccctgaa aatcatttat caaacgtatg tggcttattt tctgaaggat   100080
gtttgataat tttggaagat atgaaagtct tcatatttta caaggtttga ggtctcttta   100140
agctgcatgg ttctcatgtc agctcccaaa gcagaagacg gcatgttgaa aaatgccgta   100200
gagaagatac ttctttttcca cctgtttca actcatatca tcttgaattt cagggcacct   100260
ttccatgctc ctagtgcttg ctatctgttt attattttcc ttcctgaata ccctgaactc   100320
cagcatgttc tgctgtaatt ctggcctccc tggcatcttg actcctgtt tcctttgctc   100380 tgtcatcccc gcggtcagct cctgctgcgc agcttctcag ctgaagtgcg tttggagtgc   100440
ctggcgtgtc ttgctggatc tttgagtatt gcctctggtt tccttggttc cttctgctga   100500
gttgctcagc gtctccactc cccatttctt gtgtggccct tcctgcactc ctctgattcc   100560
ttttgtcttc cctggtttct tgcttttggtt tcgagtctcc acagaacttt tgcagctctt   100620
ctgaagacct ggaagctttt tcatcttaat tctcatctca tgacctcttt tcccttcttt   100680
gagagctaga acttcccatg gtgaacttct cttttccagaa ttccatgcct tcttttccct   100740
cccacttacc tgttgtccag gagaggtcag attgctgtgc atattggagg agaaccctt   100800 cttccctggg ctcttcatct cacatgacat caccacatca cctcgttcct tggaccctca   100860
gtggtgtcac tgctggatt tcttttcctt tggctggcct tagggcacac ccaggttgac   100920
tagcgtagtc atggtattta gatccactca cattttcagt ttctgtgtct gtctcttgcc   100980
tgcttctgac ttcgcccaga gaaagcttct cttttcacaag ggttcttaga tttatgttca   101040
ctgagcacct tctttctga ggcagtgttt taccaatatt tattttccta gtcagtctcg   101100 ccttacctttt cttgttatgc atgtctttgg tcctgaccca ttctctgagt ctgtaaaata   101160
gaattgctgt ataatttaat tacatgaaat cctttagaat cttaacacat cttacacctg   101220
atttaatatt ttattgtatc caaattgaac caaccctatg tgaatttgac agtgattct   101280 cccagggatc ctagtgtata aggaatagga cttagtattt tctattttt gatataccac   101340 ataccagata ctgattatga tggacattta acccttttt ctcattatga aagaaagtta   101400
ggaattattt cttccagtag cgccagtgta acctgaaagc ctttgaaaga gtagttttg   101460 tatagctatc tgaaaggaat ttcttttccaa aatattttc cagtgctgac aacaaacacg   101520
cagacacacc ctgcaaggtg agtgtacggc gccgcacagt ggaggcatct gctgcagccg   101580
tcgatgtttg tgtctttggt tgtacattat gagatcgtga cagggccagt aaccgtgtgt   101640
tctctccttc accttcccaa ggtcacgctg gatcttcaga acagcacgga aaagtttgga   101700
gggtttctcc gctcagcctt ggatgttctt tctcagatac tagagctggc cacactgcag   101760
```

```
gacattggga aggtttgtgt cttgtttttt ctccttgggt tgtggctggc acacttgatg  101820
tgcgtcttct gggctgagtt catctaggat ggagcctggt tctccagggt gcctccggga  101880
gactcctccc tgccccacgt gcttgcgtca caggacccaa gtctgactct gccttagcca  101940
tgaagtttag ggggaagttt ctatttgtat tctattttg tctgttatca tgtattagct  102000
tagacccagt ttagtttgga aaatcagtgg gtttcaaaat gtgtttgtag agtcctttat  102060
ttcttaactt gaccttttca agtggaaagg ggcaaaacag acgggtaagg gggcggggcg  102120
ggaggtgtga cttgctcttt tgtgcctgag gaagtaacag agctggggtt gacagtcata  102180
ttctctgaca cagatagtct ctgacttatc tcacagaaag tcagcggcag agcctgagtt  102240
aaaagtctcg tagattttct tttctttt tttggtggct aatttcagtt ttatttatat  102300
ttgtttattt atttattata ctttaagttc tgggttacat gtgcagaatg tgcagttttg  102360
ttacataggt atacacgtgc catgatggtt tgctgcaccc atcaacccat cacctacatt  102420
aggtatttct cctaatgtta tccctccccc agtcccctca ctcccatgg gccccggtgt  102480 gtgatgttct cctccctgtg cccatgtgtt ctcattgttc aatttccact tgtgagtgag  102540
aacatgcggt gtttggtttt ctgatcttgt gatagtttgc tgagaatgat ggtttccagc  102600
atcatccatg tgcctgcaaa ggacatgaac tcatccttt ttatggctgt atagtattcc  102660
atggtgtata tgtgccacat tttcttaatc cagtctatca ttgatggaca ttcgggttgg  102720
ttccaagtct ttgctattgt gactagtgcc acaataaaca tacatgtgca tgtgtcttta  102780
tcgtagaatg atttataatc ctttgggtat atgcccagta atgggattgc tgggtcaaat  102840
ggtatttcta gttctagacc tttgaggaat cgccagactg tcttccacaa tagttgaact  102900
aatttacact cccaccaaca gtgtaaaagt gttcctattt ttccacaacc tctccagcat  102960
ctgttgtttc gtgactttt aacgatcgcc atcctaactg gcgtgagatg gtatctcatt  103020
gtgattttga tctgcatttc tctaatgacc agtggtgatg agcatttttt cgtatgtctg  103080
ttggctgcat aaatgtcttc ttttgcgaag tgtctgttca tatcctttgt ccattttttg  103140
atggggttgt ttgcttttt ttcgtaaatt tgtttaagtt cttttgtagat tctggatgtt  103200 aatcttttgt cagatgggta gattgcaaaa attttatccc attctgtagg ttgcctgttc  103260
actctgatga tagtttcttt tgctatgcag aagctcttta gtttaattag atcccgtttg  103320
tcaattttgg cttttgttgc cattgctttt ggtgttttag acatgaagtc tttgcctatg  103380
cctatgtcct gaatgttatg gcccaggttt tcttctagga tttttatggt cctaggtctt  103440
atgtttaagt ctttgatcca tcttgagttg atttttgtgt aaggtataag gaaggggtcc  103500
agtttcagtt ttctgcatgt ggctagccag ttttcccaac accattatt aaatagggaa  103560 tcttttcccc attgcttatg tgtgtcaggt ttgtcaaaga tcagatgatt gtagatgtgt  103620 ggtggtatt ctgaggcctc tgttctgttc cattggtcta tatatctgtt ttggtaccag  103680
taccatgcag ttttggttac tgtagtgttg tagtatagtt tgaagtcagg tagtgtgatg  103740
cctccagctt tgttcttcta gcccaggatt gtcttggcta tgcaggctct tttttggttc  103800
catatgaagt ttaaaatagt ttttttccaat tctgtgaaga aagtcagtga tagcttgatg  103860
gggggatagc attgaatcta taaattactt tgggcagcaa ggccattttc acgatattga  103920
ttcgtcctat ccatgaacat ggaatgtttt tctatttgtt tgtgtcctct cttatttcct  103980
tgagcagtgg tttgtagttc tccttgaaga ggtccttcac atcccttgta agttgtcttc  104040
ctaggtgttt cattcccta gtagcatttg tgaatgggag ttcactcatg atttggctct  104100
```

```
ctgtttgtct gttattggtg tataggaatg cttgtgattt ttgcacattg attttgtatc    104160
ctgagacttt gctgaagttg ctaatcagct taaggagatt ttgagctgaa ccaatagggt    104220
tttctaaata tacaatcatg tcatctgcaa acagggacag ttttacttcc tctcttccta    104280
tttgaatacc ctttattgct ttctcttgcc tgattgcgct ggccagaact tccaatacta    104340
tgttgaatag gagtggtgag agagggcatc cttgtcttgt gccggttttc gaagggaatg    104400
cttccagttt ttgcccattc agtatgatat tagctgtggg tttgtcataa atagctctta    104460
ctatgttgag atacgttcca tcgatacctg gtttattgag agtttttagc atgaaaggct    104520
gttgaatttt gtcaaaggcc ttttctgcat ctgttgagat aatcatatgg ttttttgttgt   104580 tggttctgtt tatgtgatgg attacgttta ttgatttgcg tatgttgaac cagccttgca    104640
ttccagggat gaagctgact tgattgtggt ggataagctt tttgatgtgc tgctggattc    104700
agtttgccag tatttttattg aggattttca catcgatgtt catcagggat attggcctaa   104760
aattctcttt ttttgttgtg tctctgccag gctttggtat caggatgatg ctggcctcat    104820
aaaatgagtt agggaggatt ctctcttttt ctattgattg gaatagtttc agaaggaatg    104880
gtaccatctc ctctttgtac ctctggtaga attcggctgt gaatccatcc tggactttt     104940 ttggttagta ggctattaac tattgcctca agtttagaac ctgttatcag tctattcaga    105000
gattcagctt ttttctggtt tagtcttggg agggtgtatg tgtccaggaa tttatccatt    105060
tcttctagat tttctagttt atttgggtag agatgtttat agtattctct gatggtagtt    105120
tgtatttctg tgggatcggt ggtgatatcc cctttatcgt ttttattgag tctatttgat    105180
tcttctctct tttcttcttt attagtcttg ctagcggtct acctatttta ttgatctttt    105240
caaaaaacca gcacctggat tcattgattt tttttggagg gtttttttc gtgtctctat      105300 ctccttcagt tctgctctga tcttagttat tttttgtctt ctgctagctt ttgaatttgt    105360
ttgctcttgc ttttctagtt cttttaattg tgatgttagg gtgttaattt tagatctttt    105420
ctgctttctc ttgtgggcat ttagtgctat aaatttccct ctacacactg ctttaaatgt    105480
gtcccagaga ttctggtatg ttgtgtcttc gttctcattg gtttccaaga aaatttttat    105540
ttctgccttc atttcgttat ttacccagta gtcattcaag agcaggttgt tcagtttcca    105600
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtggagtct  ctttgtaggt ctctaagaac    105960
ttgcttcatg aatctgggtg ctcctgtatt gggggcgtgt atatttagga tagttagctc    106020
ttcttgttga attgatccct ttaccattat gtaatggcct tctttgtctc ctttgaactt    106080
tgttgattta aagtctgttt tatcagagac taggattgca atccctgctt ttttttttgct  106140 ttccatttgc ttgttagatc ttcctccatc ccttttatttt gagccaatga gtgtctttgc   106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
agtttcttca tagcgtcagt agtctttaca atttggcatg ttttttgcagt ggctggtact   106440 ggttgttcct ttccatgttt agtgcttcct tcaggagctc ttgtaaggca ggcctggtgg    106500
```

```
tgacaaaatc tctgcatttg cttgtctgta aaggatttta tttctcgttc acttatgaag  106560
cttagtttgg ctggatatga aattctgggt tgaaaatact ttttttaaag aatgttgaat  106620
attggctccc actcttttct ggcttgtagg atttctgcag agagatctgc tgttagtctg  106680
atgggcttcc ctttgtgggt aacccgacct ttctctctgg ctgcccttttc cttcatttca  106740
atcttggtgg atctgatgat tatgtgtctt ggggttgctc ttctcgagga gtatctttgt  106800
ggtgttctct gtatttcctg aatttgaatg ttggtctgcc ttgctaggtt ggggaagttc  106860
tcctggataa tatcctgaag agtgttttct aacttggttc tattctcccc atcactttca  106920
ggtacaccaa tcaaacgtag atttggtctt ttcacatagt cccatatttc ttggaggctt  106980
ggttcatttc ttttcactct tttttctcta atcttgtctt ctcgctttat ttcattaatt  107040
tgatcttcaa tcactgatat cctttcttct gcttgattga atcggctgtc gaagcttgtg  107100
tatacttcac aaaattctcg ttctgtggtt tttagctcca tcaggtcatt taagctcttc  107160
tctacactgg ttattctagc cattagtcta acattttttt caaggttttt agcttccttg  107220
tgatgggtta aacatgctc ctttagctcg gagaagtttg ttattaccga ccttctgaag  107280
cctacttctg tcaattcatc aaactcattc tccatccagt tttgttccct tgctggtgag  107340
gagttgtgat cctttggagg agaagaggtg ttctggtttt tggaattttc agcctttctg  107400
ctatggtttc tccccatcat tgtggtttta tctaccttttg gtctttgatg ttggtgacct  107460
acggatgggg ttttggtgtg ggtgtccttt tgttgatgt tgatgctatt cctttctgtt  107520
tgttagtttt ccttctaaca gacaggcccc tcagctgcag gtctgttgga gtttgctgga  107580
ggtccactcc aggccctgtt tgcctgggca tcaccagcag aggctgcaga acagcaaata  107640
ttgctgcctg atccttcctc tggaaacatc gtcccagagc acgaaggtgt ctgcctgtat  107700
gaggtgtttg ttggcccta ctgggaggtg tctcccagtc aggctacatg ggggtcaggg  107760
acccacttga ggcagtctgt tcattatcgg agcttgaatg ccgtaccggg agaaccactg  107820
ctctcttcag agctgtcagg cacgtatgtt taaatctgga gaagctgtct gctgccttttt  107880
gttcagatgt gcccttcccc cagaggtgga atctagagag gcagtaggcc ttgctgagct  107940
gcagtgggct ctgcccagtt cgagcttccc tgctgctttg tttacactgt gagcatagaa  108000
ccacctactc tagcctcagc agtggtggac acccctcccc cagccaagct cctgcatccc  108060
aggtcgattt cagagtgctg cgctagcagt gagcaaggcc ccatgggcgt gggacccgct  108120
gagccaggca caggagagaa tctcctggtc tgctggttgt gaagactgtg ggaaaagtgc  108180
agtatttggg caggagtgta ctgctccttc aggtacagtc actcatggct tcctttggct  108240
tggaaaggga agtcccccga cccttgtgc ttcccaggtg aggcaacacc ccgccctgct  108300
tcggcttgcc ctccgtgggc tgcacccact gtccagcaag tcccagtgag atgaactagg  108360
tacctcagtt ggaaatgcag aaatcacctg tcttctgtgt cgatctcact gggagctgta  108420
gactggagct gttcctattc ggccatttttg gaagcatccc ttgttttttg aggtggagtc  108480
ttgctctgtc gcccaggctg acgtgcatcg gcacaatctc ggcccactgc aacctttgcc  108540
tcctggtttc aagcgattct cctacctcag cctccggagt agctgggatt acaggcacct  108600
gccaccatgc ctggctaatt ttttgtattt ttagtggaga tggggtttca ccacattggc  108660
caggctagtc tcgaactcct gaccttgtga tccacccacc tcagcctcct agagtgctgg  108720
gatcacaggt gtcagccacc acgcccagcc atatttttcag atctccctct ctttgcccta  108780
aaccactgtg cttaataagt agttttttagt ggccagcagt ctccatgtat aacacatttt  108840
```

```
agcaaaatgg aaaatactat atgttttaaa tttgaacgtg agattatact gaaataaaaa    108900
tcatctaact gggattcttt aaatagtaag attttctttt ttgtatgtgg gttttttttt    108960
aaccttatta ttatgactgt catatataga aatggctgtt tttcagttac agtcagtgaa    109020
tgtatcaaat gctgccttat ccaataataa aaagtaaatt attaataagt cacaatttaa    109080
tgaagattga tgttagttga tctttatatt cttgaaatca gccatatggt tgtgtgtgta    109140
tgtatatatt tttaaaggta cataaagata ataagctcat ctctgaaaat ttttacattt    109200
ggcataagaa taactggata attaagcatc ttattctctg gcctgtgtct ttacagttaa    109260
aggtagattt actcacctct cctttttttgt ttttctaagt tcatcttttt tgctgtttca    109320
agacagaggc ccattttagc tttctcgcat atccttttgt ttgtactttg gaagcctcac    109380
ctgcttaatt gttgagtttt tatccgtggt cttttagagg gggatatgta gggtagaagc    109440
tttcacaggt tcttgtttgc acttggcccc tgactgtttt gaggaatctc cctcactgac    109500
tcacagcatg gcaaggtttc agatctcttt ctgccacaca gcagttctga ggcagctgga    109560
aagatatcca gatgcttaga ttgtcaggcc aggcttgaga tatacaaact attgagcctt    109620
atctgtgacc ttgcttaggt gaaggcatca gagcccctgc accaacatgc ataggcctct    109680
gcatgtgtgc ggggctgggt gttgaggtct gagcacaagt gtagctggag aggtgagctt    109740
gatgtggcga cgggtatgag caggttttct tcagacttct gtgagtttac ctagttccag    109800
gatttaaagg cacagagact ttagaattaa aatagaatca ttttctttttt ctaaatagca    109860 acactaggaa taaaaaataa taattccaca ttcttgacag gtaatgtttt ttcttgtctt    109920
ctaatcctta tttattccat actcattttt atacataatt gaaatgtatt atgcattgga    109980
tttttctttt gcattatatt atagacgatt tttcatgtaa ctccttactg ttccatttta    110040 tatgtttttgt ctggtttaag actttatctg caaaccggga aactgtctct acaaaaagaa    110100
aaacaaaaat agttggccgc agtggcatgc gtctgtggtc ccagctactc ggggctgagg    110160
tgggaggatt gcttgagcct tgggaggttg aggctgcaaa gagccatgat catgccattg    110220
cactccagca tgggtgacag actttatact gtctgttttg ggtgatttga taatgatatg    110280
ccctgatgta gttttttttat atcttgtgtt tcttgtgcct gggtttattg aggttgggtc    110340
tgtggcttca tagtattttt aaagtttgga aaattttagg ccattctttc tttctttctt    110400
tctttttttt tttttttgaga cagtgtctcg ctctgtcgcc tgcgttggag tgcagtgaca    110460
ctatcttggc tcactgcaag ctctgcctcc tgggttcacg ccattctcct gcctcagcct    110520
cctgagtagc tgggactaca ggcgcctgcc accacgcctg gctaattttt tgtattttta    110580
gtagagacga ggtttcactg tgttagccag gatggtctca atctcctgac ctcgtgatct    110640
gcccgcctgg gcctcccaaa gtgctgggat tacaggcgtg agccactgca cccagctagg    110700
ccattatttc ttcaaagatt ttttttctgc cctgcctccc tccttttttc cctctcttaa    110760
aggggctgtg atttcctgaa tgattgctta gtgttgtccc atagcttact gatgctcttt    110820
tcagtgtttg attgttttat gtgttttctg ttttgtatag tttctattat tgtgtttttca    110880 agttctctga tcttttcttc tacagtgtct actctgttgt taatctgtta atctgttgtt    110940
aatcctgtcc agcgtatttt tttttttgtt tttgaaacag tctcactctg ttgcccaggc    111000
tggagtttag tggtgcgata tcagctcact gcaacctcca cctcccaggc tcaagcaatt    111060
cttctgcctc agcctcccga gtagctggga ctataggcac gtgccaccac acctggctaa    111120
tttgtgtatt tttattagag atggggtttc accatgttgg ccaaactggc cttgaactcc    111180
tgacctcagg tgattcatcc gcctcggtct cccaaagtgt tgggattata ggcatgagcc    111240
```

```
accgtgtctg gcccctgttc agtgtatatc actaattttg tttttatctc tagaagtttg   111300
atttaggtct tttaaaaatg tctccctgtg tttctgttta gctttgtgaa cacaattgta   111360
ataactgttt taatatcctt ctctgctagt tctaagatct tctaataact tcccagttct   111420
tggtgtttct cattggttga ttgatactcc tcgtttttggg ttgtatttc ctgcctcttt   111480
gtatggctgc caatttttta ttggatgccc aaccttgtga attttacttt gttggatgct   111540
atatatttt gtgttcccat agatcttctt gagctttgtt ctgaggttag ttgagttaca   111600
tatagatggt ttactctttt gggtcttgct ttataatttg tcagatgggt tggagcagtg   111660
cttagtttag gactaatttt tttttttggac taattattcc tctttaggaa taattaggta   111720
ccatgcttag gaggcaagac catcctgagt actctaccta atgaaccaga aagtttgggt   111780
tttccagtcc gcctgctgag aacagtgact ttctagccct gtgtgagcgc tgagctctgc   111840
tccttctaat cctttccaat gcttctttcc ctggcctcag ggagttttct cacacacata   111900
tctctgctga gtactcgaga gggaccttcc ccagatctcc agagctctct ctgtcttgtt   111960
ttctcttctc tggtgctctg tcttatgaac tgtggctgtc ttggtctcct tagattctca   112020
gcacctcttc aattcagagg gttgcctgtc cctcctcctt gtgccacagc ctaggaactc   112080
tctcaaagca gcgagttggg gcagccatag ggctgactta gtctctcgtc tcccagggat   112140
cactgtcctt cattgctcat gtccagtgtc ttgaggactc tgggttttgt ctgttttgtt   112200
ttttggtttg ctttggttgt ctcaggcagg agggtaaacc cagtccctca ccctcattgt   112260
gctcagtagt ggaagtctca ctctattaca ttagatatta gtatttgtag cagagccctg   112320
gttccctggt acttggggag ctcttgaaag gccagaaaca gcatgctttc tcacctttc    112380
cagggcttca gtttctggtg cacatcaagc attccataca catttgttaa agtcctttgt   112440
tagacaagta gtgattcaca ggttctattt gtaatttttt cagttaacat gtattgggta   112500
tctgctggga gctagtaaaa acaaaaagtg gtgtgtgaca aattcaattc tgacaagaac   112560
aaccttaaac acttagaata tactttgagc atatcagaat tttaaaaatg tgtggccctt   112620
gagtatttga aaccaacaag aatctattgc ttattagtag aggatatttt gttaaacaag   112680
tggagagaga ggcattttca gtctaattgg tgttggcttt tagcagctga tggaaaccag   112740
ttcgtgatta gccaggcagt ggtgaaacag gctgtgcatt ctgaatgcct aggtatctag   112800
gcattcagaa tggtggcgct cttttgagtta gcatcttctt cttttcttgat tctttttttt   112860
ttttttttga gatggacttt cgctcttgtt gcccaggtaa caactccagt gcaatggcgc   112920
catctcggct cactgtaacc tctgcctccc tggttcaagc gattctcctg cctcagcctc   112980
tcaagtagct gggattacag gtgtgcgcca ccacgcctgg ctaatttttgt attttttggta  113040
gagatggggt ttcactatat tggtcaggct ggtcttgaac tcctgacctc aagtgatgca   113100
cctgcctcga tctcccaaaa tgctgggatt acaggcgtga gccaccactc ccagccccct  113160
cttgattctt gaaaaggaca ttgggtgctg tacatctcgt tatagatgtt gataaaaatg   113220
cttgtgagaa gagtaacatt aaggtagtta tttggtcatt tttgcagatt attttaagac   113280
aattctagga ctgatttgtg gtaaatcaca cattgctgta tcatagttgt gttcactgaa   113340
catattcagg ggctctacag atgcagggct cttagctgct ttgcacactt ctgaattcct   113400
gccctgcgaa caggactgga tacctaatag acaacaggta cttgataaca gtttattgaa   113460
ttaatgagtg aatgaacaga tacataaatg catgaaagaa tggttgtaat gtatataact   113520
tggatttcaa gacttttac tgactgttca aaataagaaa ttgaaaactt tcctctgatt    113580
```

```
ttcctctact atttacacaa tttaaatgga agttatcttg taccttcaat ttctgtctag   113640
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcactttttg gctcagtcca tgattgagcc aagaggccat   113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct cattttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtggaagca cgaaagagca agcaggaaat actttgtaaa agaataaaaa cgaaaaatgt   114600
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgttttttt tttttgaga cggagtcttg   115080
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
```

```
atctgacacg ttctgatcgt gtgaatgtga aattggtttg agcaggagta tatctgagtg   116040
cagaggagat tatttaaaga tattctcatt ctctgcttcc cttttattcc catttggcag   116100
atggtttgat gtcctccaga aagtgtctac ccagttgaag acaaacctca cgagtgtcac   116160
aaagaaccgt gcagataagg taaatggtgc cgtttgtggc atgtgaactc aggcgtgtca   116220
gtgctagaga ggaaactgga gctgagactt ccaggtatt ttgcttgaag cttttagttg   116280
aaggcttact tatggattct ttctttcttt ttttctttt tatagaatgc tattcataat   116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcactttt atctttcatc catcatacct   116520
gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tccctggact   116700
caaggctaac ctggggttgg ctgttaggga tttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat   116880
catctgcagt ttcaagctat ctaacaggtt cacttacctc tttaaaaagg aatgaatt   116940 agcaggacag taactgagac ccgtgctcct ggagtccatg tgggagctgt gtggctctgc   117000
acaagcattt gcacgcttcc cctcttgact gcattacctt cctcctatag ttgctgtggg   117060
caccagattc tggctagtcc tgtcccttca tgatgcacat tttcctcaag attcgtccca   117120
gttaaatcac tgcagatgaa actgcctttt catcgtcaaa atttaactgt catttttgag   117180
ccgtgatctt gggctacttt cttatgtggg gtaggaatat ttgtgagtta gaaatattac   117240
acttctctat ttccttctag acgtaaatct gttaatcctg tcagcactgt tactcacctg   117300
aaagggtctg tttccctagg agaactgagg gcactcggtc aacactgatt ttccacagtg   117360
ggtattgggg tggtatctgc ttgttttttt tgttgttgtt gtttgttttt ttttgttttt   117420
tttttgagat ggagtctcgc tctgtcaccc aggctggagt gcaggggtgc gatctcggct   117480
cactgccagc tccgcctcag aggttcacgc cattctcctg cctcagcctc ccgagtagct   117540
gggactacag gcacccacca ctacgccagg ctaattttt gtattttag tagagacgag   117600 gtttcactgt gttagccagg atggtctcca tctcctgacc tcgtgatctg cccgcctcgg   117660
cctcccaaag tgctgggatg acaggcgtga gccaccgcgc ccggcctggg gtctgctttt   117720
aatgaaggag gcatcaaggg gtgggctttg cgttggcctg atgctttcat ctttctttca   117780
caaaacctgt ccgaagaaaa tccgtctaaa tgggccattg ctctcctcag gaaatagtca   117840
ttgggaactt cttttccttt cctttgacac taggaggctg actggggaga agccctggtc   117900
tatggctgtg ggcagcaggg gctgagagga gcaggctctc aggggggcac gggtacccca   117960
agggaagcca gagccctgat ttgttccatt ctagtaagaa caaagactgc tctggtttca   118020
tgtttgttct gattgccttt catcaaccgg tcccctttct cccagttctt aagattcagt   118080
acagtgacag ttttatgaac aagaatagaa cactagaaca gacaaaccat tgaactctat   118140
gctgataaag atttattgag ctcctgctgt atgtttgcat tctgcccaga ggctctgaga   118200
aaaccaggcc atatgctcca tgctttatcc atggaagctc cccgtcaggt tgggaaagct   118260
gacagctgca gggaatacag tgtgacacaa aactggctcc catgcagccc ttacgtgtcg   118320
```

```
cctctcagat ggttggggga cgaaggtcga ctcctttggg tatcttatta ctaaaccagt   118380
ttcagggaat ctgtgccacc ctatctgcca ttaacgtgaa cagatgagtc cccaaggtgt   118440
aattttgggt attgtctgat gtctcttgga atttattatt tgttttttcca atgagatttc  118500 acctcagggt atagtaaagt tgttgagggg attcctggat gtgttctgca attatctagg   118560
ctgatttcag aatagagtta tgcttatagt caaatttatc agctgtcaag aattttatttt  118620 aaaatttatg cagataagca ggaggaaaag aagcctggtt tttacatttt aatcctatta   118680
ttgatgtgaa attttatttt ccttcctgta ggtgtttatt ggctttgtat tgaaacagtt   118740
tgaatacatt gaagtgggcc agttcaggta atagcatttt attatttttag attttttttct 118800 tcttcttgtg tacttacatg taatttaggt tattaagtga atgtttaaac tactgttagg   118860 cattttttgct gttttctttta aatggaaatc tgactaacat actgtgcatt tttgcttctc  118920
ttaaaaatta atgtatatct caagacttgt ttggaagtag ttatgtatct gaaaattcca   118980
tatgttgtca gtattcattg cacatttcaa agcatttaat tgtgttgaca gatggtggaa   119040
tgaaatcttg tggtggagca ctagttttta aatcttctta gagaaagcag ttttatataa   119100
tgttgtcttt agtaattatt atgcatttgt attctctgca gcttttttctt gctagatgtt  119160 gaggttttaa tacttcttgc tagtccatta caggtttata attattaaaa gttaaaattc   119220
ttttagtacc taaaatgctt aataaacatt gtaattagga aaatttagtg cagaaggaaa   119280
gtgttcccag attccctggg gtctggaaac atagtgttta ttctaattac atgacacctc   119340
cactgtgttt tggggcaagt tactgtttct cttttgagtt tcaatttctt caagagcaaa   119400
gaggcagagg agagctagga agatcgtagc tgctgtgccc ctgtgccgtc gggtgccttc   119460
tacctgctgc ctccgaacct ttacacatgt ccctgctctg cgcgagggca cagatgggat   119520
gcactgtggc aggggtgggg ttagagtaga tcacggacac ctgttagctt gatgtgtgct   119580
tgctgtcaag gttgaatcat gaattatttt atgttgctta tattgatatg tatcttaatt   119640
ttaaaagaaa ggtctaaatg gatgttttg tttttaggga atcagaggca atcattccaa    119700
acatcttttt cttcttggta ttactatctt atgaacgcta tcattcaaaa cagatcattg   119760
gaattcctaa aatcattcag ctctgtgatg gcatcatggc cagtggaagg aaggctgtga   119820
cacatggtaa cgggacacac cttttcactgt cgtcttcggt gtcgtgatgt gcttggcagt  119880
gttcgttttc atatacccac tttgaacgtt gtcagtggca gccatgtgct tctcaggctc   119940
tgcatgtgtg tctgtgtatg tgaaggtact ggttagagac gtttcaaaag agaagagagc   120000
atattcttta ctctcagcaa tttgtaatct tctcagggaa aaaaattcaa gaaacagtaa   120060
gataacctaa ggtacagata gattctgaat ataaagttcc tgttcattca catgaaacgc   120120
taaaagttct tcacttgatc ttagccaaaa ggccaagaag cgatgcaaca ctaaaaattc   120180
ttaaatcgaa cttgccgtga attaaatttt gatctctcat ccagtggtat tggagatata   120240
gtttgacttg ggtcagggc tttctgtttt gcctgatgat tttgctggag cttaaataag    120300
gaacccagga gatggccagc tgtgcaagcc cccagcctgt ggaaggagct agtgtggttt   120360
tatgaatgag ttgcaaatct ttcttttgagc ttttttgaact gatcttccag cattgcccta  120420
ttgacccctc cctgactcct ttgctggaat ctgtaggctt tgaactttg acagggacac    120480 atcctaagac ccttgcaaac tcccagatgt gagaatggca ctactactta gagtcttttc   120540
gactcagcgt gtgtgcagaa gagcatcaac cgggctgtgt tgcgaggcag ggccttggct   120600
gacctctcag tgtttacata gctaagccag ttagtgtttg ccacgccctc acaagggctt   120660
cagattcaca cagccaaagt atagattatt aaaggcatag gtgtttggtt tcctggactt   120720
```

```
ggagggtctt tggacagaaa atcagtaggc aaccacaccc agtactttgt gctgggaagc    120780
ttggtcatct gtgagagggt cagagagtat acccatgcgt gcatgccacc gaagggtcag    120840
tgagtattcc tgtgtgtgca tgtctcaggg ccggagagag tatgtgtcac tgagaggtca    120900
gagtgtttgt gtgtgtgtca aagagggttg cattgtgccc ttcactgagg ggtcagaggg    120960
tgcctcgcgt gtgtgtgtgt gtacgtgtgt gtgtgtcact gaggggtcag agtgtgcctg    121020
tgtgtgtgct tgtgtgtgcg tacatgtcac tgaggggtca gagtgtgcct ctgtgtgtgt    121080
gctcatgtgt gtgcatacgt gtcactgagg ggtcagagtg tgcctctgtg tgtgctcatt    121140
tgtgagcgta tgtgtcactg aggggtcag agtgtgcctc tgtgtgtgtg ctcatgtgtg    121200
agcgtatgtg tcactgaggg ggtcagagtg tgcctctgtg tgtgtgctca tgtgtgagcg    121260
tatgtgtcac tgagggtca gtgttcctat gtgctcatga cattgagggt cagagtgtgc    121320
ctgtgtgcca atgaaaggca tttcttatat tttttatat gtggtcatag tagaccagtt    121380
aatttatttt gactcctgtg ttagaccaaa ataagacttg ggggaaagtc ccttatctat    121440
ctaatgacag agtgagttta cttaaaaaag cataataatc cagtggcttt gactaaatgt    121500
attatgtgga agtctttatt gtcttttcag atgaatcaag tagattattc ttgagaccag    121560
gaatgttgct gttttggtta tttggaaagt tttatcattt tcaaattgac ttttgaattt    121620
gagtcacctt ttttcagaag tggtgttaaa ttataggagc cctaggtttt ttttctttt    121680 ttagaagtca tcacaaaatg atcagtgttc agaggaagag ctttgacctt ccacatggta    121740
taatgattga taaccttaat tcatctctta ccataaacca agtatgtgta agggttttct    121800
ttatttcttg aaagcatttt gtagatgttg agagcagttt tccaaatgta atttccatga    121860
aatgcctgat aagggtaccc ttttgtcccc acagccatac cggctctgca gcccatagtc    121920
cacgacctct ttgtattaag aggaacaaat aaagctgatg caggaaaaga gcttgaaacc    121980
caaaaagagg tggtggtgtc aatgttactg agactcatcc agtaccatca ggtaagagga    122040
atgtatgttg gaactgtcgt ggatacttta ttgacccgtg cagatggaag gaagtgccat    122100
gtggtaacgc tcactgttaa ctgtgttact ttgaaccagg tttgggcttt ctggggcctg    122160
ggtagatgcc ggtgcagggg gatggggagg gaggcggggg gtgggggggt gtggtggagt    122220
tggggaggtg cagtggcagg aggtgttgtt ggtgtgtatc cttttttttt ttttgagatg    122280
gagtctctct ccgtcgccca ggctggagtg tggtggcacg atcttggctc attgcaagct    122340
ccacctcccg ggtttaagca attctcctgc ctccacctcc cgagtagctg ggattacagg    122400
catgcaccac catgcccagc aaattttttt ttttgtattt ttagtagaga tggggtttca    122460
ccatgatggc caagctgttt cgaactcctg acctcaagtg atcctcctgc cttggcctcc    122520
caaagtgcta ggattacagg cgtgagccac catgcccagc ctggtgttta tctttaaagt    122580
gggcacagcc acaggagttc acctgactcc tggtctgaga gtcacgagat cgttcaagat    122640
agtgaggccc tcttttccaa aacgaggacc aaaaatcaat tgacagtgtt ggtcaagatg    122700
gtagaaacct taaaatgata gaaatctcaa ctctgaaata aaactttat ttgtatattt    122760 atttaccact attttgacat agggctaagg tcttttctt tgagctgatt tctggttttg    122820
ttttcttaaa gtggcataag aattcaaaga cattttgagg aaggctgagt gcagaaatct    122880 ctcttttttaa atgacttctc ctttcttta acttgcactg ttgtctagcc ctcacttatt    122940
ttgtcaattc tttttagctg tttgtctttg aatcttcata aagccatagc ttttctcata    123000
agaagcagca ctttctttgt tcattcatat tttaatgaac ccctgtagta tttaattaaa    123060
```

```
tacttaatgc ctaattaaat cacataattg caatgcaaaa gtacatgtat cataaagagg   123120
tctgaaaatg agcaactggc aagcaggtgg tggcaggcag agctgcttgg gtgggtgggt   123180
gtcatggaga ggagttcatc agccacatgt tcagtgagct ctggatatgt ctgtttagaa   123240
atgatcacta ataaacttgt gctcaaccat gtatacctct gggaagcagg tgctcttcag   123300
tagattgcct ctgcagagaa cacagaattg aagtgaatgt ccacaaaggc aatgagccac   123360
ctgcagaata gtttagtcaa ggctgtgttt gaagtttgcc aaagattaat atacatttga   123420
ttttcatgtt gtgccttttc tctgattgtg aaatattaca aattctatac aaataacaat   123480
gatggcaaat cctcctgagc aaagtgtgca ccttgtatgt gccctagagg aacttgtgtt   123540
tcgttctgat tcccctacat ttctcatgtc atagagtggg ggttgcatta gtgtcccect   123600 gtcctcgctg ggatcacatc tgtttggatc ctagagtctt ccagctgaac tgggacaagt   123660
ataacagacg gacacgtagg ggtggaaagg cgtctcttgg cagcagactt tctaattgtg   123720
cacgctctta taggtgttgg agatgttcat tcttgtcctg cagcagtgcc acaaggagaa   123780
tgaagacaag tggaagcgac tgtctcgaca gatagctgac atcatcctcc caatgttagc   123840
caaacagcag gtttgtcccc gcagccttgg cttgttgttg catagtgatg gtagcttaag   123900
gtccttgtga aaggtgggtg gctggaatca gctcttcctt cagtcctaat ctgtgccttg   123960
atagcagttc tccgtgctag tcatgggaca gctgacttca tttcttctca caatgccatc   124020
tcaggttggt attgcccacc tactttacag gggggatccc acagctccga gaggttatgg   124080
aggtgatcag gcagcacaca gctttagagt gctggggtga gggcgggcca aggctaactc   124140
taaagcccga acccttacct cctacactgc ctcctgcatt ctggtcaacc cagtgtttta   124200
tttggtggtt agatttttgt ttttgttacc ttactgcttg taatttagca gttttccttt   124260 cctttcccctt cctttccttt ccgacagggt ctcactctgt cacccaggct agagtgcagt   124320
cgtgtaatct cactgcaaca acctctgcct cccaggttca accaattctc ccacctcagc   124380
ctcctgagta gcaaggacca caggtgtgca ccactacgcc tggctagttt tttgtatttt   124440
tagtagagat gaggtctcgc tgtgttgccc aggctggttt taaactcctg ggcgcaagtg   124500
atccaccaac cttggcctgc caaagtgctg gcattacagg tgtgagccac ctcgcctggc   124560
ctattcatca ctaatcagaa tttctatgat caaatgacat gaatcattgt tccacaact   124620 gcagtggaag gaaatggcct ggcagtgcca gtttcagaag cagcctgccc ccagtcaggc   124680
acaggccact gtgcccccag tgtagcagca cctctgtagc tcacagagaa gggtggtggg   124740
gacctccttg aggcagctct gccagaaaat ctcatgagct gcctggcaca gcttgaggtt   124800
gccttttaag tggactcagc aaatacatgt ttgttcatct tgattataca caataaacaa   124860
ctactctgta tagtacgagt agtccgtggt ttttggcatt tgatttaaac ttagaggcat   124920
gtgatattga tgttactgcc ttcatgactg caccccatt ctgatttcat aatggaatgt   124980
tatcttgaga ccagttagac aacaggacag ggatcttggc ttctggtgag attgacagca   125040
gttttagtgt ggtcagggtc tccctgccta cagatggttt tagaatggtg ccctggaagc   125100
tttatcccat tcttttctgt gcgtaatctg agtagagtgg agatcgaagg cctgaataca   125160
tagtaaatac ctgacttaat atctgccgca atggaaattg tgtgatacaa catttatgaa   125220
acgcttagtg cagcacctgc caggtagctc accacaggtg catgttgcat tcagaagtag   125280
tgctagatac tatcctgtta ctggcagtgc atacatcagt gatcaaagca gattaaagaa   125340 agacccctg ccttcttgga gtgaagattt tgttgggatg cgggtaaggg gacagacaat   125400
agaaaagcaa gtgagtgaag tctataccat ggcggctgat caggaacacc gtacagaaga   125460
```

```
atccaggagg gaagagagtt aggtggtgtc tgcggtggga gtggcattgt tcagctggtg  125520
atgagaagaa gctttggtga tctggtgaca tttgagtgaa tttgcagaaa ggaaagatac  125580
aagcctagga gatacctggg gaaggaacat tccaggcaga gcaaatagca gtgcaaaggc  125640
cctggcgggg ggcggacatg ctgttagggt acaagcaatg agggtggagg agtggggcag  125700
ccatggggag ggaagggagt gaggcctggt ggggtgaggc cagtgtggag gagccttgag  125760
agggtttgcg ctgatgtggt gtaggtttta gcaggatcat tcttattcct gagttgaaga  125820
tagccttgag ggggaggtga gggcagagca gggccaccca tgtgagaccc ggcactggag  125880
tggaatggcc caagtcagca tcccttggca gcatgaaagc aaaaccagca aggtttgctg  125940
gtggcttaga tgtggcatgt gagagagagc agggctttgg gggtgatttc agggtgagga  126000
cagggtggct gtgacaagg tagggcagac attgggggca gcaggaggtc agagcctgtc  126060
tggatgtagc agttgagacc ccataggtgc ctaatgaggt gaggccagca tcaggtgtat  126120
gagcctggag ttgtcgagag actgtggggc aggggggtcag catctgagat gtccactcac  126180
agtggaccca gactggctgg agaggaggag gagcttgaat accgagcctg ctgagtccca  126240
gctccaaggt caggtaggtg aggggagcca gtgctggggc aggggggagta ggcaggtgtg  126300
gggttcctaa agccaagatt tttttttaagg cattttgtgc aggagggcga catctgctgt  126360
cagcaccttg ggaacttggc ccaggtttgg cagcaccgag ggcactgatg agtgcttttg  126420
gaggagcaaa gggagccaaa ccctaatggg aatgtgttcc tgaaaggaca ggagagagac  126480
ttgggaaaag gttttacttg aagagggaac ggagaaatag ggcagtagcc agaggaggag  126540
aggagtcggc aatgggttaa gttggcagaa atgaaggcct gtttacgcac tgagggcaga  126600
agcaacaggg aggatcagtt catgacacag gagacacaaa tcgccgttgt ggtgttcaca  126660
gacatgggtt aggattggct gcatggatga cagagcactg tgggttctcc cagagttgct  126720
ggggaggagg cagagttggt gagcacaggc gagggtccag gatgcaggaa tcctggagct  126780
caagtcagtt gttcccttgt tgtaagatgt ggccagtgtt gtgagcttca catctgtgcc  126840
ttgaaaaaca ccacatctgt ttgcagagtt gtttactatg tatacacact cagtagaaac  126900
aaaaattgga aacagtcagt gcccaccatc aataagtaat ggttgaacac actgtggtat  126960
aagcttagac tattttagct tgggctattt tgcatgatta aaaatgttct ggccaggtgt  127020
ggtggctcat gcctgtaatc ccagcacttt gggaggccaa ggcaggcaga ttgcttgagc  127080
tcaggagttt gagaccagcc tgggcaacat ggtgaaaccc tgtctctact agaaatacaa  127140
aaagtagctg ggtgtggtgg tgtgcgcctg tagtcctggc taactcagga ggctgaggtg  127200
ggaggatcac ttgagcccat tcgtgcgcca ctgcactcct ggggcacaga gtgagactct  127260
gttagaaaga gagagagaga aagaagagag agggagggag gaaggaagga aggaaataaa  127320
tggaagaaat ggaagggagg aaggggaggg aggaaggaag aaaggaagtt cagccagttg  127380
ccttgggagt tctccattgc actgggttaa gtgagaagag cagagacgtt tatgattttt  127440
caaaacaact aaaacaaaac ctctgtgggt gaggggcaa ggatatggct ataggaacat  127500
ggggcagatt aagaaaggga tatacacaca ccacttagca tttgttacaa ctgttgtggg  127560
agggatggag tgcagaaaaa gaaaaaaaaa agtgcacacc atcccatgta tgtgtataca  127620
aagggacgct tggaagactg gtccccaaaa tgttggtaat gattgtgtca gggtgctgca  127680
gtgctagttg atttttttc acacttttgt atatttgagt cttttacaga aagcatttat  127740
tatttatgta ataaaaatct aaatgacaag atttctgtta tgggaaaaat gtagctatac  127800
```

```
agtgttgttg taaaaatgtt tgcttggttc accactgaac ttaaaatgct tttaaatgag  127860
ggaaggtgac gatgagatga ttatgatgat ttgcccttga gttacatagc tggtgtacag  127920
gaagctgtcg tttcttttgg cttacgtaga aatgtttgtg gtgtctaatt ccacagatgc  127980
acattgactc tcatgaagcc cttggagtgt taaatacatt atttgagatt ttggcccctt  128040
cctccctccg tccggtagac atgcttttac ggagtatgtt cgtcactcca aacacaatgg  128100
tgagtctctc gcctggctca gcagatgaat ctggacggct tgttcaggct ctgattactg  128160
ggaccacccc cagaatgtct gagtcagtca gtttgggtag ggcttcttga gagtttgctt  128220
tttttttttt tttttttttt ggtgtggggg tggtgcggaa cagagtctca ctctgtcgcc  128280
caggctggag tacagtgtca tgatctcggc tcactgcaag ctctgccttc cagcttcaca  128340
ccattctcct gcctcagcct cccgagttgc tgggactaca gcgcccacc accacgcccg  128400 gctaattttt ttgtattttt agtagagatg gggtttcacc gtgttagcca ggatggtctt  128460
gatctcctga cctcgtgacc cgcccatctc agcctcccaa agtgctggga ttacaggcgt  128520
gagccaccgc acccggcctt tttattttt ttggagatgg agccttgctc tgtcacccag  128580
gctggagtac agtggcgcta ctcgactca ctgcaacctc cgcctccgg gttcaagcaa  128640 ttttcctgcc tcagcctccc gagtagctgg gactacaggt gcgtgccact gtgcccggct  128700
aattttttgt attttagta gagacggggt ttcactgtgt tagccaggat ggtcgcgatc  128760
tcctgacctt gtgatccgcc cgcctcggcc tcccaaagtg ttgggattac aggtggctct  128820
cgcaccaagc caagagtttg catttttagc aaattcccag gtgaaactaa tgcctgcttt  128880
tctgggagca cactttggga ctcagtgata gagaggttta ttggtaggat agtaaaatag  128940
gagttatttt ctttcacaaa attggcaatt gggggaaatt taatcttcct ttttcttca  129000 gctgtgactt atgtattatg tttattttag gcgtccgtga gcactgttca actgtggata  129060
tcgggaattc tggccatttt gagggttctg atttcccagt caactgaaga tattgttctt  129120
tctcgtattc aggagctctc cttctctccg tatttaatct cctgtacagt aattaatagg  129180
ttaagagatg gggacagtac ttcaacgcta gaagaacaca gtgaagggaa acaaataaag  129240
aatttgccag aagaaacatt ttcaaggtat gctttctatc tgagcctata actaacccat  129300
gccttttggg aagtcacgtg atgtttcaca gtcagtaagt ctggaataat acctggtctt  129360
gcttcacttc tgagttgggt aaagaagtct gtatcagtgt aattttctaa tccgtcctgc  129420
attatctatg gctcttggtt catacctgtc ttgaagttct gtcatgttct gtctcttgtc  129480
ctcagtagag atgctacagc agtggctcgc ctcaggcagg gcagggcagt ggggtggctg  129540
tcctgggggc aggcagtagg ggcacgctga cgtcagggaa gttgaaaccc aagagaagcc  129600
agtaaaagtg agtctcagat tgtcaccatg tgctggcagt tttacacgct gtcagtaata  129660
aaagtcttct ccctgcaggg cagcctgcct ccaataaata cgtgtagtat caaatcctgt  129720
cttccctcat aaattgtttg gaagctcccc aaggacagtg atgaggcact cgtaagtgct  129780
tgctgcctag atgggtccct ctccacccttt gctagattct gagcattcac tgagttagag  129840
ctgcttctgc aaatgtgctg cttctgctaa gtggctgtga cttcatgcag ccttcacttg  129900
gtttgtcatc agtggagatg ccctgtgttg tcgaaggaga taagcccagt aagcctgctg  129960 ggcaccttt ggtttgcagg ttcagcaggc agcccatggc tttccctgtg tcgcattgaa  130020
gcagctggct aaaattgatg atacattaaa ttcctgtgac agatgatcag cttgtatttg  130080
tgtaatggtg tacagttcac aaagcttaaa aaaatgctac ctgccatttc atcctcagtg  130140
aggaaggtga tacacagaga gaccaagtga ctgtgtccac ggcgacggcg ctctgcattt  130200
```

```
cactttagcg gttaatgtac tctacctata tttttacttt atatttacca tatatctttt  130260
catgtatact tggcgtaagt gctttatagt agtcacctaa ttcactgtca tcttttttgt  130320
ttcttggaag gtttctatta caactggttg gtattctttt agaagacatt gttacaaaac  130380
agctgaaggt ggaaatgagt gagcagcaac atactttcta ttgccaggaa ctaggcacac  130440
tgctaatgtg tctgatccac atcttcaagt ctggtaggtg aatcacatta gtcttcctgg  130500
agtgtctcgt tccccattct gcactataca ctctcagagt gtaggagctg tgctgcccgg  130560
tagaaactct gccttgccca gtgtgccagt tgaaaatatt tgttgctgta agagtacacc  130620
tgataccatg tgacccagca gttccactct gggtatata cccaaaagaa tggaaagcag  130680
ggtggtgaaa agatatttgc atgccagcat tcatagcagc attattcacg atagctaaaa  130740
tgtggaacca actgaagtgt ccctcgatgg atgaatggat aagcaaaatc tggtgtatat  130800
ttacagtgga atattattca gccttaaaaa aaggacattc tgacacatgc tacaacatgg  130860 gtgacccttla aggacattat gctaaatgaa ataagccagt cacaaaagga caaatactat  130920
gtgattccac ttacatgagg gacctggagt agttaattca tagatataga aagtagaatg  130980
gtggttgcca ggggctgcag gggaggggag ttattttttac aagatgaaga gagttattct  131040
agaaatgaat ggtggtgatg gttgtataac attatgaatg tacttaatgc tactgaactg  131100
tacagttaaa aatagttaag aggaccaggt gtcatggctc atgcctgaaa tccaagcact  131160
ttgagaggcc aaggcaggag gattgcttga gccaaggagt ttgagaccag cctcagcaac  131220
atggtaggac cccatctgta caaacaaact agccggggat agtggtgtgc atgtggtccc  131280
agctactcag gagactgagg ctggaggatc gcttgagccc aggaggttaa gtctctagtg  131340
agatgtgttc atgccactgc actccagcct cggctataga gtaagaccct gcctcaaaaa  131400
aacaaaacaa aacaagacaa gagccaaaaa tggttaagat gggccaatca cagtggctta  131460
tgcctgtaat cccaacactt ggggagtca aggtaaaagg atcacttgaa gccaggagct  131520
tgggaccagc ctgagcaaca tatcgagacc cctatctcta caaagaaaat caaaaactag  131580
ctagatatgg tgggcacatg cctgtagtcc cagctacttg ggaggctgag gtgggaggat  131640
ctcttgagct caggagttcg aggctgcagg gagctattat tgcactccag cctgggctac  131700
agaatgatac cctgcctctt attaaaaaaa aatccaaaaa aaaaaaaag taaacctgag  131760 agcttcctcc tcctgtgtta aatttggagg ccaagatgtt tttgttactt ttacaaatga  131820
tcaaggacgg tgaaggttgg gcatggtagc tcacacctga atcccagca ctttgggagg  131880 ctgaggcggg gtgatcgctt gagcttgaga ccagcctgga caacatagca agagaccca  131940 tctccacaaa aataaaaaaa taaaaaaaaa tagccaggag tagtggcatg agcctgagcc  132000
caggaggtca agctgtagtg agccatgatc atgccactgc actccagcct gggcgagatc  132060
gagaccatgt ctctagagaa agaaaatgac aaggacagtg aacccaagaa agtcataaga  132120
tgccagctgt gcagcaagca tggaaagcag ccagtccaaa ttaggacagt gtgttttcca  132180
agaagaacga tcgtttgtaa tgagaatgct ttgctttaaa taaatgacta aatagctaga  132240
agcctagttc taggggatag gcacgtcttt cttctctcaa gaaaatagaa aggcaattct  132300
aatttctagt aacagcaaac agcattaagt catggtccaa atatgaggca aaccaaaatg  132360
tggcttgatt gttcagcagt tgatctgttg gaagcccttg atattaaaaa ggttctcctt  132420
taagcggctt aggagtcacg atcaaagacc tatagaaaga gatgccatcc ttctaggatc  132480
cttggctctc ttgggaacta gattcagata gtcataatgt aaatactgct tgagctttct  132540
```

```
ttctttcttt ctttctttct tttttttttt gagacagagt ttcactcttg ttgcccatcc  132600
tggagtgcaa tggtgccatc tcggctcacc gcaacctctg cctcccaggt tcaagcaatt  132660
ctcctgcctc agcctcccga gtagctggga ttacgggcat gcaccaccac gcctggctaa  132720
ttttttgtat ttttagtaga cagggtttt ctccatgttg aggctggtct cgaactcctg  132780
acctcaggtg atccacccgc ctcggcctcc caaagtgctg ggattacagg tgtgagccac  132840 cgcaccoggc ccgagctttc attttttgaaa tcaatgtatg actgaaacac tgaagactta  132900
ctgacttaat tatggtttca gaacagaatg aaaatgtctt cggttctgat gaatataaaa  132960
ggaaaactaa ccaagttaat ttggcaagta gatggtagag atagaggtgg ggagtggaag  133020
gggaactaaa atcttcacct agcattgttg ggattatatg gttacatcat ctgaagttga  133080
cagaccaaaa tatagaggct tcagaggtct ccaaatagaa ctaaacatgt aattcagatt  133140
gttaggaggt agtataaatg agctaaatct catctttatt acggtagagt taatgggtga  133200
tgtctaaagt tgtctgaagt ctataaatca tgacaaatta tgatgtggtg attgtattca  133260
acagtctttc agttgcaggg ataaaacccc agtttaaact agagtaagag aaagaatgtg  133320
ttggtttaag ctcctggaaa gtgcaggcaa gggtagttgg taggactgca tctagtgttg  133380
taattctgtg gtctgcattg tatatttatg catctcagct ctgctttctt cttttcattt  133440
atataatttt taaattttat tttaaagata gggtctcact ttgtcgccta ggctgaagtg  133500
cagtggcatg aagtgcagtg cgaggctcac tctagcctcg aactcctggg ctctagagtt  133560
cttcctgcct cagccttcta agtagctgag acaataggca tgtaccaaca tgcctggata  133620
ggttttaaaa ttttttgta gaaatggaag tcttgctgtg ttgcccaggc gggtctttaa  133680
ctcttagctt caggcgatcc tcctgcctct gcctcccaaa atgctgaggt tataggtgtc  133740
acccaccacg cccagtctca tctctgcttc ctgtgttagt tttgttctct ggtgggctgt  133800
tttcacatga ccgaagatga cctctagcag gctgtgttct cagcccctca gtaggccta  133860 tgtgattggc cttgcatgag taatatgggt gaccataaac ccctgaatgc tctggtccac  133920
atgggccaaa tgggagactg acagcattc cattgatgag gaggtggggc tggtctccgg  133980
gagtaaggga gaggagcaca tgcagtaact gatggtctgc tgcaagggat agcagcacag  134040
cagttagaat tttggaggta actaccagaa ctgaaaacag aaatgataac aagtagttgc  134100
cttaaaaagg gatgggagca gggtgctttt gtgatcaaag ctcctttctc ttactggatt  134160
tttgtacaca ttttgcatac atatcttaga gtaaaagata gcatttcag ccttggtcca  134220 tttgaggata ctcttggcgt ggcccgcctc catgctagca ggctctggtt gtgccaagtt  134280
cagttgagca tcctggctct tgcctgcacg gaacttccag tcagtgcgtc agtatcacaa  134340
gtcttgatat ttcctatgaa gaagaacagt agtgcagtga cagacgaaat gggtgggcag  134400
gcagaggcag gatttctgag ggagagaagt agctagcttt ttgcagagaa gagttccggc  134460
acccaagaga gcagctgaga gtacaggcag gcaggcagga tgccggtagg gcccggccgc  134520
acggcgccac agaatcctgg agaaaggggc ctcttcatgg cctctgcatt cagctgctgt  134580
caccctccgc acaggccatg gccaaaattt aattttcata gtggactcta gttttgagc  134640 cttacttgct attattgaaa taattttctt gtttctttt aaagatcttc ggattatgct  134700
tcactgacca ctgtaataag tttaaagttg agaaaatatg gcttgttaat gaatgatagg  134760
tcaattttag tatgttggtc attttaatat tttgccacca gttggtttgg atttgatgcc  134820
aggaggagac agcctcattt ctaaggacta gtcttgcctt tgtgggataa gggtggtgtg  134880
ttctgtgtcc ttctacatgt ccgagcgatc tctgtgcagc tcaaatgtgg tcactgtctt  134940
```

```
attgcgctga tttcctctcc ttccatctca caattgaggc aaaatattgt tactgttgaa   135000
gtgttgtcca ataggacttc cagcagagac aggatgtctg cactgtctaa tttagttgcc   135060
tttagccaca tgtggtgttc tgtacctgaa atgtggctgg tctgattgga tagcttaatt   135120
tataatttta tttaattta attaacttaa atttaaacag ctctgtgtgg atagtggctc     135180
ctgtatgaga cagtgcaggt ctgttgagaa gcagctttac tggtgggagt ggagggcttg   135240
gagagggcac gtgggtttcc tgctggtatc ttttgacctt atttaatctg cccaacattt   135300
gcaagtaagt tgtgtgtgtg tgtatatata aatgtgtgtt tctgtcttct tgtttccttt   135360
gactgcattt atttgaaaga cactaggtgg cagaattact gtatttgatt ggtttcaaga   135420
taagagttga aataattcat ctcgtgtttt tatataagta aggtgtgttt agcatgtaaa   135480
attggtaata tgtattcacg tactgcttaa acaaaggcta tgaattccac ccataaaccg   135540
aaaatgaaga cctttaaatt tgtccatttc aggcgtgggt acttcttaaa taatacctgg   135600
ttcaggaact agtcagaatg gcacccttga ctttttgttt cctgcttttc ctcttgttgg   135660
gagaggaggg tattcatccc aaagtggttt gcctatttca cattccatct aggataagca   135720
gaatagccaa gaaagatagc tgtcctcctg tttacaacat tgggggtaac cagcatccct   135780
ctcttttggt ccaagataga ctggtttaga aacagatgat ggcaccagag gcccaggagg   135840
tggaaacatc agctttgttt gttgtccatg tggctgaatt agagctgtct ggccttgtag   135900
cctcaacacg gccttccagc tttgctcacc gtgattttca aggacacatc ttgtgctctt   135960
ccctgcctgc catccagact atacccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttgggg gcaaagcagg aatactggag agagagaaa gtggtccttt    136200 ctatagtaat aaagttgaca ttgattcaag ttcatgcttg gggaaggac agggctacta    136260 acaattataa tgctgggagc aatggaattt tctcatgggt atgtggtagg tttaattta     136320 attatcccag ttaattctta gaactgctct gtgaagtatt tcccgctttg tgcttaagtt   136380 ctaaagatc ctgtgccaaa accaagaatg aaaacccaag cattcttct tgcccatcga     136440 tctttctctc atcaggccac ttcttgggtt gatagtggtg agtgtagccg ctgccacttt   136500
cagaataccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800
cctcctttcc tgcactgcca tcgtggtctc cgggcacttg gtccctttct cttcccctga   136860 gtcccttttgg ctcccctgtg ccaccccttgt gatccacagg ctctgccttc tttctgtctc  136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgtttct tggttttatg   137100
acaatgtatt gagggtgttc ttggttcacg gatggttttc ctccatgtgg gaattcgggg   137160
acccaggctc ctttccttct tttggttctg ttctccaggc cttcacatcc tctgtgtctg   137220
gttggggaca aggagaggga aggtaaagaa ggctttgtgg ccttggataa gtgacaggca   137280
```

```
tgcctttgct ggtgttctct cgtggtgaca ggtcacagcc ccaccctgta aaagggact  137340
gagagacgtc gtcctgctgc ttcccagcag cagcactgtg gtctctgatg tgttttctgt  137400
gaggataaaa acaggtgatt ccaggatgag gaaagtcagg gaaacccttg gaaggagggg  137460
accaggcggg tgtcaccatg ggattagtgg tggcttcaga atgagctgca gcgagtgcca  137520
tgccttctaa agcttttgct attctgatat gcccacacca tgcccagcag gtgtctgcct  137580
tgctctccgc agagagagtg atgaatcctt ctcatgagcc tctgtccagt tgttcctccc  137640
tccacctgga agggaccctg ggttcctcat aacatcccag cggaacaggg gaccttctat  137700
cctgtcccca gttcatcct catcctcctg ccggcttcct ggcccctctt atgtctgctt  137760
cctgacgcca catccttctg gattctctgg aattgaattt tgcctttgat gcttatttaa  137820
aaatatccat tgcaggccag gtgtggtggc tcacacctgt aatcctgtgc actttgggaa  137880
gccaaggtgg gcagattgct tgagcccagg agtttgagat tagcctgagc aacatgttga  137940
aatcctgttt ctatagaaaa tacaaaaatt agctgggcat ggtggcgcac acctatactc  138000
ccagctactc aggaacctga dacaggagga tcaattgagc cccggaggcc aaagctacag  138060
tgggctgtga tcgtgccact gtactccagt ctggtcaaac agagtgagac cctgtctgaa  138120
aaaaaaaaa aaatccattg catacttcac cgtagcgaaa catgtatgtc ttacctttcc  138180
tttcctgcct gtagctgctc ttttacactt aacagccaca ctaagccagc cttaaatgaa  138240
aaacaaacca gcacttcctg tgccctcctg cttccttcat gaggggtccc tccctctgtg  138300
tacactccat tctcattgcc catggtggtt tgtttccctc ttgtttctca agccatggca  138360
gcctgcctct tgccctcttt actaaaaagg cctttgcaga ggctgcctgt gttctttctt  138420
tctaggtctc tctcatccta ggccctccag cttgattctg tggagctgcc ctcttgtcac  138480
tcagtagctt gtggggtctt ctctgtctag ccacttaatt gattgtgttc ctcgagttgc  138540
tgtccatggt ctctcgttac tgttttctct gtgtttctgc ctctctcctt ggccttggta  138600
ggtccatccc ctttgtgacc ttggctgttg ctctcatgga caactttctc ttgctggtcc  138660
ttgtagtcct ggcatccagc ttctcgacac gggacttgtc ctgccagtac ctcagacttg  138720
cacttaaaat tgaactagca ccactgtcac tctccagggc ctcttcttgt taattagatc  138780
attagggatg ttcagaatcc cagcatcata gtatgttcct cctcccgcta ccccaggaac  138840
cctaacctta cctcctcctc tctatctact aggaggtggc cctcagagtc cgtctcatct  138900
tccacctgaa cttccctaat aggctccagc agctgccacc ccgggggctg agtacttcct  138960
ccatgccttg tgcagtgctg agcccttttac ctgggttctc ctgtttgctc cttattacag  139020
ccctgcgaac agatactgct cttaattcca tcttacacct aaggaagctg aggccccagg  139080
taaggtgcat ccaaggtcac ccaggtagta gacagtagag ccacgatctg aaccaggcag  139140
tctgattcag agcctgtgtt gacactcagc cacctagaac acagcttgga ttgtgggttt  139200
ctattacctg ttcaaaaccc ctacatcccg ggtctgtccc tgcacgtgct ctgtggcctg  139260
gctgcatctt ccttgaaggc agtgcatgcc tcttcactca gggggcccat gcaggaacag  139320
agggccccac agaaggatga ggccagtgca gaatgggctg gaggggacaa tgctgaccag  139380
gaagcaagtg tagagaaatc ccaggaaacc tggaggagcc agagacaagg cattagaact  139440
cctcgtcgtg acctggtctg cattctctga gtgtgctgct tctgttagct cgcttccttg  139500
gtctcaggtt atagtttaag gcattgtgga gccctaaaaa gcctgtactc tgttttacc  139560
tgttttagga cccctttcact ttggggatgt gttgattttt ttttttttt ttttttttt  139620
tttgagatag agtctcgctc cattgcccag gctagagtgc agtggcacga tcttggccac  139680
```

```
tgctgccct   gcctcctggg   ttcaagcaat   tcttgtgctc   ccgcctccca   aatacctggg   139740
attacaggca  cccgccacca   cactcggcca   atttttgtat   ttttagtgga   gacagggttt   139800
taccatgttg  gtcaggctgg   tctcgaactc   ctgacctcaa   gtgatctgcc   caccttggcc   139860
tcccaaagtg  ctgtgattat   aggcgtgagc   caccacaccc   ggcctgaaat   ttaaatcaga   139920
aataaaattt  tgatcccaac   agtgatgcca   ggcagcccag   atctggggga   gagggtggcc   139980
ttggccagct  gggcctttct   ctgtttccca   agtcttgctg   cctctccctg   ctgggctttg   140040
cagcctgtgc  atgtctctgt   gcctttgacc   ttgtttatcc   aaaggagagg   atagaatgaa   140100
gtcatgattc  ctggagccct   gagaaggatg   ctgtggagaa   atttgccggt   agaatctagc   140160
tgagtgtgtt  gctgaggtgc   cagcattgtg   tgtggggagg   ctgaccgctt   ggcctgccta   140220
ggcccaggat  gctccatggc   cgggcacaga   ggccacttgg   ctgtcaggtg   tcaggagcct   140280
gcagagggca  cacagagcct   ggaccgcagg   ggggtcctgc   tttctcacct   ggcctccttc   140340
agcatttctg  tccctcagtc   cttagcaagc   ccaggagctg   ttgagtttgg   caggtgccga   140400
gtgctgttcc  tgcctgtgta   gctgtggctc   agtcctgtgg   gggccccgct   gtggcccgag   140460
tgcagtgatt  cgaggcgctg   agtgttccct   gactccttct   ccaggagctg   tgttcagact   140520
ttcgcagctc  ttggcttgga   gctcctggag   ggcttggcat   tgccgaccaa   tgtggaggtc   140580
gacagtgaga  gaggaggaat   gctagctttc   ttgaccagtc   cattaaataa   gtgggatatt   140640
ggccaggcac  ggcggctcac   gccttaatcc   cagcactttg   ggaggctgag   gcgggtggat   140700
cacgagctca  ggagttcaag   accagcctgg   ccaacatggt   gaaaccccct   ctatactaaa   140760
aatacaaata  ttagctgggc   gtggtggcag   gcgcctgtaa   tcctagctac   ttgggaggct   140820
gaggcaggag  aacagcttga   aaccggaagg   tggagtttgc   agtgagccaa   gattgcgcca   140880
ctgcactcca  acctgggcaa   caagagcaaa   actctatctc   aaaaaaaaaa   aaaaaagtag   140940
gatatctgtt  tctgcttaga   aaaatcagaa   ttttctaaat   gccaggtgtt   ctgaatacgt   141000
aagtatggga  gacgactcag   cctgtttcat   ttttatgtaa   aatcttcgcg   tagccatgtg   141060
gcactggacc  gagatgaaag   caaagacatt   tctccttaac   tttgtttcta   ggaatgttcc   141120
ggagaatcac  agcagctgcc   actaggctgt   tccgcagtga   tggctgtggc   ggcagtttct   141180
acaccctgga  cagcttgaac   ttgcgggctc   gttccatgat   caccacccac   ccggccctgg   141240
tgctgctctg  gtgtcagata   ctgctgcttg   tcaaccacac   cgactaccgc   tggtgggcag   141300
aagtgcagca  gaccccgaag   taggttcata   atgccccaca   gcccagggcg   ccagcccagc   141360
accctgtcct  gagactccca   gtaacctgag   ctttggccac   cgttaaagca   ttttcatttt   141420
ccattttttg  tgagggcttg   tgaaatttct   gctgcatatt   aatattcctt   tcatggacag   141480
catattattg  ggacaaacat   gcggtccagc   taaaggcatt   caaaatagca   gttgcttct   141540
aaatgcgatt  ttctttggca   ggttctttga   caccattgca   tcttgtggga   tatgcttgtc   141600
atgctctgtg  gctcctacta   agttctagtc   cttaaattgg   ttccatagcc   agacatgttg   141660
caatgtctta  acctcattat   aaagtaaatg   tggttctggt   tatccttaga   taatgaagta   141720
acagtgtagc  aaatttcaaa   acctcttgga   aatgttattt   taccattcaa   aaaggcttac   141780
taaggttctc  gttatgggtg   gccctctttt   tgcaaaaggt   tttcaggctt   aagctccatt   141840
tctaggtgct  ccaacactcc   attatttgta   tatgtatgga   aataaaagct   gtgaccaccc   141900
ccaaccctgg  ccccgccca   gctgaatcct   cagcacagta   tttctggaag   gctcaagatc   141960
ccacgctggg  gaaagaagt   tctggagaca   aaagagggca   ggtgctgccg   tgcctctctg   142020
```

```
ctcagtatgg atactggacc ttgtgctgcc agggctccca gtagggccag ttcatggcac   142080
tcagctggaa agtccactgt tgggaggcat tcttaaccat ccactctgtg ccgtatgtag   142140
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttttgtaa atgtaggtaa attctgtgac tgtttcgtga cccctctga   142560 tccagttttc ctttataacc ttctgtattg ttccttctat tatcctgaaa taacattaat   142620
agattaggct gggcgtggtg gctcatgcct ataatcccag caccttggga agccaaggcg   142680
ggcagatcac ctgaggccag gacttcgaga ccagcctggc caacatgatg aaatgctgtc   142740
tctactgaaa ataacaaaaa ttagccgagc atggtgacag tgcctgtag tccctgctac   142800 tcagaaggct gaggcgggag aatcgcttga acctaggagg aaaaggttgc agtgagctga   142860
gatcgcgcca ctgcactcta gcctgggtga cagagtgaga ctccatctca aaaaaaaaaa   142920
aaaaaaaaaa aaattaatgg atcaatggat ttttaaccta ataattaaat ttcaaaaaat   142980
atcgttcttt aatggtaatg taaaggtaaa attaagataa tatgtaacaa gcatgtgagt   143040
gtctaaggtg tccccgtggt ggaaggaaaa aataaatccc cataagtgtc caagatgccc   143100
atagagagca gagctgttct ggtttaaacc cctgctctta gcactgtgtt tttccagctg   143160
tgggtggtgg gggatgagta tctttttatt tccatgagat gagaaaaatg aattactaga   143220
agtgtgaaat acaaaacaca gctgctcttt ttttagccat agactcagca gccataaaat   143280
tgctgtatcc agttgcagaa attcctgctg cttactcttg accctctctc ggtttgtgtg   143340
catctcctct caggctggct cccagatggg agctggctcc aggcgacact gggtgctctg   143400
ctccaggagg tccttatgtg ggtcctgccc tagcctagcc cctctcttat ggactctgtc   143460
actgtgggtt tatgattcac tctcaatctg tcttacctct tggtgaactg ttagagtcct   143520
gcctatactt tggcgcttgt gggtgtgttg tggtacacat gatgtgttgg tcacttccca   143580
gctcatcttt ttctgagtca ccctagattt gggacattca ttcgccacca gtaccggggcg   143640 gtgtatggcc tgagatttgg gggggcttgt gctgctacaa attggggctg aatttgagtt   143700
gacagtggac cttctttatg tctactgctc atatttgaat tgcaaatact gcctcttctc   143760
tttcagaggc tcattaccct atagctgtat tattgcaaag tgcacaatta cagcttgagt   143820
gtaagtcaca ctgcgctggc aggacggccc actgagaaag gcacgtttc ctgttcgtta   143880 gttttcacat tgacacataa tttacaatac agtaaaatgt acttttctat caactgtagt   143940
cagtaacagc ccccctcccc caaccacatc aagatataga ggagtgctgt cacttcaaac   144000
agttccctct tcctctgcca catcctgccc ctccccaggt ctaaccacca atccgtgctc   144060
tgtccctctg ttcagcccat tgcagaaggc catagaaata gaatctatag gctaggtgtg   144120
gtggctcatg cctgtaatcc cagtattttg agaggctgaa gtgggaggat gacttgaggc   144180
tgggagttca agactagcct gggctgccta gcaagacccc atctccagaa aaaaaaaatt   144240
taaaaattac aatcacgtcc ctgtagttca gctgcttggg aggctgaggc aggaggatca   144300
cttgagctca ggagttagag gttacagtga gctatgatcg tgccactgtg ctccagccta   144360
ggtgacacag caagacgttg tctctgggga aaaagaaag aaacggaacc acgcggtgtg   144420
```

```
cagccttctg agtctggccc ctttcggtga gcagtgtcta aagttctgtc gcgtgttgcc    144480
cacgcgtcgg tggctcgctc cttgcaactg ctgagcattg tatggctagg ctgtagtttg    144540
ttttcacttc accagttggg aaacagagaa aaggcactt tta aaaagtt taaatctgta    144600 gaattttggt ttttaccagt tctcttctaa atcctgaggg attacaggaa aagttgtgt    144660 atttcagaat attcttagct tgatgtgacc tctgtccccg ttaaggccct ttgccgcaat    144720
gggaaggacg tcgctcggtc agccctgaa ggtcagaggg gcagtttggg agtgtgtcaa    144780
cattttaact gtatggacta gagccaagag tctcaaggtt tataattccc acgtattcaa    144840
aaagaaaaaa acaataaagt gagaagtcag tgtagagtga ataacctgt gttagtgggg    144900 aagaagtgtt tttaaacagg atttccataa cgtataacat caacatgttt agagtggtga    144960
tgtttcattg ggaaacgaac agtaaaacat gaaagcaggg aggttttcat tctggcagtt    145020
ggcaactttc acggcagatg gagaatttca aaagcaattg ctcaattatc aaacatagcc    145080
agtgtgagtt ctgaaataaa ggtgctgatt gaatgtgcag ctttatgtg gattttgcta    145140 ttcaggcaag catttaatt ttctgcctgt taaattctgt tttctttagt ttttcatatg    145200
tggttaattg tagcttagga atagataact gagagtatat attacacata caacatctg    145260 atatggcaat attaaaaca acttgtctgt tttagaacta gaattaaaca taatcatctt    145320 cagtatttg caaataagct cactgccatc cagaaacatt gtcaatgcat ctgttgctcc    145380
ttctagaaga cacagtctgt ccagcacaaa gttacttagt ccccagatgt ctggagaaga    145440
ggaggattct gacttggcag ccaaacttgg aatgtgcaat agagaaatag tacgaagagg    145500
ggctctcatt ctcttctgtg attatgtcgt aagtttgaaa tgcctgtaaa cggggttgag    145560
ggaggtgggg accaggagaa catcctgtgt agatgacact tgcatggacc ctctggaacc    145620
cagaccgccc ggtgtcctgc caagctccat cgaaactaaa tctagaatga atgtttactt    145680
ctgctgtgac atataattgg agaccaggcc tggccttcca gtcactggat tctaagttgg    145740
actgtgagag tttttgcagc tgactcattt atcaaatgcc cggctattgg ctcacgccta    145800
catgatgctg ggtatgtttg ttaatttgag ggaagcaatg gaataataat aactaatgat    145860
ttaaaaaaca aagtaagtgc attgactgta gtggggttct gatttaaat tttttaaaa    145920 attaatacca ggagcagtgg cttatgccta aattccagca actcgagagg ctgaggtagg    145980
aagatcactt gagcccagga gtttgagaca agcctgggct atggtgtgag acacccatct    146040
ctaaaaaaat aaaaaataaa aaattatcca agtgtggtgg ctcgtgcctg taatcacagc    146100
tctttgagaa gctgagggcg gaggatggct tgagcctggg agttcgagac cagcctggca    146160
acacagagaa accctgcctc taccaaaaaa agaaagagag gaagaaagaa aaattagcct    146220
ggcgtggtgg tgcatgcctg tggtcccagc cacctgagac actgagaagg gaggattgct    146280
tgagcccaga gtttgaggc tgcagtgagc tgtgactgtg tcactgcact ccggcctggg    146340
tgacaaggcg agaccctgc tctaaaataa tttttttaag ttaatttgta gaaaggtgt    146400 tagatgttct ttgtcacatt ttatgatgga ttcctgttta aatgccgttc tctttaaaga    146460
aaaaaaaata acttgtggga gtttttaacc ataaaactag catcacatat ttaccatgga    146520
gaatttacaa aaaacaaat aaacggagga aaataaaacc tcctgtaatc atactactca    146580
gagataactt gctgttagat tttggtctag atttaatact ttttctatat ttatattaaa    146640
aatatttaaa acatatgcat ttctttgtca caaacatggt atcttataga tactactgtc    146700
acatagcaaa acagtgttaa atattctgaa tcagaaaagg aagccgactc tccaactgaa    146760
```

```
agaggtgtta tcctagagac ttttctggt gatgacaatt tattaatagt cactttttgc   146820
tttactttct ctattgaagt agtttttcta ttttgttcta cttttaagga taatataatt   146880
tataatgctg tttttcacag aaatataaga aaaagatac taattttata agttaataaa   146940
gtttgatcat cccaaatcca aaaatctgaa atccaaaatg ctccaaattc tgaagctttt   147000
tgagtgctga cattatgttc aaaggaaatg ttcattggaa ggtttcagat tttcggattt   147060
agggagctca acaaataagt ataatgcaca tatttcaaaa cctgaaaaaa atcctaaatt   147120
cagaatactt ctgatcccaa acatttcaga taagggttat tcaacctgta ctgtcagatg   147180
atcccaaatg aaaatattta atcgttaacc aaatatcaag gaattgatca cattttacag   147240
tttctgccta ggattatgaa tcaagatgaa aaggctctgc atgttaaaa atatatattt   147300
ttattttctt ataaatctta aatatctaca cttaagattt atttgatatg tgggatccat   147360
tcatattttg gattcaacag ttctgtcaaa actgtggcag tgataggga ttctttttt    147420
cccactgaac tatcacaaaa ttggaaaaag agtaattgga gaaccccact ggcttagccg   147480
gcccgaagcc cgggagaggg caggcagtgc tgtggatggg gtcatcccag cgcaacgctg   147540
cccctgctac ctgcggatct cgctgaggcc tgccttgtc ctttgacct tggccatttg     147600
ttagtgtctc tgagagctgg actgctgtac cctacttccc cagggggcct aacttcacac   147660
agcctctgcc gcagtgcgtg gttggaggtg acggccttgg taaatcgagt ttcctacctc   147720
ctcaattatt tgtgctcata cactgtatat ttttagtgag gttatatttt gggatgtgtt   147780
ttctccttct taccctttct ggcctttcta tggcattaat acctggtctc ttcttgtgta   147840
cttgaaaatg aatctctcat catatttttc cttagtgtca gaacctccat gactccgagc   147900
acttaacgtg gctcattgta aatcacattc aagatctgat cagccttttcc cacgagcctc   147960
cagtacagga cttcatcagt gccgttcatc ggaactctgc tgccagcggc ctgttcatcc   148020
aggcaattca gtctcgttgt gaaaaccttt caactgtacg tcttcatcct gccgactatt   148080
gccagttgca gttttccctg ccttaaaaat ggagtattga aatttttaac tttaatttct   148140
gatttgcaaa atagtcatct tttgttcttt tccttcttgc tgttagccaa ccatgctgaa   148200
gaaaactctt cagtgcttgg aggggatcca tctcagccag tcgggagctg tgctcacgct   148260
gtatgtggac aggcttctgt gcacccctt ccgtgtgctg gctcgcatgg tcgacatcct    148320
tgcttgtcgc cgggtagaaa tgcttctggc tgcaaattta caggtattgg gaagagaaac   148380
cctgatattg atttatattg aaaatttagc aggccaagca aaacaggtgg ctggcttttt   148440
cctccgtaag tatggtcttg acatggtcac cgatagaaac atggaaacat ctgcaaactt   148500
gccgttactc gtgtgtccga tctgactgtt tcttgtattt ttttctagtc tgcccttact   148560
aggatgaact gtacacatca gttcatcctt tttaaatgag catgaggtta ttttgggttg   148620
ttaggtgtta caaacacact aatgtgtttt tgtctattag agcagcatgg cccagttgcc   148680
aatggaagaa ctcaacagaa tccaggaata ccttcgagc agcgggctcg ctcagaggta     148740
atgctggaaa cacaggtcgt ccttgtgtta ggacaaccca ggatataaag gatatagatt   148800
tgtacgggaa taaattcaca ggacaagaaa tcgatgtgcc ttataggtgg gtttactgca   148860
gaagtgccat aatagaacct tcctactttt aaaacaacca gatctcactt tctaaagagt   148920
aaaggatgac cggcaggatc acgtctgtga cgtgagtgga ggcagtttgc actcctggtg   148980
gctgttttgag aggtagcatt tagaatgcct gtattcactg tcctgtgatg agtgggaaaa   149040
taggttatca ggtttatctt agcaaaatca aagcatgtca tctaattgct aaacaagagt   149100
tggcaaatct gagagacatt actcaatcct tggcatgcag gacttacatc tgcatcctgt   149160
```

```
tgccatttta tgtcttcaaa gcatttaatc atttagttgt gtttgcaaag tctttgagaa   149220
gcctttgtca gaaatcccta catctcctat gtgagtgtat ttccatgact gcagaataag   149280
ttaaactttt accttttttcc ttcccttgcg gggcggggtg gggggcaggg attgtgtgtg   149340
tgagagggag agagagacag cagagaagga gaatataatt atcatgctgt gtactttgag   149400
ctgaaactgc aaaaaaggaa aaacacacaa aaattattat gcttttcagt ctttagagta   149460
ccttgtctat tatgcttttc agtctttaga gtaccttgtt gatggtgttt ttaaatggga   149520
ttgggcacaa ttaggtggac agtttgggat gattttttcag tctgtagggc caagctcttt   149580
tgtaatttgc attatgaagt tgtcactctc atagcagatg gcgggagata aactattatt   149640 acttttttgac cctagactta gtcttcagtc cagatgaggg agattaaaag attataaata   149700
tcttgtgcca gatgaggtga ttttatttttg aaatgaccat gaattcctat cagttgtctt   149760
actgggatat ttgatagtgg aatttgtgca tttgagtctt agatgatctg ttttacattt   149820
attaagaaag cctttattag ctttttatact gtgtattgcc tgttgcagtg tttgagtata   149880
aatgaaattt ctggaaaata ttaatggagt acaaactgtg atacttaaaa gtaaactagg   149940
gcctgcattt gtatcatgac ctgtttgagt attgatgaga agtagctgt gaagaaaaag   150000 gtttaaacaa gtgtattttc ctttaagaag ccactaatag tgcatctcct tagagtgtat   150060
atttctagaa tcctagtgtg cagagtttag actaagacta aaaaaaaaaa aaacaaatt   150120 atactgtaat ttcatttta tttgtatttt agacaccaaa ggctctattc cctgctggac   150180
aggtttcgtc tctccaccat gcaagactca cttagtccct ctcctccagt ctcttcccac   150240
ccgctggacg gggatgggca cgtgtcactg gaaacagtga gtccggacaa agtaagtgtc   150300
cagcgtgtct gcatgggagg cacagggcgc tgagtgcctc tgtcacctgt ggcagataca   150360
gagagtgcag aggaggtgcc gtggacccaa ggagttctgg cgctcggctc ggctcagtga   150420
agctgtggtt agagacgtgg ggggccatca aggtctgagg gagccaagca gtgctgatgt   150480 gggaccctttt tggtaggagt gtggggtgag tagttagtgg gtgaatcaag gaatagtcgg   150540
ccgtggcctg caggcccctg actgcacagg ccttcaagca catgtcaatg ccgttagcct   150600
ccctccatct cctcatacct tctggccacc tgtgagttgc actgccactg ccagccattc   150660
tggtatgttg tcagcacctc cactgctcat acctcatggt tagggaccac ctggagcctt   150720
ggtagagcct tggtagagcc ttggtactct actttcctgg acaaagttca gcttatgaat   150780
atgaatttag atttcaaaaa ccagcagccc aagtataaga agcgaaggt tcagtcctgc   150840 cttcttaggc tctattcgct aagcacctgc cctgccctgg ttgctgggga gatgagta   150900 aagcagacaa cccaggagag gatggcaaag gggccgctaa cccttagtgg tttagctata   150960 tttgaaggc ctattggaag ttcaccaggt gaagggggag gctgtgaggg tgcccaggca   151020
ggtaacagaa gtccaaaggg gaaaacctgt ggtgtggtga gccgtatagc cacagcctgc   151080
cggccggcag ccctctcagc ctagtgcggt gttcccaagc actggcctag gcctgtagct   151140
ccagggatgt gaagtcccct tgaacgccgc ccatcatgtt cccttatcc attttttttct   151200 tcccaggact ggtacgttca tcttgtcaaa tcccagtgtt ggaccaggtc agattctgca   151260
ctgctggaag gtgcagagct ggtgaatcgg attcctgctg aagatatgaa tgccttcatg   151320
atgaactcgg tacgggggga gcagtggagg caaggaatcc tcagctttc ttgtgacttc   151380 caagtggat ttgtctcatc atcatgtgac ccacttgttg acaacacatg ttggggactc   151440
cagtctgggc agggacggga tgtcggagag actccactct gaatgggcc gggaagtggg   151500
```

```
gaggactcca tttcagatgg ggtcgggaca tgggggttat gctgatcgag acagaaaagc  151560
acattgtttc agccacatta gaatccacgg aggtgttgtt ttgaaatcca gctggcccca  151620
aggctgggtg tatggtttgg gatgagaact atctggcctc cactggagga acaaacacag  151680
gatgttatca tctaagctcc atggccaaga cagaatggaa gtcaaggttg cgtatttgcc  151740
gtagacttca acacagtgtc gtaatgcgtg acgtcaataa cttgtttcta gtgtcttgga  151800
agttgatctt tagtcgtaaa agagacccct ggatgcagcg agatttcctc tactcacacc  151860
tctgttagat gtagtgaggt tcttcacccc ccaaccccag atgtcagagg gcaccctgcg  151920
cagagctagg aggccatgca aagccttggt gtccctgtcc ctcacccgtg ggcaggtcct  151980
gtgagcagtg ggggggccac ctcttgggta tggtgcagcc atggcccaag cagggcttct  152040
tctcagacct actaggacgg gagaaacctc ctggtgcttt agccctgcgt tgatatgcag  152100
caaatgggag ggaagtgggc acctggagg acaaatgcct gtagaggccg ggagtgacgg  152160
caggtgttca tgaaaagaga ccttgtgggg agggcaacac aacagtgtgt tctgatgtac  152220
tgaagagctc aactgaaaac aacaggagaa ttagcccaaa atccatttac taaaattgtt  152280
tatctttttt ttttttttttg agacaaagtc tcgctgttgt cccccaggct ggagtgcaat  152340
ggcgctatct tggctcactg caacctccgc ctcctgggtt catacgattc tcctgcctca  152400
gcctcccaaa tagctggtat taacaggcat gcaccaccac gcccggctaa ttttgtatt  152460
tttagtagag acgggatttc accatgttgg ccaggctggt ctcaaactcc tgacctcagg  152520
tgatccgccc acctcggcct cccaaagtgc tgggattata ggcctgagcc accacgcccg  152580
gcctaaaatt gtttatctta agattcatgc agtgaaagct aacttactga gtgataaatt  152640
tgcttagtga tctgtttatt aggttttcca aatttgctaa ttgggctttg aacagctgta  152700
aaagttctga ctgtaaaaga aagcttcaac ttttggcatt catgatgctt ttctgagtat  152760
taaactaaga tagatgtttt acctgaagga tcggccacca atctttaaat ggctaaacaa  152820
aagggttgct aaaacataat ccaaattgac ataagaaata ccattttttcc aaccaaaatt  152880
ttggcattca tatggctact tttacgtatt tcagctgcat ttgaacatct ttttcaaact  152940
ttagggtggt tggtgtatca ctgaggtctt ggatgcact ttagctttga ttttgttttt  153000
atgaattaaa attgtcatac caaaatttt atttcaagca aatccaagag cataaaaaat  153060
taaaatatta cttaaaatac taagagagaa cagatatata ttttactaag catatgttga  153120
atgaaattgt tcaaatattt ataacaggca tagagtagaa ttttcttaaa aatatttttg  153180
atggtatacc aatttgtatt ttctcagaaa catttgcctt attctttttt ctgttgtgtt  153240
tttcttacct gattgaaagc tcataatctg ttgttattgt ttgttaacct ttaatgctct  153300
gatttcagga gttcaaccta agcctgctag ctccatgctt aagcctaggg atgagtgaaa  153360
tttctggtgg ccagaagagt gcccttttg aagcagcccg tgaggtgact ctggcccgtg  153420
tgagcggcac cgtgcagcag ctccctgctg tccatcatgt cttccagccc gagctgcctg  153480
cagagccggc ggcctactgg agcaagttga atgatctgtt tggtaattaa aattaaaatt  153540
tatcttattt ttaaaaagca ttccagggcc agtatagtac tttgcaccaa gtaaatgtac  153600
aataaaggca gtggatctaa tacattgaaa gcgtttacag aggtagctaa agagcagcac  153660
gggtgtcctc ggctcagaat ttcttcctgt gtgtttgcca ctttgccatt cattgacatg  153720
gtcatggaca tagggctcta agcccttgag gaaggctggg ccagacctca ggggagatgc  153780
agccccaaac cacgtgcagt cctgtggacg gatgtgtaga tgtgccactg aggaacaatg  153840
tcttgagctt tcatcagatt ctcagagaat tgcttgactg cctttcgaag ttgatgcatc  153900
```

```
tgtgctcacg tttgcaccca cccacgaggt ccttctgttt cagggatgc tgcactgtat    153960 cagtccctgc ccactctggc ccgggccctg gcacagtacc tggtggtggt ctccaaactg    154020
cccagtcatt tgcaccttcc tcctgagaaa gagaaggaca ttgtgaaatt cgtggtggca    154080
acccttgagg taagaggcag ctcgggagct cagtgttgct gtggggaggg ggcatggggc    154140
tgacactgaa gagggtaaag cagttttatt tgaaaagcaa gatctctgac cagtccagtc    154200
acttttccat ctcagcctgg cagtaagtct tgtcaccgtc aagttattgt agccatcctt    154260
caccctcacc tcgccactcc tcatggtggc ctgtgaggtc agccaggtcc cttctcatc    154320 tgcacctacc atgttaggtg gatcctaatt ttagagacat gaaaaataat catctggaag    154380
tactttatgt cttaagttgg cctggacatg tcagccaagg aatacttact tggtttgtgt    154440
tagtgcttgt aattcgcccc cagaatgtgt acacgttctg gatgcattaa agtctggcct    154500
gtatccttaa agggccatcg ctgtgctgcc tgccctcagc aaggacacac tttgcagacc    154560
cacagaggct ccgcctccac ctcacaccaa agaaagggag gagtccaaag ggcatcagtg    154620
ccattactca caaaatgata aatacaccct tattctgaac cacgtggagt catatggttt    154680
gtgatccctg tccttcaggt ttcagcttag tggggaagtg ggaaagtcag cgtgtgatca    154740
cagcacaggg tgattgctgc tgattatatt atgtgcctgc tgtatgcagg atgaaatact    154800
ttatatgcgt catcttattt gactctcaca acccccgtgt agataggctc tgttactccc    154860
atttgacagg tgaggaaagc aaggcttaga gaatttcagt gacttgccca ggtcctctga    154920
gctaggaagt agccattctg gcatttgaac ccaaggcctg ctatccctag aacccacgct    154980
ctcaaattca acctatgaca gaggcaagcc ctggtgctgt gggagcccca aggaagagcc    155040
tctggcctgg tggccacgta gcccaggaga gatttctaca ggagcccaca gcgctgaagg    155100
agagagaggc agcagagtaa gggggctttg tggcagagag gggactggca ctttgggaa     155160 taggtgggtc aggactgaat gtaatgagc catgtcagag ctgtccttct ggaagggcaa    155220
gggcacctgg acgcgctgcc cctcagtgct ttggacggtt ccacaactgt gattcacacg    155280
gcttccccaa acgaaggtac acgagtgggc attctgtgac tcggtacttc cctttaggcc    155340
ctgtcctggc atttgatcca tgagcagatc ccgctgagtc tggatctcca ggcagggctg    155400
gactgctgct gcctggccct gcagctgcct ggcctctgga gcgtggtctc ctccacagag    155460
tttgtgaccc acgcctgctc cctcatctac tgtgtgcact tcatcctgga ggccggtgag    155520
tccccgtcca tgaacggtgg gttcctatca tagttcctgt ctgcttcacc atgttttat     155580 tttgtgctgc ctgtttgcca ggtactaagc taggaattgg ggatggagag gtagataaaa    155640
tatgcatcag gaagggctgg gccccatctc ttactctcca atatattgga gtctacactg    155700
gaatttaact ggaatttgct tttttagtca ttttatttag attttgaagt ttcagctttc    155760
atcaaaaata cctctaaact ttatgtctct gtgatctttg gtcttagctg ttttatgtat    155820
ttagtcttat atgatcataa gattaataac attacattca gaagattatt tgttttctgt    155880
cagagttaaa atgtttgttt ttatactgca ttgtaatatt aacgtactgt aaaataaaag    155940
tggcttgttc ttttcaagga acagtatcct caacaagggt cattagccac aatttttaaa    156000
aaattggacg tcatagttta catgttagag ggcgttttga agcttgtat ttttaaatta     156060 aatgttatag agtgatgttt tcatgtttca taattgtttt catctgtgca tttgtagcca    156120
acttgaaaac aaagatccag ggattactac ttaaaagcca gacttcttgg aggttatagt    156180
gatgattttg atagtatctt gagccgtctc ataataacct cagggtgaga gatggccaac    156240
```

```
aggagacagt cgagggactt agaaatctga atgaaatctg aagttcaaat cttcagacat   156300
ataccactaa ccaagagatt ggtacctcag tctagtattg tctgtttgtc taaaattggt   156360
tctaaggaat ctaggctagt ctgtctatcc ctttcaactt ttgtgaggct gcacaaatgt   156420
aaaatgttga ataaaaagca ctgatggaag tgtgtagaaa ttcttctctt tgttctgttg   156480
taattttagt tgcagtgcag cctggagagc agcttcttag tccagaaaga aggacaaata   156540
ccccaaaagc catcagcgag gaggaggagg aagtagatcc aaacacacag agtaagtctc   156600
aggacccatt tttttcttac atgttgttcc tccaggactt aaaaatcatt cacagagacg   156660
tgcaccgcgg tgagtgtgga ctcctggaag cgcaccgtag ctccgctgtg tcctgctgct   156720
cctccctagc tgtcagggag gctgtagtcc attgctttgc cagctctttt gtttccgagt   156780 gaacaccttta tccgtacaca tgcggctgtc tctgaccct cagaccagct gggatgccac   156840
tgggggagcg ctcccttccc cccgcacttc ccacactctg cagttattct gagatccttg   156900
agggcaggga acaggtttgt cttctttgtg ttctcagaaa ttaatgctcg gcctctggtc   156960
agcaagcaac aaccttttgt tgagtgataa tgaataaata aatgtttccc acatgagtat   157020
tcagtaacct cagtgtcagg ttcagccatc tgttttggtg gatatttaaa agaaaattcc   157080
gcttttccta cagaaaaaaa aaaaaatcca aatcccagtg atttaagcca gttatagact   157140
tagacatata ctacggcttt tcatgcactt tcctcccaat tctagagtag gtattttact   157200
aggaaaatgg tggcagtgcc tgttgggagg aagattcttt ggccaagtgt cttttgttct   157260
tgccagggcc cctaggctgc tggggtgctt cagcttcttt agcccagtgt ctggtgggga   157320
atggcccctg ttgcctgtcc cacagaggtg ggggtgcctc acctggagcc tgtccacaca   157380
ttttacacag cacgcttacc tggagcatca ggcatctttt ccatgctctg tggctcagga   157440
aacacgcctt tcaatcatg agtgcaccag tgcttttggg cttttctcc ccgcttttgt   157500 gcaatcctgg ttgtggatgg agttttcctg tctttagtct tctgcatagt acttttctct   157560
tctggttccc ggttcaaggt tttgtaatta gagaatgacc cagaagcaat ggcatttaa   157620 tgcacagcca aggacttctc tgaatttgta tctcaaacct ctgtgggtcc ttcaggcttc   157680
agtttgtgat ttcatgattt cttgttgcta cctaaggaat atgaaaacac ccacctccct   157740
actctgcatc ttccagccga gtggcacctc aggctgtgga tcctgtgctt ctgtggtgag   157800
gataagaata gtgccaaccg tgtggattga aatcaatcag ttaatccctc catgtaaagc   157860
acctggaacg gatgacagtc ttgttatgaa tactcaacaa atgctatcat gattttagt   157920 tagatttcca ttgcttaaa acagttgaga catcttggcg gtttgagtta gagcaacggg   157980
ccctgaagtg ggttctgttt gggtgaagat gattatgctt attccccatg gccctcttta   158040
ggcaagagtg ggaagctttc tttgtttttt taatcaccctc gataggacgt tacttcttaa   158100
aggtcatcca ataaatatta ataggccggg cgcggtggct cacgcctgta atcccagcac   158160
tttgggaggc cgaggcgggc ggatcacgag gtcaggagat cgagaccatc ccagctaaaa   158220
cggtgaaacc ccgtctctac taaaaataca aaaaattagc cgggcgtagt ggcgggcgcc   158280
tgtagtccca gctacttggg aggctgaggc aggagaatgg cgtgaacccg ggaggcggag   158340
cttgcagtga gccgagatcc cgccactgca ctccagcctg ggcgacagag caagactccg   158400
tctcaaaaaa aaaaaaaaat attaataaag ccaactcgtt agcgtggggc ttaattgctt   158460
aagtccaatg agaagtcctt ctctatccta ggaagttgcc caaactgtag aatctcgtgg   158520
cctgtgggta atagccacgt aatacacact cactgcctca acaaatcata ttttagtagg   158580
tatgatattc tagactcaag acaccattct gtggatcttc ccaagggtgt gaagtgtcca   158640
```

```
cagcgtctgc cttgggagtt tccatgccca ccagaaccat gccccaagcc cctcaagcac   158700
tctgacctag gaaagccagt gaagcaagga tgacaacatg gcccttttgat actagctgag  158760
ggacagacac aggtcctggg agaccagaga aagacgaggg gcagaggagg tgtcctaaag   158820
gaagtctgag gctgaggagc cacaggatgg cttccagctg tcacaggctg ctgctggcct   158880
tatcacagag agtgggccag agggctggga accaaggcca gagctcaggt tcaggaccat   158940
tccagcaatc ccagcagaaa atggggagaa ttgtatggta taggcggata tgaaggtaga   159000
atctgcaggc cttcagtggc caactcagag tctaagtgga ttccacagtt acagcttgag   159060
cagctggttg taggtcatgc tttctacact gggcatatag gatgtgtttt ttaaaaagtc   159120
ctctcttaac cgttgcttgt ttagatccta agtatatcac tgcagcctgt gagatggtgg   159180
cagaaatggt ggagtctctg cagtcggtgt tggccttggg tcataaaagg aatagcggcg   159240
tgccggcgtt tctcacgcca ttgctaagga acatcatcat cagcctggcc cgcctgcccc   159300
ttgtcaacag ctacacacgt gtgccccac  tggtgagtct gctcgttcct tgcagaagac   159360
caagtacggt gaaaggcacc ggtaggccct gggctgggca cacgtgagag ggcgggacag   159420
aatccccgca gcccagaggc tgcctgctgt ggttctggtg cccactgtgg ttctggtgcc   159480
aggctgcttt cctcaggcac cacgtgtgga ggtcgctagt agaaatactg gttttctaa    159540
aatgaactga ggccctacat ccctaagaga ttagtgttag acctgattct agagcaacta   159600
gaccactttg cttaatagca gaccagaaac cacacccct  cgagtgagtg agattttcct   159660
ttggagataa ttcatgtttt tctacacagt tttgcagttg tcttcagaat tggttttaaag  159720
taggtgttat tgccaggcgc agtagctcat gcctgtaatc ccagcacttt gggaagccaa   159780
ggtgggcgga tcacttgagg tcaggatttc gagaccagcc tggccaacat ggtgaaaccc   159840
catctctact aaaaatataa aaattagcca ggtgtggtgg tgtacgcctg taatcccagc   159900
tactcaggag actgagacag gagaatcgct tgaacccagg aggcgaaggt tgcagtaagc   159960
cgagatcgcg ccactgcact ctagcctggg caacagagca agactccgtc tcaaaaaaaa   160020
aaaaggtagg tgttattgat cagaaccctt gtttcagata acatgaggag cttagcttga   160080
ggagagtgag ggttgatgga gggggactga cttctgccca gtgaaatggc atcatctccc   160140
accagcccgc tgaaataaga tgatggggcc tgttccttag ggcctgcagc atcctcaggc   160200
aggaaagaaa ggccgacctg gcagggtgtg agccagcagg tgtaggtcag ggagaatgga   160260
gccaggtccc agggaagagg cttgtggctg cctgagaagg gtgcgtgcct gcctgtgtgt   160320
gtgtgtgcac gtgtgtgtat gtatgctgga gagtctaggg aggcttgctc caaggacgca   160380
gtattgtttg atcctgagag ataaggattc tgccgcaggg aatgaaggta ttccagatgg   160440
cgggcttatt ccgaagaaga ggccagtgcc tggcggtgct ggaagcagtt gcagaacagg   160500
gagttgtagg cttctcctggg aagagagcag caggggtgct ggagaagcag gccacacttg  160560
ctgcatgggt tgctctcgg ccccactctt ggtgcacagc gagtcactgt gggttcatta    160620
gcatctggtt atgagacagt aactgctcct ttggagggc  tcgtggagac catgcaggag   160680
ggcacggtct tgaggtcatg ccgtccagag cacacctgag gataggccag gacgggctgc   160740
acgtgtagg taaaattcct ccagcaagct cttcactgg  attgaggagt tccctgagtg    160800
cggtcatctg gaaggcagct gtaacaggca ctgcagtctc tccctgggtg gtaccagag    160860
aggagcatag gggagcataa ccgatttaaa gagagggctt tcctgtggtg aggtaagaga   160920
ttagctggtc attatcatag agcccctct  gcctttgtgc agatgggctg tgggaatcct   160980
```

```
ggggttccgt tgggtcctttt gtcacctcac tgaaggcatg taagctgagc tggccagacc  161040
gtgagctgat cctgccactt gaacagcatc aagcctgcct ctggattctt ctgtgcatgg  161100
cacttgtctg agcacctcac gcacagagaa ctggacttca gagtttacag aaataagctg  161160
tatggttcat tttcatgcct gcttgccaat aaacatatct gagctgaacc tcattgaacg  161220
cctgccttta ttctagcaca gcacctgctg tttgtgggcg aggggtgctg tctctaactc  161280
ctgcctgctt ctcccagcac tccctgagtg gggtgtgcca gcagcctcag gatgaggaca  161340
ggaagtggga gggcagagca gatttgggag ggccacttga tggggaagga agtcccagga  161400
agcagttgga gctgttttct gggggagaag gtgccagctc tgggacagtg ttggggtagt  161460
gaggagggag cccagtggag agaagtcggg cttcctgctt cctcacagta tgtctgtcct  161520
gactcaactc ggatgatgtc acttcctttt catcttctca ggtgtggaag cttggatggt  161580
cacccaaacc gggaggggat tttggcacag cattccctga gatccccgtg gagttcctcc  161640
aggaaaagga agtctttaag gagttcatct accgcatcaa cacactaggt actcttgggg  161700
cctctccttc aggtcaccat gtcggacat ctaccgggag gaaatccaga gccccagta  161760 ctgggatctt ctcatttgac tccagaaaag atttaagcat gataataata caaacctatg  161820
tgaatacatt ttgcagtgtt ggcaaaactc cttttatact gagaaaatag atcccagttc  161880
ctgtgttttg tggcttgaat cccagctttg tgtattccgg gcttgtttga agtcaggaaa  161940
ggttcatgtg tagtggacaa cgtgagacca aattctgcct tagattttgc atttaggcta  162000
aacagtggca gcacttgtct cagaatgttt tcttgtgttc accagtctga tcctgttgtg  162060
tctcagtggt ccatttttctc atatgggaac aagcagacgg gagcagatgg agtcaggttt  162120
cttggcactc gccttcccca gagcctagag gcagcatggg gagaaagcag gcttggggct  162180
cagacagtcc tggtctgctt ccagccctcc tacctgagca gcgcagggca agtccgtcta  162240
acctctagag accctcagtt ttgtcatatg taaaatgggg gtcgtgtcta tttcatagaa  162300
ttgttgcaga tttagaaatt acatttctaa acaaatgtta ccccttattt ctaaataagt  162360
gtctaaatga ataagtcacc acttttgccc ctatttgatg gcaagaggtg tgatcttgtg  162420
gtgggactgt aatcagtcag ttctcagtga ctgtgccctg ctgtggtgtt tcctggaatg  162480
ttcctgtctt gtcctagaaa gtctggcagg ggcaccctga ctccactgtc cagtcctctc  162540
cccagtccct cgggcttctg cagatttgag gcttgtttgg atcccagaag gttgtggcag  162600
gagacacctt gcctctactt tcccctttat aattcaatgt ccaaagagag ccctgagcag  162660
gtacctcacg ccagctgcct cacggagctc ctcctcttcc tggctgtgag gatcggtatc  162720
agtggcctcc tgctctctcc cccttgccta acacgagcac ctttgcttac ttgggtgccc  162780
ttgctcttga actgcccatc ggacgtgcgt gacccaagac tgtgccgcag tccttgcctt  162840
gtctgtgctc atttttctttg ttcatttttt tccctgtaac gtaaattgtt atatttgtct  162900
gtatctgtgt ctgaatcagt cctgcacgct ctccttctct ctgtctcttg ttctttcttt  162960
accccgttta tcacggggac cccgatgtcc attgctctag ttctcctgtc ctaagcaccc  163020
catcccgtct ctctggcctt accacaagtg gcgtggctgc ctcagacatc atgatgggga  163080
catgaagcac agctgtcaga aacaactgtt cgttagatac actcgaatgc agctcatcaa  163140
tagggatgga gggtctgtcg gatgtatttt cactgaatcc ccgttcctac cttgatacac  163200 tcttttttaat ctattcttct agacaggtca gaggaaccat tactttgact tttaaatttt  163260
tagcagcttt attgaggtag aattcacata ctacagattt cacccactct aagcggacag  163320
cttggtggcc attagttttta tccacagagt tgtgcagcca gctgcacagt ctcagggctg  163380
```

```
gactccaggg aagattttag cccatttagt gagtggggca gaagtggccc tggccctgca    163440
cgaggttgcc tgcatgggcg tccctgccct gtccctgtgt ctgctccact gggggttgac    163500
caggctgcca gggccgactt gggcctgtgc cacctgcctc tcatgtgtct cggacagtgc    163560
agccgatgtc tatacttcgg tttcctcaat gatgaaatgg aggggatagt gttccccgca    163620
tcatagaact gtgtgaggtt taagggactc actgcccttg gcgtggagcc ttctccaggg    163680
gccgtgctgt gtcggcgtag ctgtcagctc tccgttacag gcttgagaag ggttgacact    163740
ctctcatgta acatttatat ttctaggctg gaccagtcgt actcagtttg aagaaacttg    163800
ggccaccctc cttggtgtcc tggtgacgca gcccctcgtg atggagcagg aggagagccc    163860
accagaagta aggccacacc ctgtgctggt tggcacatgg gcagttatgg ccgcttgcag    163920
gcctttggtg gggaataaaa taaggcagca agctggtgtt cttttttttct cttacctttat   163980 ttttgaaaga gtagctgaat ggtgtcttga ctgatattcc agagcaggga caaagcctgc    164040
tgaggtctgg gggctgcgat taccaatggc tggaatgcat tttattacgg tgcattccat    164100
gttaaggatc aatacgattg tgccctttct ggaaaatatc ttttagttta tcaatattca    164160
gaggagtgta ggttgaatta aaatgaaaag gcactttata aaggccatga gtagtacctg    164220
gtttcatttt tctaatgtct tgcagagatt ttatcaggct tcttgaagtg ttcacgtaca    164280
ttacgctaac acgatattaa taataactgt gctctggtac agcggagcca gcagaatggg    164340
aagttgtgga atgcaggccc ttgattctga tagaaggtgt ggtttgaact cacagaaatg    164400
acagtttgga gggtagacat atgtcacaag tcatcaagat tgtctttaaa ttcatgcata    164460
gaagctaaca gggtgtcata agcaaggcct gtaaaatgta tgagggaatt caaagataat    164520
ttattaaaaa gtaattcatg tttggagttt tgtgcccaaa ggagtccttg atttgaaaaa    164580
tgggcttttg cccatcagat tgtttcaggg cccgtgtgtg cggaggccct gccttgtgcc    164640
ccgtgagctc agcctgacag aaatcctttg gtagcactta aggctcctct tcctcccatt    164700
gaggcaggga agactctggg ttctgcaggc agaggtggtt gtgggtgtct tgctgctctt    164760
gttgacatgt gggctctcct tccaggaaga cacagagagg acccagatca acgtcctggc    164820
cgtgcaggcc atcacctcac tggtgctcag tgcaatgact gtgcctgtgg ccggcaaccc    164880
agctgtaagc tgcttggagc agcagccccg gaacaagcct ctgaaagctc tcgacaccag    164940
gtttgcttga gttcccacgt gtctctggga catagcaggt gctggggaca gtgggttccc    165000
cgctgaagcg tccagcagct tcaaccaggc cgttttcctt cattgctaga attgaaaaca    165060
ccgtccgtgt ggcctgtgca ggagatgcag acccaaaggt ggcctcctgg tcagtgagaa    165120
gctggaaacg tgacaggaac tgacgtgggg ttattgagca tttagggaa gacgttagca    165180 gagcaggaat gagcaggcaa ctagtagaac acccacttaa gggctcacgg acaggtgctc    165240
acttaggaag tgagtttcat ttggtattac accaggttcc tttaggcaaa gcggagggaa    165300
agttctggtg ttttcactt gtaagatttt gaaggaaaca aaacactctt tacctttttt    165360
ctaaaatgta ggtttgggag gaagctgagc attatcagag ggattgtgga gcaagagatt    165420
caagcaatgg tttcaaagag agagaatatt gccacccatc atttatatca ggcatgggat    165480
cctgtccctt ctctgtctcc ggctactaca ggtacctgag ggaaagggtg cggggagcg    165540 gttgtacttg ggctagaatg agagaagact ggcatgctca ccacaccagt gatgcgggaa    165600
gacctgagtg tggtctgagt tggaggctgt ggtgctaaat acgctgcccc tttcataagc    165660
aggagtctta gtcaggccca gggaggaagt aaaatctgga aatgaatgag aagcattctc    165720
```

```
tcctgccagt caagaaatga gaagcgaaag aattctcacg ggctgtaaga ccagcaggat   165780
ttaaaagttg aattagttgc ttatgttaag aactcaacca agttcatcta cacaagctga   165840
atctccagct tttcctaaga aaccatgtgt ggcagtggct gcagggcagg gcacagctgg   165900
gcctgagcac cccgctccct gcacctctcc cctccctggg ccctgcctgt cactgcccac   165960
tctcccacca agccttccgg ttgtgtgcct gccctatcac aggcatcgga gcttgtcacc   166020
tggtttaaaa gaagagagtt gtgtggggat ttgggatgca cgttttttcac tcaaaagtat   166080
tttagcgtag agctctgtga ttccgtagct atttaggagt ttaagcacct tgaaggcttt   166140
aattgcagaa agttctatgt ggacgtgcaa tgtgttatac gcagtgtcta tgagactcaa   166200
atgtttatta gggcgttgaa gtaaactgag cacttggagg gccatggatc cagccttcaa   166260
ggagctcata agtcaggagg acccaggagc aatgacctgt catagaaggc agaaaagagg   166320
ggcacagagg tgggtgggag gcatacacag gcagctcctg gagctccaag gggagcaagt   166380
gcttccaggg aaggggggcgt ggaggccccc ttggaggagg caagttgatc tggggtctgg   166440
cagagggtta gctggggaca tttagcggga ggctggtgcc cgggaattgg ggggatgccc   166500
agcagaaaga catgaggagg ctggcctggg gcgtgggggg gtgtgaaagg ttaagtgggg   166560
gcattatcct gctcccgctc ctgccggctg tatctggtca gctgggcac cgaggtgggg   166620
ttctggaagg cactgttcac caaaatgctt atctgggtcc cccagagagc ttgcctgcct   166680
ggactgtcgg ctcgcctgca actgctgact cctaagcttt tgcagctcag cccacaacca   166740
gttcctattc acagaggtgg gagctgaggg gtgacaagtg actgctgcag tcttatttgt   166800
catagagaaa aagtgacaga gtccagcttg cccactggcc ctgccagctt aactggttat   166860
aaagtgacaa atccccaaga cccacagggc tctgcacaac ctgggccctc ctgccagtgg   166920
cggcgagggc aggtggctca cggctgggtg cctgtctggg caggagctgg gctggtatgg   166980
ggtgggcctg cggccctgcc ccctgtgca gatcaagact cagggtgctg gtgttcacag   167040
gtgccctcat cagccacgag aagctgctgc tacagatcaa ccccgagcgg gagctgggga   167100
gcatgagcta caaactcggc caggtcagtc tcgcgccccc gccgcctggc ctctgtccgt   167160
ttctgtcctc agactttggc gcttgacaca cccaggagaa aagctcagtg cacttttaaa   167220
atgaaaggaa gttttccttt tttttaaaaa aaaatttaat gttcattgtt tttatctgtt   167280
ttattcctag gtcccgcaag cagaggaagc attagttttg ttttttattta tgttctgtat   167340
tccagaaagt agttaagaga cctcacatgt agcgatagag atgtgtgtaa gagacagtga   167400
gagggcgtga cttggactta agcaaggacc gtgagacaca aaaagggggg tgaggacaga   167460
gtggagtcag ctgaaatgct caggaggaag tagacgccat gaagggccat ggtatggggg   167520
gccgcaggcg tggccgtgag tgtccctggg gccagctctt gggggctcc ctgagtgtcc   167580
ctgtccctgt ggccagttct gggtgggagc ccgtgtgca ggcagacagc tcggccactt   167640
cctagcaggt cacattggtc tgtgcttctg tttcctcctc agataagtga agggattcaa   167700
gggtctgggt gtggtggcta acacctgtaa tctataacat tttaggaggc tgaggcagga   167760
ggcttacctg agctcaggag gttgaggctg cagtgagcca tgattgcacc actgcactcc   167820
agcctgggca acagaccagt actctgtccc ttaaaaaaaa atgtaaacag aaacgtaggg   167880
ccatttgcat atgatggcac atggcgtgga gccctacagg tgtatgctgg gcggggcccg   167940
gctgtgctgg ccgacttgca cctttcccct cacccccggtg ctgtgtcttt cgctcaccgg   168000
gttcctgatt tagtgaaagc agttgtgcag gacagttctc tttgtagctt ttgtttctgt   168060
ggaaatgggt cagaatatgg tgtttagaaa cacttatgag ctctgagagt ttcctcttct   168120
```

```
gagttcctgg cctgcagcct tcacagcaga aaccctgtga tgtcacaagc ctgtttctgt  168180
tccctgctct ctgcctgtac tgtcctgttt tgtgcctgcc ggtttcagtg acaggaagca  168240
gggagctact ggaccagcct gtatttttct agacatagtt ggaaaaagaa gtcccactct  168300
tctgtccttt caccttttgac agatgtttcc accccaagat aagtgaaaat gaccaatagg  168360
atgcactgta tttttcatga aagtgtttct gaagggcagg ctgagagtga gaggcctggg  168420
gctcactggg tgcctctggc cttgtcctgg cccagggac actggtctgt gcccgaggta  168480
ttccctatcc ccccaacccc gctgcatttg ccacatcct tcaatgtttg cgttgtgtcc  168540
agcgtccgca aaccaactgt catgggatca tactggggct gaagtacggt cccacccctg  168600
ccctgtctgg ggctgaagta cagtgccacc cctgccctgt ctggggctga aggacagtgc  168660 caccctgcc ctgtctgggg ctgaagtaca gtgccacccc tgccctgtct ggggctgaag  168720
gacagtgcca ccccttccct gtctggggct gaaggacagt gccaccctg ccctgtctgg  168780 ggctgaagga cagtgccacc cctgccctgt ctggggctga aggacagtgc caccctgcc  168840 ctgtctgggg ctgaaggaca gtgccacccc tgccctgtct ggggctgaag acagtgcca  168900 cccctgccct gtctggggct gaaggacagt gccaccctg ccctgtctgg ggctgaagga  168960
cagtgccacc cctgccctgt ctggggctga aggacagtgc caccctgcc ctgtctgggg  169020 ctgaaggaca gtgccacccc tgccctgtct ggggctgaag acagtgcca ccctgccct  169080 gtctggggct gaaggacagt gccaccctg ccctgtctgg ggctgaagga cagtgccacc  169140
cctgccctgt ctggggctga aggacagtgc caccctgcc ctgtctgggg ctgaaggaca  169200
gtgccacccc tgccctgtct gggatgttta gccctagat gccactggac tgagccgcta  169260
cttgcttttg ggaagaggg gtggggtta ggggtctggg cgaggggagt gcaggggctc  169320
ctccttggcc tgagagctgt tcatacagac tcctcgccca ctccctgcag ggtgctgggt  169380 cccaggggg aaatggccct tggtgccaag aacgtgagtt ggggctagtg ccagtgatga  169440
tggagaacag ctttttatgg gcacacagcc cacagcactg tgccaagtgc tcgaggcttc  169500
ccgagaacca gcagaaagg aggacagtcg aggtgtgctg actgcgtggt ggctgcgtga  169560
tctagagcgc gggtcacaaa ggcgcgaggg agctctggcc ttgggtttac cgcaatgact  169620
gccagtgcgg gagactggaa aaggaatctc acgtattggt tccgtgtttt ggggactcca  169680
ttcagatgtc acttaggagt gaaagcatcc cttcgtagag cctctttctg tgtcaccctc  169740
ctcagctgct cctggggttg actggcccct gattcatgcc tttagcatgt gctggagctt  169800
cccagcagct gtccagcccc tgccccaccc tctctgtggg ctcccttgcc cgtaacctgg  169860
ggtgtctgaa cgaccctttgc taaggggcag actgttagac ggtaggcatg tgctgagtcc  169920
cagtggccac acccacccac caggagcctg gcactgtggc cgcagcactg agcagtgccc  169980
cgtttctgtg gcaggtgtcc atacactccg tgtggctggg aacagcatc acacccctga  170040 gggaggagga atgggacgag gaagaggagg aggaggccga cgcccctgca ccttcgtcac  170100
cacccacgtc tccagtcaac tccaggtttt ccaatggcct ttttcttttt aacagaaatt  170160
tgaaatttct tatcagtcat ttgatttgtt tgaggtgctt cttgaaatga gcctctcatc  170220
tcatgtactt ggaaaatacc catctcgcat attccacagg aaacaccggg ctggagttga  170280
catccactcc tgttcgcagt ttttgcttga gttgtacagc cgctggatcc tgccgtccag  170340
ctcagccagg aggaccccgg ccatcctgat cagtgaggtg gtcagatccg taagtgagcc  170400
ttcccattcc cctcacacct gcacgtgcca cacgcaccac acacgccaca caccccacac  170460
```

```
acacacaccg cccacacaca tgccacttgc acacacaccc ctcatgcatg caacacacac  170520
acaggccaca cgcaccatag acaccacaca cacatgccac atgcacacac atacacggca  170580
tgcaccatac acacaacaca cacagcacac atgccacaca cacacgccac accacatgca  170640
ccacacacat gccacatgca cacacactcc acatgcatgc accacacaca cacacacaca  170700
ccacacacac cacatgcacc acaccacaca ggttacatgc acacaacaca cacatgccac  170760
gtgcacacac cccacacacc acatgtatgt gccacacaca gcacacaacc acacacatgc  170820
accacacaca tgccacatgt gcatgcacca gacacatggc acacactaca cacacgccac  170880
gtgcacacac cccacacaca tgtacgcacc acacacatgc cacacacaca tgcaccacac  170940
acatgccaca tgtacacaca tgtatataca caccccacac cacacacaca ccacttgcac  171000
accacgcaca cacaccacat gcgcacacac acccacata cgccacatgt acacaccata   171060
cacacaccat acatgcacca cgtgtaccac gcacccacac agacacagca cacgcataca  171120
ccacacacac acgcacacat gcgtcccgca cagtaatgtc tcttgggtgt aagaacacga  171180
cttgccagta gtagcgttct ggatgcgttg cctggattct aacagcgcga ttctcccctt  171240
gccctcctgg ttttccacat ctccagcttc tagtggtctc agacttgttc accgagcgca  171300
accagtttga gctgatgtat gtgacgctga cagaactgcg aagggtgcac ccttcagaag  171360
acgagatcct cgctcagtac ctggtgcctg ccacctgcaa ggcagctgcc gtccttggga  171420
tggtaagtga caggtggcac agaggtttct gtgctgaagc cacgggggcc catctgcctt  171480
gggacctggt gttggccaga ggtgccgggt gcggctgcct ccttccaaga gttgacccga  171540
accggactcc acgcccacg tgagctgcag tgcttctcag atggagggg ttcagcgacg  171600 gtcagtgcca ttcacaggtc actgtgatgt gggttgtggc ggccaagcca tggtttgggg  171660
tcccgtatcc ctgggcttat gacatcattg tagtagccca tccccacaga accacggtgt  171720
gtggtggcgc tgaggcatcg tagatggtgg aaatgctact ggcttcccca tgctctgccc  171780
tgaggcctga ctgcctcact ccccttctca gttatgttcc aggccccccg agcttcctgg  171840
ctggacagct tctctcctgg gggccgtttt gtcacagtga ccctgtgttt ctagtcccaa  171900
atctgggtgc tatagtctct ttttagcgtg gtggttgtct tagtcttttt tggctgctac  171960
cacaagttac cttagactgg gtaatttata aacagtggaa atttacttct caccgttctg  172020
ggggctggaa gttttcatgg tcaaggtgcc agcagatttg gtgtgtgatg agggctgctc  172080
tctgcttcat agatggcatc ttctggctgg gtcctcacgg tggaaggagt gaacaagctc  172140
cctcaggcct tttagaaggg ccccaatcca caagggctct cccatcatga cctcatcacc  172200
tcccaaggcc ccaccttctt gtactgtggc actgcaaatt aggtgtcagt gtaggagttt  172260
caggagggat agaaacattc agaccatccc agcggtcaag tgttcatcct cttgagttcc  172320
tccttattct gcttctggtt tatcaggatt cagccagtgc agcatggtac ctgtattctg  172380
tggcacatca ccacatggta tttgccaagt atccatcacc tgcacacgtg aaatcattgc  172440
ccgtgggtcc cgacatctgg cgaagcatat tcaaggatgg cagaactgtc agagctggca  172500
cctctggttc cttgtcatgt ggcattacct agtaatccat tttatgatag caatggaaac  172560
tcatttcttc aacaaacacc tgagtggctg ccgtgtgcca gccgtctggg gcccttggtg  172620
agaatggcat ggtggtgccc atcagggcct gcctagcccg tgctctggac gggctcctgt  172680
gtgtcaggaa cgacaatgct gtcatgacgg tgaatgattt ttttttttgc catcactcca  172740
gccgctaaca tttgcggagc tcttcctccc gcaccccac ctgacaaggc caagggtgac  172800 cttggccca ccctaggcgg ccaaggtcag aggttagctg gcttgtctgg gtcacacaaa  172860
```

```
atgcagcaga ggttgaggtg agcacatgtc cgtgacctgg agcctgactc cctctctgcg  172920
agtcttgact gctcttgcct agactctgtc ctccccgagc ccaaacgcca gtcatcttcc  172980
cttgtgggtg tccttcagcc tggtgccatg ctggtgactc agcagccgtc cagggagtgg  173040
aaacaattga gtgtgtgggt tccctgtgtg ggcatctctc ttcacggcga acaccctctg  173100
ggtgttgccc acacgatgtc aaagcggctc ttggaagggg tccttctcct ttgtgggaag  173160
tttcagctgc tgggctaact tgaattgtaa ctgtggtttt gtgctcaggc ccagatcccc  173220
ctaggcaagt gttgtgccat cagtaatcaa atgagaaata atcattttga aaagcagatc  173280
ctaaggcagg atggtcatgg acactcactc ccagctcttt gtgcactcat gctttctgga  173340
agatggccat cctctgtgaa ggttttcagc gcgtcatgct tggtacccac gtatccagag  173400
catgtcgttt tgaggtattt gcccaccgtt gtgaaatccg tgccaccgcga gagcaggtcc  173460 tgatgtgggg ctttcagaag tgggacctgg ggccgtacgc agtccttagg gaggggccgt  173520
gtggcgttgt gcgtgtgagg ggatagcaca gggtgaggtg ggggcccaag aaggaagtga  173580
cccacaaaga acagcctcct cttttggtcc ttgttcctgg gatggctggg agtggcttct  173640
gtgtcgtccg gccatttccc ctgcggagag gctcctacca ctgccgagaa cctcatcatt  173700
ccacaaaaac aagaggccgc ctggccatcc agcgctccat gggaattctg tgtccccata  173760
gtcttgggct gaaggagggt gacattcctt gctgacttct gcagggctct cctcactgtt  173820
aaagagcaga ttgaaagtga agaacgtggg ctaagtgttt aggtcgatat ttaaccctgc  173880
taggttttgg atactaagtg aaattgaggc cattttggtt gaagttgaca gaaaccacta  173940
tcagggatcc ccaagactac cccaggcttt tctagaaaga ctctcagcta agatgtgtta  174000
tggtaaaagc acacaaaaca aaatcagcaa agaaaattag caagggcaga ggcccatggg  174060
gcgatgtccc gaggacacca ggcttgagct tccagaatcc tctcccagcg gggtcgtgca  174120
ggacgcactt aactcccgc acagtgagcc gtgacagcgc gtgtgcagtg tcgtcgccag  174180
gaaagcacac tagagactcg gtgccagggt ttttactggg ggctgggcac atgggcaccc  174240
tctgcctgcc tcgtgcccag actctggact cccggaggga aggcaagttc tcagcaccaa  174300
ccctggtgcc cacacaagca gctgagcaca gggagcccct cctcagtgag gatggtgggc  174360
accgtcccaa caccagccag gggccagcct tgcacacagg cctctcagga tggtctccgg  174420
cctgctgtgt agtctcttct gcacacaagc gtgagggcag cgccccgcc tcggctgtgg  174480 ggaggagcca ctgggacgtg agctctggtg gcatgcagca gcttttgtct gtgtgtgcct  174540
aggacaaggc cgtggcggag cctgtcagcc gcctgctgga gagcacgctc aggagcagcc  174600
acctgcccag cagggttgga gccctgcacg gcgtcctcta tgtgctggag tgcgacctgc  174660 tggacgcacac tgccaagcag ctcatcccgg tcatcagcga ctatctcctc tccaacctga  174720
aagggatcgc ccagtgagtg ggagcctggc tggggctggg gcggggtct cagaatgagc  174780 tgtgaaggaa gcagcatcac cctctccaag tgcccaggct cctggccaga tggcaggcca  174840
ggtatcagtg ggaacccagg tgggtgccat ggctgaggtc agtgagacgc aagagcacag  174900
gtgcgtccta gaggcttcct cgggcacctc cagcgagctg gagctctcgc ctctgctgct  174960
gtctcatgtg gcgcttagca cactctccca cgtgcccatt cctgactctg ctctcgaggc  175020
catcggctct cattctctgc tcccagaacc ctgttattac ccaggctagc ctcctctctg  175080
caccttcccc gccctggccc agtacctccc tcttgtttcc actgtgattc cgacctcacc  175140
ttatcttaaa gctgctggac ggcaggttct gtacacacgt gtccttgaca aagcacggct  175200
```

```
ggtgccgcaa ccccctcagcg agcaagtcaa gctcttcaca gcgatgtctt acaagcgcag   175260
agggctctgt gacaccctgg tctcaccgcc actcttccaa agtcgcagag gctttagcag   175320
agatgggccc agcctctctg agtcataggc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atccccttttg acaagtgggc aggaaacggg   175500
ggctaggtca aagttgagtg gaagacctgg agggagacgg gaaggtctct gtaggcacag   175560
ttcagacagg agggaggtgt gagccagggc acatgccggt ggccgtctgg caggatttgg   175620
gacatgctgg agcagggaca gcggctcatc aggggccatt gccctcatcc aggccagagt   175680
gtcacaagcc cgtggggagg cccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860 tttgggggc agccccagaa caggcccag acacaggcca aagccctgcc tgtgctggtg   175920
tgttgggctg ttctatggct cttgctgtgg gcatggagga ctcagggaag gagagttgag   175980
gtggtccagg agttgcgttt gggatgcaga gagcttgtgg catccaggta gaaatggtgc   176040
gtggggctga cctcagcacc atgggcagag gggccgtgtc acgtgcctcc gaggtggagg   176100
tgggaccacg tggtgacaga tatacgcatc actgggcacg tttttgtggg tgttgggggg   176160
catcgtattg gctcctctgt tcacagtggc cactcattca gtccctggct accaggtcct   176220
cactgtgcca tggggaaggc cggcgctgtc gggggatcac agaaggcagc acgtcatgat   176280
ggcatgtgcc atgaaggaaa agcacagggc actcaggaag tagaggggac tggcctgggg   176340
tgtgggaatc tagggcctcg ttgagggaca gagagaggaa gtgtgtggtg gccagcatgg   176400
aggtggccac aggggaggct gagttaggcc gagagggcag ggcgttgggg aggtagacgg   176460
gctcagccac tcagggagtg gtcaagcaga ggctgaaggg tcaggccagg ttgcaggggc   176520
ctgggggagc cactcagggt aggcgctccc gggagcccgc ctggcccata gctctacact   176580
cccgcgtggg gccggacatg ctgtgaagcc ctctccacgt tggatggggg tggctgagcc   176640
tggatgctgt ctcccgttttt cagctgcgtg aacattcaca gccagcagca cgtactggtc   176700
atgtgtgcca ctgcgtttta cctcattgag aactatcctc tggacgtagg gccggaattt   176760
tcagcatcaa taatacaggt gagtgggccc tggctgtctt cctctgcaca cggggagtgg   176820
gcttcccttc tcttttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc accccctcca tcatttacca   177000
ctgtgccctc agaggcctgg agcgcctcct gctctctgag cagctctccc gcctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaagggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtggctga gctgggctgg gtcctgggca agcaaggggc tgatatcacc   177420
tgctttcaga tctccaggga ctcactggac ccctgtgtac aaagcactgt ctacagagcc   177480
tattgggttg tatagaggta accttcgtac tgaacacttt tgttacagga aaggagaaag   177540
tcagtccggg tagaacttca gaccctaatc ctgcagcccc cgacagcgag tcagtgattg   177600
```

```
ttgctatgga gcgggtatct gttcttttg ataggtaaga agcgaagccc catccctcag 177660
ccgttagctt ccctagaact ttggcctgaa gctgtgcttt tgtgtgtgtc tgctgatccc 177720
ctggcgctgt tgctggagtc ctgccagtga ttccccacca cagcctgacc atgggctgcc 177780
ttggctcagg gttccactgg cgagctggtg gtccttggac cccagcactc aggtgtagcg 177840
ttgaccagtt ccaaggttgt cccagtgcct gcccatctct cctgagggct cagggacagt 177900
acctggcagt tgggggtgtg gcaggggca ggaatgacca gcctctggga gggtggggca 177960
gaagcctgta cagtgaggag gagctggctc agcctggctg cctatcgtga gagggagcc 178020
cacggggctg tgggagggg gccgtggtgc ctgtgagcag ggtgaggagc agcggcagga 178080
ggatgaaggt ggaacccaca catgcatctt tgagacccgt gtggtcagtg gcttctgccc 178140
cccaccaccc cccactgctg tgcgtgcata gaattggctt ccctcacctg ctctggaagt 178200
gggttaggag cttggtaggg ctttttctca aggacaaggg cccctgattt gctctcaggc 178260
ctcagtcctg gcgacatggt ggatctggag ccttgttgca ctgccttgcc tgtgctctcc 178320
aatcagggtg gccagtgggg agccatttgg cttttctcaa gagcatactc aggtggacct 178380
tgctccactg tttgaccaga tgaggcattc tgaacagcca agcctgtgct ggtctgtttt 178440
catgttgatt tttttttttc ttttcttttt gagatggagt ttttcccttg tcacccaggc 178500
tggagtgcaa tggtgtgatc tcggctcact gcaacctccg cctcccgggt tcaagtgatt 178560
ctcctgcctc agcctccta gtagctggga ttacaggcac acaccaccat gcccagctaa 178620
tttttgtgtt tttagtagag acggggtttc accgtgttgg ctgggctggt ctcgaactcc 178680
tgaactcaag tgatccaccc tccttggcct cccaaagtgc tgggattgca ggcgtgagcc 178740
actgcgcccg gcccccatgt cgatttttaa atgcacctct gcatcgttct tcagtcccca 178800
tatgctcact gagcaccact gcgactggca gacgggcaca gggaggcgcc acgaccagtc 178860
ctggccttca aggggcttgt ggtctagtgg gcccaatgct aggtggcgag tgctccaaag 178920
agtgtggtgc acgccttccg cttgaccgct ctccagacgc cacagggagg cacctcgcag 178980
ctgaccacag atttctctct gtggagcagt gtcttcagag cggctgccat gccactgctg 179040
ggcgagggtc tgcgggcggg tagagccagg agcacctgtg aggaagtgca ctgccatttt 179100
cgtagctgct tcccgtgtgt ctcagttaca cacggctggc atgtgtgcac tgatgagacg 179160
ggaacgtgat ggttgctttt cagcactgaa agggatactg ctcaggggc gtgtttcagg 179220
atctggttag ggaagaagca gcgagagcac agatggggcc ctgtgtggta acaagaaaaa 179280
agtcctggtt gacaacagtg ccacgaagcg ttagaacaca tagggatgtt tgtggagcat 179340
ttgcatgtgg aaagcagcaa aaacataatg ggaacgggtt cttttgttat gatttttaaa 179400
aatctctttt gtaacatcct tcccgctgcg ccgtttctgc atattccttt atgtagcttt 179460
caaactcctc ttaggagttc tggtccctac agggcgtggg agcccaggct ttacgtagct 179520
ttcaaactcc tcttaggagt tctggtccct acagggtgtg ggagcccagg cctgtgccg 179580
agcagcctgc ctccacgagc tagacagagg aagggctggg gttttgcctt tttagtctca 179640
aaattcgtac tccagttgct taggctctga ctttccccac ttggaaagtc cctcacggcc 179700
gagggtccct cccagccctg atttcacatc ggcattttcc ccagtattag agccaaggcc 179760
ctccgcgggc aggtggggca gctgtgggag ctggtgccag tctctgacct gcgtccctcc 179820
tcccaggatc aggaaaggct ttccttgtga agccagagtg gtggccagga tcctgcccca 179880
gtttctagac gacttcttcc cacccagga catcatgaac aaagtcatcg gagagtttct 179940
```

```
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg cccccacccc   180120 accccgcca cccaggcgca gcaggtgctt cccgtccccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag ggcccggtc gccatggcca   180300 cgtggagcct ctcctgcttc tttgtcagcg cgtccaccag cccgtgggtc gcggcgatgt   180360
atcctctctg ggtccctggt gctggccccg tttcccttgt caacaccgag gctcatgttt   180420
catgataagg ttttgaaacc taacctttgc aaaaacccca cagatgccag ggtgacaggc   180480
cctcagcccc agggaagtaa aatgctgaca ggggtacaga aaggagcacg tccagacatt   180540
tgctgaccag ggcctctcag agggccggt gtatggcagg agggtcgcag ctgagggcc    180600 tttctgtgga gggcctgggt gaggggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttccctttc cacagccctt ccccaagaca gaccacaaga   180840
gcctccaagc agcacagttg tcctggtgct gacagcacag ccttgcccgg cgtgcctggc   180900
acggctctgc cctcactgca ttggagcagg gctagtggag gccagcggaa gcaccggcca   180960
ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga cagggaggca gcattcccct catttgccgg   181200
cctttttcct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagccttttgg aagtctgcgc   181500 ccttgtgccc tgcctccacc gagccagctt ggtccctatg ggcttccgca catgccgcgg   181560
gcggccaggc aacgtgcgtg tctctgccat gtggcagaag tgctcttttgt ggcagtggcc   181620 aggcagggag tgtctgcagt cctggtgggg ctgagcctga ggccttccag aaagcaggag   181680
cagctgtgct gcaccccatg tgggtgacca ggtccttcct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctggggtg ctagacaccc ggcaccattc tcccttctct   181980
cttttcttct caggatttaa aatttaatta tatcagtaaa gagattaatt ttaacgtaac   182040
tctttctatg cccgtgtaaa gtatgtgaat cgcaaggcct gtgctgcatg cgacagcgtc   182100
cggggtggtg gacagggccc ccggccacgc tccctctcct gtagccactg gcatagccct   182160
cctgagcacc cgctgacatt tccgttgtac atgttcctgt ttatgcattc acaaggtgac   182220
tgggatgtag agaggcgtta gtgggcaggt ggccacagca ggactgagga caggccccca   182280
ttatcctagg ggtgcgctca cctgcagccc ctcctcctcg ggcacagacg actgtcgttc   182340
```

```
tccacccacc agtcagggac agcagcctcc ctgtcactca gctgagaagg ccagccctcc   182400
ctggctgtga gcagcctcca ctgtgtccag agacatgggc ctcccactcc tgttccttgc   182460
tagccctggg gtggcgtctg cctaggagct ggctggcagg tgttgggacc tgctgctcca   182520
tggatgcatg ccctaagagt gtcactgagc tgtgttttgt ctgagcctct ctcggtcaac   182580
agcaaagctt ggtgtcttgg cactgttagt gacagagccc agcatcccTT ctgcccccgt   182640
tccagctgac atcttgcacg gtgaccccTT ttagtcagga gagtgcagat ctgtgctcat   182700
cggagactgc cccacggccc tgtcagagcc gccactccta tccccaggcc aggtccctgg   182760
accagcctcc tgtttgcagg cccagaggag ccaagtcatt aaaatggaag tggattctgg   182820
atggccgggc tgctgctgat gtaggagctg gatttgggag ctctgcttgc cgactggctg   182880
tgagacgagg caggggctct gcttcctcag ccctagaggc gagccaggca aggttggcga   182940
ctgtcatgtg gcttggtttg gtcatgcccg tcgatgtttt gggtattgaa tgtggtaagt   183000
ggaggaaatg ttggaactct gtgcaggtgc tgccttgaga cccccaagct tccacctgtc   183060
cctctcctat gtggcagctg gggagcagct gagatgtgga cttgtatgct gcccacatac   183120
gtgaggggga gctgaaaggg agcccctcct ctgagcagcc tctgccaggc ctgtatgagg   183180
cttttcccac cagctcccaa cagaggcctc ccccagccag gaccacctcg tcctcgtggc   183240
ggggcagcag gagcggtaga aaggggtccg atgtttgagg aggcccttaa gggaagctac   183300
tgaattataa cacgtaagaa aatcaccatt ccgtattggt tgggggctcc tgtttctcat   183360
cctagctttt tcctggaaag cccgctagaa ggtttgggaa cgaggggaaa gttctcagaa   183420
ctgttggctg ctccccaccc gcctcccgcc tcccccgcag gttatgtcag cagctctgag   183480
acagcagtat cacaggccag atgttgttcc tggctagatg tttacatttg taagaaataa   183540
cactgtgaat gtaaaacaga gccattccct tggaatgcat atcgctgggc tcaacataga   183600
gtttgtcttc ctcttgttta cgacgtgatc taaaccagtc cttagcaagg ggctcagaac   183660
accccgctct ggcagtaggt gtcccccacc cccaaagacc tgcctgtgtg ctccggagat   183720
gaatatgagc tcattagtaa aaatgacttc acccacgcat atacataaag tatccatgca   183780
tgtgcatata gacacatcta taattttaca cacacacctc tcaagacgga gatgcatggc   183840
ctctaagagt gcccgtgtcg gttcttcctg gaagttgact ttccttagac ccgccaggtc   183900
aagttagccg cgtgacggac atccaggcgt gggacgtggt cagggcaggg ctcattcatt   183960
gcccactagg atcccactgg cgaagatggt ctccatatca gctctctgca gaagggagga   184020
agactttatc atgttcctaa aaatctgtgg caagcaccca tcgtattatc caaatttTGT   184080
tgcaaatgtg attaatttgg ttgtcaagtt ttggggggtgg gctgtgggga gattgctttt   184140
gttttcctgc tggtaatatc gggaaagatt ttaatgaaac cagggtagaa ttgtttggca   184200
atgcactgaa gcgtgtttct ttcccaaaat gtgcctccct tccgctgcgg gcccagctga   184260
gtctatgtag gtgatgtttc cagctgccaa gtgctctttg ttactgtcca ccctcatttc   184320
tgccagcgca tgtgtccttt caaggggaaa atgtgaagct gaaccccctc cagacaccca   184380
gaatgtagca tctgagaagg ccctgtgccc taaaggacac ccctcgcccc catcttcatg   184440
gagggggtca tttcagagcc ctcggagcca atgaacagct cctcctcttg gagctgagat   184500 gagcccacg tggagctcgg gacggatagt agacagcaat aactcggtgt gtggccgcct   184560
ggcaggtgga acttcctccc gttgcggggt ggagtgaggt tagttctgtg tgtcggtgg   184620 gtggagtcag gcttctcttg ctacctgtga gcatccttcc cagcagacat cctcatcggg   184680
```

```
ctttgtccct ccccgcttc ctccctctgc ggggaggacc cgggaccaca gctgctggcc  184740
agggtagact tggagctgtc ctccagaggg gtcacgtgta ggagtgagaa gaaggaagat  184800
cttgagagct gctgagggac cttggagagc tcaggatggc tcagacgagg acactcgctt  184860
gccgggcctg ggcctcctgg gaaggaggga gctgctcaga atgccgcatg acaactgaag  184920
gcaacctgga aggttcaggg gccgctcttc ccccatgtgc ctgtcacgct ctggtgcagt  184980
caaaggaacg ccttcccctc agttgtttct aagagcagag tctcccgctg caatctgggt  185040
ggtaactgcc agccttggag gatcgtggcc aacgtggacc tgcctacgga gggtgggctc  185100
tgacccaagt ggggcctcct tgtccaggtc tcactgcttt gcaccgtggt cagagggact  185160
gtcagctgag cttgagctcc cctggagcca gcagggctgt gatgggcgag tcccggagcc  185220
ccacccagac ctgaatgctt ctgagagcaa agggaaggac tgacgagaga tgtatattta  185280
attttttaac tgctgcaaac attgtacatc caaattaaag gaaaaaatg gaaaccatca  185340
gttgttgctg tgtgaggctt gctttgcttc atgagaacct agaccttgct gagctggagt  185400
cttaggaagc agtctcctaa gtgcttctcc agcaggggca gaaactgtcc caccagctaa  185460
catctggcat tatggagggt cccccaggca gctgccagca gggacaggcc ccgtgttttc  185520
tgtagccagg gatgaggaag tggccccagg gcatgggcct ggctgggtgc ttctgcaagg  185580
gccttcccaa accacagtac aggtggtctt cctgccctgc agatgggagc tgtgggagct  185640
gctggagctg ctggagcctt catggtcaag tgacatcata agcttatatg acatacacaa  185700
gcctcaggac ttggcccatg gcactgaagc aggtcatcag gcccagcaca gagactagag  185760
ctgtgttctc acagggccca ccaccttcc acctccttgg ccattgacac ctgcgtccct  185820
ggcccagctg ctcccaggta accccaaag cagctggcac atcccacctc tggtgtggcc  185880
ggggctgctg tgtgtccgca gggcctgccc cgtctattct agcttgtttg tcctgtctga  185940
accagcgcct actccaagaa gcctctgctc agcccagcgg ggatgcttct aagctccgga  186000
cgagcctctc ggaagccttg gtgattggtg gtgtagtcat cttgggatgc agatgtctta  186060
ccaacctgca agaacaaaaa ccctgtggct tcctctggtg cagggtattt agtcaatgtt  186120
tgctgaggtc ccgtctggtt ctggctaatt ggcaggggtc gtccacccat tctttccctg  186180
ctctgctgtc tgtgccagga gagacggggg ccagtcggcc aaggggccag ctcctgctgc  186240
ctgctcctct tgggcacgtg cggggccccc ctttctctga gcaggggatag ggatcagtct  186300
gccggaggga tgtggtggac aggcctaaag catttgggc ggggcatgcc acttgagctc  186360
cctaaatctg tctcctcata ggtgacaccg ctccagggcc ccccagtggc ctctcctttc  186420
agagctacct aaattctggt cacttcagag aaatggagca ccccttctc cctggtccag  186480
gtgtggacag cctggcacac tgagcacacc tggcatggct ggtaatttca gaaagaagag  186540
gggccggggt ccagtgggaa gcagcggtga acccctcgtg agtgggcttt gcagtccctc  186600
cccatgccac ggcagagctg ccctcaacac agccttcctc ttcctcatcg gagagcacac  186660
cctgtcccct tgccgagctg tgccctgtgc cttcggtggt atttgatttt ggctgctact  186720
ggctttgttg ggatctggaa gtcgcttccc ctgcgtggtg cgtggagcac tgtaagtcag  186780
atgagggaag tagccagggt gaggtgagta ccggtggag ccgccactga agggactggg  186840
tagggggggcc ttgcctctac atgatgtgac acagccaacc gaggacagag gaagcccgt  186900
tcctgggggt gtggggtgca cccctcaggg aagcctgcag tggggcctga ggaaaggcat  186960
cctccgcgag cccacgagtc tggtccatga gcaccgtgac agtgtctgtg ggtagaggtg  187020
gacccggcct tgtgtcatca ccaggacctc ttttgggaaa ccatgtggac atcgcttgcg  187080
```

```
ggtcccccag gctctgcagc cccagcagcc tggctgcctt ttgggcaagt ggcttgagcc 187140
acagaggacc cagtcctgtt gcagccacat cctctggggg ggcccgccag tgtggccggc 187200
tttctccacc ctacaccagg cctccaggtg tcctggtcgg gggtgtctgg gccctgggtg 187260
ggccctgtgg acctgtgagg tcaggatcag ggcatcactg gaggcagagg gctgaagttg 187320
tgggtctggg ttcccgttgt gtgcacaggc ccctgccctc catgcttggt caggcagcta 187380
cccccaaaac tgctaggaca ggctggtcct gaggtggatc ctggcccctg taccctctgg 187440
acagcccacc cgcccaacct tctaccctgc cccagcggcg gcagtgttgg ccacatcctt 187500
cccctcctgg ccccaattgc tctggggaag tccaggctcc ggagcctgcc caggggcccc 187560
ccgtgatttg ggcccaggac tccacgtggt tctctgcctt cacccaagcc ctgaactcct 187620
cagctgccaa atccccaccc atctgcacag gctgtgctca ccactgctgc tcctggaagg 187680
tgcccctcag tgggacgccc acctcctctc tgggcttctg tgtttgggag ccctgctgcc 187740
cccacccttg gtcagtcccc atgtcctgct ggcctgtcag gcagggcaga aaatccaccc 187800
agaaatgctg agcaggatga gagtctagtt gggcccagcc tcattattta aagggatgg 187860 aggcctaggg agcatgcttc tagcctgagc ccagcagggc cccgcccatg tcccaggtct 187920
gcaccaggga cagctcctgc cgaggcctga cctgcccctt ctccctcagg tgctgctggt 187980
tgaccagcct ctggcctag gagaccccgt agcgactgag ggtccagca ggccatgcag 188040 ctttgccaag gtacgagccc ctccccagca ggggacagat gtgggaccc tcccaggcag 188100 gagcagctgg gtgcctggtg ctgccatctg ctgcctgcct ggttcttgtc ctcacattgg 188160
aggtcagtgt gagggctctg cctcgggaaa ggccatggag cttgccctgt ccagggcctc 188220
ccatgtgcac tgagcctggg aagagagggt tggagttgag cctttaccc tgggaatgct 188280 gcctggagga tggtgcgggt gtggggtggc accctgccag gcagggccct gcctccctgc 188340
gcccactgga actcgggcag gcaggggtgt aggtgcctcc tctagagccg tccggtgggg 188400
gcccccggca gtggtggtgg tgtccactgg ccagcagctg cccttcagc caggacagta 188460 ggcctgacgc tgtccccagc agctccaagg tggatttgtg aaggggta gagggcacgt 188520 agaggcccca tgacctcccc agggttctgg gagggctgtg ccccccttagc cagcaccatg 188580 ctgggtgata tagtcagatc ctgttacccc tgttgtggag gtgaggaaac aggttagtgg 188640
ggaggacatg actaaggtcc atgctgagtc gctagagctg cacccagaac cactgctggg 188700
accccatgcc tttctgctta cccccttgtgc cgggagatgc caagagatgc tgggagccag 188760
ccccacctct gcccttggag tcatggctac ggaaagggca ttcggaccgg tccctgacct 188820
caccggggag ggccgaaccc tgttcctgag gagccagggc ttcctagagg aggtaggcct 188880
tctagtcact ccttcatctg caggcactcc acagagctct ctgtgccagc cccagcacg 188940 gagggctgac cttagtcgag tggagatgcc ccagtgccag gcagtaggga tgatgtctcc 189000
tgaggcccag atggaaggga ctggactagt ctcatgggc tgatggtggg gccaggcctt 189060
gaccagggac ccagtgtagg gggtgcagag acccctctga gttcctcaca catccctggg 189120
gccctcccca tacacttcct atcctgactg cgggcaagag ggagcccag ttcgccttcc 189180 ctatgctggg cacccacagt ggggctgggc acccccgcca tgcccctgcc ctgtccttcc 189240
cctgagagcc tcggtcccac ctccaaggtg cctcagagga cagcaggggc agcgggcaga 189300
ggccgagatg cctcctcatt ccaggctcag ctgcccttct tggggcagcc cacacctgag 189360
agtctcctgc agttggtcag gcctgaggag ggcagggggg tgcctgctgt ccctctgctg 189420
```

```
accacagtgg catttagcct gggcaccgcg cccagcacag tccatgctgc acaggtgccg    189480
tgggctccac agagccctgc ctgacatgca tgtgttacgt ttcgggtgcc gatgcccttg    189540
ggcggcactt ctccgggcag aaccccagg ccaccgctcc ggttccggtt ccgctgcatc     189600
tggggctctc ggcaggctgt ggtcctccgg ccagcctggg ggcatctcag tccctcagcc    189660
ccacaggggc ctgccccgca gcctgggcct cgagcccgt ctccgcacgc tgtgccgaat     189720
ctggctgccc atcagctccc tgcgtaccca gactgtgccc tgccatgccc gtggctcttc    189780
ccaggagtgc cctgtggcct cccctggct tgctgggctg attccctcct gtgtctcaaa     189840
cagagctcac ctttgccatc actgctgtcc tcaccggccg gtgccagagg cccgtgtctg    189900
tgtaccctgt gtctgcacct ctgggcaggg cctggctctg accaacccgg gcttccagtg    189960
tccacagacc taaggcccag ggcgcctggg ggctggagca agagaagcaa aaggagccaa    190020
gggtgggggt ttggggttct tgtgagggcc cagccccagg accccaggac caggacaccc    190080
aggagcccca gggcccagcc ccagttcaga aggcaggggc cttctgaggg agcttaaggg    190140
tcccacagcc caggaccccc accagggcca gtggccagcc ttgggggact cagcctcctc    190200
gtcgctcgtc ctctctgttt ctcccacctt ttgccccctt tctccttgcc tgttcccacc    190260
cgaggccccc tcttggcctg cgtgagccgg ggcggcactg aactggggc cgatccgcct     190320 gggcggcggt gagaggcagg gccgggagcc gggccgctgg gtttgggcct ggcccgctcg    190380
ccgcaatatt gatgggccgt cagtgcagcc ctgattcctg tgctttcagt taaaaggttt    190440
ctgttgttgt agcttatgca gttgctctgt tgctatggaa acgtgacatc aaaatgacgt    190500
ttcccgttta aaagctttta actaaaattcc tgcctgtcag atgtaggccc cattttgagc    190560
gtggagctgc cttcgagcga gcgtgagcgg cgcctcccgc ccatggtgcg tggggccggg    190620
ccggggccct cgctgagcgc gctctctcac cccacaggcg cctccggcat ggcggcggcc    190680
gagggggccg gctacctcgt gtctccccag gcggagaagc accggcgggc ccgcaactgg    190740
acggacgccg agatgcgcgg cctcatgctg gtctgggagg agttcttcga cgagctcaag    190800
cagaccaagc gcaacgccaa ggtgtacgag aagatggcca gcaagctctt cgagatgacc    190860
ggcgagcgca ggctgggcga ggagatcaag atcaagatca ccaacatgac cttccagtac    190920
aggtgggcga gcggcagtg tgggccccac caggacgggc gggcccgggc gtggcgggcc     190980
gctcctgact tcttggagc tctgagtcgg gacgatgtgt gggtcgtggc ctgcctgtcg     191040
gtctcctctg gccgggtatg ggcagaaccc cacggggtga cacggggccc acggaaaccg    191100
tgtgtgcagc cttccattgg ggaagtgggg aaactgaggc ccagcaaggg caggaaacca    191160
gtctaagagc tgaggggtag caggggtggg gctggtgctg ggcagaggcc aggatggctc    191220
ccaggacgta tgggcggtct gggcactgtc cctcggaggc agcaacactc atggtggtgc    191280
ccactgacct cacaccctgc tcccccatag ggaggcggcg gctgccagtg ccctccccac    191340
caccaagctc ccaagctcag cagggggttc aggggcctac tgcgtcattg gggaaattga    191400
gactgcaagt gagaaggagg ctcagtgctc tgcgacttgg agcatccact gagcctctgc    191460
catgagccgg tgagccccac tggggctggc cctagggtca cggtggggta tttccagaaa    191520
tcaccaggtg aggtgcagga ccagccacgc atgggtggg gcttacggtg cgaagaagaa    191580
agaggtggag gcctgccctg gcccaggact cccagcgtgg gggctcccgg cctggcccca    191640
cctctgctcc tgctacatgg caggtggcc cttcctgccc tggcaacctg cagggaaggc    191700 cggagggac cacccagcca gggagatgtt ggcgtcctgg aggggacagg tgtggtccca    191760
cacacccagc atcttaaagt gcgtgggtcc ccagcccatt aggacagggt cccgggtggg    191820
```

```
caggggtcat ggtggggtga aggtctcagg cacaggcaag gtcacaggtg cggtgagggt    191880
cttgcagggt gtgaaggtca taggtgtgcg gtgaaggtca caggtgtggg gtgatggttt    191940
tgggtgtggg gagggtcttg cacggagcga gggtggcagc aagagctgga agctgcaggg    192000
ggagaatggc agcagagagc acccggccct gtgggcggcc tggacagggc tgggcctggg    192060
gctgccggag agcctgtcag cttccaggat gggagtggcc tcactcagct gctccacctc    192120
cgggtcaggc aggtgagcct ggggcagaga ggctgagagc acctgagcca cttgtgggag    192180
aggccacccc cactgccccc ctcaggcgag gagccggcct ccagcacagc agaagggaac    192240
ccccagtccc cagccctagt gggagtgggg aagaggccca gcaaggcccc ggacagaccg    192300
ccagcctgtg aggtctccgc tttcagttgc gttgatttga tttttctga gccttgaagg     192360 aggggtccgg ggcctggccc tgcccaaagg cccctaggca ggcccaaag ccgggaccta     192420 gggtgctgag catgacggat gttgggtttg agcggctggc ttgcgacgtg agggctgagg    192480
tgtgagcctg ggtatcttca gaggttcggt ggacacaggc agctgcccgc ggccccactg    192540
ttcccgtggc ctcctagtcc tgctcaggca cctggtgagg aagggacgca gagggcagtg    192600
ggaggtggcc acgactgttc cagcaggctc ccctctgact caggaattca cgggcaccac    192660
ctccctggct ggctctggtt ggtgtctggc caggttattc attatttatg ctgaaagcct    192720
cttcagagtc ccaggggagg gtttctgtct ccattcctgg aggctgagag atgagggtgc    192780
agcagagtgg gggcctccac tccagaccct gcagtctggg ctggccaagg gctgcaccgg    192840
tgcactgcac gtcatggctg atgaagcact tccacaccgc agcccctcag agctgccaca    192900
gtcagcctta gttcaccgag ggggaagctg aggcccagag catgagaggg acttgcccag    192960
ggccacatag tccttagcag aggaagctgt ggctgggtga ctcgatcttt gtccttttc     193020 tttatacccg cagtctcccc atagcagagg cttttctttt tttttcttt ttcttttttt    193080 ttttttaca agaactcttt atatattaag gctgttgggc tgaagaagcc tgagagggtg     193140
gctggttctg tggagcatgg tttgttgaag tacagtttgg gggcctccta cactgagaat    193200 aggcctttc tcgtttctcc aaagagtggg ctggctcaag tagggcagag agagaagcct     193260
ggggcagagg ttagggatgg gcacccagcg cctgccctca cacgctctgt gctggtgtct    193320
tcacagccac gtgccaccct gggcagcatc ccctgctcac catctggctg tgcctgtttg    193380
ctgggggcac ctcattcaga atccagctta ttgtttccaa cggccaatgg ccacaccctg    193440
gcaggtagca agagtaggag agaggagaca cccactccga gcacaggttg ggtttggagc    193500
ccggccttgg ggcactctgt cactcaaagg cagagtgggg agtgggcact gggccttagg    193560
aggtactggg tccagtgagg cagagatgcc cctgccccac ccccaccttg tggcttcttc    193620
cctggcctgg ccagagctgt ctggccgcca tgggccctg tgtctcctgc cttgacctcc     193680
cagagggcag ccgaggccca gggaggcct gggacttag cctctcaggg caggacctgt      193740
ctgcaggagt aggtgggtgc tgggggtccc agtggtaatg aggcatcagg cagtgtggga    193800
aggggcccat ccggcccacc ccagggcctc tgggcaggtt gcaggttgta gcgctggatc    193860
taggctcctg cccagactgt aggttcaacc aagaatggca tgggagccca gcctgctgtt    193920
tgctttatta aatctgccct gtagctgggg gagggcttta ctttgatcat cactatgtca    193980
ttgatataaa aatagaggct cagagaggtg aatgaacctg cccaaagtca cacagcaaag    194040
tgtggagatg agatactgac tcagggctgt ggacactgaa gcctgtgctc taacgccagt    194100
ggctgtcgct ccctgaggca ttctctcccg aacaacacag ttattatatt acaaaatatt    194160
```

```
atcactatat ttatatatct tataataacct tattattaca ataaaacctt attactctac 194220
ctttcaaaat gaattattta aaaagcagta tttgctcatt gcagagagtc tagaaactat 194280
agaaaagcaa gggaaaagca ataggaccag ccccaaggtc ccagcatgca cagataacct 194340
tagtaatact gggacgtgtg cttccttttt aacatctgag cccgtgtagg tcctgaagcc 194400
cagcttcttt ctaagtccat tgtcatcttg accctggagc ctggccgatt ttgctgggga 194460
ggcccttgcc agccgagagc ggctcctgcc tgtgccggcg tggcgcgccc ctctgctgag 194520
gctgggcagg acaggggctg ggccagctct gtttctcacc cttggctctt gtgtctctcg 194580
tttcaggaaa ttaaaatgca tgacagatag cgagtccgcc ccgcccgact ggccctatta 194640
cctagccatt gatgggattc tggccaaggt ccccgagtcc tgtgatggca aactgccgga 194700
cagccagccg ccggggccct ccacgtccca gaccgaggcg tccctgtcgc cgcccgctaa 194760 gtccaccccct ctgtacttcc cgtataacca gtgctcctac gaaggccgct tcgaggatga 194820
tcgctccgac agctcctcca gcttactgtc ccttaagttc aggtagtgtg tctgcttgtc 194880
cttcccctgc cctggggtat ctcagccccc accatttaga gaaagggact gggagtggca 194940
aggccggcgg cggcggccac agtggttgca gaggccgtgg ctgcgggcag cgcctccagg 195000
gacaggcggc ctcagaccag ggagggcttt agtgtccaca gcagaccga gtttgtctcc 195060 cagctccatc acttttgagc tgcacggaaa gttccttgac ttctctggcc tcagtctccc 195120
tcctataaaa tggggtaaa tcagtacctt tctcagaggg tggctgggag catcacagga 195180
gagaagacgc agcatgggc cggcacacg agggagacc aagccccaga ccccagaatg 195240
cgccccctgg cctcccttag cccacacaga ccccacccctc acaggctagc tgccctctca 195300
gcactgggga gggtgtcggg ctgcacctca tcacgtgttg ccgtgggcat gacccgtccc 195360
ctctgccatc catcccacac ctcagacccg tcccgtgctg gccacgtgac tgtgcctgca 195420
agatgctcac agggcagccg ggagccaggc agcatgcagg acagacacct gcggggtggg 195480
cctggggagc ccagagaagg tgcttttgag gaggggacat ttggggtggg cttttcaaggt 195540 aaaatagaag ttggccattt ggaggcaaga acaggaagat tgtggatttg agtcacagct 195600
tctcccctgc cctggtcttc aagtcttcct gacaggaggt gtcagaaaag tatctttagt 195660
agagaaggcg tctccgagga gggtccctct catgccgggg gccgctgctt gactcaggat 195720
ttctcattga agacctgaga caaaaacgct tttgctggca gctagaagga accagcagga 195780
ggcctgagat ttgtggctgt tgttcccgtg gactgagccc agttctcaga ctcagctgcc 195840
tggggccttg cacaggactg gggcgtgggg gctgccctcc ctgatcaggc ccaaagcgcg 195900
gatctcacgc ccctgaggtt ggctgtaccc tctcagctca gagcagagtg tgggccaggg 195960
atgagcaggc actggagcag ggccctgggg tctgtgggtt ttggcagctc cctgcccttc 196020
agggaggtct gctgagacca cgggtggccc ctaccccagc agcagagctc tcaggaggcg 196080
cccacagggc tggactgcct ttactcacca cctctaccag agctctgagg tcctggggag 196140
agagcccagg cctcttgtgg gccccacacc ctctaggtgc ctgtccttct gcctctctac 196200
caaggtgtgc cggccccatt tctaggccgc cgggagataa gggggctcac atctcaggcc 196260
cttccttctg ggacctcagt ttccccatct gcctaaggcc gggtgggct ggtggtcttg 196320 gcttccctac aggggtcctg agtactctgc actacccagc acccccacc cctgccttca 196380 tctctccctg ggggtggtct ctccacccct ggccccaaac tggggctgag cccccacctg 196440
cccagtttgg tgggtgaagg gtgctccctg gcaggatatg cccctctgca gcccagaaca 196500 tcccacccctt tccagaccga aggggtgtgg attgtcctgg gaccctggtc attggggtca 196560
```

```
tccgctagtc gcaaaggacg gcaatgcctg tggcctctct ttctttcttt ttctttttt  196620
ttttttttga gacggagtct cgctcttgtg cagagagcag tggcgcgatc ttggctcact  196680
gcaacctccg cctcgtgggt tcaagcgatt ctcctgcctc agcctcccga gtagctggga  196740
ttacaggcac ccgccacaac gcctggctaa ttttgtatt tttagtagag atgggtttc   196800
accatgttgg ccaggctggt cttgaactcc tgacctcagg tgatccacct gcctctgcct  196860
cccaaagtgc tgggattaca ggcataagcc tccacacccg gccacccctg ttactttctg  196920
tcaaaggcgg tgggttctgg cccctccttt gcacatggaa tatgagaccc tgagtaagtg  196980
acctgactcc ctggggcctc agtttcccca tttgcccagt aggattgtcg ggagggtccg  197040
gtgaggcccc tggtgtgccc aggctctgtg ccagcacgt ccacagccgg cactgtcctt   197100
ccaggtcgga ggagcggccg gtgaagaagc gcaaggtgca gagctgccac ctgcagaaga  197160
agcagctgcg gctgctggag gccatggtgg aggagcagcg ccggctgagc cgcgccgtgg  197220
aggagacctg ccgcgaggtg cgccgcgtgc tggaccagca gcacatcctg caggtgcaga  197280
gcctgcagct gcaggagcgc atgatgagtc tgctggagag gatcatcacc aagtccagcg  197340
tctaggccag caggcggcgg cggcggcggg gccgggcggc tggtggtact gctcaggcca  197400
cccagggcag gccactcagg ccaggcgggc aaggggccg ccccgcgagc ggagaccgcc   197460
ttccacctgg cctctggcag gatgtccctt ctgaggggta ttttgaggaa ccccaggcc   197520
ctggggaccg tgaggctcca gtctccagca tgaatgccct tcctcggaca caggccaggg  197580
cctctggggt tcactccgag taagaacgtc ctagagccac tctccagtgt cgttactatc  197640
aatgatactt gacgtggctt tgatattaaa cgtatacttt tcattcttg cctggaacgc   197700
acagtttgct gttgctggct tggtgaggat gccctgattg atggatcccg aaaatgaaag  197760
cagatggaaa cgggttgggg caggctggag ctggggagc tctctcctga agggaaccct   197820
gtgtcctccc tcaccaggac ctctgcgtct tccttaaat ggcctctgac gcctgatgaa   197880
aaccccagcg accttccagg aggcttttat tcagctctgt ttggagcatc aggtgtttcc  197940
actgcctcct tagcaatgac actaataaaa gtcgtaacac ctgttcacat gcacagccct  198000
gttgagtgtt ctgggtgctg agatatcat ggtggatgac acaaaggccc tggcctcttg   198060
gagcttatgc tcccatgcgg ggaagacaca tgggtcagta gagaaatggt tgcaggttgt  198120
gataagtgct ggaagggagg ggttggcctg aggacacgga ggcagacata cgtggagctg  198180
ggaacagtgg ccacacaggg aacggccagt gcgaaggccc agaggcagag gacactggag  198240
caagcccagg agcagctagg aggctggtgg ccagcagcca ggcacgaaa gcccgtgcag   198300
cccgtgggga ggagtgttca tgcttttcaa gcttagtggg agtcttttgg ccagtgcagc  198360
tctgggtctg acatcggtgg gggacagagg ggtggtggag cggccacagc tgcaagctca  198420
cctcactgcc ggcccttcca ccagtttcaa actctttcta gaagctccag ctttcccaaa  198480
gctgaattct ctatgagcct ccttggccgg gactcgggcg tctggttgcc ctggctgcaa  198540
aggaggctgg ggccaggtgt gtttgagtca cctcctggaa ttaggcaagt tgctgcccaa  198600
atagaaggtt gttggcaggt gggtcagcag gtgaacagca tggtttgact cagggttcag  198660
aaaaatctcc ctctggctgc caagcgagca ggccgtggag acaggtgcag aggcaggtgt  198720
ggcagcaggc atcctgccag gcagtgctgc agtcatcctg cgacaagcag cagcagctca  198780
tcctaccctc taggggtct tgaggtcagc caggcaagag agcagcttgg actccactgg   198840
gtgtgggacc agcctgtgga ccatggtggt gtggagggtg ccctcggcct gcctgtgtga  198900
```

```
aggagaggcc ggcgtgttct gtggagccca aaggggagct gggcaagcag gattcacttc  198960
actctgaggg tcctggagct cccacccctcc tcagccatct ccccagagcc tgtgtgccga  199020
ggactcggcc catgttgctg tgggatgaga ggcagagtgt cgtgagggtg taaggagcgg  199080
cggcagtggt gggaggaggg agcagcagcc agcgctacgg tgccagtttc cagctgccag  199140
atgacgccgc tgaccctgtg gttgagaaga gatgcacaga gccagctctt gcaagccagt  199200
gtggctgcca tagcacctgc cgagaagcag aaggaagggt ggcccagga ggacagagga  199260 tgcgggcaca tctgatgcgg gcctgagttt tgggagcttt tgctctagcc agtttccagc  199320
tccgggaccc acccgcctcg taggcaagac accacccaag aaatcatttg cttaacaaac  199380
acactgggct ccaactggac acctgtgcca ccctagatgc tgggaaccca gccatgacac  199440
aggcacctgc ccccagctgc tgaccactga ggctggctag cagctcccat ggggccagtg  199500
tggggttccc cagcctccta acagggagcc agtcacaagc cctcgagagg aagggtgcc   199560 cgcggccctg gcaggaaggt taggctggac gctcccacaa gacataacag atggaggttc  199620
taaatgatgt agcaacttct tcaccctgaa actgctgtag agtcagccat gacgcaccgg  199680
tacttcagta actgccaggc atccgggaca gcacaccgcg agtcgctgct gtgcttgggt  199740
tagaagtggt ttggtctgtt ttcttctcgc cctctctaat cagagtcagt gattcatgcc  199800
cttccatcac cttagagaag gggcaggcgc tgcccgacct tctccaggct ggagcagcat  199860
cgcctcatgt cagcagaact cagctgtaga atatcgtggg gttggtgcct ttcatcagca  199920
gcatgtcctt aacaactttc tgatttcttc cttagttgtt ggtccattaa ggagaaaaaa  199980
aatgatctca gccattgcta aaatatttga taagattcag caaagcagca tgttaacatt  200040
gaaaactaga atcaggagcc aggcagatgt gcttgctttt cacctgtagt atttcatgtt  200100
gttttgacgt ttttagctaa tgcattaaga taaataaaca aaagccgggc acggtggttc  200160
acgcctgtaa tcccagcact ttgggaggct gaggcgggag gatcctctga ggtcaggagt  200220
tcaagaccag cctgaccaac atggagaaac ctcgtcatta ctaaaaatac aaaattagct  200280
gggcgtggtg gtgcatgcct gtaatcccag ctacttggga ggctgaggca ggagaatcgc  200340
ttgaacccgg gaggcggagg ttgcagtgag ctgagattgc accactgcac tccagcctgg  200400
gtgacagtga aactcggtct caaaaaaaaa aaaaattaa aaaagataa ataaaataag    200460 caggataaga aatgaagaaa gtagagttac ctttgttttc agatttcatt tttgtatacc  200520
cagaaagcca aatgtacaaa agactgggag ctctttaaac cagcttaaac ttgttgaaaa  200580
tgaggatgaa gaaatatccc attcagagtt ggaatgaatt taacccagaa ggaacaggac  200640
ctctactgaa gagaactatg cagtcttact gaaaaatcta aataatacct gagcgctgga  200700
gaaacttcgc acactcctga aagctccaaa gtcaatgtca tcattttatt aatgtcattc  200760
caaacatagt ctcaataata tcacttcttg gttttgacat ggacgcgatg atgtttaaat  200820
tcatatgaaa aaagaacggg gccaaaagtc caaggccagt cagcgtgaga agaccgctcg  200880
gcctccctcg gagtcgggga gttggaaccg cagactgaga tcatgtggct gctgaggcc   200940 aggacgaacg tcgggaaatg gagactcctg cgttgctggt gggatgtggt gcagccgctt  201000
ccaggagcaa tttggtgtcc cgtcctaaag ctgaagaaac gcatttcctc tggtcagtgc  201060
cactcctaga caggccaccc tgcggcagcc gtcctcaaac tggtctgagg acccctcaac  201120
gctcttaaaa atcattaaaa gtgggccagg tgcggtggct cacacctgta atcccagcac  201180
tttgggaggc caagacaggc ggatcacgag gtcaggacat tgagatcatc ctggctaaca  201240
cggtgaaacc ccgtctctac taaaaataca aaaaattagc cgggcgtggt ggcgggcgcc  201300
```

-continued

```
tgtagtccca gctacttggg aggctgagcc aggagaatgg cgtgaaccca ggaggtggag    201360
cttgcagtga gctgagatca ctccactgca ctccagcctg ggcagcagag cgagactctg    201420
tctcaaaaaa aaataataaa taaataaata aaaataaaat aaaataaaat tcattaaaag    201480
tgccaaagaa cttttgctta tgtgagttct aatgaccaat attaatacac attagaatat    201540
cttattagaa attaaacctg agaccttttag aaaacatgta ttcatttcaa aatagcaata    201600
aacccatgac atattaacat aaataacaat tgtatgaaaa atatattttc caaaacaaaa    201660
agttttcggg agaagtgtgg catagtttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaaggaac    201840
attttaataa cctttgcaaa taatcggtat attcttccgt gatcctattc caacactgga    201900
caggtggtgg tttgttttt tttttggag acggagtccc gctctgtcac tcaggctgga    201960
gtgcagtggc gcgatttcag ctcactgcaa gctccgcctc c                        202001

<210> SEQ ID NO 2
<211> LENGTH: 13481
<212> TYPE: DNA
<213> ORGANISM: Homo sapiens

<400> SEQUENCE: 2
gctgccggga cgggtccaag atggacggcc gctcaggttc tgcttttacc tgcggcccag         60
agccccattc attgccccgg tgctgagcgg cgccgcgagt cggcccgagg cctccgggga        120
ctgccgtgcc gggcgggaga ccgccatggc gaccctggaa aagctgatga aggccttcga        180
gtccctcaag tccttccagc agcagcagca gcagcagcag cagcagcagc agcagcagca        240
gcagcagcag cagcagcagc aacagccgcc accgccgccg ccgccgccgc cgcctcctca        300
gcttcctcag ccgccgccgc aggcacagcc gctgctgcct cagccgcagc cgccccgcc        360
gccgccccg ccgccacccg gcccggctgt ggctgaggag ccgctgcacc gaccaaagaa        420
agaactttca gctaccaaga aagaccgtgt gaatcattgt ctgacaatat gtgaaaacat        480
agtggcacag tctgtcagaa attctccaga atttcagaaa cttctgggca tcgctatgga        540
acttttctg ctgtgcagtg atgacgcaga gtcagatgtc aggatggtgg ctgacgaatg        600
cctcaacaaa gttatcaaag cttttgatgga ttctaatctt ccaaggttac agctcgagct        660
ctataaggaa attaaaaaga atggtgcccc tcggagtttg cgtgctgccc tgtggaggtt        720
tgctgagctg gctcacctgg ttcggcctca gaaatgcagg ccttacctgg tgaaccttct        780
gccgtgcctg actcgaacaa gcaagagacc cgaagaatca gtccaggaga ccttggctgc        840
agctgttccc aaaattatgg cttcttttgg caatttgca aatgacaatg aaattaaggt        900
tttgttaaag gccttcatag cgaacctgaa gtcaagctcc ccaccattc ggcggacagc        960
ggctggatca gcagtgagca tctgccagca ctcaagaagg acacaatatt tctatagttg       1020
gctactaaat gtgctcttag gcttactcgt tcctgtcgag gatgaacact ccactctgct       1080
gattcttggc gtgctgctca cctgaggta tttggtgccc ttgctgcagc agcaggtcaa       1140
ggacacaagc ctgaaaggca gcttcggagt gacaaggaaa gaaatggaag tctctccttc       1200
tgcagagcag cttgtccagg tttatgaact gacgttacat catacacagc accaagacca       1260
caatgttgtg accggagccc tggagctgtt gcagcagctc ttcagaacgc ctccaccgga       1320
gcttctgcaa accctgaccg cagtcggggg cattgggcag ctcaccgctg ctaaggagga       1380
```

```
gtctggtggc cgaagccgta gtgggagtat tgtggaactt atagctggag ggggttcctc   1440
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aggtgacat   2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa tacctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagcttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taaccttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
ctctgaagaa gaagccaacc cagcagccac caagcaagag gaggtctggc cagccctggg   3540
ggaccgggcc ctggtgccca tggtggagca gctcttctct cacctgctga aggtgattaa   3600
catttgtgcc cacgtcctgg atgacgtggc tcctggaccc gcaataaagg cagccttgcc   3660
ttctctaaca aaccccccctt ctctaagtcc catccgacga aaggggaagg agaaagaacc   3720
aggagaacaa gcatctgtac cgttgagtcc caagaaaggc agtgaggcca gtgcagcttc   3780
```

```
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt ctttctcaga tactagagct ggccacactg caggacattg gaagtgtgt     4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aacccagca agtcacaagg ccgagcacag cgccttggct cctccagtgt     4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga acagtttga atacattgaa gtgggccagt tcagggaatc    4620
agaggcaatc attccaaaca tcttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta aagaacaca gtgaagggaa    5340
acaaataaag aatttgccag aagaaacatt ttcaaggttt ctattacaac tggttggtat    5400
tctttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac acctggaca gcttgaactt gcgggctcgt tccatgatca ccacccaccc     5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccagcaa ttcagtctcg ttgtgaaaac ctttcaactc caaccatgct    6060
gaagaaaact cttcagtgct tggaggggat ccatctcagc cagtcgggag ctgtgctcac    6120
```

```
gctgtatgtg acaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg aagaactca acagaatcca ggaataccct cagagcagcg ggctcgctca    6300
gagacaccaa aggctctatt ccctgctgga caggtttcgt ctctccacca tgcaagactc    6360
acttagtccc tctcctccag tctcttccca cccgctggac ggggatgggc acgtgtcact    6420
ggaaacagtg agtccggaca aagactggta cgttcatctt gtcaaatccc agtgttggac    6480
caggtcagat tctgcactgc tggaaggtgc agagctggtg aatcggattc ctgctgaaga    6540
tatgaatgcc ttcatgatga actcggagtt caacctaagc ctgctagctc catgcttaag    6600
cctagggatg agtgaaattt ctggtggcca gaagagtgcc cttttttgaag cagcccgtga    6660 ggtgactctg gcccgtgtga gcggcaccgt gcagcagctc cctgctgtcc atcatgtctt    6720
ccagcccgag ctgcctgcag agccggcggc ctactggagc aagttgaatg atctgtttgg    6780
ggatgctgca ctgtatcagt ccctgcccac tctggcccgg gccctggcac agtacctggt    6840
ggtggtctcc aaactgccca gtcatttgca ccttcctcct gagaaagaga aggacattgt    6900
gaaattcgtg gtggcaaccc ttgaggccct gtcctggcat ttgatccatg agcagatccc    6960
gctgagtctg gatctccagg cagggctgga ctgctgctgc ctggccctgc agctgcctgg    7020
cctctggagc gtggtctcct ccacagagtt tgtgacccac gcctgctccc tcatctactg    7080
tgtgcacttc atcctggagg ccgttgcagt gcagcctgga gagcagcttc ttagtccaga    7140
aagaaggaca aataccccaa aagccatcag cgaggaggag gaggaagtag atccaaacac    7200
acagaatcct aagtatatca ctgcagcctg tgagatggtg gcagaaatgg tggagtctct    7260
gcagtcggtg ttggccttgg gtcataaaag gaatagcggc gtgccggcgt ttctcacgcc    7320
attgctaagg aacatcatca tcagcctggc ccgcctgccc cttgtcaaca gctacacacg    7380
tgtgccccca ctggtgtgga agcttggatg gtcacccaaa ccgggagggg attttggcac    7440
agcattccct gagatccccg tggagttcct ccaggaaaag gaagtctttta aggagttcat    7500 ctaccgcatc aacacactag gctggaccag tcgtactcag tttgaagaaa cttgggccac    7560
cctccttggt gtcctggtga cgcagcccct cgtgatggag caggaggaga gcccaccaga    7620
agaagacaca gagaggaccc agatcaacgt cctggccgtg caggccatca cctcactggt    7680
gctcagtgca atgactgtgc ctgtggccgg caacccagct gtaagctgct tggagcagca    7740
gccccggaac aagcctctga aagctctcga caccaggttt gggaggaagc tgagcattat    7800
cagagggatt gtggagcaag agattcaagc aatggtttca aagagagaga atattgccac    7860
ccatcattta tatcaggcat gggatcctgt cccttctctg tctccggcta ctacaggtgc    7920
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag gaggaatggg acgaggaaga ggaggaggag gccgacgccc ctgcaccttc    8100
gtcaccaccc acgtctccag tcaactccag gaaacaccgg gctggagttg acatccactc    8160
ctgttcgcag tttttgcttg agttgtacag ccgctggatc ctgccgtcca gctcagccag    8220
gaggaccccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca gaagacgaga tcctcgctca gtacctggtg cctgccacct gcaaggcagc    8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
```

```
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000
agtgattgtt gctatggagc gggtatctgt tcttttgat aggatcagga aaggctttcc     9060
ttgtgaagcc agagtggtgg ccaggatcct gccccagttt ctagacgact tcttcccacc    9120
ccaggacatc atgaacaaag tcatcggaga gtttctgtcc aaccagcagc catccccca     9180
gttcatggcc accgtggtgt ataaggtgtt tcagactctg cacagcaccg ggcagtcgtc    9240
catggtccgg gactgggtca tgctgtccct ctccaacttc acgcagaggg ccccggtcgc    9300
catgccacag tggagcctct cctgcttctt tgtcagcgcg tccaccagcc cgtgggtcgc    9360
ggcgatcctc ccacatgtca tcagcaggat gggcaagctg agcaggtgg acgtgaacct     9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat ggcttccgc acatgccgcg ggcggccagg caacgtgcgt     9720
gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctggggt gctagacacc cggcaccatt ctcccttctc tcttttcttc tcaggattta     10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggcccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtgcgtct    10620
gcctaggagc tggctggcag gtgttgggac ctgctgctcc atggatgcat gcctaagag    10680
tgtcactgag ctgtgttttg tctgagcctc tctcggtcaa cagcaaagct tggtgtcttg    10740
gcactgttag tgacagagcc cagcatccct tctgccccccg ttccagctga catcttgcac   10800
ggtgacccct tttagtcagg agagtgcaga tctgtgctca tcggagactg ccccacggcc    10860
```

```
ctgtcagagc cgccactcct atccccaggc caggtccctg gaccagcctc ctgtttgcag   10920
gcccagagga gccaagtcat taaaatggaa gtggattctg gatggccggg ctgctgctga   10980
tgtaggagct ggatttggga gctctgcttg ccgactggct gtgagacgag gcagggctc    11040 tgcttcctca gccctagagg cgagccaggc aaggttggcg actgtcatgt ggcttggttt   11100
ggtcatgccc gtcgatgttt tgggtattga atgtggtaag tggaggaaat gttggaactc   11160
tgtgcaggtg ctgccttgag accccccaagc ttccacctgt ccctctccta tgtggcagct  11220
ggggagcagc tgagatgtgg acttgtatgc tgcccacata cgtgagggg agctgaaagg    11280 gagcccctcc tctgagcagc ctctgccagg cctgtatgag cttttccca ccagctccca    11340 acagaggcct cccccagcca ggaccacctc gtcctcgtgg cggggcagca ggagcggtag   11400
aaaggggtcc gatgtttgag gagcccctta agggaagcta ctgaattata acacgtaaga   11460
aaatcaccat tccgtattgg ttgggggctc ctgtttctca tcctagcttt ttcctggaaa   11520
gcccgctaga aggtttggga acgagggaa agttctcaga actgttggct gctccccacc    11580
cgcctcccgc ctcccccgca ggttatgtca gcagctctga cacagcagta tcacaggcca   11640
gatgttgttc ctggctagat gtttacattt gtaagaaata acactgtgaa tgtaaaacag   11700
agccattccc ttgaatgca tatcgctggg ctcaacatag agtttgtctt cctcttgttt    11760
acgacgtgat ctaaaccagt ccttagcaag gggctcagaa caccccgctc tggcagtagg   11820
tgtcccccac ccccaaagac ctgcctgtgt gctccggaga tgaatatgag ctcattagta   11880
aaaatgactt cacccacgca tatacataaa gtatccatgc atgtgcatat agacacatct   11940
ataattttac acacacacct ctcaagacg agatgcatgg cctctaagag tgcccgtgtc    12000
ggttcttcct ggaagttgac tttccttaga cccgccaggt caagttagcc gcgtgacgga   12060
catccaggcg tgggacgtgg tcagggcagg gctcattcat tgcccactag atcccactg    12120 gcgaagatgg tctccatatc agctctctgc agaagggagg aagactttat catgttccta   12180
aaaatctgtg gcaagcaccc atcgtattat ccaaattttg ttgcaaatgt gattaatttg   12240
gttgtcaagt tttgggggtg ggctgtgggg agattgcttt tgttttcctg ctggtaatat   12300
cgggaaagat tttaatgaaa ccagggtaga attgttggc aatgcactga gcgtgtttc     12360 tttcccaaaa tgtgcctccc ttccgctgcg ggcccagctg agtctatgta ggtgatgttt   12420
ccagctgcca agtgctcttt gttactgtcc accctcattt ctgccagcgc atgtgtcctt   12480
tcaaggggaa aatgtgaagc tgaaccccct ccagacaccc agaatgtagc atctgagaag   12540
gccctgtgcc ctaaaggaca ccctcgccc ccatcttcat ggaggggtc atttcagagc     12600 cctcggagcc aatgaacagc tcctcctctt ggagctgaga tgagcccac gtggagctcg    12660 ggacggatag tagacagcaa taactcggtg tgtggccgcc tggcaggtgg aacttcctcc   12720
cgttgcgggg tggagtgagg ttagttctgt gtgtctggtg ggtggagtca ggcttctctt   12780
gctacctgtg agcatccttc ccagcagaca tcctcatcgg gctttgtccc tcccccgctt   12840
cctccctctg cggggaggac ccgggaccac agctgctggc cagggtagac ttggagctgt   12900
cctccagagg ggtcacgtgt aggagtgaga agaaggaaga tcttgagagc tgctgaggga   12960
ccttggagag ctcaggatgg ctcagacgag gacactcgct tgccgggcct gggcctcctg   13020
ggaaggaggg agctgctcag aatgccgcat gacaactgaa ggcaacctgg aaggttcagg   13080
ggccgctctt cccccatgtg cctgtcacgc tctggtgcag tcaaaggaac gccttcccct   13140
cagttgtttc taagagcaga gtctcccgct gcaatctggg tggtaactgc cagccttgga   13200
ggatcgtggc caacgtggac ctgcctacgg agggtgggct ctgacccaag tggggcctcc   13260
```

| | |
|---|---|
| ttgtccaggt ctcactgctt tgcaccgtgg tcagagggac tgtcagctga gcttgagctc | 13320 |
| ccctggagcc agcagggctg tgatgggcga gtcccggagc cccacccaga cctgaatgct | 13380 |
| tctgagagca aagggaagga ctgacgagag atgtatattt aattttttaa ctgctgcaaa | 13440 |
| cattgtacat ccaaattaaa ggaaaaaaat ggaaaccatc a | 13481 |

<210> SEQ ID NO 3
<211> LENGTH: 3160
<212> TYPE: DNA
<213> ORGANISM: Homo sapiens

<400> SEQUENCE: 3

| | |
|---|---|
| cctcccctcg cccggcgcgg tcccgtccgc ctctcgctcg cctcccgcct ccccctcggtc | 60 |
| ttccgaggcg cccgggctcc cggcgcggcg gcggaggggg cgggcaggcc ggcgggcggt | 120 |
| gatgtggcag gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gccctctca gcgcctgtga gcagccgcg gggcagcgcc ctcggggagc cggccggcct | 360 |
| gcggcggcgg cagcggcggc gtttctcgcc tcctcttcgt cttttctaac cgtgcagcct | 420 |
| cttcctcggc ttctcctgaa agggaaggtg aagccgtgg gctcgggcgg gagccggctg | 480 |
| aggcgcggcg gcggcggcgg cggcacctcc cgctcctgga gcggggggga gaagcggcgg | 540 |
| cggcggcggc cgcggcggct gcagctccag ggaggggggtc tgagtcgcct gtcaccattt | 600 |
| ccagggctgg gaacgccgga gagttggtct ctccccttct actgcctcca acacggcggc | 660 |
| ggcggcggcg gcacatccag ggacccgggc cggttttaaa cctcccgtcc gccgccgccg | 720 |
| caccccccgt ggcccgggct ccggaggccg ccggcggagg cagccgttcg gaggattatt | 780 |
| cgtcttctcc ccattccgct gccgccgctg ccaggcctct ggctgctgag gagaagcagg | 840 |
| cccagtcgct gcaaccatcc agcagccgcc gcagcagcca ttacccggct gcggtccaga | 900 |
| gccaagcggc ggcagagcga ggggcatcag ctaccgccaa gtccagagcc atttccatcc | 960 |
| tgcagaagaa gccccgccac cagcagcttc tgccatctct ctcctccttt tcttcagcc | 1020 |
| acaggctccc agacatgaca gccatcatca agagatcgt tagcagaaac aaaaggagat | 1080 |
| atcaagagga tggattcgac ttagacttga cctatattta tccaaacatt attgctatgg | 1140 |
| gatttcctgc agaaagactt gaaggcgtat acaggaacaa tattgatgat gtagtaaggt | 1200 |
| ttttggattc aaagcataaa aaccattaca agatatacaa tctttgtgct gaaagacatt | 1260 |
| atgacaccgc caaatttaat tgcagagttg cacaatatcc ttttgaagac cataacccac | 1320 |
| cacagctaga acttatcaaa cccttttgtg aagatcttga ccaatggcta agtgaagatg | 1380 |
| acaatcatgt tgcagcaatt cactgtaaag ctggaaaggg acgaactggt gtaatgatat | 1440 |
| gtgcatattt attacatcgg ggcaaatttt taaaggcaca agaggcccta gatttctatg | 1500 |
| gggaagtaag gaccagagac aaaaagggag taactattcc cagtcagagg cgctatgtgt | 1560 |
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |

```
atacattctt cataccagga ccagaggaaa cctcagaaaa agtagaaaat ggaagtctat      1920
gtgatcaaga aatcgatagc atttgcagta tagagcgtgc agataatgac aaggaatatc      1980
tagtacttac tttaacaaaa aatgatcttg acaaagcaaa taaagacaaa gccaaccgat      2040
acttttctcc aaattttaag gtgaagctgt acttcacaaa aacagtagag gagccgtcaa      2100
atccagaggc tagcagttca acttctgtaa caccagatgt tagtgacaat gaacctgatc      2160
attatagata ttctgacacc actgactctg atccagagaa tgaacctttt gatgaagatc      2220
agcatacaca aattacaaaa gtctgaattt ttttttatca agagggataa acaccatga       2280 aaataaactt gaataaactg aaaatggacc ttttttttt taatggcaat aggacattgt       2340
gtcagattac cagttatagg aacaattctc ttttcctgac caatcttgtt ttaccctata      2400
catccacagg gttttgacac ttgttgtcca gttgaaaaaa ggttgtgtag ctgtgtcatg      2460
tatataccdt tttgtgtcaa aaggacatt aaaattcaat taggattaat aaagatggca      2520
ctttcccgtt ttattccagt tttataaaaa gtggagacag actgatgtgt atacgtagga     2580
attttttcct tttgtgttct gtcaccaact gaagtggcta aagagctttg tgatatactg      2640
gttcacatcc tacccctttg cacttgtggc aacagataag tttgcagttg gctaagagag      2700
gtttccgaaa ggttttgcta ccattctaat gcatgtattc gggttagggc aatggagggg      2760
aatgctcaga aaggaaataa ttttatgctg gactctggac catataccat ctccagctat      2820
ttacacacac cttctcttag catgctacag ttattaatct ggacattcga ggaattggcc      2880
gctgtcactg cttgttgttt gcgcattttt ttttaaagca tattggtgct agaaaaggca      2940
gctaaaggaa gtgaatctgt attggggtac aggaatgaac cttctgcaac atcttaagat      3000
ccacaaatga agggatataa aaataatgtc ataggtaaga aacacagcaa caatgactta     3060
accatataaa tgtggaggct atcaacaaag aatgggcttg aaacattata aaaattgaca      3120
atgatttatt aaatatgttt tctcaattgt aaaaaaaaaa                            3160
```

<210> SEQ ID NO 4
<211> LENGTH: 26
<212> TYPE: DNA
<213> ORGANISM: Artificial sequence
<220> FEATURE:
<223> OTHER INFORMATION: Primer

<400> SEQUENCE: 4
aatggctaag tgaagatgac aatcat      26

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
tgcacatatc attacaccag ttcgt      25

<210> SEQ ID NO 6
<211> LENGTH: 30
<212> TYPE: DNA
<213> ORGANISM: Artificial sequence
<220> FEATURE:
<223> OTHER INFORMATION: Probe

<400> SEQUENCE: 6
ttgcagcaat tcactgtaaa gctggaaagg      30

```
<210> SEQ ID NO 7
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 7
ucgagaacau cc                                                          12

<210> SEQ ID NO 8
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 8
ggatgttctc ga                                                          12

<210> SEQ ID NO 9
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 9
taaattgtca tcacc                                                       15

<210> SEQ ID NO 10
<211> LENGTH: 30
<212> TYPE: RNA
<213> ORGANISM: Artificial sequence
<220> FEATURE:
<223> OTHER INFORMATION: Synthetic oligonucleotide

<400> SEQUENCE: 10
agacuuuuuc uggugaugac aauuuauuaa                                       30

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
gtctgtgcat ctctcc                                                      16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ttcagtcatg acttcc                                                      16

<210> SEQ ID NO 13
<211> LENGTH: 20
<212> TYPE: DNA
<213> ORGANISM: Artificial sequence
<220> FEATURE:
```

```
<223> OTHER INFORMATION: Synthetic oligonucleotide

<400> SEQUENCE: 13
gccaggctgg ttatgactca                                              20

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
aagttgtagt agtcgc                                                  16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
gcatgttctc acatta                                                  16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
acatcttcag atcatt                                                  16

<210> SEQ ID NO 17
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 17
aaggaaguca ugacugaagc                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgctagcct ctggatttga                                              20
```